US007696322B2

(12) United States Patent
Bleck et al.

(10) Patent No.: US 7,696,322 B2
(45) Date of Patent: Apr. 13, 2010

(54) FUSION ANTIBODIES

(75) Inventors: Gregory T. Bleck, Cross Plains, WI (US); Dona York, Wisconsin Dells, WI (US); Ian Collins, Prairie du Sac, WI (US)

(73) Assignee: Catalent Pharma Solutions, Inc., Somerset, NJ (US)

( * ) Notice: Subject to any disclaimer, the term of this patent is extended or adjusted under 35 U.S.C. 154(b) by 377 days.

(21) Appl. No.: 10/900,928

(22) Filed: Jul. 28, 2004

(65) Prior Publication Data

US 2005/0069552 A1 Mar. 31, 2005

Related U.S. Application Data

(60) Provisional application No. 60/490,569, filed on Jul. 28, 2003.

(51) Int. Cl.
*C12P 21/08* (2006.01)
*C07K 16/00* (2006.01)
*A61K 39/395* (2006.01)
*C12P 21/04* (2006.01)
*C07H 21/04* (2006.01)

(52) U.S. Cl. .............. 530/387.3; 424/133.1; 424/136.1; 424/141.1; 435/69.6; 435/70.21; 530/388.1

(58) Field of Classification Search .............. 530/387.1, 530/387.3, 387.5, 387.7, 387.8; 424/133.1, 424/134.1, 135.1, 136.1; 435/70.21, 451, 435/452, 455, 328; 536/23.4, 23.53
See application file for complete search history.

(56) References Cited

U.S. PATENT DOCUMENTS 5,132,405 A * 7/1992 Huston et al.
5,512,421 A 4/1996 Burns et al.
5,514,548 A 5/1996 Krebber et al.
5,583,202 A 12/1996 Zanetti
5,658,762 A 8/1997 Zanetti et al.
5,674,486 A 10/1997 Sobol et al.
5,686,120 A 11/1997 Mertz et al.
5,792,455 A 8/1998 Chapman et al.
5,798,100 A 8/1998 Hansen
5,904,920 A 5/1999 Dranoff et al.
5,914,267 A 6/1999 Mertz et al.
5,972,334 A 10/1999 Denney, Jr.
5,994,136 A 11/1999 Naldini et al.
5,994,523 A 11/1999 Kawakami et al.
6,013,516 A 1/2000 Verma et al.
6,051,230 A 4/2000 Thorpe
6,132,718 A 10/2000 Hansen
6,136,597 A 10/2000 Hope et al.
6,180,357 B1 1/2001 Young et al.
6,180,370 B1 1/2001 Queen
6,207,147 B1 3/2001 Hiserodt et al.
6,277,969 B1 8/2001 Le et al.
6,291,650 B1 9/2001 Winter et al.
6,852,510 B2 2/2005 Bremel et al.
6,972,324 B2 * 12/2005 Adolf et al. ............ 530/388.85
2003/0092882 A1 5/2003 Bremel et al.
2003/0224415 A1 12/2003 Bremel
2004/0002062 A1 1/2004 Bremel et al.
2004/0038304 A1 2/2004 Bremel et al.
2004/0235173 A1 11/2004 Bleck et al.
2005/0100952 A1 5/2005 Bremel et al.
2006/0160220 A1 7/2006 Bremel et al.

FOREIGN PATENT DOCUMENTS

WO 94/13806 * 6/1994

OTHER PUBLICATIONS

Alberts et al (Molecular Biology of the Cell, 3rd Edition, 1994, Chapter 23, in particular pp. 1206-1211).*
Rudikoff et al (Proc. Natl. Acad. Sci. USA 1982 vol. 79 p. 1979).*
Ibragimova and Eade (Biophysical Journal, Oct 1999, vol. 77, pp. 2191-2198).*
Todorovska et al. 2001. J. Immunological Methods. 248:47-66.*
Luo et al. 1995. J. Biochem. 118:825-831.*
Paul, Fundamental Immunology, 3rd Edition, 1993, pp. 292-295.*
Rudikoff et al. Proc. Natl. Acad. Sci. USA, 79:1979-1983, Mar. 1982.*
Colman, Research in Immunology, 145:33-36, 1994.*
Bendig M. M. Methods: A Companion to Methods in Enzymology, 1995; 8:83-93.*
Arndt et al. Biochemistry, 37:12918-12926, 1998.*
Whitlow et al. Protein Engineering, 7(8):1017-1026, 1994.*
Miller and Baltimore, "Redesign of retrovirus packaging cell lines to avoid recombination leading to helper virus production,". Mol. Cell. Biol. 6:2895 [1986].

(Continued)

*Primary Examiner*—David J. Blanchard
(74) *Attorney, Agent, or Firm*—Casimir Jones, S.C.

(57) ABSTRACT

The present invention provides novel antibodies. In particular, the present invention provides fusion antibodies comprising antibody heavy and light chain fusions. The present invention further provides multivalent antibodies comprising multiple fusion antibody chains. The present invention further provides methods of generating splice resistant antibody genes.

2 Claims, 39 Drawing Sheets

OTHER PUBLICATIONS

Markowitz et al., "A safe packaging line for gene transfer: separating viral genes on two different plasmids," J. Virol. 62:1120 [1988].

Miller et al., "Gene transfer by retrovirus vectors occurs only in cells that are actively replicating at the time of infection," Mol. Cell. Biol. 10:4239 [1990].

Miller and Rosman, "Improved retroviral vectors for gene transfer and expression," BioTechniques 7: 980 [1986] —.

Miller, "Human gene therapy comes of age," Nature 357: 455 [1990].

Adams et al., "Transduction of primary human hepatocytes with amphotropic and xenotropic retroviral vectors," Proc. Natl. Acad. Sci. USA 89:8981 [1992].

Mastromarino et al., "Characterization of membrane components of the erythrocyte involved in vesicular stomatitis virus attachment and fusion at acidic pH," J. Gen. Virol. 68:2359 [1987 ].

Burns et al. Proc. Natl. Acad. Sci. USA 90:8033 [1993].

* cited by examiner

Figure 1
Antibody Heavy Chain
Linker
Antibody Light Chain

Figure 2

SEQ ID NO:1

ATG/GGA/TGG/AGC/TGT/ATC/ATC/CTC/TTC/TTG/GTA/GCA/ACA/GCT/ACA/GGT/GTC/CAC
/TCC/GAG/GTC/CAA/CTG/GTG/GAG/AGC/GGT/GGA/GGT/GTT/GTG/CAA/CCT/GGC/CGG/TC
C/CTG/CGC/CTG/TCC/TGC/TCC/GCA/TCT/GGC/TTC/GAT/TTC/ACC/ACA/TAT/TGG/ATG/A
GT/TGG/GTG/AGA/CAG/GCA/CCT/GGA/AAA/GGT/CTT/GAG/TGG/ATT/GGA/GAA/ATT/CAT/
CCA/GAT/AGC/AGT/ACG/ATT/AAC/TAT/GCG/CCG/TCT/CTA/AAG/GAT/AGA/TTT/ACA/ATA
/TCG/CGA/GAC/AAC/GCC/AAG/AAC/ACA/TTG/TTC/CTG/CAA/ATG/GAC/AGC/CTG/AGA/CC
C/GAA/GAC/ACC/GGG/GTC/TAT/TTT/TGT/GCA/AGC/CTT/TAC/TTC/GGC/TTC/CCC/TGG/T
TT/GCT/TAT/TGG/GGC/CAA/GGG/ACC/CCG/GTC/ACC/GTC/TCC/TCA/GCC/TCC/ACC/AAG/
GGC/CCA/TCG/GTC/TTC/CCC/CTG/GCA/CCC/TCC/TCC/AAG/AGC/ACC/TCT/GGG/GGC/ACA
/GCG/GCC/CTG/GGC/TGC/CTG/GTC/AAG/GAC/TAC/TTC/CCC/GAA/CCG/GTG/ACG/GTG/TC
G/TGG/AAC/TCA/GGC/GCC/CTG/ACC/AGC/GGC/GTG/CAC/ACC/TTC/CCG/GCT/GTC/CTA/C
AG/TCC/TCA/GGA/CTC/TAC/TCC/CTC/AGC/AGC/GTG/GTG/ACC/GTG/CCC/TCC/AGC/AGC/
TTG/GGC/ACC/CAG/ACC/TAC/ATC/TGC/AAC/GTG/AAT/CAC/AAG/CCC/AGC/AAC/ACC/AAG
/GTG/GAC/AAG/AGA/GTT/GAG/CCC/AAA/TCT/TGT/GAC/AAA/ACT/CAC/ACA/TGC/CCA/CC
G/TGC/CCA/GCA/CCT/GAA/CTC/CTG/GGG/GGA/CCG/TCA/GTC/TTC/CTC/TTC/CCC/CCA/A
AA/CCC/AAG/GAC/ACC/CTC/ATG/ATC/TCC/CGG/ACC/CCT/GAG/GTC/ACA/TGC/GTG/GTG/
GTG/GAC/GTG/AGC/CAC/GAA/GAC/CCT/GAG/GTC/AAG/TTC/AAC/TGG/TAC/GTG/GAC/GGC
/GTG/GAG/GTG/CAT/AAT/GCC/AAG/ACA/AAG/CCG/CGG/GAG/GAG/CAG/TAC/AAC/AGC/AC
G/TAC/CGT/GTG/GTC/AGC/GTC/CTC/ACC/GTC/CTG/CAC/CAG/GAC/TGG/CTG/AAT/GGC/A
AG/GAG/TAC/AAG/TGC/AAG/GTC/TCC/AAC/AAA/GCC/CTC/CCA/GCC/CCC/ATC/GAG/AAA/
ACC/ATC/TCC/AAA/GCC/AAA/GGG/CAG/CCC/CGA/GAA/CCA/CAG/GTG/TAC/ACC/CTG/CCC
/CCA/TCC/CGG/GAG/GAG/ATG/ACC/AAG/AAC/CAG/GTC/AGC/CTG/ACC/TGC/CTG/GTC/AA
A/GGC/TTC/TAT/CCC/AGC/GAC/ATC/GCC/GTG/GAG/TGG/GAG/AGC/AAT/GGG/CAG/CCG/G
AG/AAC/AAC/TAC/AAG/ACC/ACG/CCT/CCC/GTG/CTG/GAC/TCC/GAC/GGC/TCC/TTC/TTC/
CTC/TAT/AGC/AAG/CTC/ACC/GTG/GAC/AAG/AGC/AGG/TGG/CAG/CAG/
GGG/AAC/GTC/TTC/TCA/TGC/TCC/GTG/ATG/CAT/GAG/GCT/CTG/CAC/AAC/CAC/TAC/ACG
/CAG/AAG/AGC/CTC/TCC/CTG/TCT/CCG/GGC/ATC/CTA/TTC/CAT/GCC/ACC/CAG/GCC/GA
C/ATC/CAG/CTG/ACC/CAG/AGC/CCA/AGC/AGC/CTG/AGC/GCC/AGC/GTG/GGT/GAC/AGA/G
TG/ACC/ATC/ACC/TGT/AAG/GCC/AGT/CAG/GAT/GTG/GGT/ACT/TCT/GTA/GCC/TGG/TAC/
CAG/CAG/AAG/CCA/GGT/AAG/GCT/CCA/AAG/CTG/CTG/ATC/TAC/TGG/ACA/TCC/ACC/CGG
/CAC/ACT/GGT/GTG/CCA/AGC/AGA/TTC/AGC/GGT/AGC/GGT/AGC/GGT/ACC/GAC/TTC/AC
C/TTC/ACC/ATC/AGC/AGC/CTC/CAG/CCA/GAG/GAC/ATC/GCC/ACC/TAC/TAC/TGC/CAG/C
AA/TAT/AGC/CTC/TAT/CGG/TCG/TTC/GGC/CAA/GGG/ACC/AAG/GTG/GAA/ATC/AAA/CGA/
ACT/GTG/GCT/GCA/CCA/TCT/GTC/TTC/ATC/TTC/CCG/CCA/TCT/GAT/GAG/CAG/TTG/AAA
/TCT/GGA/ACT/GCC/TCT/GTT/GTG/TGC/CTG/CTG/AAT/AAC/TTC/TAT/CCC/AGA/GAG/GC
C/AAA/GTA/CAG/TGG/AAG/GTG/GAT/AAC/GCC/CTC/CAA/TCG/GGT/AAC/TCC/CAG/GAG/A
GT/GTC/ACA/GAG/CAG/GAC/AGC/AAG/GAC/AGC/ACC/TAC/AGC/CTC/AGC/AGC/ACC/CTG/
ACG/CTG/AGC/AAA/GCA/GAC/TAC/GAG/AAA/CAC/AAA/GTC/TAC/GCC/TGC/GAA/GTC/ACC
/CAT/CAG/GGC/CTG/AGC/TCG/CCC/GTC/ACA/AAG/AGC/TTC/AAC/AGG/GGA/GAG/TGT/**TA
G**

Antibody Fusion Gene #2 (SEQ ID NO:2):

ATG/GGA/TGG/AGC/TGT/ATC/ATC/CTC/TTC/TTG/GTA/GCA/ACA/GCT/ACA
/GGT/GTC/CAC/TCC/CAG/GTC/CAG/CTG/GTC/CAA/TCA/GGG/GCT/GAA/GT
C/AAG/AAA/CCT/GGG/TCA/TCA/GTG/AAG/GTC/TCC/TGC/AAG/GCT/TCT/G
GC/TAC/ACC/TTT/ACT/AGC/TAC/TGG/CTG/CAC/TGG/GTC/AGG/CAG/GCA/
CCT/GGA/CAG/GGT/CTG/GAA/TGG/ATT/GGA/TAC/ATT/AAT/CCT/AGG/AAT

SEQ ID NO:2 (CONT)

/GAT/TAT/ACT/GAG/TAC/AAT/CAG/AAC/TTC/AAG/GAC/AAG/GCC/ACA/AT
A/ACT/GCA/GAC/GAA/TCC/ACC/AAT/ACA/GCC/TAC/ATG/GAG/CTG/AGC/A
GC/CTG/AGG/TCT/GAG/GAC/ACG/GCA/TTT/TAT/TTT/TGT/GCA/AGA/AGG/
GAT/ATT/ACT/ACG/TTC/TAC/TGG/GGC/CAA/GGC/ACC/ACG/GTC/ACC/GTC
/TCC/TCA/GCC/TCC/ACC/AAG/GGC/CCA/TCG/GTC/TTC/CCC/CTG/GCA/CC
C/TCC/TCC/AAG/AGC/ACC/TCT/GGG/GGC/ACA/GCG/GCC/CTG/GGC/TGC/C
TG/GTC/AAG/GAC/TAC/TTC/CCC/GAA/CCG/GTG/ACG/GTG/TCG/TGG/AAC/
TCA/GGC/GCC/CTG/ACC/AGC/GGC/GTG/CAC/ACC/TTC/CCG/GCT/GTC/CTA
/CAG/TCC/TCA/GGA/CTC/TAC/TCC/CTC/AGC/AGC/GTG/GTG/ACC/GTG/CC
C/TCC/AGC/AGC/TTG/GGC/ACC/CAG/ACC/TAC/ATC/TGC/AAC/GTG/AAT/C
AC/AAG/CCC/AGC/AAC/ACC/AAG/GTG/GAC/AAG/AGA/GTT/GAG/CCC/AAA/
TCT/TGT/GAC/AAA/ACT/CAC/ACA/TGC/CCA/CCG/TGC/CCA/GCA/CCT/GAA
/CTC/CTG/GGG/GGA/CCG/TCA/GTC/TTC/CTC/TTC/CCC/CCA/AAA/CCC/AA
G/GAC/ACC/CTC/ATG/ATC/TCC/CGG/ACC/CCT/GAG/GTC/ACA/TGC/GTG/G
TG/GTG/GAC/GTG/AGC/CAC/GAA/GAC/CCT/GAG/GTC/AAG/TTC/AAC/TGG/
TAC/GTG/GAC/GGC/GTG/GAG/GTG/CAT/AAT/GCC/AAG/ACA/AAG/CCG/CGG
/GAG/GAG/CAG/TAC/AAC/AGC/ACG/TAC/CGT/GTG/GTC/AGC/GTC/CTC/AC
C/GTC/CTG/CAC/CAG/GAC/TGG/CTG/AAT/GGC/AAG/GAG/TAC/AAG/TGC/A
AG/GTC/TCC/AAC/AAA/GCC/CTC/CCA/GCC/CCC/ATC/GAG/AAA/ACC/ATC/
TCC/AAA/GCC/AAA/GGG/CAG/CCC/CGA/GAA/CCA/CAG/GTG/TAC/ACC/CTG
/CCC/CCA/TCC/CGG/GAG/GAG/ATG/ACC/AAG/AAC/CAG/GTC/AGC/CTG/AC
C/TGC/CTG/GTC/AAA/GGC/TTC/TAT/CCC/AGC/GAC/ATC/GCC/GTG/GAG/T
GG/GAG/AGC/AAT/GGG/CAG/CCG/GAG/AAC/AAC/TAC/AAG/ACC/ACG/CCT/
CCC/GTG/CTG/GAC/TCC/GAC/GGC/TCC/TTC/TTC/CTC/TAT/AGC/AAG/CTC
/ACC/GTG/GAC/AAG/AGC/AGG/TGG/CAG/CAG/GGG/AAC/GTC/TTC/TCA/TG
C/TCC/GTG/ATG/CAT/GAG/GCT/CTG/CAC/AAC/CAC/TAC/ACG/CAG/AAG/A
GC/CTC/TCC/CTG/TCT/CCG/GGC/ATC/CTA/TTC/CAT/GCC/ACC/CAG/GCC/
GAC/ATC/CAG/CTG/ACC/CAG/TCT/CCA/TCA/TCT/CTG/AGC/GCA/TCT/GTT
/GGA/GAT/AGG/GTC/ACT/ATG/AGC/TGT/AAG/TCC/AGT/CAA/AGT/GTT/TT
A/TAC/AGT/GCA/AAT/CAC/AAG/AAC/TAC/TTG/GCC/TGG/TAC/CAG/CAG/A
AA/CCA/GGG/AAA/GCA/CCT/AAA/CTG/CTG/ATC/TAC/TGG/GCA/TCC/ACT/
AGG/GAA/TCT/GGT/GTC/CCT/TCG/CGA/TTC/TCT/GGC/AGC/GGA/TCT/GGG
/ACA/GAT/TTT/ACT/TTC/ACC/ATC/AGC/TCT/CTT/CAA/CCA/GAA/GAC/AT
T/GCA/ACA/TAT/TAT/TGT/CAC/CAA/TAC/CTC/TCC/TCG/TGG/ACG/TTC/G
GT/GGA/GGG/ACC/AAG/GTG/CAG/ATC/AAA/CGA/ACT/GTG/GCT/GCA/CCA/
TCT/GTC/TTC/ATC/TTC/CCG/CCA/TCT/GAT/GAG/CAG/TTG/AAA/TCT/GGA
/ACT/GCC/TCT/GTT/GTG/TGC/CTG/CTG/AAT/AAC/TTC/TAT/CCC/AGA/GA
G/GCC/AAA/GTA/CAG/TGG/AAG/GTG/GAT/AAC/GCC/CTC/CAA/TCG/GGT/A
AC/TCC/CAG/GAG/AGT/GTC/ACA/GAG/CAG/GAC/AGC/AAG/GAC/AGC/ACC/
TAC/AGC/CTC/AGC/AGC/ACC/CTG/ACG/CTG/AGC/AAA/GCA/GAC/TAC/GAG
/AAA/CAC/AAA/GTC/TAC/GCC/TGC/GAA/GTC/ACC/CAT/CAG/GGC/CTG/AG
C/TCG/CCC/GTC/ACA/AAG/AGC/TTC/AAC/AGG/GGA/GAG/TGT/TAG

Figure 3
SEQ ID NO:3

EVQLVESGGGVVQPGRSLRLSCSASGFDFTTYWMSWVRQAPGKGLEWIGEIHPDSSTIN
YAPSLKDRFTISRDNAKNTLFLQMDSLRPEDTGVYFCASLYFGFPWFAYWGQGTPVTVS
SASTKGPSVFPLAPSSKSTSGGTAALGCLVKDYFPEPVTVSWNSGALTSGVHTFPAVLQ
SSGLYSLSSVVTVPSSSLGTQTYICNVNHKPSNTKVDKRVEPKSCDKTHTCPPCPAPEL
LGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLP
PSREEMTKNQVSLTCLVKGFYPSDIAVEWESNGQPENNYKTTPPVLDSDGSFFLYSKLT
VDKSRWQQGNVFSCSVMHEALHNHYTQKSLSLSPGilfhatqa*DIQLTQSPSSLSASVG*
*DRVTITCKASQDVGTSVAWYQQKPGKAPKLLIYWTSTRHTGVPSRFSGSGSGTDFTFTI*
*SSLQPEDIATYYCQQYSLYRSFGQGTKVEIKRTVAAPSVFIFPPSDEQLKSGTASVVCL*
*LNNFYPREAKVQWKVDNALQSGNSQESVTEQDSKDSTYSLSSTLTLSKADYEKHKVYAC*
*EVTHQGLSSPVTKSFNRGEC*

Figure 5

Initial Retrovector Gene Construct for Antibody #1 (SEQ ID NO:4):

TTTGAAAGACCCCACCCGTAGGTGGCAAGCTAGCTTAAGTAACGCCACTTTGCAAGGCATGGAAAAATACA
TAACTGAGAATAGAAAAGTTCAGATCAAGGTCAGGAACAAAGAAACAGCTGAATACCAAACAGGATATCTG
TGGTAAGCGGTTCCTGCCCCGGCTCAGGGCCAAGAACAGATGAGACAGCTGAGTGATGGGCCAAACAGGAT
ATCTGTGGTAAGCAGTTCCTGCCCCGGCTCGGGGCCAAGAACAGATGGTCCCCAGATGCGGTCCAGCCCTC
AGCAGTTTCTAGTGAATCATCAGATGTTTCCAGGGTGCCCCAAGGACCTGAAAATGACCCTGTACCTTATT
TGAACTAACCAATCAGTTCGCTTCTCGCTTCTGTTCGCGCGCTTCCGCTCTCCGAGCTCAATAAAAGAGCC
CACAACCCCTCACTCGGCGCGCCAGTCTTCCGATAGACTGCGTCGCCCGGGTACCCGTATTCCCAATAAAG
CCTCTTGCTGTTTGCATCCGAATCGTGGTCTCGCTGTTCCTTGGGAGGGTCTCCTCTGAGTGATTGACTAC
CCACGACGGGGGTCTTTCATTTGGGGGCTCGTCCGGGATTTGGAGACCCCTGCCCAGGGACCACCGACCCA
CCACCGGGAGGTAAGCTGGCCAGCAACTTATCTGTGTCTGTCCGATTGTCTAGTGTCTATGTTTGATGTTA
TGCGCCTGCGTCTGTACTAGTTAGCTAACTAGCTCTGTATCTGGCGGACCCGTGGTGGAACTGACGAGTTC
TGAACACCCGGCCGCAACCCTGGGAGACGTCCCAGGGACTTTGGGGGCCGTTTTTGTGGCCCGACCTGAGG
AAGGGAGTCGATGTGGAATCCGACCCCGTCAGGATATGTGGTTCTGGTAGGAGACGAGAACCTAAAACAGT
TCCCGCCTCCGTCTGAATTTTTGCTTTCGGTTTGGAACCGAAGCCGCGCGTCTTGTCTGCTGCAGCGCTGC
AGCATCGTTCTGTGTTGTCTCTGTCTGACTGTGTTTCTGTATTTGTCTGAAAATTAGGGCCAGACTGTTAC
CACTCCCTTAAGTTTGACCTTAGGTCACTGGAAAGATGTCGAGCGGATCGCTCACAACCAGTCGGTAGATG
TCAAGAAGAGACGTTGGGTTACCTTCTGCTCTGCAGAATGGCCAACCTTTAACGTCGGATGGCCGCGAGAC
GGCACCTTTAACCGAGACCTCATCACCCAGGTTAAGATCAAGGTCTTTTCACCTGGCCCGCATGGACACCC
AGACCAGGTCCCCTACATCGTGACCTGGGAAGCCTTGGCTTTTGACCCCCCTCCCTGGGTCAAGCCCTTTG
TACACCCTAAGCCTCCGCCTCCTCTTCCTCCATCCGCCCCGTCTCTCCCCCTTGAACCTCCTCGTTCGACC
CCGCCTCGATCCTCCCTTTATCCAGCCCTCACTCCTTCTCTAGGCGCCGGAATTCCGATCTGATCAAGAGA
CAGGATGAGGATCGTTTCGCATGATTGAACAAGATGGATTGCACGCAGGTTCTCCGGCCGCTTGGGTGGAG
AGGCTATTCGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAGGACGAGGCAG
CGCGGCTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCATTCGACCACC
AAGCGAAACATCGCATCGAGCGAGCACGTACTCGGATGGAAGCCGGTCTTGTCGATCAGGATGATCTGGAC
GAAGAGCATCAGGGGCTCGCGCCAGCCGAACTGTTCGCCAGGCTCAAGGCGCGCATGCCCGACGGCGAGGA
TCTCGTCGTGACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGATATTGCTGAA
GAGCTTGGCGGCGAATGGGCTGACCGCTTCCTCGTGCTTTACGGTATCGCCGCTCCCGATTCGCAGCGCAT
CGCCTTCTATCGCCTTCTTGACGAGTTCTTCTGAGCGGGACTCTGGGGTTCGAAATGACCGACCAAGCGAC
GCCCAACCTGCCATCACGAGATTTCGATTCCACCGCCGCCTTCTATGAAAGGTTGGGCTTCGGAATCGTTT
TCCGGGACGCCGGCTGGATGATCCTCCAGCGCGGGGATCTCATGCTGGAGTTCTTCGCCCACCCCGGGCTC
GATCCCCTCGCGAGTTGGTTCAGCTGCTGCCTGAGGCTGGACGACCTCGCGGAGTTCTACCGGCAGTGCAA
ATCCGTCGGCATCCAGGAAACCAGCAGCGGCTATCCGCGCATCCATGCCCCCGAACTGCAGGAGTGGGGAG
GCACGATGGCCGCTTTGGTCGAGGCGGATCCGGCCATTAGCCATATTATTCATTGGTTATATAGCATAAAT
CAATATTGGCTATTGGCCATTGCATACGTTGTATCCATATCATAATATGTACATTTATATTGGCTCATGTC
CAACATTACCGCCATGTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGGACTTTCC
TACTTGGCAGTACATCTACGTATTAGTCATCGCTATTACCATGGTGATGCGGTTTTGGCAGTACATCAATG
GGCGTGGATAGCGGTTTGACTCACGGGGATTTCCAAGTCTCCACCCCATTGACGTCAATGGGAGTTTGTTT
TGGCACCAAAATCAACGGGACTTTCCAAAATGTCGTAACAACTCCGCCCCATTGACGCAAATGGGCGGTAG
GCATGTACGGTGGGAGGTCTATATAAGCAGAGCTCGTTTAGTGAACCGTCAGATCGCCTGGAGACGCCATC
CACGCTGTTTTGACCTCCATAGAAGACACCGGGACCGATCCAGCCTCCGCGGCCCCAAGCTTCTCGACGGA
TCCCCGGGAATTCAGGACCTCACCATGGGATGGAGCTGTATCATCCTCTTCTTGGTAGCAACAGCTACAGG
TGTCCACTCCGAGGTCCAACTGGTGGAGAGCGGTGGAGGTGTTGTGCAACCTGGCCGGTCCCTGCGCCTGT
CCTGCTCCGCATCTGGCTTCGATTTCACCACATATTGGATGAGTTGGGTGAGACAGGCACCTGGAAAAGGT

SEQ ID NO: 4 (CONT)

```
CTTGAGTGGATTGGAGAAATTCATCCAGATAGCAGTACGATTAACTATGCGCCGTCTCTAAAGGATAGATT
TACAATATCGCGAGACAACGCCAAGAACACATTGTTCCTGCAAATGGACAGCCTGAGACCCGAAGACACCG
GGGTCTATTTTTGTGCAAGCCTTTACTTCGGCTTCCCCTGGTTTGCTTATTGGGGCCAAGGGACCCCGGTC
ACCGTCTCCTCAGCCTCCACCAAGGGCCCATCGGTCTTCCCCCTGGCACCCTCCTCCAAGAGCACCTCTGG
GGGCACAGCGGCCCTGGGCTGCCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATCACAAGCCCAGCAA
CACCAAGGTGGACAAGAGAGTTGAGCCCAAATCTTGTGACAAAACTCACACATGCCCACCGTGCCCAGCAC
CTGAACTCCTGGGGGGACCGTCAGTCTTCCTCTTCCCCCCAAAACCCAAGGACACCCTCATGATCTCCCGG
ACCCCTGAGGTCACATGCGTGGTGGTGGACGTGAGCCACGAAGACCCTGAGGTCAAGTTCAACTGGTACGT
GGACGGCGTGGAGGTGCATAATGCCAAGACAAAGCCGCGGGAGGAGCAGTACAACAGCACGTACCGTGTGG
TCAGCGTCCTCACCGTCCTGCACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCCCCGAGAACCACAGGTGTACAC
CCTGCCCCCATCCCGGGAGGAGATGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGCCTCCCGTG
CTGGACTCCGACGGCTCCTTCTTCCTCTATAGCAAGCTCACCGTGGACAAGAGCAGGTGGCAGCAGGGGAA
CGTCTTCTCATGCTCCGTGATGCATGAGGCTCTGCACAACCACTACACGCAGAAGAGCCTCTCCCTGTCTC
CGGGTAAATGAAAGCCGAATTCGCCCCTCTCCCTCCCCCCCCCCTAACGTTACTGGCCGAAGCCGCTTGGA
ATAAGGCCGGTGTGCGTTTGTCTATATGTTATTTTCCACCATATTGCCGTCTTTTGGCAATGTGAGGGCCC
GGAAACCTGGCCCTGTCTTCTTGACGAGCATTCCTAGGGGTCTTTCCCCTCTCGCCAAAGGAATGCAAGGT
CTGTTGAATGTCGTGAAGGAAGCAGTTCCTCTGGAAGCTTCTTGAAGACAAACAACGTCTGTAGCGACCCT
TTGCAGGCAGCGGAACCCCCCACCTGGCGACAGGTGCCTCTGCGGCCAAAAGCCACGTGTATAAGATACAC
CTGCAAAGGCGGCACAACCCCAGTGCCACGTTGTGAGTTGGATAGTTGTGGAAAGAGTCAAATGGCTCTCC
TCAAGCGTATTCAACAAGGGGCTGAAGGATGCCCAGAAGGTACCCCATTGTATGGGATCTGATCTGGGGCC
TCGGTGCACATGCTTTACATGTGTTTAGTCGAGGTTAAAAAAACGTCTAGGCCCCCCGAACCACGGGGACG
TGGTTTTCCTTTGAAAAACACGATGATAATATGGCCTCCTTTGTCTCTCTGCTCCTGGTAGGCATCCTATT
CCATGCCACCCAGGCCGACATCCAGCTGACCCAGAGCCCAAGCAGCCTGAGCGCCAGCGTGGGTGACAGAG
TGACCATCACCTGTAAGGCCAGTCAGGATGTGGGTACTTCTGTAGCCTGGTACCAGCAGAAGCCAGGTAAG
GCTCCAAAGCTGCTGATCTACTGGACATCCACCCGGCACACTGGTGTGCCAAGCAGATTCAGCGGTAGCGG
TAGCGGTACCGACTTCACCTTCACCATCAGCAGCCTCCAGCCAGAGGACATCGCCACCTACTACTGCCAGC
AATATAGCCTCTATCGGTCGTTCGGCCAAGGGACCAAGGTGGAAATCAAACGAACTGTGGCTGCACCATCT
GTCTTCATCTTCCCGCCATCTGATGAGCAGTTGAAATCTGGAACTGCCTCTGTTGTGTGCCTGCTGAATAA
CTTCTATCCCAGAGAGGCCAAAGTACAGTGGAAGGTGGATAACGCCCTCCAATCGGGTAACTCCCAGGAGA
GTGTCACAGAGCAGGACAGCAAGGACAGCACCTACAGCCTCAGCAGCACCCTGACGCTGAGCAAAGCAGAC
TACGAGAAACACAAAGTCTACGCCTGCGAAGTCACCCATCAGGGCCTGAGCTCGCCCGTCACAAAGAGCTT
CAACAGGGGAGAGTGTTAGAGATCTAGGCCTCCTAGGTCGACATCGATAAAATAAAAGATTTTATTTAGTC
TCCAGAAAAAGGGGGGAATGAAAGACCCCACCTGTAGGTTTGGCAAGCTAGCTTAAGTAACGCCATTTTGC
AAGGCATGGAAAAATACATAACTGAGAATAGAGAAGTTCAGATCAAGGTCAGGAACAGATGGAACAGCTGA
ATATGGGCCAAACAGGATATCTGTGGTAAGCAGTTCCTGCCCCGGCTCAGGGCCAAGAACAGATGGAACAG
CTGAATATGGGCCAAACAGGATATCTGTGGTAAGCAGTTCCTGCCCCGGCTCAGGGCCAAGAACAGATGGT
CCCCAGATGCGGTCCAGCCCTCAGCAGTTTCTAGAGAACCATCAGATGTTTCCAGGGTGCCCCAAGGACCT
GAAATGACCCTGTGCCTTATTTGAACTAACCAATCAGTTCGCTTCTCGCTTCTGTTCGCGCGCTTCTGCTC
CCCGAGCTCAATAAAAGAGCCCACAACCCCTCACTCGGGGCGCCAGTCCTCCGATTGACTGAGTCGCCCGG
GTACCCGTGTATCCAATAAACCCTCTTGCAGTTGCATCCGACTTGTGGTCTCGCTGTTCCTTGGGAGGGTC
TCCTCTGAGTGATTGACTACCCGTCAGCGGGGGTCTTTCATT
```

| | |
|---|---|
| 1 - 589 | 5'LTR Moloney murine sarcoma virus |
| 659 - 1468 | Extended packaging signal Moloney murine leukemia virus |
| 1512 - 2306 | Neomycin resistance gene |
| 2656 - 3473 | Human cytomegalovirus major immediate early promoter/enhancer |
| 3504 - 3506 | MN14 heavy chain gene signal peptide start codon |
| 4908 - 4910 | Stop codon for MN14 heavy chain gene |

SEQ ID NO: 4 (CONT)

| | |
|---|---|
| 4922 - 5497 | Encephalomyocarditis virus internal ribosome entry site |
| 5498 - 5500 | Bovine α-Lactalbumin signal peptide start codon |
| 5555 - 5557 | First codon encoding mature MN14 light chain |
| 6194 - 6196 | Stop codon for MN14 light chain |
| 6265 - 6858 | 3'LTR Moloney murine leukemia virus |

Initial Retrovector Gene Construct for Antibody #2 (SEQ ID NO:5):

TTTGAAAGACCCCACCCGTAGGTGGCAAGCTAGCTTAAGTAACGCCACTTTGCAAGGCATGGAAAAATACA
TAACTGAGAATAGAAAAGTTCAGATCAAGGTCAGGAACAAAGAAACAGCTGAATACCAAACAGGATATCTG
TGGTAAGCGGTTCCTGCCCCGGCTCAGGGCCAAGAACAGATGAGACAGCTGAGTGATGGGCCAAACAGGAT
ATCTGTGGTAAGCAGTTCCTGCCCCGGCTCGGGGCCAAGAACAGATGGTCCCCAGATGCGGTCCAGCCCTC
AGCAGTTTCTAGTGAATCATCAGATGTTTCCAGGGTGCCCCAAGGACCTGAAAATGACCCTGTACCTTATT
TGAACTAACCAATCAGTTCGCTTCTCGCTTCTGTTCGCGCGCTTCCGCTCTCCGAGCTCAATAAAAGAGCC
CACAACCCCTCACTCGGCGCGCCAGTCTTCCGATAGACTGCGTCGCCCGGGTACCCGTATTCCCAATAAAG
CCTCTTGCTGTTTGCATCCGAATCGTGGTCTCGCTGTTCCTTGGGAGGGTCTCCTCTGAGTGATTGACTAC
CCACGACGGGGGTCTTTCATTTGGGGGCTCGTCCGGGATTTGGAGACCCCTGCCCAGGGACCACCGACCCA
CCACCGGGAGGTAAGCTGGCCAGCAACTTATCTGTGTCTGTCCGATTGTCTAGTGTCTATGTTTGATGTTA
TGCGCCTGCGTCTGTACTAGTTAGCTAACTAGCTCTGTATCTGGCGGACCCGTGGTGGAACTGACGAGTTC
TGAACACCCGGCCGCAACCCTGGGAGACGTCCCAGGGACTTTGGGGGCCGTTTTTGTGGCCCGACCTGAGG
AAGGGAGTCGATGTGGAATCCGACCCCGTCAGGATATGTGGTTCTGGTAGGAGACGAGAACCTAAAACAGT
TCCCGCCTCCGTCTGAATTTTTGCTTTCGGTTTGGAACCGAAGCCGCGCGTCTTGTCTGCTGCAGCGCTGC
AGCATCGTTCTGTGTTGTCTCTGTCTGACTGTGTTTCTGTATTTGTCTGAAAATTAGGGCCAGACTGTTAC
CACTCCCTTAAGTTTGACCTTAGGTCACTGGAAAGATGTCGAGCGGATCGCTCACAACCAGTCGGTAGATG
TCAAGAAGAGACGTTGGGTTACCTTCTGCTCTGCAGAATGGCCAACCTTTAACGTCGGATGGCCGCGAGAC
GGCACCTTTAACCGAGACCTCATCACCCAGGTTAAGATCAAGGTCTTTTCACCTGGCCCGCATGGACACCC
AGACCAGGTCCCCTACATCGTGACCTGGGAAGCCTTGGCTTTTGACCCCCCTCCCTGGGTCAAGCCCTTTG
TACACCCTAAGCCTCCGCCTCCTCTTCCTCCATCCGCCCCGTCTCTCCCCCTTGAACCTCCTCGTTCGACC
CCGCCTCGATCCTCCCTTTATCCAGCCCTCACTCCTTCTCTAGGCGCCGGAATTCCGATCTGATCAAGAGA
CAGGATGAGGATCGTTTCGCATGATTGAACAAGATGGATTGCACGCAGGTTCTCCGGCCGCTTGGGTGGAG
AGGCTATTCGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAGGACGAGGCAG
CGCGGCTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCATTCGACCACC
AAGCGAAACATCGCATCGAGCGAGCACGTACTCGGATGGAAGCCGGTCTTGTCGATCAGGATGATCTGGAC
GAAGAGCATCAGGGGCTCGCGCCAGCCGAACTGTTCGCCAGGCTCAAGGCGCGCATGCCCGACGGCGAGGA
TCTCGTCGTGACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGATATTGCTGAA
GAGCTTGGCGGCGAATGGGCTGACCGCTTCCTCGTGCTTTACGGTATCGCCGCTCCCGATTCGCAGCGCAT
CGCCTTCTATCGCCTTCTTGACGAGTTCTTCTGAGCGGGACTCTGGGGTTCGAAATGACCGACCAAGCGAC
GCCCAACCTGCCATCACGAGATTTCGATTCCACCGCCGCCTTCTATGAAAGGTTGGGCTTCGGAATCGTTT
TCCGGGACGCCGGCTGGATGATCCTCCAGCGCGGGGATCTCATGCTGGAGTTCTTCGCCCACCCCGGGCTC
GATCCCCTCGCGAGTTGGTTCAGCTGCTGCCTGAGGCTGGACGACCTCGCGGAGTTCTACCGGCAGTGCAA
ATCCGTCGGCATCCAGGAAACCAGCAGCGGCTATCCGCGCATCCATGCCCCCGAACTGCAGGAGTGGGGAG
GCACGATGGCCGCTTTGGTCGAGGCGGATCCGGCCATTAGCCATATTATTCATTGGTTATATAGCATAAAT
CAATATTGGCTATTGGCCATTGCATACGTTGTATCCATATCATAATATGTACATTTATATTGGCTCATGTC
CAACATTACCGCCATGTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGACTTTCC

SEQ ID NO: 5 (CONT)

TACTTGGCAGTACATCTACGTATTAGTCATCGCTATTACCATGGTGATGCGGTTTTGGCAGTACATCAATG
GGCGTGGATAGCGGTTTGACTCACGGGGATTTCCAAGTCTCCACCCCATTGACGTCAATGGGAGTTTGTTT
TGGCACCAAAATCAACGGGACTTTCCAAAATGTCGTAACAACTCCGCCCCATTGACGCAAATGGGCGGTAG
GCATGTACGGTGGGAGGTCTATATAAGCAGAGCTCGTTTAGTGAACCGTCAGATCGCCTGGAGACGCCATC
CACGCTGTTTTGACCTCCATAGAAGACACCGGGACCGATCCAGCCTCCGCGGCCCCAAGCTTCTCGACGGA
TCCCCGGGAATTCAGGACCTCACCATGGGATGGAGCTGTATCATCCTCTTCTTGGTAGCAACAGCTACAGG
TGTCCACTCCCAGGTCCAGCTGGTCCAATCAGGGGCTGAAGTCAAGAAACCTGGGTCATCAGTGAAGGTCT
CCTGCAAGGCTTCTGGCTACACCTTTACTAGCTACTGGCTGCACTGGGTCAGGCAGGCACCTGGACAGGGT
CTGGAATGGATTGGATACATTAATCCTAGGAATGATTATACTGAGTACAATCAGAACTTCAAGGACAAGGC
CACAATAACTGCAGACGAATCCACCAATACAGCCTACATGGAGCTGAGCAGCCTGAGGTCTGAGGACACGG
CATTTTATTTTTGTGCAAGAAGGGATATTACTACGTTCTACTGGGGCCAAGGCACCACGGTCACCGTCTCC
TCAGCCTCCACCAAGGGCCCATCGGTCTTCCCCCTGGCACCCTCCTCCAAGAGCACCTCTGGGGGCACAGC
GGCCCTGGGCTGCCTGGTCAAGGACTACTTCCCCGAACCGGTGACGGTGTCGTGGAACTCAGGCGCCCTGA
CCAGCGGCGTGCACACCTTCCCGGCTGTCCTACAGTCCTCAGGACTCTACTCCCTCAGCAGCGTGGTGACC
GTGCCCTCCAGCAGCTTGGGCACCCAGACCTACATCTGCAACGTGAATCACAAGCCCAGCAACACCAAGGT
GGACAAGAGAGTTGAGCCCAAATCTTGTGACAAAACTCACACATGCCCACCGTGCCCAGCACCTGAACTCC
TGGGGGGACCGTCAGTCTTCCTCTTCCCCCCAAAACCCAAGGACACCCTCATGATCTCCCGGACCCCTGAG
GTCACATGCGTGGTGGTGGACGTGAGCCACGAAGACCCTGAGGTCAAGTTCAACTGGTACGTGGACGGCGT
GGAGGTGCATAATGCCAAGACAAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAGGTCTCCAACAAAGCCCTCCCA
GCCCCCATCGAGAAAACCATCTCCAAAGCCAAAGGGCAGCCCCGAGAACCACAGGTGTACACCCTGCCCCC
ATCCCGGGAGGAGATGACCAAGAACCAGGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCCGTGCTGGACTCC
GACGGCTCCTTCTTCCTCTATAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCGGGTAAAT
GAAAGCCGAATTCGCCCCTCTCCCTCCCCCCCCCCTAACGTTACTGGCCGAAGCCGCTTGGAATAAGGCCG
GTGTGCGTTTGTCTATATGTTATTTTCCACCATATTGCCGTCTTTTGGCAATGTGAGGGCCCGGAAACCTG
GCCCTGTCTTCTTGACGAGCATTCCTAGGGGTCTTTCCCCTCTCGCCAAAGGAATGCAAGGTCTGTTGAAT
GTCGTGAAGGAAGCAGTTCCTCTGGAAGCTTCTTGAAGACAAACAACGTCTGTAGCGACCCTTTGCAGGCA
GCGGAACCCCCCACCTGGCGACAGGTGCCTCTGCGGCCAAAAGCCACGTGTATAAGATACACCTGCAAAGG
CGGCACAACCCCAGTGCCACGTTGTGAGTTGGATAGTTGTGGAAAGAGTCAAATGGCTCTCCTCAAGCGTA
TTCAACAAGGGGCTGAAGGATGCCCAGAAGGTACCCCATTGTATGGGATCTGATCTGGGGCCTCGGTGCAC
ATGCTTTACATGTGTTTAGTCGAGGTTAAAAAAACGTCTAGGCCCCCCGAACCACGGGGACGTGGTTTTCC
TTTGAAAAACACGATGATAATATGGCCTCCTTTGTCTCTCTGCTCCTGGTAGGCATCCTATTCCATGCCAC
CCAGGCCGACATCCAGCTGACCCAGTCTCCATCATCTCTGAGCGCATCTGTTGGAGATAGGGTCACTATGA
GCTGTAAGTCCAGTCAAAGTGTTTTATACAGTGCAAATCACAAGAACTACTTGGCCTGGTACCAGCAGAAA
CCAGGGAAAGCACCTAAACTGCTGATCTACTGGGCATCCACTAGGGAATCTGGTGTCCCTTCGCGATTCTC
TGGCAGCGGATCTGGGACAGATTTTACTTTCACCATCAGCTCTCTTCAACCAGAAGACATTGCAACATATT
ATTGTCACCAATACCTCTCCTCGTGGACGTTCGGTGGAGGGACCAAGGTGCAGATCAAACGAACTGTGGCT
GCACCATCTGTCTTCATCTTCCCGCCATCTGATGAGCAGTTGAAATCTGGAACTGCCTCTGTTGTGTGCCT
GCTGAATAACTTCTATCCCAGAGAGGCCAAAGTACAGTGGAAGGTGGATAACGCCCTCCAATCGGGTAACT
CCCAGGAGAGTGTCACAGAGCAGGACAGCAAGGACAGCACCTACAGCCTCAGCAGCACCCTGACGCTGAGC
AAAGCAGACTACGAGAAACACAAAGTCTACGCCTGCGAAGTCACCCATCAGGGCCTGAGCTCGCCCGTCAC
AAAGAGCTTCAACAGGGGAGAGTGTTAGAGATCTAGGCCTCCTAGGTCGACATCGATAAAATAAAAGATTT
TATTTAGTCTCCAGAAAAAGGGGGGAATGAAAGACCCCACCTGTAGGTTTGGCAAGCTAGCTTAAGTAACG
CCATTTTGCAAGGCATGGAAAAATACATAACTGAGAATAGAGAAGTTCAGATCAAGGTCAGGAACAGATGG
AACAGCTGAATATGGGCCAAACAGGATATCTGTGGTAAGCAGTTCCTGCCCCGGCTCAGGGCCAAGAACAG
ATGGAACAGCTGAATATGGGCCAAACAGGATATCTGTGGTAAGCAGTTCCTGCCCCGGCTCAGGGCCAAGA
ACAGATGGTCCCCAGATGCGGTCCAGCCCTCAGCAGTTTCTAGAGAACCATCAGATGTTTCCAGGGTGCCC
CAAGGACCTGAAATGACCCTGTGCCTTATTTGAACTAACCAATCAGTTCGCTTCTCGCTTCTGTTCGCGCG
CTTCTGCTCCCCGAGCTCAATAAAAGAGCCCACAACCCCTCACTCGGGGCGCCAGTCCTCCGATTGACTGA
GTCGCCCGGGTACCCGTGTATCCAATAAACCCTCTTGCAGTTGCATCCGACTTGTGGTCTCGCTGTTCCTT
GGGAGGGTCTCCTCTGAGTGATTGACTACCCGTCAGCGGGGGTCTTTCATT

1 - 589 5'LTR Moloney murine sarcoma virus
659 - 1468 Extended packaging signal Moloney murine

SEQ ID NO: 5 (CONT)

| | |
|---|---|
| | leukemia virus |
| 1512 - 2306 | Neomycin resistance gene |
| 2656 - 3473 | Human cytomegalovirus major immediate early promoter/enhancer |
| 3504 - 3506 | LL2 heavy chain gene signal peptide start codon |
| 4899 - 4901 | Stop codon for LL2 heavy chain gene |
| 4913 - 5488 | Encephalomyocarditis virus internal ribosome entry site |
| 5489 - 5491 | Bovine α-Lactalbumin signal peptide start codon |
| 5546 - 5548 | First codon encoding mature LL2 light chain |
| 6203 - 6205 | Stop codon for LL2 light chain gene |
| 6274 - 6867 | 3'LTR Moloney murine leukemia virus |

Initial Retrovector Gene Construct for Antibody #3 (SEQ ID NO:6):

TTTGAAAGACCCCACCCGTAGGTGGCAAGCTAGCTTAAGTAACGCCACTTTGCAAGGCATGGAAAAATACA
TAACTGAGAATAGAAAAGTTCAGATCAAGGTCAGGAACAAAGAAACAGCTGAATACCAAACAGGATATCTG
TGGTAAGCGGTTCCTGCCCCGGCTCAGGGCCAAGAACAGATGAGACAGCTGAGTGATGGGCCAAACAGGAT
ATCTGTGGTAAGCAGTTCCTGCCCCGGCTCGGGGCCAAGAACAGATGGTCCCCAGATGCGGTCCAGCCCTC
AGCAGTTTCTAGTGAATCATCAGATGTTTCCAGGGTGCCCCAAGGACCTGAAAATGACCCTGTACCTTATT
TGAACTAACCAATCAGTTCGCTTCTCGCTTCTGTTCGCGCGCTTCCGCTCTCCGAGCTCAATAAAAGAGCC
CACAACCCCTCACTCGGCGCGCCAGTCTTCCGATAGACTGCGTCGCCCGGGTACCCGTATTCCCAATAAAG
CCTCTTGCTGTTTGCATCCGAATCGTGGTCTCGCTGTTCCTTGGGAGGGTCTCCTCTGAGTGATTGACTAC
CCACGACGGGGGTCTTTCATTTGGGGGCTCGTCCGGGATTTGGAGACCCCTGCCCAGGGACCACCGACCCA
CCACCGGGAGGTAAGCTGGCCAGCAACTTATCTGTGTCTGTCCGATTGTCTAGTGTCTATGTTTGATGTTA
TGCGCCTGCGTCTGTACTAGTTAGCTAACTAGCTCTGTATCTGGCGGACCCGTGGTGGAACTGACGAGTTC
TGAACACCCGGCCGCAACCCTGGGAGACGTCCCAGGGACTTTGGGGGCCGTTTTTGTGGCCCGACCTGAGG
AAGGGAGTCGATGTGGAATCCGACCCCGTCAGGATATGTGGTTCTGGTAGGAGACGAGAACCTAAAACAGT
TCCCGCCTCCGTCTGAATTTTTGCTTTCGGTTTGGAACCGAAGCCGCGCGTCTTGTCTGCTGCAGCGCTGC
AGCATCGTTCTGTGTTGTCTCTGTCTGACTGTGTTTCTGTATTTGTCTGAAAATTAGGGCCAGACTGTTAC
CACTCCCTTAAGTTTGACCTTAGGTCACTGGAAAGATGTCGAGCGGATCGCTCACAACCAGTCGGTAGATG
TCAAGAAGAGACGTTGGGTTACCTTCTGCTCTGCAGAATGGCCAACCTTTAACGTCGGATGGCCGCGAGAC
GGCACCTTTAACCGAGACCTCATCACCCAGGTTAAGATCAAGGTCTTTTCACCTGGCCCGCATGGACACCC
AGACCAGGTCCCCTACATCGTGACCTGGGAAGCCTTGGCTTTTGACCCCCCTCCCTGGGTCAAGCCCTTTG
TACACCCTAAGCCTCCGCCTCCTCTTCCTCCATCCGCCCCGTCTCTCCCCCTTGAACCTCCTCGTTCGACC
CCGCCTCGATCCTCCCTTTATCCAGCCCTCACTCCTTCTCTAGGCGCCGGAATTCCGATCTGATCAAGAGA
CAGGATGAGGATCGTTTCGCATGATTGAACAAGATGGATTGCACGCAGGTTCTCCGGCCGCTTGGGTGGAG
AGGCTATTCGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAGGACGAGGCAG
CGCGGCTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCATTCGACCACC
AAGCGAAACATCGCATCGAGCGAGCACGTACTCGGATGGAAGCCGGTCTTGTCGATCAGGATGATCTGGAC
GAAGAGCATCAGGGGCTCGCGCCAGCCGAACTGTTCGCCAGGCTCAAGGCGCGCATGCCCGACGGCGAGGA
TCTCGTCGTGACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGATATTGCTGAA
GAGCTTGGCGGCGAATGGGCTGACCGCTTCCTCGTGCTTTACGGTATCGCCGCTCCCGATTCGCAGCGCAT
CGCCTTCTATCGCCTTCTTGACGAGTTCTTCTGAGCGGGACTCTGGGGTTCGAAATGACCGACCAAGCGAC
GCCCAACCTGCCATCACGAGATTTCGATTCCACCGCCGCCTTCTATGAAAGGTTGGGCTTCGGAATCGTTT
TCCGGGACGCCGGCTGGATGATCCTCCAGCGCGGGGATCTCATGCTGGAGTTCTTCGCCCACCCCGGGCTC

SEQ ID NO: 6 (CONT)

GATCCCCTCGCGAGTTGGTTCAGCTGCTGCCTGAGGCTGGACGACCTCGCGGAGTTCTACCGGCAGTGCAA
ATCCGTCGGCATCCAGGAAACCAGCAGCGGCTATCCGCGCATCCATGCCCCCGAACTGCAGGAGTGGGGAG
GCACGATGGCCGCTTTGGTCGAGGCGGATCCGGCCATTAGCCATATTATTCATTGGTTATATAGCATAAAT
CAATATTGGCTATTGGCCATTGCATACGTTGTATCCATATCATAATATGTACATTTATATTGGCTCATGTC
CAACATTACCGCCATGTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGGACTTTCC
TACTTGGCAGTACATCTACGTATTAGTCATCGCTATTACCATGGTGATGCGGTTTTGGCAGTACATCAATG
GGCGTGGATAGCGGTTTGACTCACGGGGATTTCCAAGTCTCCACCCCATTGACGTCAATGGGAGTTTGTTT
TGGCACCAAAATCAACGGGACTTTCCAAAATGTCGTAACAACTCCGCCCCATTGACGCAAATGGGCGGTAG
GCATGTACGGTGGGAGGTCTATATAAGCAGAGCTCGTTTAGTGAACCGTCAGATCGCCTGGAGACGCCATC
CACGCTGTTTTGACCTCCATAGAAGACACCGGGACCGATCCAGCCTCCGCGGCCCCAAGCTTGGATCTCAC
CATGGAGTTGGGACTGCGCTGGGGCTTCCTCGTTGCTCTTTTAAGAGGTGTCCAGTGTCAGGTGCAATTGG
TGGAGTCTGGGGGAGGCGTGGTCCAGCCTGGGAGGTCCCTGAGACTCTCCTGTGCAGCGTCTGGATTCGCC
TTCAGTAGATATGGCATGCACTGGGTCCGCCAGGCTCCAGGCAAGGGGCTGGAGTGGGTGGCAGTTATATG
GTATGATGGAAGTAATAAATACTATGCAGACTCCGTGAAGGGCCGATTCACCATCTCCAGAGACAATTCCA
AGAACACGCAGTATCTGCAAATGAACAGCCTGAGAGCCGAGGACACGGCTGTGTATTACTGTGCGAGAGGC
GGTGACTTCCTCTACTACTACTATTACGGTATGGACGTCTGGGGCCAAGGGACCACGGTCACCGTCTCCTC
AGCCTCCACCAAGGGCCCATCGGTCTTCCCCCTGGCACCCTCTAGCAAGAGCACCTCTGGGGGCACAGCGG
CCCTGGGCTGCCTGGTCAAGGACTACTTCCCCGAACCGGTGACGGTGTCGTGGAACTCAGGCGCCCTGACC
AGCGGCGTGCACACCTTCCCGGCTGTCCTACAGTCCTCAGGACTCTACTCCCTCAGCAGCGTGGTGACCGT
GCCCTCCAGCAGCTTGGGCACCCAGACCTACATCTGCAACGTGAATCACAAGCCCAGCAACACCAAGGTGG
ACAAGAGAGTTGAGCCCAAATCTTGTGACAAAACTCACACATGCCCACCGTGCCCAGCACCTGAACTCCTG
GGGGGACCGTCAGTCTTCCTCTTCCCCCCAAAACCCAAGGACACCCTCATGATCTCCCGGACCCCTGAGGT
CACATGCGTGGTGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAACAAAGCCCTCCCAGC
CCCCATCGAGAAAACCATCTCCAAAGCCAAAGGGCAGCCCCGAGAACCACAGGTGTACACCCTGCCCCCAT
CCCGGGAGGAGATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTGCTGGACTCCGA
CGGCTCCTTCTTCCTCTATAGCAAGCTCACCGTGGACAAGAGCAGGTGGCAGCAGGGGAACGTCTTCTCAT
GCTCCGTGATGCATGAGGCTCTGCACAACCACTACACGCAGAAGAGCCTCTCCCTGTCTCCGGGTAAATGA
GAATTCCTCGAGTTAACAGATCCCCGGGAATTCGCCCCTCTCCCTCCCCCCCCCCTAACGTTACTGGCCGA
AGCCGCTTGGAATAAGGCCGGTGTGCGTTTGTCTATATGTTATTTTCCACCATATTGCCGTCTTTTGGCAA
TGTGAGGGCCCGGAAACCTGGCCCTGTCTTCTTGACGAGCATTCCTAGGGGTCTTTCCCCTCTCGCCAAAG
GAATGCAAGGTCTGTTGAATGTCGTGAAGGAAGCAGTTCCTCTGGAAGCTTCTTGAAGACAAACAACGTCT
GTAGCGACCCTTTGCAGGCAGCGGAACCCCCCACCTGGCGACAGGTGCCTCTGCGGCCAAAAGCCACGTGT
ATAAGATACACCTGCAAAGGCGGCACAACCCCAGTGCCACGTTGTGAGTTGGATAGTTGTGGAAAGAGTCA
AATGGCTCTCCTCAAGCGTATTCAACAAGGGGCTGAAGGATGCCCAGAAGGTACCCCATTGTATGGGATCT
GATCTGGGGCCTCGGTGCACATGCTTTACATGTGTTTAGTCGAGGTTAAAAAAACGTCTAGGCCCCCCGAA
CCACGGGGACGTGGTTTTCCTTTGAAAAACACGATGATAATATGGCCTCCTTTGTCTCTCTGCTCCTGGTA
GGCATCCTATTCCATGCCACCCAGGCCGACATCCAGATGACCCAGTCTCCATCCTCCCTGTCTGCATCTGT
AGGAGACAGAGTCACCATCACTTGCCGGGCGAGTCAGGGCATTAGCAATTATTTAGCCTGGTATCAGCAGA
AAACAGGGAAAGTTCCTAAGTTCCTGATCTATGAAGCATCCACTTTGCAATCAGGGGTCCCATCTCGGTTC
AGTGGCGGTGGATCTGGGACAGATTTCACTCTCACCATCAGCAGCCTGCAGCCTGAAGATGTTGCAACTTA
TTACTGTCAAAATTATAACAGTGCCCCATTCACTTTCGGCCCTGGGACCAAAGTGGATATCAAACGAACTG
TGGCTGCACCCTCTGTCTTCATCTTCCCGCCATCTGATGAGCAGTTGAAATCTGGAACTGCTAGCGTTGTG
TGCCTGCTGAATAACTTCTATCCCAGAGAGGCCAAAGTACAGTGGAAGGTGGATAACGCCCTCCAATCGGG
TAACTCCCAGGAGAGTGTCACAGAGCAGGACAGCAAGGACAGCACCTACAGCCTCAGCAGCACCCTGACGC
TGAGCAAAGCAGACTACGAGAAACACAAAGTCTACGCCTGCGAAGTCACCCATCAGGGCCTGAGCTCGCCC
GTCACAAAGAGCTTCAACAGGGGAGAGTGTTAGGAATTCGCGGCCGCTCGACATCGATAATCAACCTCTGG
ATTACAAAATTTGTGAAAGATTGACTGGTATTCTTAACTATGTTGCTCCTTTTACGCTATGTGGATACGCT
GCTTTAATGCCTTTGTATCATGCTATTGCTTCCCGTATGGCTTTCATTTTCTCCTCCTTGTATAAATCCTG
GTTGCTGTCTCTTTATGAGGAGTTGTGGCCCGTTGTCAGGCAACGTGGCGTGGTGTGCACTGTGTTTGCTG
ACGCAACCCCCACTGGTTGGGGCATTGCCACCACCTGTCAGCTCCTTTCCGGGACTTTCGCTTTCCCCCTC

SEQ ID NO: 6 (CONT)

CCTATTGCCACGGCGGAACTCATCGCCGCCTGCCTTGCCCGCTGCTGGACAGGGGCTCGGCTGTTGGGCAC
TGACAATTCCGTGGTGTTGTCGGGGAAATCATCGTCCTTTCCTTGGCTGCTCGCCTGTGTTGCCACCTGGA
TTCTGCGCGGGACGTCCTTCTGCTACGTCCCTTCGGCCCTCAATCCAGCGGACCTTCCTTCCCGCGGCCTG
CTGCCGGCTCTGCGGCCTCTTCCGCGTCTTCGCCTTCGCCCTCAGACGAGTCGGATCTCCCTTTGGGCCGC
CTCCCCGCCTGATCGATAAAATAAAAGATTTTATTTAGTCTCCAGAAAAAGGGGGGAATGAAAGACCCCAC
CTGTAGGTTTGGCAAGCTAGCTTAAGTAACGCCATTTTGCAAGGCATGGAAAAATACATAACTGAGAATAG
AGAAGTTCAGATCAAGGTCAGGAACAGATGGAACAGCTGAATATGGGCCAAACAGGATATCTGTGGTAAGC
AGTTCCTGCCCCGGCTCAGGGCCAAGAACAGATGGAACAGCTGAATATGGGCCAAACAGGATATCTGTGGT
AAGCAGTTCCTGCCCCGGCTCAGGGCCAAGAACAGATGGTCCCCAGATGCGGTCCAGCCCTCAGCAGTTTC
TAGAGAACCATCAGATGTTTCCAGGGTGCCCCAAGGACCTGAAATGACCCTGTGCCTTATTTGAACTAACC
AATCAGTTCGCTTCTCGCTTCTGTTCGCGCGCTTCTGCTCCCCGAGCTCAATAAAAGAGCCCACAACCCCT
CACTCGGGGCGCCAGTCCTCCGATTGACTGAGTCGCCCGGGTACCCGTGTATCCAATAAACCCTCTTGCAG
TTGCATCCGACTTGTGGTCTCGCTGTTCCTTGGGAGGGTCTCCTCTGAGTGATTGACTACCCGTCAGCGGG
GGTCTTTCATT

| | |
|---|---|
| 1 - 589 | 5'LTR Moloney murine sarcoma virus |
| 659 - 1468 | Extended packaging region Moloney murine leukemia virus |
| 1512 - 2306 | Neomycin resistance gene |
| 2656 - 3473 | Human cytomegalovirus major immediate early promoter/enhancer |
| 3481 - 3483 | First codon encoding PSMA heavy chain |
| 4897 - 4899 | PSMA heavy chain gene stop codon |
| 4927 - 5508 | Encephalomyocarditis virus internal ribosome entry site |
| 5509 - 5511 | Bovine α-lactalbumin signal peptide start codon |
| 5563 - 5565 | Bovine α-lactalbumin signal peptide ending codon |
| 5566 - 5568 | First codon encoding mature PSMA light chain |
| 6208 - 6210 | PSMA light chain stop codon |
| 6230 - 6830 | Woodchuck Hepatitis B virus RNA export and stability element |
| 6873 - 7466 | 3' LTR Moloney murine leukemia virus |

Initial Retrovector Gene Construct for Antibody #4 (SEQ ID NO:7):

TTTGAAAGACCCCACCCGTAGGTGGCAAGCTAGCTTAAGTAACGCCACTTTGCAAGGCA
TGGAAAAATACATAACTGAGAATAGAAAAGTTCAGATCAAGGTCAGGAACAAAGAAACA
GCTGAATACCAAACAGGATATCTGTGGTAAGCGGTTCCTGCCCCGGCTCAGGGCCAAGA
ACAGATGAGACAGCTGAGTGATGGGCCAAACAGGATATCTGTGGTAAGCAGTTCCTGCC
CCGGCTCGGGGCCAAGAACAGATGGTCCCCAGATGCGGTCCAGCCCTCAGCAGTTTCTA
GTGAATCATCAGATGTTTCCAGGGTGCCCCAAGGACCTGAAAATGACCCTGTACCTTAT
TTGAACTAACCAATCAGTTCGCTTCTCGCTTCTGTTCGCGCGCTTCCGCTCTCCGAGCT
CAATAAAAGAGCCCACAACCCCTCACTCGGCGCGCCAGTCTTCCGATAGACTGCGTCGC
CCGGGTACCCGTATTCCCAATAAAGCCTCTTGCTGTTTGCATCCGAATCGTGGTCTCGC
TGTTCCTTGGGAGGGTCTCCTCTGAGTGATTGACTACCCACGACGGGGGTCTTTCATTT
GGGGGCTCGTCCGGGATTTGGAGACCCCTGCCCAGGGACCACCGACCCACCACCGGGAG

SEQ ID NO: 7 (CONT)

GTAAGCTGGCCAGCAACTTATCTGTGTCTGTCCGATTGTCTAGTGTCTATGTTTGATGT
TATGCGCCTGCGTCTGTACTAGTTAGCTAACTAGCTCTGTATCTGGCGGACCCGTGGTG
GAACTGACGAGTTCTGAACACCCGGCCGCAACCCTGGGAGACGTCCCAGGGACTTTGGG
GGCCGTTTTTGTGGCCCGACCTGAGGAAGGGAGTCGATGTGGAATCCGACCCCGTCAGG
ATATGTGGTTCTGGTAGGAGACGAGAACCTAAAACAGTTCCCGCCTCCGTCTGAATTTT
TGCTTTCGGTTTGGAACCGAAGCCGCGCGTCTTGTCTGCTGCAGCGCTGCAGCATCGTT
CTGTGTTGTCTCTGTCTGACTGTGTTTCTGTATTTGTCTGAAAATTAGGGCCAGACTGT
TACCACTCCCTTAAGTTTGACCTTAGGTCACTGGAAAGATGTCGAGCGGATCGCTCACA
ACCAGTCGGTAGATGTCAAGAAGAGACGTTGGGTTACCTTCTGCTCTGCAGAATGGCCA
ACCTTTAACGTCGGATGGCCGCGAGACGGCACCTTTAACCGAGACCTCATCACCCAGGT
TAAGATCAAGGTCTTTTCACCTGGCCCGCATGGACACCCAGACCAGGTCCCCTACATCG
TGACCTGGGAAGCCTTGGCTTTTGACCCCCCTCCCTGGGTCAAGCCCTTTGTACACCCT
AAGCCTCCGCCTCCTCTTCCTCCATCCGCCCCGTCTCTCCCCCTTGAACCTCCTCGTTC
GACCCCGCCTCGATCCTCCCTTTATCCAGCCCTCACTCCTTCTCTAGGCGCCGGAATTC
CGATCTGATCAAGAGACAGGATGAGGATCGTTTCGCATGATTGAACAAGATGGATTGCA
CGCAGGTTCTCCGGCCGCTTGGGTGGAGAGGCTATTCGGCTATGACTGGGCACAACAGA
CAATCGGCTGCTCTGATGCCGCCGTGTTCCGGCTGTCAGCGCAGGGGCGCCCGGTTCTT
TTTGTCAAGACCGACCTGTCCGGTGCCCTGAATGAACTGCAGGACGAGGCAGCGCGGCT
ATCGTGGCTGGCCACGACGGGCGTTCCTTGCGCAGCTGTGCTCGACGTTGTCACTGAAG
CGGGAAGGGACTGGCTGCTATTGGGCGAAGTGCCGGGGCAGGATCTCCTGTCATCTCAC
CTTGCTCCTGCCGAGAAAGTATCCATCATGGCTGATGCAATGCGGCGGCTGCATACGCT
TGATCCGGCTACCTGCCCATTCGACCACCAAGCGAAACATCGCATCGAGCGAGCACGTA
CTCGGATGGAAGCCGGTCTTGTCGATCAGGATGATCTGGACGAAGAGCATCAGGGGCTC
GCGCCAGCCGAACTGTTCGCCAGGCTCAAGGCGCGCATGCCCGACGGCGAGGATCTCGT
CGTGACCCATGGCGATGCCTGCTTGCCGAATATCATGGTGGAAAATGGCCGCTTTTCTG
GATTCATCGACTGTGGCCGGCTGGGTGTGGCGGACCGCTATCAGGACATAGCGTTGGCT
ACCCGTGATATTGCTGAAGAGCTTGGCGGCGAATGGGCTGACCGCTTCCTCGTGCTTTA
CGGTATCGCCGCTCCCGATTCGCAGCGCATCGCCTTCTATCGCCTTCTTGACGAGTTCT
TCTGAGCGGGACTCTGGGGTTCGAAATGACCGACCAAGCGACGCCCAACCTGCCATCAC
GAGATTTCGATTCCACCGCCGCCTTCTATGAAAGGTTGGGCTTCGGAATCGTTTTCCGG
GACGCCGGCTGGATGATCCTCCAGCGCGGGGATCTCATGCTGGAGTTCTTCGCCCACCC
CGGGCTCGATCCCCTCGCGAGTTGGTTCAGCTGCTGCCTGAGGCTGGACGACCTCGCGG
AGTTCTACCGGCAGTGCAAATCCGTCGGCATCCAGGAAACCAGCAGCGGCTATCCGCGC
ATCCATGCCCCCGAACTGCAGGAGTGGGGAGGCACGATGGCCGCTTTGGTCGAGGCGGA
TCCGGCCATTAGCCATATTATTCATTGGTTATATAGCATAAATCAATATTGGCTATTGG
CCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGT
CATTAGTTCATAGCCCATATATGGAGTTCCGCGTTACATAACTTACGGTAAATGGCCCG
CCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTG
CCCACTTGGCAGTACATCAAGTGTATCATATGCCAAGTACGCCCCCTATTGACGTCAAT
GACGGTAAATGGCCCGCCTGGCATTATGCCCAGTACATGACCTTATGGGACTTTCCTAC
TTGGCAGTACATCTACGTATTAGTCATCGCTATTACCATGGTGATGCGGTTTTGGCAGT
ACATCAATGGGCGTGGATAGCGGTTTGACTCACGGGGATTTCCAAGTCTCCACCCCATT
GACGTCAATGGGAGTTTGTTTTGGCACCAAAATCAACGGGACTTTCCAAAATGTCGTAA
CAACTCCGCCCCATTGACGCAAATGGGCGGTAGGCATGTACGGTGGGAGGTCTATATAA
GCAGAGCTCGTTTAGTGAACCGTCAGATCGCCTGGAGACGCCATCCACGCTGTTTTGAC

SEQ ID NO: 7 (CONT)

CTCCATAGAAGACACCGGGACCGATCCAGCCTCCGCGGCCCCAAGCTTCTCGAGCACCA
TGGAATGGAGCGGAGTCTTTATCTTTCTCCTGTCAGTAACTGCAGGTGTCCACTCCGAG
GTGCAGCTGGTGGAGTCTGGTGGAGGCTTGGTAAAGCCTGGAGGTTCCCTTAGACTCTC
CTGTGCAGCCTCTGGTTACACTTTCAGTAACTATTGGATCGGATGGGTCCGCCAGGCTC
CAGGCAAAGGGCTGGAGTGGATTGGCGATATCTACCCTGGAGGGAACTACATCAGGAAC
AATGAGAAGTTCAAGGACAAGACCACCCTGTCAGCAGATACTTCCAAGAACACAGCCTA
TCTGCAAATGAACAGCCTGAAAACCGAGGACACAGCCGTGTATTACTGTGGAAGCAGCT
TCGGTAGTAACTACGTGTTCGCCTGGTTTACTTACTGGGGCCAAGGGACTCTGGTCACA
GTCTCCTCAGCTTCCACCAAGGGCCCATCCGTCTTCCCCCTGGCGCCCTGCTCCAGGAG
CACCTCCGAGAGCACAGCCGCCCTGGGCTGCCTGGTCAAGGACTACTTCCCCGAACCGG
TGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTT
GGGCACGAAGACCTACACCTGCAACGTAGATCACAAGCCCAGCAACACCAAGGTGGACA
AGAGAGTTGAGTCCAAATATGGTCCCCCATGCCCATCATGCCCAGCACCTGAGTTCCTG
GGGGGACCATCAGTCTTCCTGTTCCCCCCAAAACCCAAGGACACTCTCATGATCTCCCG
GACCCCTGAGGTCACGTGCGTGGTGGTGGACGTGAGCCAGGAAGACCCCGAGGTCCAGT
TCAACTGGTACGTGGATGGCGTGGAGGTGCATAATGCCAAGACAAAGCCGCGGGAGGAG
CAGTTCAACAGCACGTACCGTGTGGTCAGCGTCCTCACCGTCCTGCACCAGGACTGGCT
GAACGGCAAGGAGTACAAGTGCAAGGTCTCCAACAAAGGCCTCCCGTCCTCCATCGAGA
AAACCATCTCCAAAGCCAAAGGGCAGCCCCGAGAGCCACAGGTGTACACCCTGCCCCCA
TCCCAGGAGGAGATGACCAAGAACCAGGTCAGCCTGACCTGCCTGGTCAAAGGCTTCTA
CCCCAGCGACATCGCCGTGGAGTGGGAGAGCAATGGGCAGCCGGAGAACAACTACAAGA
CCACGCCTCCCGTGCTGGACTCCGACGGCTCCTTCTTCCTCTACAGCAGGCTAACCGTG
GACAAGAGCAGGTGGCAGGAGGGGAATGTCTTCTCATGCTCCGTGATGCATGAGGCTCT
GCACAACCACTACACACAGAAGAGCCTCTCCCTGTCTCTGGGTAAATGAGTGCCAGATC
CCCGGGAATTCGCCCCTCTCCCTCCCCCCCCCCTAACGTTACTGGCCGAAGCCGCTTGG
AATAAGGCCGGTGTGCGTTTGTCTATATGTTATTTTCCACCATATTGCCGTCTTTTGGC
AATGTGAGGGCCCGGAAACCTGGCCCTGTCTTCTTGACGAGCATTCCTAGGGGTCTTTC
CCCTCTCGCCAAAGGAATGCAAGGTCTGTTGAATGTCGTGAAGGAAGCAGTTCCTCTGG
AAGCTTCTTGAAGACAAACAACGTCTGTAGCGACCCTTTGCAGGCAGCGGAACCCCCCA
CCTGGCGACAGGTGCCTCTGCGGCCAAAAGCCACGTGTATAAGATACACCTGCAAAGGC
GGCACAACCCCAGTGCCACGTTGTGAGTTGGATAGTTGTGGAAAGAGTCAAATGGCTCT
CCTCAAGCGTATTCAACAAGGGGCTGAAGGATGCCCAGAAGGTACCCCATTGTATGGGA
TCTGATCTGGGGCCTCGGTGCACATGCTTTACATGTGTTTAGTCGAGGTTAAAAAAACG
TCTAGGCCCCCCGAACCACGGGGACGTGGTTTTCCTTTGAAAAACACGATGATAATATG
GCCTCCTTTGTCTCTCTGCTCCTGGTAGGCATCCTATTCCATGCCACCCAGGCCGACAT
TGTGATGACCCAATCTCCACTCTCCCTGCCTGTCACTCCTGGAGAGCCAGCCTCCATCT
CTTGCAGATCTAGTCAGCGCCTTCTGAGCAGTTATGGACATACCTATTTACATTGGTAC
CTACAGAAGCCAGGCCAGTCTCCACAGCTCCTGATCTACGAAGTTTCCAACCGATTTTC
TGGGGTCCCAGACAGGTTCAGTGGCAGTGGGTCAGGGACAGATTTCACACTTAAGATCA
GTAGAGTGGAGGCTGAGGATGTGGGAGTTTATTACTGCTCTCAAAGTACACATGTTCCT
CTCACGTTCGGACAGGGGACCAAGGTGGAAATAAAACGAACTGTGGCTGCACCATCTGT
CTTCATCTTCCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGATAACGCCCTC
CAATCGGGTAACTCCCAGGAGAGTGTCACAGAGCAGGACAGCAAGGACAGCACCTACAG
CCTCAGCAGCACCCTGACGCTGAGCAAAGCAGACTACGAGAAACACAAAGTCTACGCCT
GCGAAGTCACCCATCAGGGCCTGAGCTCGCCCGTCACAAAGAGCTTCAACAGGGGAGAG

SEQ ID NO: 7 (CONT)

TGTTAGAGGGAGAAGTGCCCCCACCTGCTCCTCGACATCGATAATCAACCTCTGGATTA
CAAAATTTGTGAAAGATTGACTGGTATTCTTAACTATGTTGCTCCTTTTACGCTATGTG
GATACGCTGCTTTAATGCCTTTGTATCATGCTATTGCTTCCCGTATGGCTTTCATTTTC
TCCTCCTTGTATAAATCCTGGTTGCTGTCTCTTTATGAGGAGTTGTGGCCCGTTGTCAG
GCAACGTGGCGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATTGCCACGGCG
GAACTCATCGCCGCCTGCCTTGCCCGCTGCTGGACAGGGGCTCGGCTGTTGGGCACTGA
CAATTCCGTGGTGTTGTCGGGGAAATCATCGTCCTTTCCTTGGCTGCTCGCCTGTGTTG
CCACCTGGATTCTGCGCGGGACGTCCTTCTGCTACGTCCCTTCGGCCCTCAATCCAGCG
GACCTTCCTTCCCGCGGCCTGCTGCCGGCTCTGCGGCCTCTTCCGCGTCTTCGCCTTCG
CCCTCAGACGAGTCGGATCTCCCTTTGGGCCGCCTCCCCGCATCGATAAAATAAAAGAT
TTTATTTAGTCTCCAGAAAAAGGGGGGAATGAAAGACCCCACCTGTAGGTTTGGCAAGC
TAGCTTAAGTAACGCCATTTTGCAAGGCATGGAAAAATACATAACTGAGAATAGAGAAG
TTCAGATCAAGGTCAGGAACAGATGGAACAGCTGAATATGGGCCAAACAGGATATCTGT
GGTAAGCAGTTCCTGCCCCGGCTCAGGGCCAAGAACAGATGGAACAGCTGAATATGGGC
CAAACAGGATATCTGTGGTAAGCAGTTCCTGCCCCGGCTCAGGGCCAAGAACAGATGGT
CCCCAGATGCGGTCCAGCCCTCAGCAGTTTCTAGAGAACCATCAGATGTTTCCAGGGTG
CCCCAAGGACCTGAAATGACCCTGTGCCTTATTTGAACTAACCAATCAGTTCGCTTCTC
GCTTCTGTTCGCGCGCTTCTGCTCCCCGAGCTCAATAAAAGAGCCCACAACCCCTCACT
CGGGGCGCCAGTCCTCCGATTGACTGAGTCGCCCGGGTACCCGTGTATCCAATAAACCC
TCTTGCAGTTGCATCCGACTTGTGGTCTCGCTGTTCCTTGGGAGGGTCTCCTCTGAGTG
ATTGACTACCCGTCAGCGGGGGTCTTTCATT

| | |
|---|---|
| 1 - 589 | 5'LTR Moloney murine sarcoma virus |
| 659 - 1468 | Extended Packaging Region Moloney murine leukemia virus |
| 1512 - 2306 | Neomycin resistance gene |
| 2656 - 3473 | Human cytomegalovirus major immediate early promoter/enhancer |
| 3481 - 3483 | First codon encoding Pro140 heavy chain |
| 4885 - 4887 | Pro140 heavy chain gene stop codon |
| 4903 - 5484 | Encephalomyocarditis virus internal ribosome entry site |
| 5485 - 5487 | Bovine α-lactalbumin signal peptide start codon |
| 5539 - 5541 | Bovine α-lactalbumin signal peptide ending codon |
| 5542 - 5544 | First codon encoding mature Pro140 light chain |
| 6199 - 6201 | Pro140 light chain stop codon |
| 6232 - 6832 | Woodchuck Hepatitis B virus RNA export and stability element |
| 6872 - 7465 | 3' LTR Moloney murine leukemia virus |

Figure 6

Spliced Retrovector Gene Construct for Antibody #1 (SEQ ID NO:8):

TTTGAAAGACCCCACCCGTAGGTGGCAAGCTAGCTTAAGTAACGCCACTTTGCAAGGCATGGAAAAATACA
TAACTGAGAATAGAAAAGTTCAGATCAAGGTCAGGAACAAAGAAACAGCTGAATACCAAACAGGATATCTG
TGGTAAGCGGTTCCTGCCCCGGCTCAGGGCCAAGAACAGATGAGACAGCTGAGTGATGGGCCAAACAGGAT
ATCTGTGGTAAGCAGTTCCTGCCCCGGCTCGGGGCCAAGAACAGATGGTCCCCAGATGCGGTCCAGCCCTC
AGCAGTTTCTAGTGAATCATCAGATGTTTCCAGGGTGCCCCAAGGACCTGAAAATGACCCTGTACCTTATT
TGAACTAACCAATCAGTTCGCTTCTCGCTTCTGTTCGCGCGCTTCCGCTCTCCGAGCTCAATAAAAGAGCC
CACAACCCCTCACTCGGCGCGCCAGTCTTCCGATAGACTGCGTCGCCCGGGTACCCGTATTCCCAATAAAG
CCTCTTGCTGTTTGCATCCGAATCGTGGTCTCGCTGTTCCTTGGGAGGGTCTCCTCTGAGTGATTGACTAC
CCACGACGGGGGTCTTTCATTTGGGGGCTCGTCCGGGATTTGGAGACCCCTGCCCAGGGACCACCGACCCA
CCACCGGGAGGTAAGCTGGCCAGCAACTTATCTGTGTCTGTCCGATTGTCTAGTGTCTATGTTTGATGTTA
TGCGCCTGCGTCTGTACTAGTTAGCTAACTAGCTCTGTATCTGGCGGACCCGTGGTGGAACTGACGAGTTC
TGAACACCCGGCCGCAACCCTGGGAGACGTCCCAGGGACTTTGGGGGCCGTTTTTGTGGCCCGACCTGAGG
AAGGGAGTCGATGTGGAATCCGACCCCGTCAGGATATGTGGTTCTGGTAGGAGACGAGAACCTAAAACAGT
TCCCGCCTCCGTCTGAATTTTTGCTTTCGGTTTGGAACCGAAGCCGCGCGTCTTGTCTGCTGCAGCGCTGC
AGCATCGTTCTGTGTTGTCTCTGTCTGACTGTGTTTCTGTATTTGTCTGAAAATTAGGGCCAGACTGTTAC
CACTCCCTTAAGTTTGACCTTAGGTCACTGGAAAGATGTCGAGCGGATCGCTCACAACCAGTCGGTAGATG
TCAAGAAGAGACGTTGGGTTACCTTCTGCTCTGCAGAATGGCCAACCTTTAACGTCGGATGGCCGCGAGAC
GGCACCTTTAACCGAGACCTCATCACCCAGGTTAAGATCAAGGTCTTTTCACCTGGCCCGCATGGACACCC
AGACCAGGTCCCCTACATCGTGACCTGGGAAGCCTTGGCTTTTGACCCCCCTCCCTGGGTCAAGCCCTTTG
TACACCCTAAGCCTCCGCCTCCTCTTCCTCCATCCGCCCCGTCTCTCCCCCTTGAACCTCCTCGTTCGACC
CCGCCTCGATCCTCCCTTTATCCAGCCCTCACTCCTTCTCTAGGCGCCGGAATTCCGATCTGATCAAGAGA
CAGGATGAGGATCGTTTCGCATGATTGAACAAGATGGATTGCACGCAGGTTCTCCGGCCGCTTGGGTGGAG
AGGCTATTCGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAGGACGAGGCAG
CGCGGCTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCATTCGACCACC
AAGCGAAACATCGCATCGAGCGAGCACGTACTCGGATGGAAGCCGGTCTTGTCGATCAGGATGATCTGGAC
GAAGAGCATCAGGGGCTCGCGCCAGCCGAACTGTTCGCCAGGCTCAAGGCGCGCATGCCCGACGGCGAGGA
TCTCGTCGTGACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGATATTGCTGAA
GAGCTTGGCGGCGAATGGGCTGACCGCTTCCTCGTGCTTTACGGTATCGCCGCTCCCGATTCGCAGCGCAT
CGCCTTCTATCGCCTTCTTGACGAGTTCTTCTGAGCGGGACTCTGGGGTTCGAAATGACCGACCAAGCGAC
GCCCAACCTGCCATCACGAGATTTCGATTCCACCGCCGCCTTCTATGAAAGGTTGGGCTTCGGAATCGTTT
TCCGGGACGCCGGCTGGATGATCCTCCAGCGCGGGGATCTCATGCTGGAGTTCTTCGCCCACCCCGGGCTC
GATCCCCTCGCGAGTTGGTTCAGCTGCTGCCTGAGGCTGGACGACCTCGCGGAGTTCTACCGGCAGTGCAA
ATCCGTCGGCATCCAGGAAACCAGCAGCGGCTATCCGCGCATCCATGCCCCCGAACTGCAGGAGTGGGGAG
GCACGATGGCCGCTTTGGTCGAGGCGGATCCGGCCATTAGCCATATTATTCATTGGTTATATAGCATAAAT
CAATATTGGCTATTGGCCATTGCATACGTTGTATCCATATCATAATATGTACATTTATATTGGCTCATGTC
CAACATTACCGCCATGTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGGACTTTCC
TACTTGGCAGTACATCTACGTATTAGTCATCGCTATTACCATGGTGATGCGGTTTTGGCAGTACATCAATG
GGCGTGGATAGCGGTTTGACTCACGGGGATTTCCAAGTCTCCACCCCATTGACGTCAATGGGAGTTTGTTT
TGGCACCAAAATCAACGGGACTTTCCAAAATGTCGTAACAACTCCGCCCCATTGACGCAAATGGGCGGTAG
GCATGTACGGTGGGAGGTCTATATAAGCAGAGCTCGTTTAGTGAACCGTCAGATCGCCTGGAGACGCCATC
CACGCTGTTTTGACCTCCATAGAAGACACCGGGACCGATCCAGCCTCCGCGGCCCCAAGCTTCTCGACGGA
TCCCCGGGAATTCAGGACCTCACCATGGGATGGAGCTGTATCATCCTCTTCTTGGTAGCAACAGCTACAGG
TGTCCACTCCGAGGTCCAACTGGTGGAGAGCGGTGGAGGTGTTGTGCAACCTGGCCGGTCCCTGCGCCTGT
CCTGCTCCGCATCTGGCTTCGATTTCACCACATATTGGATGAGTTGGGTGAGACAGGCACCTGGAAAAGGT

SEQ ID NO: 8 (CONT)

CTTGAGTGGATTGGAGAAATTCATCCAGATAGCAGTACGATTAACTATGCGCCGTCTCTAAAGGATAGATT
TACAATATCGCGAGACAACGCCAAGAACACATTGTTCCTGCAAATGGACAGCCTGAGACCCGAAGACACCG
GGGTCTATTTTTGTGCAAGCCTTTACTTCGGCTTCCCCTGGTTTGCTTATTGGGGCCAAGGGACCCCGGTC
ACCGTCTCCTCAGCCTCCACCAAGGGCCCATCGGTCTTCCCCCTGGCACCCTCCTCCAAGAGCACCTCTGG
GGGCACAGCGGCCCTGGGCTGCCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATCACAAGCCCAGCAA
CACCAAGGTGGACAAGAGAGTTGAGCCCAAATCTTGTGACAAAACTCACACATGCCCACCGTGCCCAGCAC
CTGAACTCCTGGGGGGACCGTCAGTCTTCCTCTTCCCCCCAAAACCCAAGGACACCCTCATGATCTCCCGG
ACCCCTGAGGTCACATGCGTGGTGGTGGACGTGAGCCACGAAGACCCTGAGGTCAAGTTCAACTGGTACGT
GGACGGCGTGGAGGTGCATAATGCCAAGACAAAGCCGCGGGAGGAGCAGTACAACAGCACGTACCGTGTGG
TCAGCGTCCTCACCGTCCTGCACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCCCCGAGAACCACAGGTGTACAC
CCTGCCCCCATCCCGGGAGGAGATGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGCCTCCCGTG
CTGGACTCCGACGGCTCCTTCTTCCTCTATAGCAAGCTCACCGTGGACAAGAGCAGGTGGCAGCAGGGGAA
CGTCTTCTCATGCTCCGTGATGCATGAGGCTCTGCACAACCACTACACGCAGAAGAGCCTCTCCCTGTCTC
CGGGCATCCTATTCCATGCCACCCAGGCCGACATCCAGCTGACCCAGAGCCCAAGCAGCCTGAGCGCCAGC
GTGGGTGACAGAGTGACCATCACCTGTAAGGCCAGTCAGGATGTGGGTACTTCTGTAGCCTGGTACCAGCA
GAAGCCAGGTAAGGCTCCAAAGCTGCTGATCTACTGGACATCCACCCGGCACACTGGTGTGCCAAGCAGAT
TCAGCGGTAGCGGTAGCGGTACCGACTTCACCTTCACCATCAGCAGCCTCCAGCCAGAGGACATCGCCACC
TACTACTGCCAGCAATATAGCCTCTATCGGTCGTTCGGCCAAGGGACCAAGGTGGAAATCAAACGAACTGT
GGCTGCACCATCTGTCTTCATCTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTGGATAACGCCCTCCAATCGGGT
AACTCCCAGGAGAGTGTCACAGAGCAGGACAGCAAGGACAGCACCTACAGCCTCAGCAGCACCCTGACGCT
GAGCAAAGCAGACTACGAGAAACACAAAGTCTACGCCTGCGAAGTCACCCATCAGGGCCTGAGCTCGCCCG
TCACAAAGAGCTTCAACAGGGGAGAGTGTTAGAGATCTAGGCCTCCTAGGTCGACATCGATAAAATAAAAG
ATTTTATTTAGTCTCCAGAAAAAGGGGGGAATGAAAGACCCCACCTGTAGGTTTGGCAAGCTAGCTTAAGT
AACGCCATTTTGCAAGGCATGGAAAAATACATAACTGAGAATAGAGAAGTTCAGATCAAGGTCAGGAACAG
ATGGAACAGCTGAATATGGGCCAAACAGGATATCTGTGGTAAGCAGTTCCTGCCCCGGCTCAGGGCCAAGA
ACAGATGGAACAGCTGAATATGGGCCAAACAGGATATCTGTGGTAAGCAGTTCCTGCCCCGGCTCAGGGCC
AAGAACAGATGGTCCCCAGATGCGGTCCAGCCCTCAGCAGTTTCTAGAGAACCATCAGATGTTTCCAGGGT
GCCCCAAGGACCTGAAATGACCCTGTGCCTTATTTGAACTAACCAATCAGTTCGCTTCTCGCTTCTGTTCG
CGCGCTTCTGCTCCCCGAGCTCAATAAAAGAGCCCACAACCCCTCACTCGGGGCGCCAGTCCTCCGATTGA
CTGAGTCGCCCGGGTACCCGTGTATCCAATAAACCCTCTTGCAGTTGCATCCGACTTGTGGTCTCGCTGTT
CCTTGGGAGGGTCTCCTCTGAGTGATTGACTACCCGTCAGCGGGGGTCTTTCATT

| | |
|---|---|
| 1 - 589 | 5'LTR Moloney murine sarcoma virus |
| 659 - 1468 | Extended packaging signal Moloney murine leukemia virus |
| 1512 - 2306 | Neomycin resistance gene |
| 2656 - 3473 | Human cytomegalovirus major immediate early promoter/enhancer |
| 3504 - 3506 | MN14 heavy chain gene signal peptide start codon |
| 4902 - 4904 | Codon encoding the second to last amino acid of MN14 heavy chain |
| 4905 - 4928 | Linker sequence originally encoding part of the Bovine α-Lactalbumin signal peptide |
| 4929 - 4931 | First codon encoding mature MN14 light chain |
| 5568 - 5570 | Stop codon for MN14 light chain |
| 5639 - 6232 | 3'LTR Moloney murine leukemia virus |

Spliced Retrovector Gene Construct for Antibody #2 (SEQ ID NO:9):

TTTGAAAGACCCCACCCGTAGGTGGCAAGCTAGCTTAAGTAACGCCACTTTGCAAGGCATGGAAAAATACA
TAACTGAGAATAGAAAAGTTCAGATCAAGGTCAGGAACAAAGAAACAGCTGAATACCAAACAGGATATCTG
TGGTAAGCGGTTCCTGCCCCGGCTCAGGGCCAAGAACAGATGAGACAGCTGAGTGATGGGCCAAACAGGAT
ATCTGTGGTAAGCAGTTCCTGCCCCGGCTCGGGGCCAAGAACAGATGGTCCCCAGATGCGGTCCAGCCCTC
AGCAGTTTCTAGTGAATCATCAGATGTTTCCAGGGTGCCCCAAGGACCTGAAAATGACCCTGTACCTTATT
TGAACTAACCAATCAGTTCGCTTCTCGCTTCTGTTCGCGCGCTTCCGCTCTCCGAGCTCAATAAAAGAGCC
CACAACCCCTCACTCGGCGCGCCAGTCTTCCGATAGACTGCGTCGCCCGGGTACCCGTATTCCCAATAAAG
CCTCTTGCTGTTTGCATCCGAATCGTGGTCTCGCTGTTCCTTGGGAGGGTCTCCTCTGAGTGATTGACTAC
CCACGACGGGGGTCTTTCATTTGGGGGCTCGTCCGGGATTTGGAGACCCCTGCCCAGGGACCACCGACCCA
CCACCGGGAGGTAAGCTGGCCAGCAACTTATCTGTGTCTGTCCGATTGTCTAGTGTCTATGTTTGATGTTA
TGCGCCTGCGTCTGTACTAGTTAGCTAACTAGCTCTGTATCTGGCGGACCCGTGGTGGAACTGACGAGTTC
TGAACACCCGGCCGCAACCCTGGGAGACGTCCCAGGGACTTTGGGGGCCGTTTTTGTGGCCCGACCTGAGG
AAGGGAGTCGATGTGGAATCCGACCCCGTCAGGATATGTGGTTCTGGTAGGAGACGAGAACCTAAAACAGT
TCCCGCCTCCGTCTGAATTTTTGCTTTCGGTTTGGAACCGAAGCCGCGCGTCTTGTCTGCTGCAGCGCTGC
AGCATCGTTCTGTGTTGTCTCTGTCTGACTGTGTTTCTGTATTTGTCTGAAAATTAGGGCCAGACTGTTAC
CACTCCCTTAAGTTTGACCTTAGGTCACTGGAAAGATGTCGAGCGGATCGCTCACAACCAGTCGGTAGATG
TCAAGAAGAGACGTTGGGTTACCTTCTGCTCTGCAGAATGGCCAACCTTTAACGTCGGATGGCCGCGAGAC
GGCACCTTTAACCGAGACCTCATCACCCAGGTTAAGATCAAGGTCTTTTCACCTGGCCCGCATGGACACCC
AGACCAGGTCCCCTACATCGTGACCTGGGAAGCCTTGGCTTTTGACCCCCCTCCCTGGGTCAAGCCCTTTG
TACACCCTAAGCCTCCGCCTCCTCTTCCTCCATCCGCCCCGTCTCTCCCCCTTGAACCTCCTCGTTCGACC
CCGCCTCGATCCTCCCTTTATCCAGCCCTCACTCCTTCTCTAGGCGCCGGAATTCCGATCTGATCAAGAGA
CAGGATGAGGATCGTTTCGCATGATTGAACAAGATGGATTGCACGCAGGTTCTCCGGCCGCTTGGGTGGAG
AGGCTATTCGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAGGACGAGGCAG
CGCGGCTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCATTCGACCACC
AAGCGAAACATCGCATCGAGCGAGCACGTACTCGGATGGAAGCCGGTCTTGTCGATCAGGATGATCTGGAC
GAAGAGCATCAGGGGCTCGCGCCAGCCGAACTGTTCGCCAGGCTCAAGGCGCGCATGCCCGACGGCGAGGA
TCTCGTCGTGACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGATATTGCTGAA
GAGCTTGGCGGCGAATGGGCTGACCGCTTCCTCGTGCTTTACGGTATCGCCGCTCCCGATTCGCAGCGCAT
CGCCTTCTATCGCCTTCTTGACGAGTTCTTCTGAGCGGGACTCTGGGGTTCGAAATGACCGACCAAGCGAC
GCCCAACCTGCCATCACGAGATTTCGATTCCACCGCCGCCTTCTATGAAAGGTTGGGCTTCGGAATCGTTT
TCCGGGACGCCGGCTGGATGATCCTCCAGCGCGGGGATCTCATGCTGGAGTTCTTCGCCCACCCCGGGCTC
GATCCCCTCGCGAGTTGGTTCAGCTGCTGCCTGAGGCTGGACGACCTCGCGGAGTTCTACCGGCAGTGCAA
ATCCGTCGGCATCCAGGAAACCAGCAGCGGCTATCCGCGCATCCATGCCCCCGAACTGCAGGAGTGGGGAG
GCACGATGGCCGCTTTGGTCGAGGCGGATCCGGCCATTAGCCATATTATTCATTGGTTATATAGCATAAAT
CAATATTGGCTATTGGCCATTGCATACGTTGTATCCATATCATAATATGTACATTTATATTGGCTCATGTC
CAACATTACCGCCATGTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGGACTTTCC
TACTTGGCAGTACATCTACGTATTAGTCATCGCTATTACCATGGTGATGCGGTTTTGGCAGTACATCAATG
GGCGTGGATAGCGGTTTGACTCACGGGGATTTCCAAGTCTCCACCCCATTGACGTCAATGGGAGTTTGTTT
TGGCACCAAAATCAACGGGACTTTCCAAAATGTCGTAACAACTCCGCCCCATTGACGCAAATGGGCGGTAG
GCATGTACGGTGGGAGGTCTATATAAGCAGAGCTCGTTTAGTGAACCGTCAGATCGCCTGGAGACGCCATC
CACGCTGTTTTGACCTCCATAGAAGACACCGGGACCGATCCAGCCTCCGCGGCCCCAAGCTTCTCGACGGA
TCCCCGGGAATTCAGGACCTCACCATGGGATGGAGCTGTATCATCCTCTTCTTGGTAGCAACAGCTACAGG
TGTCCACTCCCAGGTCCAGCTGGTCCAATCAGGGGCTGAAGTCAAGAAACCTGGGTCATCAGTGAAGGTCT
CCTGCAAGGCTTCTGGCTACACCTTTACTAGCTACTGGCTGCACTGGGTCAGGCAGGCACCTGGACAGGGT
CTGGAATGGATTGGATACATTAATCCTAGGAATGATTATACTGAGTACAATCAGAACTTCAAGGACAAGGC
CACAATAACTGCAGACGAATCCACCAATACAGCCTACATGGAGCTGAGCAGCCTGAGGTCTGAGGACACGG

SEQ ID NO: 9 (CONT)

```
CATTTTATTTTTGTGCAAGAAGGGATATTACTACGTTCTACTGGGGCCAAGGCACCACGGTCACCGTCTCC
TCAGCCTCCACCAAGGGCCCATCGGTCTTCCCCCTGGCACCCTCCTCCAAGAGCACCTCTGGGGGCACAGC
GGCCCTGGGCTGCCTGGTCAAGGACTACTTCCCCGAACCGGTGACGGTGTCGTGGAACTCAGGCGCCCTGA
CCAGCGGCGTGCACACCTTCCCGGCTGTCCTACAGTCCTCAGGACTCTACTCCCTCAGCAGCGTGGTGACC
GTGCCCTCCAGCAGCTTGGGCACCCAGACCTACATCTGCAACGTGAATCACAAGCCCAGCAACACCAAGGT
GGACAAGAGAGTTGAGCCCAAATCTTGTGACAAAACTCACACATGCCCACCGTGCCCAGCACCTGAACTCC
TGGGGGGACCGTCAGTCTTCCTCTTCCCCCCAAAACCCAAGGACACCCTCATGATCTCCCGGACCCCTGAG
GTCACATGCGTGGTGGTGGACGTGAGCCACGAAGACCCTGAGGTCAAGTTCAACTGGTACGTGGACGGCGT
GGAGGTGCATAATGCCAAGACAAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAGGTCTCCAACAAAGCCCTCCCA
GCCCCCATCGAGAAAACCATCTCCAAAGCCAAAGGGCAGCCCCGAGAACCACAGGTGTACACCCTGCCCCC
ATCCCGGGAGGAGATGACCAAGAACCAGGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCCGTGCTGGACTCC
GACGGCTCCTTCTTCCTCTATAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCGGGCATCC
TATTCCATGCCACCCAGGCCGACATCCAGCTGACCCAGTCTCCATCATCTCTGAGCGCATCTGTTGGAGAT
AGGGTCACTATGAGCTGTAAGTCCAGTCAAAGTGTTTTATACAGTGCAAATCACAAGAACTACTTGGCCTG
GTACCAGCAGAAACCAGGGAAAGCACCTAAACTGCTGATCTACTGGGCATCCACTAGGGAATCTGGTGTCC
CTTCGCGATTCTCTGGCAGCGGATCTGGGACAGATTTTACTTTCACCATCAGCTCTCTTCAACCAGAAGAC
ATTGCAACATATTATTGTCACCAATACCTCTCCTCGTGGACGTTCGGTGGAGGGACCAAGGTGCAGATCAA
ACGAACTGTGGCTGCACCATCTGTCTTCATCTTCCCGCCATCTGATGAGCAGTTGAAATCTGGAACTGCCT
CTGTTGTGTGCCTGCTGAATAACTTCTATCCCAGAGAGGCCAAAGTACAGTGGAAGGTGGATAACGCCCTC
CAATCGGGTAACTCCCAGGAGAGTGTCACAGAGCAGGACAGCAAGGACAGCACCTACAGCCTCAGCAGCAC
CCTGACGCTGAGCAAAGCAGACTACGAGAAACACAAAGTCTACGCCTGCGAAGTCACCCATCAGGGCCTGA
GCTCGCCCGTCACAAAGAGCTTCAACAGGGGAGAGTGTTAGAGATCTAGGCCTCCTAGGTCGACATCGATA
AAATAAAAGATTTTATTTAGTCTCCAGAAAAAGGGGGGAATGAAAGACCCCACCTGTAGGTTTGGCAAGCT
AGCTTAAGTAACGCCATTTTGCAAGGCATGGAAAAATACATAACTGAGAATAGAGAAGTTCAGATCAAGGT
CAGGAACAGATGGAACAGCTGAATATGGGCCAAACAGGATATCTGTGGTAAGCAGTTCCTGCCCCGGCTCA
GGGCCAAGAACAGATGGAACAGCTGAATATGGGCCAAACAGGATATCTGTGGTAAGCAGTTCCTGCCCCGG
CTCAGGGCCAAGAACAGATGGTCCCCAGATGCGGTCCAGCCCTCAGCAGTTTCTAGAGAACCATCAGATGT
TTCCAGGGTGCCCCAAGGACCTGAAATGACCCTGTGCCTTATTTGAACTAACCAATCAGTTCGCTTCTCGC
TTCTGTTCGCGCGCTTCTGCTCCCCGAGCTCAATAAAAGAGCCCACAACCCCTCACTCGGGGCGCCAGTCC
TCCGATTGACTGAGTCGCCCGGGTACCCGTGTATCCAATAAACCCTCTTGCAGTTGCATCCGACTTGTGGT
CTCGCTGTTCCTTGGGAGGGTCTCCTCTGAGTGATTGACTACCCGTCAGCGGGGGTCTTTCATT
```

| | |
|---|---|
| 1 - 589 | 5'LTR Moloney murine sarcoma virus |
| 659 - 1468 | Extended packaging signal Moloney murine leukemia virus |
| 1512 - 2306 | Neomycin resistance gene |
| 2656 - 3473 | Human cytomegalovirus major immediate early promoter/enhancer |
| 3504 - 3506 | LL2 heavy chain gene signal peptide start codon |
| 4893 - 4895 | Codon encoding the second to last amino acid of LL2 heavy chain |
| 4896 - 4919 | Linker sequence originally encoding part of the Bovine α-Lactalbumin signal peptide |
| 4920 - 4922 | First codon encoding mature LL2 light chain |
| 5577 - 5579 | Stop codon for LL2 light chain gene |
| 5648 - 6241 | 3'LTR Moloney murine leukemia virus |

Spliced Retrovector Gene Construct for Antibody #3 (SEQ ID NO:10):

SEQ ID NO: 10 (CONT)

TTTGAAAGACCCCACCCGTAGGTGGCAAGCTAGCTTAAGTAACGCCACTTTGCAAGGCATGGAAAAATACA
TAACTGAGAATAGAAAAGTTCAGATCAAGGTCAGGAACAAAGAAACAGCTGAATACCAAACAGGATATCTG
TGGTAAGCGGTTCCTGCCCCGGCTCAGGGCCAAGAACAGATGAGACAGCTGAGTGATGGGCCAAACAGGAT
ATCTGTGGTAAGCAGTTCCTGCCCCGGCTCGGGGCCAAGAACAGATGGTCCCCAGATGCGGTCCAGCCCTC
AGCAGTTTCTAGTGAATCATCAGATGTTTCCAGGGTGCCCCAAGGACCTGAAAATGACCCTGTACCTTATT
TGAACTAACCAATCAGTTCGCTTCTCGCTTCTGTTCGCGCGCTTCCGCTCTCCGAGCTCAATAAAAGAGCC
CACAACCCCTCACTCGGCGCGCCAGTCTTCCGATAGACTGCGTCGCCCGGGTACCCGTATTCCCAATAAAG
CCTCTTGCTGTTTGCATCCGAATCGTGGTCTCGCTGTTCCTTGGGAGGGTCTCCTCTGAGTGATTGACTAC
CCACGACGGGGGTCTTTCATTTGGGGGCTCGTCCGGGATTTGGAGACCCCTGCCCAGGGACCACCGACCCA
CCACCGGGAGGTAAGCTGGCCAGCAACTTATCTGTGTCTGTCCGATTGTCTAGTGTCTATGTTTGATGTTA
TGCGCCTGCGTCTGTACTAGTTAGCTAACTAGCTCTGTATCTGGCGGACCCGTGGTGGAACTGACGAGTTC
TGAACACCCGGCCGCAACCCTGGGAGACGTCCCAGGGACTTTGGGGGCCGTTTTTGTGGCCCGACCTGAGG
AAGGGAGTCGATGTGGAATCCGACCCCGTCAGGATATGTGGTTCTGGTAGGAGACGAGAACCTAAAACAGT
TCCCGCCTCCGTCTGAATTTTTGCTTTCGGTTTGGAACCGAAGCCGCGCGTCTTGTCTGCTGCAGCGCTGC
AGCATCGTTCTGTGTTGTCTCTGTCTGACTGTGTTTCTGTATTTGTCTGAAAATTAGGGCCAGACTGTTAC
CACTCCCTTAAGTTTGACCTTAGGTCACTGGAAAGATGTCGAGCGGATCGCTCACAACCAGTCGGTAGATG
TCAAGAAGAGACGTTGGGTTACCTTCTGCTCTGCAGAATGGCCAACCTTTAACGTCGGATGGCCGCGAGAC
GGCACCTTTAACCGAGACCTCATCACCCAGGTTAAGATCAAGGTCTTTTCACCTGGCCCGCATGGACACCC
AGACCAGGTCCCCTACATCGTGACCTGGGAAGCCTTGGCTTTTGACCCCCCTCCCTGGGTCAAGCCCTTTG
TACACCCTAAGCCTCCGCCTCCTCTTCCTCCATCCGCCCCGTCTCTCCCCCTTGAACCTCCTCGTTCGACC
CCGCCTCGATCCTCCCTTTATCCAGCCCTCACTCCTTCTCTAGGCGCCGGAATTCCGATCTGATCAAGAGA
CAGGATGAGGATCGTTTCGCATGATTGAACAAGATGGATTGCACGCAGGTTCTCCGGCCGCTTGGGTGGAG
AGGCTATTCGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAGGACGAGGCAG
CGCGGCTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCATTCGACCACC
AAGCGAAACATCGCATCGAGCGAGCACGTACTCGGATGGAAGCCGGTCTTGTCGATCAGGATGATCTGGAC
GAAGAGCATCAGGGGCTCGCGCCAGCCGAACTGTTCGCCAGGCTCAAGGCGCGCATGCCCGACGGCGAGGA
TCTCGTCGTGACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGATATTGCTGAA
GAGCTTGGCGGCGAATGGGCTGACCGCTTCCTCGTGCTTTACGGTATCGCCGCTCCCGATTCGCAGCGCAT
CGCCTTCTATCGCCTTCTTGACGAGTTCTTCTGAGCGGGACTCTGGGGTTCGAAATGACCGACCAAGCGAC
GCCCAACCTGCCATCACGAGATTTCGATTCCACCGCCGCCTTCTATGAAAGGTTGGGCTTCGGAATCGTTT
TCCGGGACGCCGGCTGGATGATCCTCCAGCGCGGGGATCTCATGCTGGAGTTCTTCGCCCACCCCGGGCTC
GATCCCCTCGCGAGTTGGTTCAGCTGCTGCCTGAGGCTGGACGACCTCGCGGAGTTCTACCGGCAGTGCAA
ATCCGTCGGCATCCAGGAAACCAGCAGCGGCTATCCGCGCATCCATGCCCCCGAACTGCAGGAGTGGGGAG
GCACGATGGCCGCTTTGGTCGAGGCGGATCCGGCCATTAGCCATATTATTCATTGGTTATATAGCATAAAT
CAATATTGGCTATTGGCCATTGCATACGTTGTATCCATATCATAATATGTACATTTATATTGGCTCATGTC
CAACATTACCGCCATGTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGGACTTTCC
TACTTGGCAGTACATCTACGTATTAGTCATCGCTATTACCATGGTGATGCGGTTTTGGCAGTACATCAATG
GGCGTGGATAGCGGTTTGACTCACGGGGATTTCCAAGTCTCCACCCCATTGACGTCAATGGGAGTTTGTTT
TGGCACCAAAATCAACGGGACTTTCCAAAATGTCGTAACAACTCCGCCCCATTGACGCAAATGGGCGGTAG
GCATGTACGGTGGGAGGTCTATATAAGCAGAGCTCGTTTAGTGAACCGTCAGATCGCCTGGAGACGCCATC
CACGCTGTTTTGACCTCCATAGAAGACACCGGGACCGATCCAGCCTCCGCGGCCCCAAGCTTGGATCTCAC
CATGGAGTTGGGACTGCGCTGGGGCTTCCTCGTTGCTCTTTTAAGAGGTGTCCAGTGTCAGGTGCAATTGG
TGGAGTCTGGGGGAGGCGTGGTCCAGCCTGGGAGGTCCCTGAGACTCTCCTGTGCAGCGTCTGGATTCGCC
TTCAGTAGATATGGCATGCACTGGGTCCGCCAGGCTCCAGGCAAGGGGCTGGAGTGGGTGGCAGTTATATG
GTATGATGGAAGTAATAAATACTATGCAGACTCCGTGAAGGGCCGATTCACCATCTCCAGAGACAATTCCA
AGAACACGCAGTATCTGCAAATGAACAGCCTGAGAGCCGAGGACACGGCTGTGTATTACTGTGCGAGAGGC
GGTGACTTCCTCTACTACTACTATTACGGTATGGACGTCTGGGGCCAAGGGACCACGGTCACCGTCTCCTC

SEQ ID NO: 10 (CONT)

AGCCTCCACCAAGGGCCCATCGGTCTTCCCCCTGGCACCCTCTAGCAAGAGCACCTCTGGGGGCACAGCGG
CCCTGGGCTGCCTGGTCAAGGACTACTTCCCCGAACCGGTGACGGTGTCGTGGAACTCAGGCGCCCTGACC
AGCGGCGTGCACACCTTCCCGGCTGTCCTACAGTCCTCAGGACTCTACTCCCTCAGCAGCGTGGTGACCGT
GCCCTCCAGCAGCTTGGGCACCCAGACCTACATCTGCAACGTGAATCACAAGCCCAGCAACACCAAGGTGG
ACAAGAGAGTTGAGCCCAAATCTTGTGACAAAACTCACACATGCCCACCGTGCCCAGCACCTGAACTCCTG
GGGGGACCGTCAGTCTTCCTCTTCCCCCCAAAACCCAAGGACACCCTCATGATCTCCCGGACCCCTGAGGT
CACATGCGTGGTGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAACAAAGCCCTCCCAGC
CCCCATCGAGAAAACCATCTCCAAAGCCAAAGGGCAGCCCCGAGAACCACAGGTGTACACCCTGCCCCCAT
CCCGGGAGGAGATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTGCTGGACTCCGA
CGGCTCCTTCTTCCTCTATAGCAAGCTCACCGTGGACAAGAGCAGGTGGCAGCAGGGGAACGTCTTCTCAT
GCTCCGTGATGCATGAGGCTCTGCACAACCACTACACGCAGAAGAGCCTCTCCCTGTCTCCGGGCATCCTA
TTCCATGCCACCCAGGCCGACATCCAGATGACCCAGTCTCCATCCTCCCTGTCTGCATCTGTAGGAGACAG
AGTCACCATCACTTGCCGGGCGAGTCAGGGCATTAGCAATTATTTAGCCTGGTATCAGCAGAAAACAGGGA
AAGTTCCTAAGTTCCTGATCTATGAAGCATCCACTTTGCAATCAGGGGTCCCATCTCGGTTCAGTGGCGGT
GGATCTGGGACAGATTTCACTCTCACCATCAGCAGCCTGCAGCCTGAAGATGTTGCAACTTATTACTGTCA
AAATTATAACAGTGCCCCATTCACTTTCGGCCCTGGGACCAAAGTGGATATCAAACGAACTGTGGCTGCAC
CCTCTGTCTTCATCTTCCCGCCATCTGATGAGCAGTTGAAATCTGGAACTGCTAGCGTTGTGTGCCTGCTG
AATAACTTCTATCCCAGAGAGGCCAAAGTACAGTGGAAGGTGGATAACGCCCTCCAATCGGGTAACTCCCA
GGAGAGTGTCACAGAGCAGGACAGCAAGGACAGCACCTACAGCCTCAGCAGCACCCTGACGCTGAGCAAAG
CAGACTACGAGAAACACAAAGTCTACGCCTGCGAAGTCACCCATCAGGGCCTGAGCTCGCCCGTCACAAAG
AGCTTCAACAGGGGAGAGTGTTAGGAATTCGCGGCCGCTCGACATCGATAATCAACCTCTGGATTACAAAA
TTTGTGAAAGATTGACTGGTATTCTTAACTATGTTGCTCCTTTTACGCTATGTGGATACGCTGCTTTAATG
CCTTTGTATCATGCTATTGCTTCCCGTATGGCTTTCATTTTCTCCTCCTTGTATAAATCCTGGTTGCTGTC
TCTTTATGAGGAGTTGTGGCCCGTTGTCAGGCAACGTGGCGTGGTGTGCACTGTGTTTGCTGACGCAACCC
CCACTGGTTGGGGCATTGCCACCACCTGTCAGCTCCTTTCCGGGACTTTCGCTTTCCCCCTCCCTATTGCC
ACGGCGGAACTCATCGCCGCCTGCCTTGCCCGCTGCTGGACAGGGGCTCGGCTGTTGGGCACTGACAATTC
CGTGGTGTTGTCGGGGAAATCATCGTCCTTTCCTTGGCTGCTCGCCTGTGTTGCCACCTGGATTCTGCGCG
GGACGTCCTTCTGCTACGTCCCTTCGGCCCTCAATCCAGCGGACCTTCCTTCCCGCGGCCTGCTGCCGGCT
CTGCGGCCTCTTCCGCGTCTTCGCCTTCGCCCTCAGACGAGTCGGATCTCCCTTTGGGCCGCCTCCCCGCC
TGATCGATAAAATAAAAGATTTTATTTAGTCTCCAGAAAAAGGGGGGAATGAAAGACCCCACCTGTAGGTT
TGGCAAGCTAGCTTAAGTAACGCCATTTTGCAAGGCATGGAAAAATACATAACTGAGAATAGAGAAGTTCA
GATCAAGGTCAGGAACAGATGGAACAGCTGAATATGGGCCAAACAGGATATCTGTGGTAAGCAGTTCCTGC
CCCGGCTCAGGGCCAAGAACAGATGGAACAGCTGAATATGGGCCAAACAGGATATCTGTGGTAAGCAGTTC
CTGCCCCGGCTCAGGGCCAAGAACAGATGGTCCCCAGATGCGGTCCAGCCCTCAGCAGTTTCTAGAGAACC
ATCAGATGTTTCCAGGGTGCCCCAAGGACCTGAAATGACCCTGTGCCTTATTTGAACTAACCAATCAGTTC
GCTTCTCGCTTCTGTTCGCGCGCTTCTGCTCCCCGAGCTCAATAAAAGAGCCCACAACCCCTCACTCGGGG
CGCCAGTCCTCCGATTGACTGAGTCGCCCGGGTACCCGTGTATCCAATAAACCCTCTTGCAGTTGCATCCG
ACTTGTGGTCTCGCTGTTCCTTGGGAGGGTCTCCTCTGAGTGATTGACTACCCGTCAGCGGGGGTCTTTCA
TT

| | |
|---|---|
| 1 - 589 | 5'LTR Moloney murine sarcoma virus |
| 659 - 1468 | Extended packaging region Moloney murine leukemia virus |
| 1512 - 2306 | Neomycin resistance gene |
| 2656 - 3473 | Human cytomegalovirus major immediate early promoter/enhancer |
| 3481 - 3483 | First codon encoding PSMA heavy chain |
| 4891 - 4893 | Codon encoding the second to last amino acid of PSMA heavy chain |
| 4894 - 4917 | Linker sequence originally encoding part of the Bovine α-Lactalbumin signal peptide |

SEQ ID NO: 10 (CONT)

| | |
|---|---|
| 4918 - 4920 | First codon encoding mature PSMA light chain |
| 5560 - 5562 | PSMA light chain stop codon |
| 5582 - 6182 | Woodchuck Hepatitis B virus RNA export and stability element |
| 6225 - 6818 | 3' LTR Moloney murine leukemia virus |

Spliced Retrovector Gene Construct for Antibody #4 (SEQ ID NO:11):

TTTGAAAGACCCCACCCGTAGGTGGCAAGCTAGCTTAAGTAACGCCACTTTGCAAGGCA
TGGAAAAATACATAACTGAGAATAGAAAAGTTCAGATCAAGGTCAGGAACAAAGAAACA
GCTGAATACCAAACAGGATATCTGTGGTAAGCGGTTCCTGCCCCGGCTCAGGGCCAAGA
ACAGATGAGACAGCTGAGTGATGGGCCAAACAGGATATCTGTGGTAAGCAGTTCCTGCC
CCGGCTCGGGGCCAAGAACAGATGGTCCCCAGATGCGGTCCAGCCCTCAGCAGTTTCTA
GTGAATCATCAGATGTTTCCAGGGTGCCCCAAGGACCTGAAAATGACCCTGTACCTTAT
TTGAACTAACCAATCAGTTCGCTTCTCGCTTCTGTTCGCGCGCTTCCGCTCTCCGAGCT
CAATAAAAGAGCCCACAACCCCTCACTCGGCGCGCCAGTCTTCCGATAGACTGCGTCGC
CCGGGTACCCGTATTCCCAATAAAGCCTCTTGCTGTTTGCATCCGAATCGTGGTCTCGC
TGTTCCTTGGGAGGGTCTCCTCTGAGTGATTGACTACCCACGACGGGGGTCTTTCATTT
GGGGGCTCGTCCGGGATTTGGAGACCCCTGCCCAGGGACCACCGACCCACCACCGGGAG
GTAAGCTGGCCAGCAACTTATCTGTGTCTGTCCGATTGTCTAGTGTCTATGTTTGATGT
TATGCGCCTGCGTCTGTACTAGTTAGCTAACTAGCTCTGTATCTGGCGGACCCGTGGTG
GAACTGACGAGTTCTGAACACCCGGCCGCAACCCTGGGAGACGTCCCAGGGACTTTGGG
GGCCGTTTTTGTGGCCCGACCTGAGGAAGGGAGTCGATGTGGAATCCGACCCCGTCAGG
ATATGTGGTTCTGGTAGGAGACGAGAACCTAAAACAGTTCCCGCCTCCGTCTGAATTTT
TGCTTTCGGTTTGGAACCGAAGCCGCGCGTCTTGTCTGCTGCAGCGCTGCAGCATCGTT
CTGTGTTGTCTCTGTCTGACTGTGTTTCTGTATTTGTCTGAAAATTAGGGCCAGACTGT
TACCACTCCCTTAAGTTTGACCTTAGGTCACTGGAAAGATGTCGAGCGGATCGCTCACA
ACCAGTCGGTAGATGTCAAGAAGAGACGTTGGGTTACCTTCTGCTCTGCAGAATGGCCA
ACCTTTAACGTCGGATGGCCGCGAGACGGCACCTTTAACCGAGACCTCATCACCCAGGT
TAAGATCAAGGTCTTTTCACCTGGCCCGCATGGACACCCAGACCAGGTCCCCTACATCG
TGACCTGGGAAGCCTTGGCTTTTGACCCCCCTCCCTGGGTCAAGCCCTTTGTACACCCT
AAGCCTCCGCCTCCTCTTCCTCCATCCGCCCCGTCTCTCCCCCTTGAACCTCCTCGTTC
GACCCCGCCTCGATCCTCCCTTTATCCAGCCCTCACTCCTTCTCTAGGCGCCGGAATTC
CGATCTGATCAAGAGACAGGATGAGGATCGTTTCGCATGATTGAACAAGATGGATTGCA
CGCAGGTTCTCCGGCCGCTTGGGTGGAGAGGCTATTCGGCTATGACTGGGCACAACAGA
CAATCGGCTGCTCTGATGCCGCCGTGTTCCGGCTGTCAGCGCAGGGGCGCCCGGTTCTT
TTTGTCAAGACCGACCTGTCCGGTGCCCTGAATGAACTGCAGGACGAGGCAGCGCGGCT
ATCGTGGCTGGCCACGACGGGCGTTCCTTGCGCAGCTGTGCTCGACGTTGTCACTGAAG
CGGGAAGGGACTGGCTGCTATTGGGCGAAGTGCCGGGGCAGGATCTCCTGTCATCTCAC
CTTGCTCCTGCCGAGAAAGTATCCATCATGGCTGATGCAATGCGGCGGCTGCATACGCT
TGATCCGGCTACCTGCCCATTCGACCACCAAGCGAAACATCGCATCGAGCGAGCACGTA
CTCGGATGGAAGCCGGTCTTGTCGATCAGGATGATCTGGACGAAGAGCATCAGGGGCTC
GCGCCAGCCGAACTGTTCGCCAGGCTCAAGGCGCGCATGCCCGACGGCGAGGATCTCGT
CGTGACCCATGGCGATGCCTGCTTGCCGAATATCATGGTGGAAAATGGCCGCTTTTCTG
GATTCATCGACTGTGGCCGGCTGGGTGTGGCGGACCGCTATCAGGACATAGCGTTGGCT
ACCCGTGATATTGCTGAAGAGCTTGGCGGCGAATGGGCTGACCGCTTCCTCGTGCTTTA

SEQ ID NO: 11 (CONT)

CGGTATCGCCGCTCCCGATTCGCAGCGCATCGCCTTCTATCGCCTTCTTGACGAGTTCT
TCTGAGCGGGACTCTGGGGTTCGAAATGACCGACCAAGCGACGCCCAACCTGCCATCAC
GAGATTTCGATTCCACCGCCGCCTTCTATGAAAGGTTGGGCTTCGGAATCGTTTTCCGG
GACGCCGGCTGGATGATCCTCCAGCGCGGGGATCTCATGCTGGAGTTCTTCGCCCACCC
CGGGCTCGATCCCCTCGCGAGTTGGTTCAGCTGCTGCCTGAGGCTGGACGACCTCGCGG
AGTTCTACCGGCAGTGCAAATCCGTCGGCATCCAGGAAACCAGCAGCGGCTATCCGCGC
ATCCATGCCCCCGAACTGCAGGAGTGGGGAGGCACGATGGCCGCTTTGGTCGAGGCGGA
TCCGGCCATTAGCCATATTATTCATTGGTTATATAGCATAAATCAATATTGGCTATTGG
CCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGT
CATTAGTTCATAGCCCATATATGGAGTTCCGCGTTACATAACTTACGGTAAATGGCCCG
CCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTG
CCCACTTGGCAGTACATCAAGTGTATCATATGCCAAGTACGCCCCCTATTGACGTCAAT
GACGGTAAATGGCCCGCCTGGCATTATGCCCAGTACATGACCTTATGGGACTTTCCTAC
TTGGCAGTACATCTACGTATTAGTCATCGCTATTACCATGGTGATGCGGTTTTGGCAGT
ACATCAATGGGCGTGGATAGCGGTTTGACTCACGGGGATTTCCAAGTCTCCACCCCATT
GACGTCAATGGGAGTTTGTTTTGGCACCAAAATCAACGGGACTTTCCAAAATGTCGTAA
CAACTCCGCCCCATTGACGCAAATGGGCGGTAGGCATGTACGGTGGGAGGTCTATATAA
GCAGAGCTCGTTTAGTGAACCGTCAGATCGCCTGGAGACGCCATCCACGCTGTTTTGAC
CTCCATAGAAGACACCGGGACCGATCCAGCCTCCGCGGCCCCAAGCTTCTCGAGCACCA
TGGAATGGAGCGGAGTCTTTATCTTTCTCCTGTCAGTAACTGCAGGTGTCCACTCCGAG
GTGCAGCTGGTGGAGTCTGGTGGAGGCTTGGTAAAGCCTGGAGGTTCCCTTAGACTCTC
CTGTGCAGCCTCTGGTTACACTTTCAGTAACTATTGGATCGGATGGGTCCGCCAGGCTC
CAGGCAAAGGGCTGGAGTGGATTGGCGATATCTACCCTGGAGGGAACTACATCAGGAAC
AATGAGAAGTTCAAGGACAAGACCACCCTGTCAGCAGATACTTCCAAGAACACAGCCTA
TCTGCAAATGAACAGCCTGAAAACCGAGGACACAGCCGTGTATTACTGTGGAAGCAGCT
TCGGTAGTAACTACGTGTTCGCCTGGTTTACTTACTGGGGCCAAGGGACTCTGGTCACA
GTCTCCTCAGCTTCCACCAAGGGCCCATCCGTCTTCCCCCTGGCGCCCTGCTCCAGGAG
CACCTCCGAGAGCACAGCCGCCCTGGGCTGCCTGGTCAAGGACTACTTCCCCGAACCGG
TGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTT
GGGCACGAAGACCTACACCTGCAACGTAGATCACAAGCCCAGCAACACCAAGGTGGACA
AGAGAGTTGAGTCCAAATATGGTCCCCCATGCCCATCATGCCCAGCACCTGAGTTCCTG
GGGGGACCATCAGTCTTCCTGTTCCCCCCAAAACCCAAGGACACTCTCATGATCTCCCG
GACCCCTGAGGTCACGTGCGTGGTGGTGGACGTGAGCCAGGAAGACCCCGAGGTCCAGT
TCAACTGGTACGTGGATGGCGTGGAGGTGCATAATGCCAAGACAAAGCCGCGGGAGGAG
CAGTTCAACAGCACGTACCGTGTGGTCAGCGTCCTCACCGTCCTGCACCAGGACTGGCT
GAACGGCAAGGAGTACAAGTGCAAGGTCTCCAACAAAGGCCTCCCGTCCTCCATCGAGA
AAACCATCTCCAAAGCCAAAGGGCAGCCCCGAGAGCCACAGGTGTACACCCTGCCCCCA
TCCCAGGAGGAGATGACCAAGAACCAGGTCAGCCTGACCTGCCTGGTCAAAGGCTTCTA
CCCCAGCGACATCGCCGTGGAGTGGGAGAGCAATGGGCAGCCGGAGAACAACTACAAGA
CCACGCCTCCCGTGCTGGACTCCGACGGCTCCTTCTTCCTCTACAGCAGGCTAACCGTG
GACAAGAGCAGGTGGCAGGAGGGGAATGTCTTCTCATGCTCCGTGATGCATGAGGCTCT
GCACAACCACTACACACAGAAGAGCCTCTCCCTGTCTCTGGGCATCCTATTCCATGCCA
CCCAGGCCGACATTGTGATGACCCAATCTCCACTCTCCCTGCCTGTCACTCCTGGAGAG
CCAGCCTCCATCTCTTGCAGATCTAGTCAGCGCCTTCTGAGCAGTTATGGACATACCTA

SEQ ID NO: 11 (CONT)

TTTACATTGGTACCTACAGAAGCCAGGCCAGTCTCCACAGCTCCTGATCTACGAAGTTT
CCAACCGATTTTCTGGGGTCCCAGACAGGTTCAGTGGCAGTGGGTCAGGGACAGATTTC
ACACTTAAGATCAGTAGAGTGGAGGCTGAGGATGTGGGAGTTTATTACTGCTCTCAAAG
TACACATGTTCCTCTCACGTTCGGACAGGGGACCAAGGTGGAAATAAAACGAACTGTGG
CTGCACCATCTGTCTTCATCTTCCCGCCATCTGATGAGCAGTTGAAATCTGGAACTGCC
TCTGTTGTGTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGACAGCAAGG
ACAGCACCTACAGCCTCAGCAGCACCCTGACGCTGAGCAAAGCAGACTACGAGAAACAC
AAAGTCTACGCCTGCGAAGTCACCCATCAGGGCCTGAGCTCGCCCGTCACAAAGAGCTT
CAACAGGGGAGAGTGTTAGAGGGAGAAGTGCCCCCACCTGCTCCTCGACATCGATAATC
AACCTCTGGATTACAAAATTTGTGAAAGATTGACTGGTATTCTTAACTATGTTGCTCCT
TTTACGCTATGTGGATACGCTGCTTTAATGCCTTTGTATCATGCTATTGCTTCCCGTAT
GGCTTTCATTTTCTCCTCCTTGTATAAATCCTGGTTGCTGTCTCTTTATGAGGAGTTGT
GGCCCGTTGTCAGGCAACGTGGCGTGGTGTGCACTGTGTTTGCTGACGCAACCCCCACT
GGTTGGGGCATTGCCACCACCTGTCAGCTCCTTTCCGGGACTTTCGCTTTCCCCCTCCC
TATTGCCACGGCGGAACTCATCGCCGCCTGCCTTGCCCGCTGCTGGACAGGGGCTCGGC
TGTTGGGCACTGACAATTCCGTGGTGTTGTCGGGGAAATCATCGTCCTTTCCTTGGCTG
CTCGCCTGTGTTGCCACCTGGATTCTGCGCGGGACGTCCTTCTGCTACGTCCCTTCGGC
CCTCAATCCAGCGGACCTTCCTTCCCGCGGCCTGCTGCCGGCTCTGCGGCCTCTTCCGC
GTCTTCGCCTTCGCCCTCAGACGAGTCGGATCTCCCTTTGGGCCGCCTCCCCGCATCGA
TAAAATAAAAGATTTTATTTAGTCTCCAGAAAAAGGGGGGAATGAAAGACCCCACCTGT
AGGTTTGGCAAGCTAGCTTAAGTAACGCCATTTTGCAAGGCATGGAAAAATACATAACT
GAGAATAGAGAAGTTCAGATCAAGGTCAGGAACAGATGGAACAGCTGAATATGGGCCAA
ACAGGATATCTGTGGTAAGCAGTTCCTGCCCCGGCTCAGGGCCAAGAACAGATGGAACA
GCTGAATATGGGCCAAACAGGATATCTGTGGTAAGCAGTTCCTGCCCCGGCTCAGGGCC
AAGAACAGATGGTCCCCAGATGCGGTCCAGCCCTCAGCAGTTTCTAGAGAACCATCAGA
TGTTTCCAGGGTGCCCCAAGGACCTGAAATGACCCTGTGCCTTATTTGAACTAACCAAT
CAGTTCGCTTCTCGCTTCTGTTCGCGCGCTTCTGCTCCCCGAGCTCAATAAAAGAGCCC
ACAACCCCTCACTCGGGGCGCCAGTCCTCCGATTGACTGAGTCGCCCGGGTACCCGTGT
ATCCAATAAACCCTCTTGCAGTTGCATCCGACTTGTGGTCTCGCTGTTCCTTGGGAGGG
TCTCCTCTGAGTGATTGACTACCCGTCAGCGGGGGTCTTTCATT

| | |
|---|---|
| 1 - 589 | 5'LTR Moloney murine sarcoma virus |
| 659 - 1468 | Extended Packaging Region Moloney murine leukemia virus |
| 1512 - 2306 | Neomycin resistance gene |
| 2656 - 3473 | Human cytomegalovirus major immediate early promoter/enhancer |
| 3481 - 3483 | First codon encoding Pro140 heavy chain |
| 4879 - 4881 | Codon encoding the second to last amino acid of Pro140 heavy chain |
| 4882 - 4905 | Linker sequence originally encoding part of the Bovine α-Lactalbumin signal peptide |
| 4906 - 4908 | First codon encoding mature Pro140 light chain |
| 5563 - 5565 | Pro140 light chain stop codon |

SEQ ID NO: 11 (CONT)

| | |
|---|---|
| 5596 - 6196 | Woodchuck Hepatitis B virus RNA export and stability element |
| 6236 - 6829 | 3' LTR Moloney murine leukemia virus |

Figure 7

Mutatated Retrovector Gene Construct to Prevent Splicing for Antibody #1 (SEQ ID NO:12):

TTTGAAAGACCCCACCCGTAGGTGGCAAGCTAGCTTAAGTAACGCCACTTTGCAAGGCATGGAAAAATACA
TAACTGAGAATAGAAAAGTTCAGATCAAGGTCAGGAACAAAGAAACAGCTGAATACCAAACAGGATATCTG
TGGTAAGCGGTTCCTGCCCCGGCTCAGGGCCAAGAACAGATGAGACAGCTGAGTGATGGGCCAAACAGGAT
ATCTGTGGTAAGCAGTTCCTGCCCCGGCTCGGGGCCAAGAACAGATGGTCCCCAGATGCGGTCCAGCCCTC
AGCAGTTTCTAGTGAATCATCAGATGTTTCCAGGGTGCCCCAAGGACCTGAAAATGACCCTGTACCTTATT
TGAACTAACCAATCAGTTCGCTTCTCGCTTCTGTTCGCGCGCTTCCGCTCTCCGAGCTCAATAAAAGAGCC
CACAACCCCTCACTCGGCGCGCCAGTCTTCCGATAGACTGCGTCGCCCGGGTACCCGTATTCCCAATAAAG
CCTCTTGCTGTTTGCATCCGAATCGTGGTCTCGCTGTTCCTTGGGAGGGTCTCCTCTGAGTGATTGACTAC
CCACGACGGGGGTCTTTCATTTGGGGGCTCGTCCGGGATTTGGAGACCCCTGCCCAGGGACCACCGACCCA
CCACCGGGAGGTAAGCTGGCCAGCAACTTATCTGTGTCTGTCCGATTGTCTAGTGTCTATGTTTGATGTTA
TGCGCCTGCGTCTGTACTAGTTAGCTAACTAGCTCTGTATCTGGCGGACCCGTGGTGGAACTGACGAGTTC
TGAACACCCGGCCGCAACCCTGGGAGACGTCCCAGGGACTTTGGGGGCCGTTTTTGTGGCCCGACCTGAGG
AAGGGAGTCGATGTGGAATCCGACCCCGTCAGGATATGTGGTTCTGGTAGGAGACGAGAACCTAAAACAGT
TCCCGCCTCCGTCTGAATTTTTGCTTTCGGTTTGGAACCGAAGCCGCGCGTCTTGTCTGCTGCAGCGCTGC
AGCATCGTTCTGTGTTGTCTCTGTCTGACTGTGTTTCTGTATTTGTCTGAAAATTAGGGCCAGACTGTTAC
CACTCCCTTAAGTTTGACCTTAGGTCACTGGAAAGATGTCGAGCGGATCGCTCACAACCAGTCGGTAGATG
TCAAGAAGAGACGTTGGGTTACCTTCTGCTCTGCAGAATGGCCAACCTTTAACGTCGGATGGCCGCGAGAC
GGCACCTTTAACCGAGACCTCATCACCCAGGTTAAGATCAAGGTCTTTTCACCTGGCCCGCATGGACACCC
AGACCAGGTCCCCTACATCGTGACCTGGGAAGCCTTGGCTTTTGACCCCCCTCCCTGGGTCAAGCCCTTTG
TACACCCTAAGCCTCCGCCTCCTCTTCCTCCATCCGCCCCGTCTCTCCCCCTTGAACCTCCTCGTTCGACC
CCGCCTCGATCCTCCCTTTATCCAGCCCTCACTCCTTCTCTAGGCGCCGGAATTCCGATCTGATCAAGAGA
CAGGATGAGGATCGTTTCGCATGATTGAACAAGATGGATTGCACGCAGGTTCTCCGGCCGCTTGGGTGGAG
AGGCTATTCGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAGGACGAGGCAG
CGCGGCTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCATTCGACCACC
AAGCGAAACATCGCATCGAGCGAGCACGTACTCGGATGGAAGCCGGTCTTGTCGATCAGGATGATCTGGAC
GAAGAGCATCAGGGGCTCGCGCCAGCCGAACTGTTCGCCAGGCTCAAGGCGCGCATGCCCGACGGCGAGGA
TCTCGTCGTGACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGATATTGCTGAA
GAGCTTGGCGGCGAATGGGCTGACCGCTTCCTCGTGCTTTACGGTATCGCCGCTCCCGATTCGCAGCGCAT
CGCCTTCTATCGCCTTCTTGACGAGTTCTTCTGAGCGGGACTCTGGGGTTCGAAATGACCGACCAAGCGAC
GCCCAACCTGCCATCACGAGATTTCGATTCCACCGCCGCCTTCTATGAAAGGTTGGGCTTCGGAATCGTTT
TCCGGGACGCCGGCTGGATGATCCTCCAGCGCGGGGATCTCATGCTGGAGTTCTTCGCCCACCCCGGGCTC
GATCCCCTCGCGAGTTGGTTCAGCTGCTGCCTGAGGCTGGACGACCTCGCGGAGTTCTACCGGCAGTGCAA
ATCCGTCGGCATCCAGGAAACCAGCAGCGGCTATCCGCGCATCCATGCCCCCGAACTGCAGGAGTGGGGAG
GCACGATGGCCGCTTTGGTCGAGGCGGATCCGGCCATTAGCCATATTATTCATTGGTTATATAGCATAAAT
CAATATTGGCTATTGGCCATTGCATACGTTGTATCCATATCATAATATGTACATTTATATTGGCTCATGTC
CAACATTACCGCCATGTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGGACTTTCC
TACTTGGCAGTACATCTACGTATTAGTCATCGCTATTACCATGGTGATGCGGTTTTGGCAGTACATCAATG
GGCGTGGATAGCGGTTTGACTCACGGGGATTTCCAAGTCTCCACCCCATTGACGTCAATGGGAGTTTGTTT
TGGCACCAAAATCAACGGGACTTTCCAAAATGTCGTAACAACTCCGCCCCATTGACGCAAATGGGCGGTAG
GCATGTACGGTGGGAGGTCTATATAAGCAGAGCTCGTTTAGTGAACCGTCAGATCGCCTGGAGACGCCATC
CACGCTGTTTTGACCTCCATAGAAGACACCGGGACCGATCCAGCCTCCGCGGCCCCAAGCTTCTCGACGGA
TCCCCGGGAATTCAGGACCTCACCATGGGATGGAGCTGTATCATCCTCTTCTTGGTAGCAACAGCTACAGG
TGTCCACTCCGAGGTCCAACTGGTGGAGAGCGGTGGAGGTGTTGTGCAACCTGGCCGGTCCCTGCGCCTGT

SEQ ID NO: 12 (CONT)

CCTGCTCCGCATCTGGCTTCGATTTCACCACATATTGGATGAGTTGGGTGAGACAGGCACCTGGAAAAGGT
CTTGAGTGGATTGGAGAAATTCATCCAGATAGCAGTACGATTAACTATGCGCCGTCTCTAAAGGATAGATT
TACAATATCGCGAGACAACGCCAAGAACACATTGTTCCTGCAAATGGACAGCCTGAGACCCGAAGACACCG
GGGTCTATTTTTGTGCAAGCCTTTACTTCGGCTTCCCCTGGTTTGCTTATTGGGGCCAAGGGACCCCGGTC
ACCGTCTCCTCAGCCTCCACCAAGGGCCCATCGGTCTTCCCCCTGGCACCCTCCTCCAAGAGCACCTCTGG
GGGCACAGCGGCCCTGGGCTGCCTGGTCAAGGACTACTTCCCCGAACCGGTGACGGTGTCGTGGAACTCAG
GCGCCCTGACCAGCGGCGTGCACACCTTCCCGGCTGTCCTACAGTCCTCAGGACTCTACTCCCTCAGCAGC
GTGGTGACCGTGCCCTCCAGCAGCTTGGGCACCCAGACCTACATCTGCAACGTGAATCACAAGCCCAGCAA
CACCAAGGTGGACAAGAGAGTTGAGCCCAAATCTTGTGACAAAACTCACACATGCCCACCGTGCCCAGCAC
CTGAACTCCTGGGGGGACCGTCAGTCTTCCTCTTCCCCCCAAAACCCAAGGACACCCTCATGATCTCCCGG
ACCCCTGAGGTCACATGCGTGGTGGTGGACGTGAGCCACGAAGACCCTGAGGTCAAGTTCAACTGGTACGT
GGACGGCGTGGAGGTGCATAATGCCAAGACAAAGCCGCGGGAGGAGCAGTACAACAGCACGTACCGTGTGG
TCAGCGTCCTCACCGTCCTGCACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCCCCGAGAACCACAGGTGTACAC
CCTGCCCCCATCCCGGGAGGAGATGACCAAGAACCAGGTCAGCCTGACCTGCCTGGTCAAAGGCTTCTATC
CCAGCGACATCGCCGTGGAGTGGGAGAGCAATGGGCAGCCGGAGAACAACTACAAGACCACGCCTCCCGTG
CTGGACTCCGACGGCTCCTTCTTCCTCTATAGCAAGCTCACCGTGGACAAGAGCAGGTGGCAGCAGGGGAA
CGTCTTCTCATGCTCCGTGATGCATGAGGCTCTGCACAACCACTACACGCAGAAGAGCCTCTCCCTGTCTC
CCGGGAAATGAAAGCCGAATTCGCCCCTCTCCCTCCCCCCCCCCTAACGTTACTGGCCGAAGCCGCTTGGA
ATAAGGCCGGTGTGCGTTTGTCTATATGTTATTTTCCACCATATTGCCGTCTTTTGGCAATGTGAGGGCCC
GGAAACCTGGCCCTGTCTTCTTGACGAGCATTCCTAGGGGTCTTTCCCCTCTCGCCAAAGGAATGCAAGGT
CTGTTGAATGTCGTGAAGGAAGCAGTTCCTCTGGAAGCTTCTTGAAGACAAACAACGTCTGTAGCGACCCT
TTGCAGGCAGCGGAACCCCCCACCTGGCGACAGGTGCCTCTGCGGCCAAAAGCCACGTGTATAAGATACAC
CTGCAAAGGCGGCACAACCCCAGTGCCACGTTGTGAGTTGGATAGTTGTGGAAAGAGTCAAATGGCTCTCC
TCAAGCGTATTCAACAAGGGGCTGAAGGATGCCCAGAAGGTACCCCATTGTATGGGATCTGATCTGGGGCC
TCGGTGCACATGCTTTACATGTGTTTAGTCGAGGTTAAAAAAACGTCTAGGCCCCCCGAACCACGGGGACG
TGGTTTTCCTTTGAAAAACACGATGATAATATGGCCTCCTTTGTCTCTCTGCTCCTGGTAGGCATCCTATT
CCATGCCACCCAGGCCGACATCCAGCTGACCCAGAGCCCAAGCAGCCTGAGCGCCAGCGTGGGTGACAGAG
TGACCATCACCTGTAAGGCCAGTCAGGATGTGGGTACTTCTGTAGCCTGGTACCAGCAGAAGCCAGGTAAG
GCTCCAAAGCTGCTGATCTACTGGACATCCACCCGGCACACTGGTGTGCCAAGCAGATTCAGCGGTAGCGG
TAGCGGTACCGACTTCACCTTCACCATCAGCAGCCTCCAGCCAGAGGACATCGCCACCTACTACTGCCAGC
AATATAGCCTCTATCGGTCGTTCGGCCAAGGGACCAAGGTGGAAATCAAACGAACTGTGGCTGCACCATCT
GTCTTCATCTTCCCGCCATCTGATGAGCAGTTGAAATCTGGAACTGCCTCTGTTGTGTGCCTGCTGAATAA
CTTCTATCCCAGAGAGGCCAAAGTACAGTGGAAGGTGGATAACGCCCTCCAATCGGGTAACTCCCAGGAGA
GTGTCACAGAGCAGGACAGCAAGGACAGCACCTACAGCCTCAGCAGCACCCTGACGCTGAGCAAAGCAGAC
TACGAGAAACACAAAGTCTACGCCTGCGAAGTCACCCATCAGGGCCTGAGCTCGCCCGTCACAAAGAGCTT
CAACAGGGGAGAGTGTTAGAGATCTAGGCCTCCTAGGTCGACATCGATAAAATAAAAGATTTTATTTAGTC
TCCAGAAAAAGGGGGGAATGAAAGACCCCACCTGTAGGTTTGGCAAGCTAGCTTAAGTAACGCCATTTTGC
AAGGCATGGAAAAATACATAACTGAGAATAGAGAAGTTCAGATCAAGGTCAGGAACAGATGGAACAGCTGA
ATATGGGCCAAACAGGATATCTGTGGTAAGCAGTTCCTGCCCCGGCTCAGGGCCAAGAACAGATGGAACAG
CTGAATATGGGCCAAACAGGATATCTGTGGTAAGCAGTTCCTGCCCCGGCTCAGGGCCAAGAACAGATGGT
CCCCAGATGCGGTCCAGCCCTCAGCAGTTTCTAGAGAACCATCAGATGTTTCCAGGGTGCCCCAAGGACCT
GAAATGACCCTGTGCCTTATTTGAACTAACCAATCAGTTCGCTTCTCGCTTCTGTTCGCGCGCTTCTGCTC
CCCGAGCTCAATAAAAGAGCCCACAACCCCTCACTCGGGGCGCCAGTCCTCCGATTGACTGAGTCGCCCGG
GTACCCGTGTATCCAATAAACCCTCTTGCAGTTGCATCCGACTTGTGGTCTCGCTGTTCCTTGGGAGGGTC
TCCTCTGAGTGATTGACTACCCGTCAGCGGGGGTCTTTCATT

| | | |
|---|---|
| 1 - 589 | 5'LTR Moloney murine sarcoma virus |
| 659 - 1468 | Extended packaging signal Moloney murine leukemia virus |
| 1512 - 2306 | Neomycin resistance gene |
| 2656 - 3473 | Human cytomegalovirus major immediate early promoter/enhancer |
| 3504 - 3506 | MN14 heavy chain gene signal peptide start codon |

SEQ ID NO: 12 (CONT)

| | |
|---|---|
| 4901 | Splicing prevention mutation G to C |
| 4904 | Splicing prevention mutation T to G |
| 4908 - 4910 | Stop codon for MN14 heavy chain gene |
| 4922 - 5497 | Encephalomyocarditis virus internal ribosome entry site |
| 5498 - 5500 | Bovine α-Lactalbumin signal peptide start codon |
| 5555 - 5557 | First codon encoding mature MN14 light chain |
| 6194 - 6196 | Stop codon for MN14 light chain |
| 6265 - 6858 | 3'LTR Moloney murine leukemia virus |

Mutatated Retrovector Gene Construct to Prevent Splicing for Antibody #2 (SEQ ID NO:13):

TTTGAAAGACCCCACCCGTAGGTGGCAAGCTAGCTTAAGTAACGCCACTTTGCAAGGCATGGAAAAATACA
TAACTGAGAATAGAAAAGTTCAGATCAAGGTCAGGAACAAAGAAACAGCTGAATACCAAACAGGATATCTG
TGGTAAGCGGTTCCTGCCCCGGCTCAGGGCCAAGAACAGATGAGACAGCTGAGTGATGGGCCAAACAGGAT
ATCTGTGGTAAGCAGTTCCTGCCCCGGCTCGGGGCCAAGAACAGATGGTCCCCAGATGCGGTCCAGCCCTC
AGCAGTTTCTAGTGAATCATCAGATGTTTCCAGGGTGCCCCAAGGACCTGAAAATGACCCTGTACCTTATT
TGAACTAACCAATCAGTTCGCTTCTCGCTTCTGTTCGCGCGCTTCCGCTCTCCGAGCTCAATAAAAGAGCC
CACAACCCCTCACTCGGCGCGCCAGTCTTCCGATAGACTGCGTCGCCCGGGTACCCGTATTCCCAATAAAG
CCTCTTGCTGTTTGCATCCGAATCGTGGTCTCGCTGTTCCTTGGGAGGGTCTCCTCTGAGTGATTGACTAC
CCACGACGGGGGTCTTTCATTTGGGGGCTCGTCCGGGATTTGGAGACCCCTGCCCAGGGACCACCGACCCA
CCACCGGGAGGTAAGCTGGCCAGCAACTTATCTGTGTCTGTCCGATTGTCTAGTGTCTATGTTTGATGTTA
TGCGCCTGCGTCTGTACTAGTTAGCTAACTAGCTCTGTATCTGGCGGACCCGTGGTGGAACTGACGAGTTC
TGAACACCCGGCCGCAACCCTGGGAGACGTCCCAGGGACTTTGGGGGCCGTTTTTGTGGCCCGACCTGAGG
AAGGGAGTCGATGTGGAATCCGACCCCGTCAGGATATGTGGTTCTGGTAGGAGACGAGAACCTAAAACAGT
TCCCGCCTCCGTCTGAATTTTTGCTTTCGGTTTGGAACCGAAGCCGCGCGTCTTGTCTGCTGCAGCGCTGC
AGCATCGTTCTGTGTTGTCTCTGTCTGACTGTGTTTCTGTATTTGTCTGAAAATTAGGGCCAGACTGTTAC
CACTCCCTTAAGTTTGACCTTAGGTCACTGGAAAGATGTCGAGCGGATCGCTCACAACCAGTCGGTAGATG
TCAAGAAGAGACGTTGGGTTACCTTCTGCTCTGCAGAATGGCCAACCTTTAACGTCGGATGGCCGCGAGAC
GGCACCTTTAACCGAGACCTCATCACCCAGGTTAAGATCAAGGTCTTTTCACCTGGCCCGCATGGACACCC
AGACCAGGTCCCCTACATCGTGACCTGGGAAGCCTTGGCTTTTGACCCCCCTCCCTGGGTCAAGCCCTTTG
TACACCCTAAGCCTCCGCCTCCTCTTCCTCCATCCGCCCCGTCTCTCCCCCTTGAACCTCCTCGTTCGACC
CCGCCTCGATCCTCCCTTTATCCAGCCCTCACTCCTTCTCTAGGCGCCGGAATTCCGATCTGATCAAGAGA
CAGGATGAGGATCGTTTCGCATGATTGAACAAGATGGATTGCACGCAGGTTCTCCGGCCGCTTGGGTGGAG
AGGCTATTCGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAGGACGAGGCAG
CGCGGCTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCATTCGACCACC
AAGCGAAACATCGCATCGAGCGAGCACGTACTCGGATGGAAGCCGGTCTTGTCGATCAGGATGATCTGGAC
GAAGAGCATCAGGGGCTCGCGCCAGCCGAACTGTTCGCCAGGCTCAAGGCGCGCATGCCCGACGGCGAGGA
TCTCGTCGTGACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGATATTGCTGAA
GAGCTTGGCGGCGAATGGGCTGACCGCTTCCTCGTGCTTTACGGTATCGCCGCTCCCGATTCGCAGCGCAT
CGCCTTCTATCGCCTTCTTGACGAGTTCTTCTGAGCGGGACTCTGGGGTTCGAAATGACCGACCAAGCGAC
GCCCAACCTGCCATCACGAGATTTCGATTCCACCGCCGCCTTCTATGAAAGGTTGGGCTTCGGAATCGTTT
TCCGGGACGCCGGCTGGATGATCCTCCAGCGCGGGGATCTCATGCTGGAGTTCTTCGCCCACCCCGGGCTC
GATCCCCTCGCGAGTTGGTTCAGCTGCTGCCTGAGGCTGGACGACCTCGCGGAGTTCTACCGGCAGTGCAA
ATCCGTCGGCATCCAGGAAACCAGCAGCGGCTATCCGCGCATCCATGCCCCCGAACTGCAGGAGTGGGGAG
GCACGATGGCCGCTTTGGTCGAGGCGGATCCGGCCATTAGCCATATTATTCATTGGTTATATAGCATAAAT
CAATATTGGCTATTGGCCATTGCATACGTTGTATCCATATCATAATATGTACATTTATATTGGCTCATGTC
CAACATTACCGCCATGTTGACATTGATTATTGACTAGTTATTAATAGTAATCAATTACGGGGTCATTAGTT

SEQ ID NO: 13 (CONT)

CATAGCCCATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGGACTTTCC
TACTTGGCAGTACATCTACGTATTAGTCATCGCTATTACCATGGTGATGCGGTTTTGGCAGTACATCAATG
GGCGTGGATAGCGGTTTGACTCACGGGGATTTCCAAGTCTCCACCCCATTGACGTCAATGGGAGTTTGTTT
TGGCACCAAAATCAACGGGACTTTCCAAAATGTCGTAACAACTCCGCCCCATTGACGCAAATGGGCGGTAG
GCATGTACGGTGGGAGGTCTATATAAGCAGAGCTCGTTTAGTGAACCGTCAGATCGCCTGGAGACGCCATC
CACGCTGTTTTGACCTCCATAGAAGACACCGGGACCGATCCAGCCTCCGCGGCCCCAAGCTTCTCGACGGA
TCCCCGGGAATTCAGGACCTCACCATGGGATGGAGCTGTATCATCCTCTTCTTGGTAGCAACAGCTACAGG
TGTCCACTCCCAGGTCCAGCTGGTCCAATCAGGGGCTGAAGTCAAGAAACCTGGGTCATCAGTGAAGGTCT
CCTGCAAGGCTTCTGGCTACACCTTTACTAGCTACTGGCTGCACTGGGTCAGGCAGGCACCTGGACAGGGT
CTGGAATGGATTGGATACATTAATCCTAGGAATGATTATACTGAGTACAATCAGAACTTCAAGGACAAGGC
CACAATAACTGCAGACGAATCCACCAATACAGCCTACATGGAGCTGAGCAGCCTGAGGTCTGAGGACACGG
CATTTTATTTTTGTGCAAGAAGGGATATTACTACGTTCTACTGGGGCCAAGGCACCACGGTCACCGTCTCC
TCAGCCTCCACCAAGGGCCCATCGGTCTTCCCCCTGGCACCCTCCTCCAAGAGCACCTCTGGGGGCACAGC
GGCCCTGGGCTGCCTGGTCAAGGACTACTTCCCCGAACCGGTGACGGTGTCGTGGAACTCAGGCGCCCTGA
CCAGCGGCGTGCACACCTTCCCGGCTGTCCTACAGTCCTCAGGACTCTACTCCCTCAGCAGCGTGGTGACC
GTGCCCTCCAGCAGCTTGGGCACCCAGACCTACATCTGCAACGTGAATCACAAGCCCAGCAACACCAAGGT
GGACAAGAGAGTTGAGCCCAAATCTTGTGACAAAACTCACACATGCCCACCGTGCCCAGCACCTGAACTCC
TGGGGGGACCGTCAGTCTTCCTCTTCCCCCCAAAACCCAAGGACACCCTCATGATCTCCCGGACCCCTGAG
GTCACATGCGTGGTGGTGGACGTGAGCCACGAAGACCCTGAGGTCAAGTTCAACTGGTACGTGGACGGCGT
GGAGGTGCATAATGCCAAGACAAAGCCGCGGGAGGAGCAGTACAACAGCACGTACCGTGTGGTCAGCGTCC
TCACCGTCCTGCACCAGGACTGGCTGAATGGCAAGGAGTACAAGTGCAAGGTCTCCAACAAAGCCCTCCCA
GCCCCCATCGAGAAAACCATCTCCAAAGCCAAAGGGCAGCCCCGAGAACCACAGGTGTACACCCTGCCCCC
ATCCCGGGAGGAGATGACCAAGAACCAGGTCAGCCTGACCTGCCTGGTCAAAGGCTTCTATCCCAGCGACA
TCGCCGTGGAGTGGGAGAGCAATGGGCAGCCGGAGAACAACTACAAGACCACGCCTCCCGTGCTGGACTCC
GACGGCTCCTTCTTCCTCTATAGCAAGCTCACCGTGGACAAGAGCAGGTGGCAGCAGGGGAACGTCTTCTC
ATGCTCCGTGATGCATGAGGCTCTGCACAACCACTACACGCAGAAGAGCCTCTCCCTGTCTCCCGGGAAAT
GAAAGCCGAATTCGCCCCTCTCCCTCCCCCCCCCCTAACGTTACTGGCCGAAGCCGCTTGGAATAAGGCCG
GTGTGCGTTTGTCTATATGTTATTTTCCACCATATTGCCGTCTTTTGGCAATGTGAGGGCCCGGAAACCTG
GCCCTGTCTTCTTGACGAGCATTCCTAGGGGTCTTTCCCCTCTCGCCAAAGGAATGCAAGGTCTGTTGAAT
GTCGTGAAGGAAGCAGTTCCTCTGGAAGCTTCTTGAAGACAAACAACGTCTGTAGCGACCCTTTGCAGGCA
GCGGAACCCCCCACCTGGCGACAGGTGCCTCTGCGGCCAAAAGCCACGTGTATAAGATACACCTGCAAAGG
CGGCACAACCCCAGTGCCACGTTGTGAGTTGGATAGTTGTGGAAAGAGTCAAATGGCTCTCCTCAAGCGTA
TTCAACAAGGGGCTGAAGGATGCCCAGAAGGTACCCCATTGTATGGGATCTGATCTGGGGCCTCGGTGCAC
ATGCTTTACATGTGTTTAGTCGAGGTTAAAAAAACGTCTAGGCCCCCCGAACCACGGGGACGTGGTTTTCC
TTTGAAAAACACGATGATAATATGGCCTCCTTTGTCTCTCTGCTCCTGGTAGGCATCCTATTCCATGCCAC
CCAGGCCGACATCCAGCTGACCCAGTCTCCATCATCTCTGAGCGCATCTGTTGGAGATAGGGTCACTATGA
GCTGTAAGTCCAGTCAAAGTGTTTTATACAGTGCAAATCACAAGAACTACTTGGCCTGGTACCAGCAGAAA
CCAGGGAAAGCACCTAAACTGCTGATCTACTGGGCATCCACTAGGGAATCTGGTGTCCCTTCGCGATTCTC
TGGCAGCGGATCTGGGACAGATTTTACTTTCACCATCAGCTCTCTTCAACCAGAAGACATTGCAACATATT
ATTGTCACCAATACCTCTCCTCGTGGACGTTCGGTGGAGGGACCAAGGTGCAGATCAAACGAACTGTGGCT
GCACCATCTGTCTTCATCTTCCCGCCATCTGATGAGCAGTTGAAATCTGGAACTGCCTCTGTTGTGTGCCT
GCTGAATAACTTCTATCCCAGAGAGGCCAAAGTACAGTGGAAGGTGGATAACGCCCTCCAATCGGGTAACT
CCCAGGAGAGTGTCACAGAGCAGGACAGCAAGGACAGCACCTACAGCCTCAGCAGCACCCTGACGCTGAGC
AAAGCAGACTACGAGAAACACAAAGTCTACGCCTGCGAAGTCACCCATCAGGGCCTGAGCTCGCCCGTCAC
AAAGAGCTTCAACAGGGGAGAGTGTTAGAGATCTAGGCCTCCTAGGTCGACATCGATAAAATAAAAGATTT
TATTTAGTCTCCAGAAAAAGGGGGGAATGAAAGACCCCACCTGTAGGTTTGGCAAGCTAGCTTAAGTAACG
CCATTTTGCAAGGCATGGAAAAATACATAACTGAGAATAGAGAAGTTCAGATCAAGGTCAGGAACAGATGG
AACAGCTGAATATGGGCCAAACAGGATATCTGTGGTAAGCAGTTCCTGCCCCGGCTCAGGGCCAAGAACAG
ATGGAACAGCTGAATATGGGCCAAACAGGATATCTGTGGTAAGCAGTTCCTGCCCCGGCTCAGGGCCAAGA
ACAGATGGTCCCCAGATGCGGTCCAGCCCTCAGCAGTTTCTAGAGAACCATCAGATGTTTCCAGGGTGCCC
CAAGGACCTGAAATGACCCTGTGCCTTATTTGAACTAACCAATCAGTTCGCTTCTCGCTTCTGTTCGCGCG
CTTCTGCTCCCCGAGCTCAATAAAAGAGCCCACAACCCCTCACTCGGGGCGCCAGTCCTCCGATTGACTGA
GTCGCCCGGGTACCCGTGTATCCAATAAACCCTCTTGCAGTTGCATCCGACTTGTGGTCTCGCTGTTCCTT
GGGAGGGTCTCCTCTGAGTGATTGACTACCCGTCAGCGGGGGTCTTTCATT

SEQ ID NO: 13 (CONT)

| | |
|---|---|
| 1 - 589 | 5'LTR Moloney murine sarcoma virus |
| 659 - 1468 | Extended packaging signal Moloney murine leukemia virus |
| 1512 - 2306 | Neomycin resistance gene |
| 2656 - 3473 | Human cytomegalovirus major immediate early promoter/enhancer |
| 3504 - 3506 | LL2 heavy chain gene signal peptide start codon |
| 4892 | Splicing prevention mutation G to C |
| 4895 | Splicing prevention mutation T to G |
| 4899 - 4901 | Stop codon for LL2 heavy chain gene |
| 4913 - 5488 | Encephalomyocarditis virus internal ribosome entry site |
| 5489 - 5491 | Bovine α-Lactalbumin signal peptide start codon |
| 5546 - 5548 | First codon encoding mature LL2 light chain |
| 6203 - 6205 | Stop codon for LL2 light chain gene |
| 6274 - 6867 | 3'LTR Moloney murine leukemia virus |

Mutatated Retrovector Gene Construct to Prevent Splicing for Antibody #3 (SEQ ID NO:14):

TTTGAAAGACCCCACCCGTAGGTGGCAAGCTAGCTTAAGTAACGCCACTTTGCAAGGCATGGAAAAATACA
TAACTGAGAATAGAAAAGTTCAGATCAAGGTCAGGAACAAAGAAACAGCTGAATACCAAACAGGATATCTG
TGGTAAGCGGTTCCTGCCCCGGCTCAGGGCCAAGAACAGATGAGACAGCTGAGTGATGGGCCAAACAGGAT
ATCTGTGGTAAGCAGTTCCTGCCCCGGCTCGGGGCCAAGAACAGATGGTCCCCAGATGCGGTCCAGCCCTC
AGCAGTTTCTAGTGAATCATCAGATGTTTCCAGGGTGCCCCAAGGACCTGAAAATGACCCTGTACCTTATT
TGAACTAACCAATCAGTTCGCTTCTCGCTTCTGTTCGCGCGCTTCCGCTCTCCGAGCTCAATAAAAGAGCC
CACAACCCCTCACTCGGCGCGCCAGTCTTCCGATAGACTGCGTCGCCCGGGTACCCGTATTCCCAATAAAG
CCTCTTGCTGTTTGCATCCGAATCGTGGTCTCGCTGTTCCTTGGGAGGGTCTCCTCTGAGTGATTGACTAC
CCACGACGGGGGTCTTTCATTTGGGGGCTCGTCCGGGATTTGGAGACCCCTGCCCAGGGACCACCGACCCA
CCACCGGGAGGTAAGCTGGCCAGCAACTTATCTGTGTCTGTCCGATTGTCTAGTGTCTATGTTTGATGTTA
TGCGCCTGCGTCTGTACTAGTTAGCTAACTAGCTCTGTATCTGGCGGACCCGTGGTGGAACTGACGAGTTC
TGAACACCCGGCCGCAACCCTGGGAGACGTCCCAGGGACTTTGGGGGCCGTTTTTGTGGCCCGACCTGAGG
AAGGGAGTCGATGTGGAATCCGACCCCGTCAGGATATGTGGTTCTGGTAGGAGACGAGAACCTAAAACAGT
TCCCGCCTCCGTCTGAATTTTTGCTTTCGGTTTGGAACCGAAGCCGCGCGTCTTGTCTGCTGCAGCGCTGC
AGCATCGTTCTGTGTTGTCTCTGTCTGACTGTGTTTCTGTATTTGTCTGAAAATTAGGGCCAGACTGTTAC
CACTCCCTTAAGTTTGACCTTAGGTCACTGGAAAGATGTCGAGCGGATCGCTCACAACCAGTCGGTAGATG
TCAAGAAGAGACGTTGGGTTACCTTCTGCTCTGCAGAATGGCCAACCTTTAACGTCGGATGGCCGCGAGAC
GGCACCTTTAACCGAGACCTCATCACCCAGGTTAAGATCAAGGTCTTTTCACCTGGCCCGCATGGACACCC
AGACCAGGTCCCCTACATCGTGACCTGGGAAGCCTTGGCTTTTGACCCCCCTCCCTGGGTCAAGCCCTTTG
TACACCCTAAGCCTCCGCCTCCTCTTCCTCCATCCGCCCCGTCTCTCCCCCTTGAACCTCCTCGTTCGACC
CCGCCTCGATCCTCCCTTTATCCAGCCCTCACTCCTTCTCTAGGCGCCGGAATTCCGATCTGATCAAGAGA
CAGGATGAGGATCGTTTCGCATGATTGAACAAGATGGATTGCACGCAGGTTCTCCGGCCGCTTGGGTGGAG
AGGCTATTCGGCTATGACTGGGCACAACAGACAATCGGCTGCTCTGATGCCGCCGTGTTCCGGCTGTCAGC
GCAGGGGCGCCCGGTTCTTTTTGTCAAGACCGACCTGTCCGGTGCCCTGAATGAACTGCAGGACGAGGCAG
CGCGGCTATCGTGGCTGGCCACGACGGGCGTTCCTTGCGCAGCTGTGCTCGACGTTGTCACTGAAGCGGGA
AGGGACTGGCTGCTATTGGGCGAAGTGCCGGGGCAGGATCTCCTGTCATCTCACCTTGCTCCTGCCGAGAA
AGTATCCATCATGGCTGATGCAATGCGGCGGCTGCATACGCTTGATCCGGCTACCTGCCCATTCGACCACC
AAGCGAAACATCGCATCGAGCGAGCACGTACTCGGATGGAAGCCGGTCTTGTCGATCAGGATGATCTGGAC

SEQ ID NO: 14 (CONT)

GAAGAGCATCAGGGGCTCGCGCCAGCCGAACTGTTCGCCAGGCTCAAGGCGCGCATGCCCGACGGCGAGGA
TCTCGTCGTGACCCATGGCGATGCCTGCTTGCCGAATATCATGGTGGAAAATGGCCGCTTTTCTGGATTCA
TCGACTGTGGCCGGCTGGGTGTGGCGGACCGCTATCAGGACATAGCGTTGGCTACCCGTGATATTGCTGAA
GAGCTTGGCGGCGAATGGGCTGACCGCTTCCTCGTGCTTTACGGTATCGCCGCTCCCGATTCGCAGCGCAT
CGCCTTCTATCGCCTTCTTGACGAGTTCTTCTGAGCGGGACTCTGGGGTTCGAAATGACCGACCAAGCGAC
GCCCAACCTGCCATCACGAGATTTCGATTCCACCGCCGCCTTCTATGAAAGGTTGGGCTTCGGAATCGTTT
TCCGGGACGCCGGCTGGATGATCCTCCAGCGCGGGGATCTCATGCTGGAGTTCTTCGCCCACCCCGGGCTC
GATCCCCTCGCGAGTTGGTTCAGCTGCTGCCTGAGGCTGGACGACCTCGCGGAGTTCTACCGGCAGTGCAA
ATCCGTCGGCATCCAGGAAACCAGCAGCGGCTATCCGCGCATCCATGCCCCCGAACTGCAGGAGTGGGGAG
GCACGATGGCCGCTTTGGTCGAGGCGGATCCGGCCATTAGCCATATTATTCATTGGTTATATAGCATAAAT
CAATATTGGCTATTGGCCATTGCATACGTTGTATCCATATCATAATATGTACATTTATATTGGCTCATGTC
CAACATTACCGCCATGTTGACATTGATTATTGACTAGTTATTAATAGTAATCAATTACGGGGTCATTAGTT
CATAGCCCATATATGGAGTTCCGCGTTACATAACTTACGGTAAATGGCCCGCCTGGCTGACCGCCCAACGA
CCCCCGCCCATTGACGTCAATAATGACGTATGTTCCCATAGTAACGCCAATAGGGACTTTCCATTGACGTC
AATGGGTGGAGTATTTACGGTAAACTGCCCACTTGGCAGTACATCAAGTGTATCATATGCCAAGTACGCCC
CCTATTGACGTCAATGACGGTAAATGGCCCGCCTGGCATTATGCCCAGTACATGACCTTATGGGACTTTCC
TACTTGGCAGTACATCTACGTATTAGTCATCGCTATTACCATGGTGATGCGGTTTTGGCAGTACATCAATG
GGCGTGGATAGCGGTTTGACTCACGGGGATTTCCAAGTCTCCACCCCATTGACGTCAATGGGAGTTTGTTT
TGGCACCAAAATCAACGGGACTTTCCAAAATGTCGTAACAACTCCGCCCCATTGACGCAAATGGGCGGTAG
GCATGTACGGTGGGAGGTCTATATAAGCAGAGCTCGTTTAGTGAACCGTCAGATCGCCTGGAGACGCCATC
CACGCTGTTTTGACCTCCATAGAAGACACCGGGACCGATCCAGCCTCCGCGGCCCCAAGCTTGGATCTCAC
CATGGAGTTGGGACTGCGCTGGGGCTTCCTCGTTGCTCTTTTAAGAGGTGTCCAGTGTCAGGTGCAATTGG
TGGAGTCTGGGGGAGGCGTGGTCCAGCCTGGGAGGTCCCTGAGACTCTCCTGTGCAGCGTCTGGATTCGCC
TTCAGTAGATATGGCATGCACTGGGTCCGCCAGGCTCCAGGCAAGGGGCTGGAGTGGGTGGCAGTTATATG
GTATGATGGAAGTAATAAATACTATGCAGACTCCGTGAAGGGCCGATTCACCATCTCCAGAGACAATTCCA
AGAACACGCAGTATCTGCAAATGAACAGCCTGAGAGCCGAGGACACGGCTGTGTATTACTGTGCGAGAGGC
GGTGACTTCCTCTACTACTACTATTACGGTATGGACGTCTGGGGCCAAGGGACCACGGTCACCGTCTCCTC
AGCCTCCACCAAGGGCCCATCGGTCTTCCCCCTGGCACCCTCTAGCAAGAGCACCTCTGGGGGCACAGCGG
CCCTGGGCTGCCTGGTCAAGGACTACTTCCCCGAACCGGTGACGGTGTCGTGGAACTCAGGCGCCCTGACC
AGCGGCGTGCACACCTTCCCGGCTGTCCTACAGTCCTCAGGACTCTACTCCCTCAGCAGCGTGGTGACCGT
GCCCTCCAGCAGCTTGGGCACCCAGACCTACATCTGCAACGTGAATCACAAGCCCAGCAACACCAAGGTGG
ACAAGAGAGTTGAGCCCAAATCTTGTGACAAAACTCACACATGCCCACCGTGCCCAGCACCTGAACTCCTG
GGGGGACCGTCAGTCTTCCTCTTCCCCCCAAAACCCAAGGACACCCTCATGATCTCCCGGACCCCTGAGGT
CACATGCGTGGTGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGTGTGGTCAGCGTCCTC
ACCGTCCTGCACCAGGACTGGCTGAATGGCAAGGAGTACAAGTGCAAGGTCTCCAACAAAGCCCTCCCAGC
CCCCATCGAGAAAACCATCTCCAAAGCCAAAGGGCAGCCCCGAGAACCACAGGTGTACACCCTGCCCCCAT
CCCGGGAGGAGATGACCAAGAACCAGGTCAGCCTGACCTGCCTGGTCAAAGGCTTCTATCCCAGCGACATC
GCCGTGGAGTGGGAGAGCAATGGGCAGCCGGAGAACAACTACAAGACCACGCCTCCCGTGCTGGACTCCGA
CGGCTCCTTCTTCCTCTATAGCAAGCTCACCGTGGACAAGAGCAGGTGGCAGCAGGGGAACGTCTTCTCAT
GCTCCGTGATGCATGAGGCTCTGCACAACCACTACACGCAGAAGAGCCTCTCCCTGTCTCCCGGGAAATGA
GAATTCCTCGAGTTAACAGATCCCCGGGAATTCGCCCCTCTCCCTCCCCCCCCCCTAACGTTACTGGCCGA
AGCCGCTTGGAATAAGGCCGGTGTGCGTTTGTCTATATGTTATTTTCCACCATATTGCCGTCTTTTGGCAA
TGTGAGGGCCCGGAAACCTGGCCCTGTCTTCTTGACGAGCATTCCTAGGGGTCTTTCCCCTCTCGCCAAAG
GAATGCAAGGTCTGTTGAATGTCGTGAAGGAAGCAGTTCCTCTGGAAGCTTCTTGAAGACAAACAACGTCT
GTAGCGACCCTTTGCAGGCAGCGGAACCCCCCACCTGGCGACAGGTGCCTCTGCGGCCAAAAGCCACGTGT
ATAAGATACACCTGCAAAGGCGGCACAACCCCAGTGCCACGTTGTGAGTTGGATAGTTGTGGAAAGAGTCA
AATGGCTCTCCTCAAGCGTATTCAACAAGGGGCTGAAGGATGCCCAGAAGGTACCCCATTGTATGGGATCT
GATCTGGGGCCTCGGTGCACATGCTTTACATGTGTTTAGTCGAGGTTAAAAAAACGTCTAGGCCCCCCGAA
CCACGGGGACGTGGTTTTCCTTTGAAAAACACGATGATAATATGGCCTCCTTTGTCTCTCTGCTCCTGGTA
GGCATCCTATTCCATGCCACCCAGGCCGACATCCAGATGACCCAGTCTCCATCCTCCCTGTCTGCATCTGT
AGGAGACAGAGTCACCATCACTTGCCGGGCGAGTCAGGGCATTAGCAATTATTTAGCCTGGTATCAGCAGA
AAACAGGGAAAGTTCCTAAGTTCCTGATCTATGAAGCATCCACTTTGCAATCAGGGGTCCCATCTCGGTTC
AGTGGCGGTGGATCTGGGACAGATTTCACTCTCACCATCAGCAGCCTGCAGCCTGAAGATGTTGCAACTTA
TTACTGTCAAAATTATAACAGTGCCCCATTCACTTTCGGCCCTGGGACCAAAGTGGATATCAAACGAACTG
TGGCTGCACCCTCTGTCTTCATCTTCCCGCCATCTGATGAGCAGTTGAAATCTGGAACTGCTAGCGTTGTG
TGCCTGCTGAATAACTTCTATCCCAGAGAGGCCAAAGTACAGTGGAAGGTGGATAACGCCCTCCAATCGGG

SEQ ID NO: 14 (CONT)

TAACTCCCAGGAGAGTGTCACAGAGCAGGACAGCAAGGACAGCACCTACAGCCTCAGCAGCACCCTGACGC
TGAGCAAAGCAGACTACGAGAAACACAAAGTCTACGCCTGCGAAGTCACCCATCAGGGCCTGAGCTCGCCC
GTCACAAAGAGCTTCAACAGGGGAGAGTGTTAGGAATTCGCGGCCGCTCGACATCGATAATCAACCTCTGG
ATTACAAAATTTGTGAAAGATTGACTGGTATTCTTAACTATGTTGCTCCTTTTACGCTATGTGGATACGCT
GCTTTAATGCCTTTGTATCATGCTATTGCTTCCCGTATGGCTTTCATTTTCTCCTCCTTGTATAAATCCTG
GTTGCTGTCTCTTTATGAGGAGTTGTGGCCCGTTGTCAGGCAACGTGGCGTGGTGTGCACTGTGTTTGCTG
ACGCAACCCCCACTGGTTGGGGCATTGCCACCACCTGTCAGCTCCTTTCCGGGACTTTCGCTTTCCCCCTC
CCTATTGCCACGGCGGAACTCATCGCCGCCTGCCTTGCCCGCTGCTGGACAGGGGCTCGGCTGTTGGGCAC
TGACAATTCCGTGGTGTTGTCGGGGAAATCATCGTCCTTTCCTTGGCTGCTCGCCTGTGTTGCCACCTGGA
TTCTGCGCGGGACGTCCTTCTGCTACGTCCCTTCGGCCCTCAATCCAGCGGACCTTCCTTCCCGCGGCCTG
CTGCCGGCTCTGCGGCCTCTTCCGCGTCTTCGCCTTCGCCCTCAGACGAGTCGGATCTCCCTTTGGGCCGC
CTCCCCGCCTGATCGATAAAATAAAAGATTTTATTTAGTCTCCAGAAAAAGGGGGGAATGAAAGACCCCAC
CTGTAGGTTTGGCAAGCTAGCTTAAGTAACGCCATTTTGCAAGGCATGGAAAAATACATAACTGAGAATAG
AGAAGTTCAGATCAAGGTCAGGAACAGATGGAACAGCTGAATATGGGCCAAACAGGATATCTGTGGTAAGC
AGTTCCTGCCCCGGCTCAGGGCCAAGAACAGATGGAACAGCTGAATATGGGCCAAACAGGATATCTGTGGT
AAGCAGTTCCTGCCCCGGCTCAGGGCCAAGAACAGATGGTCCCCAGATGCGGTCCAGCCCTCAGCAGTTTC
TAGAGAACCATCAGATGTTTCCAGGGTGCCCCAAGGACCTGAAATGACCCTGTGCCTTATTTGAACTAACC
AATCAGTTCGCTTCTCGCTTCTGTTCGCGCGCTTCTGCTCCCCGAGCTCAATAAAAGAGCCCACAACCCCT
CACTCGGGGCGCCAGTCCTCCGATTGACTGAGTCGCCCGGGTACCCGTGTATCCAATAAACCCTCTTGCAG
TTGCATCCGACTTGTGGTCTCGCTGTTCCTTGGGAGGGTCTCCTCTGAGTGATTGACTACCCGTCAGCGGG
GGTCTTTCATT

| | |
|---|---|
| 1 - 589 | 5'LTR Moloney murine sarcoma virus |
| 659 - 1468 | Extended packaging region Moloney murine leukemia virus |
| 1512 - 2306 | Neomycin resistance gene |
| 2656 - 3473 | Human cytomegalovirus major immediate early promoter/enhancer |
| 3481 - 3483 | First codon encoding PSMA heavy chain |
| 4890 | Splicing prevention mutation G to C |
| 4893 | Splicing prevention mutation T to G |
| 4897 - 4899 | PSMA heavy chain gene stop codon |
| 4927 - 5508 | Encephalomyocarditis virus internal ribosome entry site |
| 5509 - 5511 | Bovine α-lactalbumin signal peptide start codon |
| 5563 - 5565 | Bovine α-lactalbumin signal peptide ending codon |
| 5566 - 5568 | First codon encoding mature PSMA light chain |
| 6208 - 6210 | PSMA light chain stop codon |
| 6230 - 6830 | Woodchuck Hepatitis B virus RNA export and stability element |
| 6873 - 7466 | 3' LTR Moloney murine leukemia virus |

Mutatated Retrovector Gene Construct to Prevent Splicing for Antibody #4 (SEQ ID NO:15):

TTTGAAAGACCCCACCCGTAGGTGGCAAGCTAGCTTAAGTAACGCCACTTTGCAAGGCA
TGGAAAAATACATAACTGAGAATAGAAAAGTTCAGATCAAGGTCAGGAACAAAGAAACA

SEQ ID NO: 15 (CONT)

GCTGAATACCAAACAGGATATCTGTGGTAAGCGGTTCCTGCCCCGGCTCAGGGCCAAGA
ACAGATGAGACAGCTGAGTGATGGGCCAAACAGGATATCTGTGGTAAGCAGTTCCTGCC
CCGGCTCGGGGCCAAGAACAGATGGTCCCCAGATGCGGTCCAGCCCTCAGCAGTTTCTA
GTGAATCATCAGATGTTTCCAGGGTGCCCCAAGGACCTGAAAATGACCCTGTACCTTAT
TTGAACTAACCAATCAGTTCGCTTCTCGCTTCTGTTCGCGCGCTTCCGCTCTCCGAGCT
CAATAAAAGAGCCCACAACCCCTCACTCGGCGCGCCAGTCTTCCGATAGACTGCGTCGC
CCGGGTACCCGTATTCCCAATAAAGCCTCTTGCTGTTTGCATCCGAATCGTGGTCTCGC
TGTTCCTTGGGAGGGTCTCCTCTGAGTGATTGACTACCCACGACGGGGGTCTTTCATTT
GGGGGCTCGTCCGGGATTTGGAGACCCCTGCCCAGGGACCACCGACCCACCACCGGGAG
GTAAGCTGGCCAGCAACTTATCTGTGTCTGTCCGATTGTCTAGTGTCTATGTTTGATGT
TATGCGCCTGCGTCTGTACTAGTTAGCTAACTAGCTCTGTATCTGGCGGACCCGTGGTG
GAACTGACGAGTTCTGAACACCCGGCCGCAACCCTGGGAGACGTCCCAGGGACTTTGGG
GGCCGTTTTTGTGGCCCGACCTGAGGAAGGGAGTCGATGTGGAATCCGACCCCGTCAGG
ATATGTGGTTCTGGTAGGAGACGAGAACCTAAAACAGTTCCCGCCTCCGTCTGAATTTT
TGCTTTCGGTTTGGAACCGAAGCCGCGCGTCTTGTCTGCTGCAGCGCTGCAGCATCGTT
CTGTGTTGTCTCTGTCTGACTGTGTTTCTGTATTTGTCTGAAAATTAGGGCCAGACTGT
TACCACTCCCTTAAGTTTGACCTTAGGTCACTGGAAAGATGTCGAGCGGATCGCTCACA
ACCAGTCGGTAGATGTCAAGAAGAGACGTTGGGTTACCTTCTGCTCTGCAGAATGGCCA
ACCTTTAACGTCGGATGGCCGCGAGACGGCACCTTTAACCGAGACCTCATCACCCAGGT
TAAGATCAAGGTCTTTTCACCTGGCCCGCATGGACACCCAGACCAGGTCCCCTACATCG
TGACCTGGGAAGCCTTGGCTTTTGACCCCCCTCCCTGGGTCAAGCCCTTTGTACACCCT
AAGCCTCCGCCTCCTCTTCCTCCATCCGCCCCGTCTCTCCCCCTTGAACCTCCTCGTTC
GACCCCGCCTCGATCCTCCCTTTATCCAGCCCTCACTCCTTCTCTAGGCGCCGGAATTC
CGATCTGATCAAGAGACAGGATGAGGATCGTTTCGCATGATTGAACAAGATGGATTGCA
CGCAGGTTCTCCGGCCGCTTGGGTGGAGAGGCTATTCGGCTATGACTGGGCACAACAGA
CAATCGGCTGCTCTGATGCCGCCGTGTTCCGGCTGTCAGCGCAGGGGCGCCCGGTTCTT
TTTGTCAAGACCGACCTGTCCGGTGCCCTGAATGAACTGCAGGACGAGGCAGCGCGGCT
ATCGTGGCTGGCCACGACGGGCGTTCCTTGCGCAGCTGTGCTCGACGTTGTCACTGAAG
CGGGAAGGGACTGGCTGCTATTGGGCGAAGTGCCGGGGCAGGATCTCCTGTCATCTCAC
CTTGCTCCTGCCGAGAAAGTATCCATCATGGCTGATGCAATGCGGCGGCTGCATACGCT
TGATCCGGCTACCTGCCCATTCGACCACCAAGCGAAACATCGCATCGAGCGAGCACGTA
CTCGGATGGAAGCCGGTCTTGTCGATCAGGATGATCTGGACGAAGAGCATCAGGGGCTC
GCGCCAGCCGAACTGTTCGCCAGGCTCAAGGCGCGCATGCCCGACGGCGAGGATCTCGT
CGTGACCCATGGCGATGCCTGCTTGCCGAATATCATGGTGGAAAATGGCCGCTTTTCTG
GATTCATCGACTGTGGCCGGCTGGGTGTGGCGGACCGCTATCAGGACATAGCGTTGGCT
ACCCGTGATATTGCTGAAGAGCTTGGCGGCGAATGGGCTGACCGCTTCCTCGTGCTTTA
CGGTATCGCCGCTCCCGATTCGCAGCGCATCGCCTTCTATCGCCTTCTTGACGAGTTCT
TCTGAGCGGGACTCTGGGGTTCGAAATGACCGACCAAGCGACGCCCAACCTGCCATCAC
GAGATTTCGATTCCACCGCCGCCTTCTATGAAAGGTTGGGCTTCGGAATCGTTTTCCGG
GACGCCGGCTGGATGATCCTCCAGCGCGGGGATCTCATGCTGGAGTTCTTCGCCCACCC
CGGGCTCGATCCCCTCGCGAGTTGGTTCAGCTGCTGCCTGAGGCTGGACGACCTCGCGG
AGTTCTACCGGCAGTGCAAATCCGTCGGCATCCAGGAAACCAGCAGCGGCTATCCGCGC
ATCCATGCCCCCGAACTGCAGGAGTGGGGAGGCACGATGGCCGCTTTGGTCGAGGCGGA
TCCGGCCATTAGCCATATTATTCATTGGTTATATAGCATAAATCAATATTGGCTATTGG
CCATTGCATACGTTGTATCCATATCATAATATGTACATTTATATTGGCTCATGTCCAAC
ATTACCGCCATGTTGACATTGATTATTGACTAGTTATTAATAGTAATCAATTACGGGGT
CATTAGTTCATAGCCCATATATGGAGTTCCGCGTTACATAACTTACGGTAAATGGCCCG

SEQ ID NO: 15 (CONT)

CCTGGCTGACCGCCCAACGACCCCCGCCCATTGACGTCAATAATGACGTATGTTCCCAT
AGTAACGCCAATAGGGACTTTCCATTGACGTCAATGGGTGGAGTATTTACGGTAAACTG
CCCACTTGGCAGTACATCAAGTGTATCATATGCCAAGTACGCCCCCTATTGACGTCAAT
GACGGTAAATGGCCCGCCTGGCATTATGCCCAGTACATGACCTTATGGGACTTTCCTAC
TTGGCAGTACATCTACGTATTAGTCATCGCTATTACCATGGTGATGCGGTTTTGGCAGT
ACATCAATGGGCGTGGATAGCGGTTTGACTCACGGGGATTTCCAAGTCTCCACCCCATT
GACGTCAATGGGAGTTTGTTTTGGCACCAAAATCAACGGGACTTTCCAAAATGTCGTAA
CAACTCCGCCCCATTGACGCAAATGGGCGGTAGGCATGTACGGTGGGAGGTCTATATAA
GCAGAGCTCGTTTAGTGAACCGTCAGATCGCCTGGAGACGCCATCCACGCTGTTTTGAC
CTCCATAGAAGACACCGGGACCGATCCAGCCTCCGCGGCCCCAAGCTTCTCGAGCACCA
TGGAATGGAGCGGAGTCTTTATCTTTCTCCTGTCAGTAACTGCAGGTGTCCACTCCGAG
GTGCAGCTGGTGGAGTCTGGTGGAGGCTTGGTAAAGCCTGGAGGTTCCCTTAGACTCTC
CTGTGCAGCCTCTGGTTACACTTTCAGTAACTATTGGATCGGATGGGTCCGCCAGGCTC
CAGGCAAAGGGCTGGAGTGGATTGGCGATATCTACCCTGGAGGGAACTACATCAGGAAC
AATGAGAAGTTCAAGGACAAGACCACCCTGTCAGCAGATACTTCCAAGAACACAGCCTA
TCTGCAAATGAACAGCCTGAAAACCGAGGACACAGCCGTGTATTACTGTGGAAGCAGCT
TCGGTAGTAACTACGTGTTCGCCTGGTTTACTTACTGGGGCCAAGGGACTCTGGTCACA
GTCTCCTCAGCTTCCACCAAGGGCCCATCCGTCTTCCCCCTGGCGCCCTGCTCCAGGAG
CACCTCCGAGAGCACAGCCGCCCTGGGCTGCCTGGTCAAGGACTACTTCCCCGAACCGG
TGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTT
GGGCACGAAGACCTACACCTGCAACGTAGATCACAAGCCCAGCAACACCAAGGTGGACA
AGAGAGTTGAGTCCAAATATGGTCCCCCATGCCCATCATGCCCAGCACCTGAGTTCCTG
GGGGGACCATCAGTCTTCCTGTTCCCCCCAAAACCCAAGGACACTCTCATGATCTCCCG
GACCCCTGAGGTCACGTGCGTGGTGGTGGACGTGAGCCAGGAAGACCCCGAGGTCCAGT
TCAACTGGTACGTGGATGGCGTGGAGGTGCATAATGCCAAGACAAAGCCGCGGGAGGAG
CAGTTCAACAGCACGTACCGTGTGGTCAGCGTCCTCACCGTCCTGCACCAGGACTGGCT
GAACGGCAAGGAGTACAAGTGCAAGGTCTCCAACAAAGGCCTCCCGTCCTCCATCGAGA
AAACCATCTCCAAAGCCAAAGGGCAGCCCCGAGAGCCACAGGTGTACACCCTGCCCCCA
TCCCAGGAGGAGATGACCAAGAACCAGGTCAGCCTGACCTGCCTGGTCAAAGGCTTCTA
CCCCAGCGACATCGCCGTGGAGTGGGAGAGCAATGGGCAGCCGGAGAACAACTACAAGA
CCACGCCTCCCGTGCTGGACTCCGACGGCTCCTTCTTCCTCTACAGCAGGCTAACCGTG
GACAAGAGCAGGTGGCAGGAGGGGAATGTCTTCTCATGCTCCGTGATGCATGAGGCTCT
GCACAACCACTACACACAGAAGAGCCTCTCCCTGTCTCTCGGGAAATGAGTGCCAGATC
CCCGGGAATTCGCCCCTCTCCCTCCCCCCCCCCTAACGTTACTGGCCGAAGCCGCTTGG
AATAAGGCCGGTGTGCGTTTGTCTATATGTTATTTTCCACCATATTGCCGTCTTTTGGC
AATGTGAGGGCCCGGAAACCTGGCCCTGTCTTCTTGACGAGCATTCCTAGGGGTCTTTC
CCCTCTCGCCAAAGGAATGCAAGGTCTGTTGAATGTCGTGAAGGAAGCAGTTCCTCTGG
AAGCTTCTTGAAGACAAACAACGTCTGTAGCGACCCTTTGCAGGCAGCGGAACCCCCCA
CCTGGCGACAGGTGCCTCTGCGGCCAAAAGCCACGTGTATAAGATACACCTGCAAAGGC
GGCACAACCCCAGTGCCACGTTGTGAGTTGGATAGTTGTGGAAAGAGTCAAATGGCTCT
CCTCAAGCGTATTCAACAAGGGGCTGAAGGATGCCCAGAAGGTACCCCATTGTATGGGA
TCTGATCTGGGGCCTCGGTGCACATGCTTTACATGTGTTTAGTCGAGGTTAAAAAAACG
TCTAGGCCCCCCGAACCACGGGGACGTGGTTTTCCTTTGAAAAACACGATGATAATATG
GCCTCCTTTGTCTCTCTGCTCCTGGTAGGCATCCTATTCCATGCCACCCAGGCCGACAT
TGTGATGACCCAATCTCCACTCTCCCTGCCTGTCACTCCTGGAGAGCCAGCCTCCATCT
CTTGCAGATCTAGTCAGCGCCTTCTGAGCAGTTATGGACATACCTATTTACATTGGTAC

SEQ ID NO: 15 (CONT)

CTACAGAAGCCAGGCCAGTCTCCACAGCTCCTGATCTACGAAGTTTCCAACCGATTTTC
TGGGGTCCCAGACAGGTTCAGTGGCAGTGGGTCAGGGACAGATTTCACACTTAAGATCA
GTAGAGTGGAGGCTGAGGATGTGGGAGTTTATTACTGCTCTCAAAGTACACATGTTCCT
CTCACGTTCGGACAGGGGACCAAGGTGGAAATAAAACGAACTGTGGCTGCACCATCTGT
CTTCATCTTCCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGATAACGCCCTC
CAATCGGGTAACTCCCAGGAGAGTGTCACAGAGCAGGACAGCAAGGACAGCACCTACAG
CCTCAGCAGCACCCTGACGCTGAGCAAAGCAGACTACGAGAAACACAAAGTCTACGCCT
GCGAAGTCACCCATCAGGGCCTGAGCTCGCCCGTCACAAAGAGCTTCAACAGGGGAGAG
TGTTAGAGGGAGAAGTGCCCCCACCTGCTCCTCGACATCGATAATCAACCTCTGGATTA
CAAAATTTGTGAAAGATTGACTGGTATTCTTAACTATGTTGCTCCTTTTACGCTATGTG
GATACGCTGCTTTAATGCCTTTGTATCATGCTATTGCTTCCCGTATGGCTTTCATTTTC
TCCTCCTTGTATAAATCCTGGTTGCTGTCTCTTTATGAGGAGTTGTGGCCCGTTGTCAG
GCAACGTGGCGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATTGCCACGGCG
GAACTCATCGCCGCCTGCCTTGCCCGCTGCTGGACAGGGGCTCGGCTGTTGGGCACTGA
CAATTCCGTGGTGTTGTCGGGGAAATCATCGTCCTTTCCTTGGCTGCTCGCCTGTGTTG
CCACCTGGATTCTGCGCGGGACGTCCTTCTGCTACGTCCCTTCGGCCCTCAATCCAGCG
GACCTTCCTTCCCGCGGCCTGCTGCCGGCTCTGCGGCCTCTTCCGCGTCTTCGCCTTCG
CCCTCAGACGAGTCGGATCTCCCTTTGGGCCGCCTCCCCGCATCGATAAAATAAAAGAT
TTTATTTAGTCTCCAGAAAAAGGGGGGAATGAAAGACCCCACCTGTAGGTTTGGCAAGC
TAGCTTAAGTAACGCCATTTTGCAAGGCATGGAAAAATACATAACTGAGAATAGAGAAG
TTCAGATCAAGGTCAGGAACAGATGGAACAGCTGAATATGGGCCAAACAGGATATCTGT
GGTAAGCAGTTCCTGCCCCGGCTCAGGGCCAAGAACAGATGGAACAGCTGAATATGGGC
CAAACAGGATATCTGTGGTAAGCAGTTCCTGCCCCGGCTCAGGGCCAAGAACAGATGGT
CCCCAGATGCGGTCCAGCCCTCAGCAGTTTCTAGAGAACCATCAGATGTTTCCAGGGTG
CCCCAAGGACCTGAAATGACCCTGTGCCTTATTTGAACTAACCAATCAGTTCGCTTCTC
GCTTCTGTTCGCGCGCTTCTGCTCCCCGAGCTCAATAAAAGAGCCCACAACCCCTCACT
CGGGGCGCCAGTCCTCCGATTGACTGAGTCGCCCGGGTACCCGTGTATCCAATAAACCC
TCTTGCAGTTGCATCCGACTTGTGGTCTCGCTGTTCCTTGGGAGGGTCTCCTCTGAGTG
ATTGACTACCCGTCAGCGGGGGTCTTTCATT

| | |
|---|---|
| 1 - 589 | 5'LTR Moloney murine sarcoma virus |
| 659 - 1468 | Extended Packaging Region Moloney murine leukemia virus |
| 1512 - 2306 | Neomycin resistance gene |
| 2656 - 3473 | Human cytomegalovirus major immediate early promoter/enhancer |
| 3481 - 3483 | First codon encoding Pro140 heavy chain |
| 4878 | Splicing prevention mutation G to C |
| 4881 | Splicing prevention mutation T to G |
| 4885 - 4887 | Pro140 heavy chain gene stop codon |
| 4903 - 5484 | Encephalomyocarditis virus internal ribosome entry site |
| 5485 - 5487 | Bovine α-lactalbumin signal peptide start codon |

SEQ ID NO: 15 (CONT)

| | |
|---|---|
| 5539 - 5541 | Bovine α-lactalbumin signal peptide ending codon |
| 5542 - 5544 | First codon encoding mature Pro140 light chain |
| 6199 - 6201 | Pro140 light chain stop codon |
| 6232 - 6832 | Woodchuck Hepatitis B virus RNA export and stability element |
| 6872 - 7465 | 3' LTR Moloney murine leukemia virus |

Figure 8

Antibody Fusion Gene #3 (SEQ ID NO:16):

ATG/GAG/TTG/GGA/CTG/CGC/TGG/GGC/TTC/CTC/GTT/GCT/CTT/TTA/AGA
/GGT/GTC/CAG/TGT/CAG/GTG/CAA/TTG/GTG/GAG/TCT/GGG/GGA/GGC/GT
G/GTC/CAG/CCT/GGG/AGG/TCC/CTG/AGA/CTC/TCC/TGT/GCA/GCG/TCT/G
GA/TTC/GCC/TTC/AGT/AGA/TAT/GGC/ATG/CAC/TGG/GTC/CGC/CAG/GCT/
CCA/GGC/AAG/GGG/CTG/GAG/TGG/GTG/GCA/GTT/ATA/TGG/TAT/GAT/GGA
/AGT/AAT/AAA/TAC/TAT/GCA/GAC/TCC/GTG/AAG/GGC/CGA/TTC/ACC/AT
C/TCC/AGA/GAC/AAT/TCC/AAG/AAC/ACG/CAG/TAT/CTG/CAA/ATG/AAC/A
GC/CTG/AGA/GCC/GAG/GAC/ACG/GCT/GTG/TAT/TAC/TGT/GCG/AGA/GGC/
GGT/GAC/TTC/CTC/TAC/TAC/TAC/TAT/TAC/GGT/ATG/GAC/GTC/TGG/GGC
/CAA/GGG/ACC/ACG/GTC/ACC/GTC/TCC/TCA/GCC/TCC/ACC/AAG/GGC/CC
A/TCG/GTC/TTC/CCC/CTG/GCA/CCC/TCT/AGC/AAG/AGC/ACC/TCT/GGG/G
GC/ACA/GCG/GCC/CTG/GGC/TGC/CTG/GTC/AAG/GAC/TAC/TTC/CCC/GAA/
CCG/GTG/ACG/GTG/TCG/TGG/AAC/TCA/GGC/GCC/CTG/ACC/AGC/GGC/GTG
/CAC/ACC/TTC/CCG/GCT/GTC/CTA/CAG/TCC/TCA/GGA/CTC/TAC/TCC/CT
C/AGC/AGC/GTG/GTG/ACC/GTG/CCC/TCC/AGC/AGC/TTG/GGC/ACC/CAG/A
CC/TAC/ATC/TGC/AAC/GTG/AAT/CAC/AAG/CCC/AGC/AAC/ACC/AAG/GTG/
GAC/AAG/AGA/GTT/GAG/CCC/AAA/TCT/TGT/GAC/AAA/ACT/CAC/ACA/TGC
/CCA/CCG/TGC/CCA/GCA/CCT/GAA/CTC/CTG/GGG/GGA/CCG/TCA/GTC/TT
C/CTC/TTC/CCC/CCA/AAA/CCC/AAG/GAC/ACC/CTC/ATG/ATC/TCC/CGG/A
CC/CCT/GAG/GTC/ACA/TGC/GTG/GTG/GTG/GAC/GTG/AGC/CAC/GAA/GAC/
CCT/GAG/GTC/AAG/TTC/AAC/TGG/TAC/GTG/GAC/GGC/GTG/GAG/GTG/CAT
/AAT/GCC/AAG/ACA/AAG/CCG/CGG/GAG/GAG/CAG/TAC/AAC/AGC/ACG/TA
C/CGT/GTG/GTC/AGC/GTC/CTC/ACC/GTC/CTG/CAC/CAG/GAC/TGG/CTG/A
AT/GGC/AAG/GAG/TAC/AAG/TGC/AAG/GTC/TCC/AAC/AAA/GCC/CTC/CCA/
GCC/CCC/ATC/GAG/AAA/ACC/ATC/TCC/AAA/GCC/AAA/GGG/CAG/CCC/CGA
/GAA/CCA/CAG/GTG/TAC/ACC/CTG/CCC/CCA/TCC/CGG/GAG/GAG/ATG/AC
C/AAG/AAC/CAG/GTC/AGC/CTG/ACC/TGC/CTG/GTC/AAA/GGC/TTC/TAT/C
CC/AGC/GAC/ATC/GCC/GTG/GAG/TGG/GAG/AGC/AAT/GGG/CAG/CCG/GAG/
AAC/AAC/TAC/AAG/ACC/ACG/CCT/CCC/GTG/CTG/GAC/TCC/GAC/GGC/TCC
/TTC/TTC/CTC/TAT/AGC/AAG/CTC/ACC/GTG/GAC/AAG/AGC/AGG/TGG/CA
G/CAG/GGG/AAC/GTC/TTC/TCA/TGC/TCC/GTG/ATG/CAT/GAG/GCT/CTG/C
AC/AAC/CAC/TAC/ACG/CAG/AAG/AGC/CTC/TCC/CTG/TCT/CCG/GGC/ATC/
CTA/TTC/CAT/GCC/ACC/CAG/GCC/GAC/ATC/CAG/ATG/ACC/CAG/TCT/CCA
/TCC/TCC/CTG/TCT/GCA/TCT/GTA/GGA/GAC/AGA/GTC/ACC/ATC/ACT/TG
C/CGG/GCG/AGT/CAG/GGC/ATT/AGC/AAT/TAT/TTA/GCC/TGG/TAT/CAG/C
AG/AAA/ACA/GGG/AAA/GTT/CCT/AAG/TTC/CTG/ATC/TAT/GAA/GCA/TCC/
ACT/TTG/CAA/TCA/GGG/GTC/CCA/TCT/CGG/TTC/AGT/GGC/GGT/GGA/TCT
/GGG/ACA/GAT/TTC/ACT/CTC/ACC/ATC/AGC/AGC/CTG/CAG/CCT/GAA/GA
T/GTT/GCA/ACT/TAT/TAC/TGT/CAA/AAT/TAT/AAC/AGT/GCC/CCA/TTC/A
CT/TTC/GGC/CCT/GGG/ACC/AAA/GTG/GAT/ATC/AAA/CGA/ACT/GTG/GCT/
GCA/CCC/TCT/GTC/TTC/ATC/TTC/CCG/CCA/TCT/GAT/GAG/CAG/TTG/AAA
/TCT/GGA/ACT/GCT/AGC/GTT/GTG/TGC/CTG/CTG/AAT/AAC/TTC/TAT/CC
C/AGA/GAG/GCC/AAA/GTA/CAG/TGG/AAG/GTG/GAT/AAC/GCC/CTC/CAA/T

SEQ ID NO: 16 (CONT)

CG/GGT/AAC/TCC/CAG/GAG/AGT/GTC/ACA/GAG/CAG/GAC/AGC/AAG/GAC/
AGC/ACC/TAC/AGC/CTC/AGC/AGC/ACC/CTG/ACG/CTG/AGC/AAA/GCA/GAC
/TAC/GAG/AAA/CAC/AAA/GTC/TAC/GCC/TGC/GAA/GTC/ACC/CAT/CAG/GG
C/CTG/AGC/TCG/CCC/GTC/ACA/AAG/AGC/TTC/AAC/AGG/GGA/GAG/TGT/T
AG

Antibody Fusion Gene #4 (SEQ ID NO:17):

ATG/GAA/TGG/AGC/GGA/GTC/TTT/ATC/TTT/CTC/CTG/TCA/GTA/ACT/GCA
/GGT/GTC/CAC/TCC/GAG/GTG/CAG/CTG/GTG/GAG/TCT/GGT/GGA/GGC/TT
G/GTA/AAG/CCT/GGA/GGT/TCC/CTT/AGA/CTC/TCC/TGT/GCA/GCC/TCT/G
GT/TAC/ACT/TTC/AGT/AAC/TAT/TGG/ATC/GGA/TGG/GTC/CGC/CAG/GCT/
CCA/GGC/AAA/GGG/CTG/GAG/TGG/ATT/GGC/GAT/ATC/TAC/CCT/GGA/GGG
/AAC/TAC/ATC/AGG/AAC/AAT/GAG/AAG/TTC/AAG/GAC/AAG/ACC/ACC/CT
G/TCA/GCA/GAT/ACT/TCC/AAG/AAC/ACA/GCC/TAT/CTG/CAA/ATG/AAC/A
GC/CTG/AAA/ACC/GAG/GAC/ACA/GCC/GTG/TAT/TAC/TGT/GGA/AGC/AGC/
TTC/GGT/AGT/AAC/TAC/GTG/TTC/GCC/TGG/TTT/ACT/TAC/TGG/GGC/CAA
/GGG/ACT/CTG/GTC/ACA/GTC/TCC/TCA/GCT/TCC/ACC/AAG/GGC/CCA/TC
C/GTC/TTC/CCC/CTG/GCG/CCC/TGC/TCC/AGG/AGC/ACC/TCC/GAG/AGC/A
CA/GCC/GCC/CTG/GGC/TGC/CTG/GTC/AAG/GAC/TAC/TTC/CCC/GAA/CCG/
GTG/ACG/GTG/TCG/TGG/AAC/TCA/GGC/GCC/CTG/ACC/AGC/GGC/GTG/CAC
/ACC/TTC/CCG/GCT/GTC/CTA/CAG/TCC/TCA/GGA/CTC/TAC/TCC/CTC/AG
C/AGC/GTG/GTG/ACC/GTG/CCC/TCC/AGC/AGC/TTG/GGC/ACG/AAG/ACC/T
AC/ACC/TGC/AAC/GTA/GAT/CAC/AAG/CCC/AGC/AAC/ACC/AAG/GTG/GAC/
AAG/AGA/GTT/GAG/TCC/AAA/TAT/GGT/CCC/CCA/TGC/CCA/TCA/TGC/CCA
/GCA/CCT/GAG/TTC/CTG/GGG/GGA/CCA/TCA/GTC/TTC/CTG/TTC/CCC/CC
A/AAA/CCC/AAG/GAC/ACT/CTC/ATG/ATC/TCC/CGG/ACC/CCT/GAG/GTC/A
CG/TGC/GTG/GTG/GTG/GAC/GTG/AGC/CAG/GAA/GAC/CCC/GAG/GTC/CAG/
TTC/AAC/TGG/TAC/GTG/GAT/GGC/GTG/GAG/GTG/CAT/AAT/GCC/AAG/ACA
/AAG/CCG/CGG/GAG/GAG/CAG/TTC/AAC/AGC/ACG/TAC/CGT/GTG/GTC/AG
C/GTC/CTC/ACC/GTC/CTG/CAC/CAG/GAC/TGG/CTG/AAC/GGC/AAG/GAG/T
AC/AAG/TGC/AAG/GTC/TCC/AAC/AAA/GGC/CTC/CCG/TCC/TCC/ATC/GAG/
AAA/ACC/ATC/TCC/AAA/GCC/AAA/GGG/CAG/CCC/CGA/GAG/CCA/CAG/GTG
/TAC/ACC/CTG/CCC/CCA/TCC/CAG/GAG/GAG/ATG/ACC/AAG/AAC/CAG/GT
C/AGC/CTG/ACC/TGC/CTG/GTC/AAA/GGC/TTC/TAC/CCC/AGC/GAC/ATC/G
CC/GTG/GAG/TGG/GAG/AGC/AAT/GGG/CAG/CCG/GAG/AAC/AAC/TAC/AAG/
ACC/ACG/CCT/CCC/GTG/CTG/GAC/TCC/GAC/GGC/TCC/TTC/TTC/CTC/TAC
/AGC/AGG/CTA/ACC/GTG/GAC/AAG/AGC/AGG/TGG/CAG/GAG/GGG/AAT/GT
C/TTC/TCA/TGC/TCC/GTG/ATG/CAT/GAG/GCT/CTG/CAC/AAC/CAC/TAC/A
CA/CAG/AAG/AGC/CTC/TCC/CTG/TCT/CTG/GGC/ATC/CTA/TTC/CAT/GCC/
ACC/CAG/GCC/GAC/ATT/GTG/ATG/ACC/CAA/TCT/CCA/CTC/TCC/CTG/CCT
/GTC/ACT/CCT/GGA/GAG/CCA/GCC/TCC/ATC/TCT/TGC/AGA/TCT/AGT/CA
G/CGC/CTT/CTG/AGC/AGT/TAT/GGA/CAT/ACC/TAT/TTA/CAT/TGG/TAC/C
TA/CAG/AAG/CCA/GGC/CAG/TCT/CCA/CAG/CTC/CTG/ATC/TAC/GAA/GTT/
TCC/AAC/CGA/TTT/TCT/GGG/GTC/CCA/GAC/AGG/TTC/AGT/GGC/AGT/GGG
/TCA/GGG/ACA/GAT/TTC/ACA/CTT/AAG/ATC/AGT/AGA/GTG/GAG/GCT/GA

SEQ ID NO: 17 (CONT)

G/GAT/GTG/GGA/GTT/TAT/TAC/TGC/TCT/CAA/AGT/ACA/CAT/GTT/CCT/C
TC/ACG/TTC/GGA/CAG/GGG/ACC/AAG/GTG/GAA/ATA/AAA/CGA/ACT/GTG/
GCT/GCA/CCA/TCT/GTC/TTC/ATC/TTC/CCG/CCA/TCT/GAT/GAG/CAG/TTG
/AAA/TCT/GGA/ACT/GCC/TCT/GTT/GTG/TGC/CTG/CTG/AAT/AAC/TTC/TA
T/CCC/AGA/GAG/GCC/AAA/GTA/CAG/TGG/AAG/GTG/GAT/AAC/GCC/CTC/C
AA/TCG/GGT/AAC/TCC/CAG/GAG/AGT/GTC/ACA/GAG/CAG/GAC/AGC/AAG/
GAC/AGC/ACC/TAC/AGC/CTC/AGC/AGC/ACC/CTG/ACG/CTG/AGC/AAA/GCA
/GAC/TAC/GAG/AAA/CAC/AAA/GTC/TAC/GCC/TGC/GAA/GTC/ACC/CAT/CA
G/GGC/CTG/AGC/TCG/CCC/GTC/ACA/AAG/AGC/TTC/AAC/AGG/GGA/GAG/T
GT/*TAG*

SEQUENCE LISTING

```
<160> NUMBER OF SEQ ID NOS: 20

<210> SEQ ID NO 1
<211> LENGTH: 2067
<212> TYPE: DNA
<213> ORGANISM: Artificial Sequence
<220> FEATURE:
<223> OTHER INFORMATION: Synthetic

<400> SEQUENCE: 1

atgggatgga gctgtatcat cctcttcttg gtagcaacag ctacaggtgt ccactccgag     60

gtccaactgg tggagagcgg tggaggtgtt gtgcaacctg gccggtccct gcgcctgtcc    120

tgctccgcat ctggcttcga tttcaccaca tattggatga gttgggtgag acaggcacct    180

ggaaaaggtc ttgagtggat tggagaaatt catccagata gcagtacgat taactatgcg    240

ccgtctctaa aggatagatt tacaatatcg cgagacaacg ccaagaacac attgttcctg    300

caaatggaca gcctgagacc cgaagacacc ggggtctatt tttgtgcaag cctttacttc    360

ggcttcccct ggtttgctta ttggggccaa gggaccccgg tcaccgtctc ctcagcctcc    420

accaagggcc catcggtctt ccccctggca ccctcctcca agagcacctc tgggggcaca    480

gcggccctgg gctgcctggt caaggactac ttccccgaac cggtgacggt gtcgtggaac    540

tcaggcgccc tgaccagcgg cgtgcacacc ttcccggctg tcctacagtc ctcaggactc    600

tactccctca gcagcgtggt gaccgtgccc tccagcagct tgggcaccca gacctacatc    660

tgcaacgtga atcacaagcc cagcaacacc aaggtggaca agagagttga gcccaaatct    720

tgtgacaaaa ctcacacatg cccaccgtgc ccagcacctg aactcctggg gggaccgtca    780

gtcttcctct tccccccaaa acccaaggac accctcatga tctcccggac ccctgaggtc    840

acatgcgtgg tggtggacgt gagccacgaa gaccctgagg tcaagttcaa ctggtacgtg    900

gacggcgtgg aggtgcataa tgccaagaca aagccgcggg aggagcagta caacagcacg    960

taccgtgtgg tcagcgtcct caccgtcctg caccaggact ggctgaatgg caaggagtac   1020

aagtgcaagg tctccaacaa agccctccca gcccccatcg agaaaaccat ctccaaagcc   1080

aaagggcagc cccgagaacc acaggtgtac accctgcccc catcccggga ggagatgacc   1140

aagaaccagg tcagcctgac ctgcctggtc aaaggcttct atcccagcga catcgccgtg   1200

gagtgggaga gcaatgggca gccggagaac aactacaaga ccacgcctcc cgtgctggac   1260

tccgacggct ccttcttcct ctatagcaag ctcaccgtgg acaagagcag gtggcagcag   1320
```

-continued gggaacgtct tctcatgctc cgtgatgcat gaggctctgc acaaccacta cacgcagaag 1380
agcctctccc tgtctccggg catcctattc catgccaccc aggccgacat ccagctgacc 1440
cagagcccaa gcagcctgag cgccagcgtg ggtgacagag tgaccatcac ctgtaaggcc 1500
agtcaggatg tgggtacttc tgtagcctgg taccagcaga agccaggtaa ggctccaaag 1560
ctgctgatct actggacatc cacccggcac actggtgtgc caagcagatt cagcggtagc 1620
ggtagcggta ccgacttcac cttcaccatc agcagcctcc agccagagga catcgccacc 1680
tactactgcc agcaatatag cctctatcgg tcgttcggcc aagggaccaa ggtggaaatc 1740
aaacgaactg tggctgcacc atctgtcttc atcttcccgc catctgatga gcagttgaaa 1800
tctggaactg cctctgttgt gtgcctgctg aataacttct atcccagaga ggccaaagta 1860
cagtggaagg tggataacgc cctccaatcg ggtaactccc aggagagtgt cacagagcag 1920
gacagcaagg acagcaccta cagcctcagc agcaccctga cgctgagcaa agcagactac 1980
gagaaacaca aagtctacgc ctgcgaagtc acccatcagg gcctgagctc gcccgtcaca 2040
aagagcttca acaggggaga gtgttag 2067

<210> SEQ ID NO 2
<211> LENGTH: 2076
<212> TYPE: DNA
<213> ORGANISM: Artificial Sequence
<220> FEATURE:
<223> OTHER INFORMATION: Synthetic

<400> SEQUENCE: 2
atgggatgga gctgtatcat cctcttcttg gtagcaacag ctacaggtgt ccactcccag 60
gtccagctgg tccaatcagg ggctgaagtc aagaaacctg ggtcatcagt gaaggtctcc 120
tgcaaggctt ctggctacac ctttactagc tactggctgc actgggtcag gcaggcacct 180
ggacagggtc tggaatggat tggatacatt aatcctagga atgattatac tgagtacaat 240
cagaacttca aggacaaggc cacaataact gcagacgaat ccaccaatac agcctacatg 300
gagctgagca gcctgaggtc tgaggacacg gcattttatt tttgtgcaag aagggatatt 360
actacgttct actggggcca aggcaccacg gtcaccgtct cctcagcctc caccaagggc 420
ccatcggtct tccccctggc accctcctcc aagagcacct ctgggggcac agcggccctg 480
ggctgcctgg tcaaggacta cttccccgaa ccggtgacgg tgtcgtggaa ctcaggcgcc 540
ctgaccagcg gcgtgcacac cttcccggct gtcctacagt cctcaggact ctactccctc 600
agcagcgtgg tgaccgtgcc ctccagcagc ttgggcaccc agacctacat ctgcaacgtg 660
aatcacaagc ccagcaacac caaggtggac aagagagttg agcccaaatc ttgtgacaaa 720
actcacacat gcccaccgtg cccagcacct gaactcctgg ggggaccgtc agtcttcctc 780
ttccccccaa aacccaagga caccctcatg atctcccgga cccctgaggt cacatgcgtg 840
gtggtggacg tgagccacga agaccctgag gtcaagttca actggtacgt ggacggcgtg 900
gaggtgcata atgccaagac aaagccgcgg gaggagcagt acaacagcac gtaccgtgtg 960
gtcagcgtcc tcaccgtcct gcaccaggac tggctgaatg gcaaggagta caagtgcaag 1020
gtctccaaca aagccctccc agcccccatc gagaaaacca tctccaaagc caaagggcag 1080
ccccgagaac cacaggtgta caccctgccc ccatcccggg aggagatgac caagaaccag 1140
gtcagcctga cctgcctggt caaaggcttc tatcccagcg acatcgccgt ggagtgggag 1200
agcaatgggc agccggagaa caactacaag accacgcctc ccgtgctgga ctccgacggc 1260

-continued

```
tccttcttcc tctatagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gcatcctatt ccatgccacc caggccgaca tccagctgac ccagtctcca   1440

tcatctctga gcgcatctgt tggagatagg gtcactatga gctgtaagtc cagtcaaagt   1500

gttttataca gtgcaaatca caagaactac ttggcctggt accagcagaa accagggaaa   1560

gcacctaaac tgctgatcta ctgggcatcc actagggaat ctggtgtccc ttcgcgattc   1620

tctggcagcg gatctgggac agattttact ttcaccatca gctctcttca accagaagac   1680

attgcaacat attattgtca ccaatacctc tcctcgtgga cgttcggtgg agggaccaag   1740

gtgcagatca aacgaactgt ggctgcacca tctgtcttca tcttcccgcc atctgatgag   1800

cagttgaaat ctggaactgc ctctgttgtg tgcctgctga ataacttcta tcccagagag   1860

gccaaagtac agtggaaggt ggataacgcc ctccaatcgg gtaactccca ggagagtgtc   1920

acagagcagg acagcaagga cagcacctac agcctcagca gcaccctgac gctgagcaaa   1980

gcagactacg agaaacacaa agtctacgcc tgcgaagtca cccatcaggg cctgagctcg   2040

cccgtcacaa agagcttcaa caggggagag tgttag                             2076
```

```
<210> SEQ ID NO 3
<211> LENGTH: 669
<212> TYPE: PRT
<213> ORGANISM: Artificial Sequence
<220> FEATURE:
<223> OTHER INFORMATION: Synthetic

<400> SEQUENCE: 3

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Asp Phe Thr Thr Tyr
            20                  25                  30

Trp Met Ser Trp Val Arg Gln Ala Pro Gly Lys Gly Leu Glu Trp Ile
        35                  40                  45

Gly Glu Ile His Pro Asp Ser Ser Thr Ile Asn Tyr Ala Pro Ser Leu
    50                  55                  60

Lys Asp Arg Phe Thr Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Ser Leu Tyr Phe Gly Phe Pro Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220
```

-continued

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Ile Leu Phe His Ala Thr Gln Ala Asp Ile Gln Leu Thr Gln Ser Pro
    450                 455                 460

Ser Ser Leu Ser Ala Ser Val Gly Asp Arg Val Thr Ile Thr Cys Lys
465                 470                 475                 480

Ala Ser Gln Asp Val Gly Thr Ser Val Ala Trp Tyr Gln Gln Lys Pro
                485                 490                 495

Gly Lys Ala Pro Lys Leu Leu Ile Tyr Trp Thr Ser Thr Arg His Thr
            500                 505                 510

Gly Val Pro Ser Arg Phe Ser Gly Ser Gly Ser Gly Thr Asp Phe Thr
        515                 520                 525

Phe Thr Ile Ser Ser Leu Gln Pro Glu Asp Ile Ala Thr Tyr Tyr Cys
    530                 535                 540

Gln Gln Tyr Ser Leu Tyr Arg Ser Phe Gly Gln Gly Thr Lys Val Glu
545                 550                 555                 560

Ile Lys Arg Thr Val Ala Ala Pro Ser Val Phe Ile Phe Pro Pro Ser
                565                 570                 575

Asp Glu Gln Leu Lys Ser Gly Thr Ala Ser Val Val Cys Leu Leu Asn
            580                 585                 590

Asn Phe Tyr Pro Arg Glu Ala Lys Val Gln Trp Lys Val Asp Asn Ala
        595                 600                 605

Leu Gln Ser Gly Asn Ser Gln Glu Ser Val Thr Glu Gln Asp Ser Lys
    610                 615                 620

Asp Ser Thr Tyr Ser Leu Ser Ser Thr Leu Thr Leu Ser Lys Ala Asp
625                 630                 635                 640
```

-continued

```
Tyr Glu Lys His Lys Val Tyr Ala Cys Glu Val Thr His Gln Gly Leu
                645                 650                 655

Ser Ser Pro Val Thr Lys Ser Phe Asn Arg Gly Glu Cys
            660                 665
```

<210> SEQ ID NO 4
<211> LENGTH: 6858
<212> TYPE: DNA
<213> ORGANISM: Artificial Sequence
<220> FEATURE:
<223> OTHER INFORMATION: Synthetic

<400> SEQUENCE: 4

```
tttgaaagac cccacccgta ggtggcaagc tagcttaagt aacgccactt tgcaaggcat     60

ggaaaaatac ataactgaga atagaaaagt tcagatcaag gtcaggaaca aagaaacagc    120

tgaataccaa acaggatatc tgtggtaagc ggttcctgcc ccggctcagg gccaagaaca    180

gatgagacag ctgagtgatg ggccaaacag gatatctgtg gtaagcagtt cctgccccgg    240

ctcggggcca agaacagatg gtccccagat gcggtccagc cctcagcagt ttctagtgaa    300

tcatcagatg tttccagggt gccccaagga cctgaaaatg accctgtacc ttatttgaac    360

taaccaatca gttcgcttct cgcttctgtt cgcgcgcttc cgctctccga gctcaataaa    420

agagcccaca acccctcact cggcgcgcca gtcttccgat agactgcgtc gcccgggtac    480

ccgtattccc aataaagcct cttgctgttt gcatccgaat cgtggtctcg ctgttccttg    540

ggagggtctc ctctgagtga ttgactaccc acgacggggg tctttcattt gggggctcgt    600

ccgggatttg gagacccctg cccagggacc accgacccac caccgggagg taagctggcc    660

agcaacttat ctgtgtctgt ccgattgtct agtgtctatg tttgatgtta tgcgcctgcg    720

tctgtactag ttagctaact agctctgtat ctggcggacc cgtggtggaa ctgacgagtt    780

ctgaacaccc ggccgcaacc ctgggagacg tcccagggac tttgggggcc gtttttgtgg    840

cccgacctga ggaagggagt cgatgtggaa tccgaccccg tcaggatatg tggttctggt    900

aggagacgag aacctaaaac agttcccgcc tccgtctgaa tttttgcttt cggtttggaa    960

ccgaagccgc gcgtcttgtc tgctgcagcg ctgcagcatc gttctgtgtt gtctctgtct   1020

gactgtgttt ctgtatttgt ctgaaaatta gggccagact gttaccactc ccttaagttt   1080

gaccttaggt cactggaaag atgtcgagcg gatcgctcac aaccagtcgg tagatgtcaa   1140

gaagagacgt tgggttacct tctgctctgc agaatggcca acctttaacg tcggatggcc   1200

gcgagacggc acctttaacc gagacctcat cacccaggtt aagatcaagg tcttttcacc   1260

tggcccgcat ggacacccag accaggtccc ctacatcgtg acctgggaag ccttggcttt   1320

tgacccccct ccctgggtca agccctttgt acaccctaag cctccgcctc ctcttcctcc   1380

atccgccccg tctctccccc ttgaacctcc tcgttcgacc ccgcctcgat cctcccttta   1440

tccagccctc actccttctc taggcgccgg aattccgatc tgatcaagag acaggatgag   1500

gatcgtttcg catgattgaa caagatggat tgcacgcagg ttctccggcc gcttgggtgg   1560

agaggctatt cggctatgac tgggcacaac agacaatcgg ctgctctgat gccgccgtgt   1620

tccggctgtc agcgcagggg cgcccggttc tttttgtcaa gaccgacctg tccggtgccc   1680

tgaatgaact gcaggacgag gcagcgcggc tatcgtggct ggccacgacg ggcgttcctt   1740

gcgcagctgt gctcgacgtt gtcactgaag cgggaaggga ctggctgcta ttgggcgaag   1800

tgccggggca ggatctcctg tcatctcacc ttgctcctgc cgagaaagta tccatcatgg   1860

ctgatgcaat gcggcggctg catacgcttg atccggctac ctgcccattc gaccaccaag   1920
```

-continued

```
cgaaacatcg catcgagcga gcacgtactc ggatggaagc cggtcttgtc gatcaggatg   1980
atctggacga agagcatcag gggctcgcgc cagccgaact gttcgccagg ctcaaggcgc   2040
gcatgcccga cggcgaggat ctcgtcgtga cccatggcga tgcctgcttg ccgaatatca   2100
tggtggaaaa tggccgcttt tctggattca tcgactgtgg ccggctgggt gtggcggacc   2160
gctatcagga catagcgttg gctacccgtg atattgctga agagcttggc ggcgaatggg   2220
ctgaccgctt cctcgtgctt tacggtatcg ccgctcccga ttcgcagcgc atcgccttct   2280
atcgccttct tgacgagttc ttctgagcgg gactctgggg ttcgaaatga ccgaccaagc   2340
gacgcccaac ctgccatcac gagatttcga ttccaccgcc gccttctatg aaaggttggg   2400
cttcggaatc gttttccggg acgccggctg gatgatcctc cagcgcgggg atctcatgct   2460
ggagttcttc gcccaccccg ggctcgatcc cctcgcgagt tggttcagct gctgcctgag   2520
gctggacgac ctcgcggagt tctaccggca gtgcaaatcc gtcggcatcc aggaaaccag   2580
cagcggctat ccgcgcatcc atgcccccga actgcaggag tggggaggca cgatggccgc   2640
tttggtcgag gcggatccgg ccattagcca tattattcat tggttatata gcataaatca   2700
atattggcta ttggccattg catacgttgt atccatatca taatatgtac atttatattg   2760
gctcatgtcc aacattaccg ccatgttgac attgattatt gactagttat taatagtaat   2820
caattacggg gtcattagtt catagcccat atatggagtt ccgcgttaca taacttacgg   2880
taaatggccc gcctggctga ccgcccaacg acccccgccc attgacgtca ataatgacgt   2940
atgttcccat agtaacgcca atagggactt tccattgacg tcaatgggtg gagtatttac   3000
ggtaaactgc ccacttggca gtacatcaag tgtatcatat gccaagtacg ccccctattg   3060
acgtcaatga cggtaaatgg cccgcctggc attatgccca gtacatgacc ttatgggact   3120
ttcctacttg gcagtacatc tacgtattag tcatcgctat taccatggtg atgcggtttt   3180
ggcagtacat caatgggcgt ggatagcggt ttgactcacg gggatttcca agtctccacc   3240
ccattgacgt caatgggagt ttgttttggc accaaaatca acgggacttt ccaaaatgtc   3300
gtaacaactc cgccccattg acgcaaatgg gcggtaggca tgtacggtgg gaggtctata   3360
taagcagagc tcgtttagtg aaccgtcaga tcgcctggag acgccatcca cgctgttttg   3420
acctccatag aagacaccgg gaccgatcca gcctccgcgg ccccaagctt ctcgacggat   3480
ccccgggaat tcaggacctc accatgggat ggagctgtat catcctcttc ttggtagcaa   3540
cagctacagg tgtccactcc gaggtccaac tggtggagag cggtggaggt gttgtgcaac   3600
ctggccggtc cctgcgcctg tcctgctccg catctggctt cgatttcacc acatattgga   3660
tgagttgggt gagacaggca cctggaaaag gtcttgagtg gattggagaa attcatccag   3720
atagcagtac gattaactat gcgccgtctc taaaggatag atttacaata tcgcgagaca   3780
acgccaagaa cacattgttc ctgcaaatgg acagcctgag acccgaagac accggggtct   3840
atttttgtgc aagcctttac ttcggcttcc cctggtttgc ttattggggc caagggaccc   3900
cggtcaccgt ctcctcagcc tccaccaagg gcccatcggt cttccccctg gcaccctcct   3960
ccaagagcac ctctgggggc acagcggccc tgggctgcct ggtcaaggac tacttccccg   4020
aaccggtgac ggtgtcgtgg aactcaggcg ccctgaccag cggcgtgcac accttcccgg   4080
ctgtcctaca gtcctcagga ctctactccc tcagcagcgt ggtgaccgtg ccctccagca   4140
gcttgggcac ccagacctac atctgcaacg tgaatcacaa gcccagcaac accaaggtgg   4200
acaagagagt tgagcccaaa tcttgtgaca aaactcacac atgcccaccg tgcccagcac   4260
```

-continued

```
ctgaactcct ggggggaccg tcagtcttcc tcttcccccc aaaacccaag gacaccctca   4320
tgatctcccg gacccctgag gtcacatgcg tggtggtgga cgtgagccac gaagaccctg   4380
aggtcaagtt caactggtac gtggacggcg tggaggtgca taatgccaag acaaagccgc   4440
gggaggagca gtacaacagc acgtaccgtg tggtcagcgt cctcaccgtc ctgcaccagg   4500
actggctgaa tggcaaggag tacaagtgca aggtctccaa caaagccctc ccagccccca   4560
tcgagaaaac catctccaaa gccaaagggc agccccgaga accacaggtg tacaccctgc   4620
ccccatcccg ggaggagatg accaagaacc aggtcagcct gacctgcctg gtcaaaggct   4680
tctatcccag cgacatcgcc gtggagtggg agagcaatgg gcagccggag aacaactaca   4740
agaccacgcc tcccgtgctg gactccgacg gctccttctt cctctatagc aagctcaccg   4800
tggacaagag caggtggcag caggggaacg tcttctcatg ctccgtgatg catgaggctc   4860
tgcacaacca ctacacgcag aagagcctct ccctgtctcc gggtaaatga aagccgaatt   4920
cgcccctctc cctccccccc ccctaacgtt actggccgaa gccgcttgga ataaggccgg   4980
tgtgcgtttg tctatatgtt attttccacc atattgccgt cttttggcaa tgtgagggcc   5040
cggaaacctg gccctgtctt cttgacgagc attcctaggg gtctttcccc tctcgccaaa   5100
ggaatgcaag gtctgttgaa tgtcgtgaag gaagcagttc ctctggaagc ttcttgaaga   5160
caaacaacgt ctgtagcgac cctttgcagg cagcggaacc ccccacctgg cgacaggtgc   5220
ctctgcggcc aaaagccacg tgtataagat acacctgcaa aggcggcaca accccagtgc   5280
cacgttgtga gttggatagt tgtggaaaga gtcaaatggc tctcctcaag cgtattcaac   5340
aaggggctga aggatgccca gaaggtaccc cattgtatgg gatctgatct ggggcctcgg   5400
tgcacatgct ttacatgtgt ttagtcgagg ttaaaaaaac gtctaggccc cccgaaccac   5460
ggggacgtgg ttttcctttg aaaaacacga tgataatatg gcctcctttg tctctctgct   5520
cctggtaggc atcctattcc atgccaccca ggccgacatc cagctgaccc agagcccaag   5580
cagcctgagc gccagcgtgg gtgacagagt gaccatcacc tgtaaggcca gtcaggatgt   5640
gggtacttct gtagcctggt accagcagaa gccaggtaag gctccaaagc tgctgatcta   5700
ctggacatcc acccggcaca ctggtgtgcc aagcagattc agcggtagcg gtagcggtac   5760
cgacttcacc ttcaccatca gcagcctcca gccagaggac atcgccacct actactgcca   5820
gcaatatagc ctctatcggt cgttcggcca agggaccaag gtggaaatca aacgaactgt   5880
ggctgcacca tctgtcttca tcttcccgcc atctgatgag cagttgaaat ctggaactgc   5940
ctctgttgtg tgcctgctga ataacttcta tcccagagag gccaaagtac agtggaaggt   6000
ggataacgcc ctccaatcgg gtaactccca ggagagtgtc acagagcagg acagcaagga   6060
cagcacctac agcctcagca gcaccctgac gctgagcaaa gcagactacg agaaacacaa   6120
agtctacgcc tgcgaagtca cccatcaggg cctgagctcg cccgtcacaa agagcttcaa   6180
caggggagag tgttagagat ctaggcctcc taggtcgaca tcgataaaat aaaagatttt   6240
atttagtctc cagaaaaagg ggggaatgaa agaccccacc tgtaggtttg gcaagctagc   6300
ttaagtaacg ccattttgca aggcatggaa aaatacataa ctgagaatag agaagttcag   6360
atcaaggtca ggaacagatg gaacagctga atatgggcca aacaggatat ctgtggtaag   6420
cagttcctgc cccggctcag ggccaagaac agatggaaca gctgaatatg ggccaaacag   6480
gatatctgtg gtaagcagtt cctgccccgg ctcagggcca agaacagatg gtccccagat   6540
gcggtccagc cctcagcagt ttctagagaa ccatcagatg tttccagggt gccccaagga   6600
cctgaaatga ccctgtgcct tatttgaact aaccaatcag ttcgcttctc gcttctgttc   6660
```

-continued

```
gcgcgcttct gctccccgag ctcaataaaa gagcccacaa cccctcactc ggggcgccag   6720

tcctccgatt gactgagtcg cccgggtacc cgtgtatcca ataaaccctc ttgcagttgc   6780

atccgacttg tggtctcgct gttccttggg agggtctcct ctgagtgatt gactacccgt   6840

cagcgggggt ctttcatt                                                 6858


<210> SEQ ID NO 5
<211> LENGTH: 6867
<212> TYPE: DNA
<213> ORGANISM: Artificial Sequence
<220> FEATURE:
<223> OTHER INFORMATION: Synthetic

<400> SEQUENCE: 5

tttgaaagac cccacccgta ggtggcaagc tagcttaagt aacgccactt tgcaaggcat     60

ggaaaaatac ataactgaga atagaaaagt tcagatcaag gtcaggaaca aagaaacagc    120

tgaataccaa acaggatatc tgtggtaagc ggttcctgcc ccggctcagg gccaagaaca    180

gatgagacag ctgagtgatg ggccaaacag gatatctgtg gtaagcagtt cctgccccgg    240

ctcggggcca agaacagatg gtccccagat gcggtccagc cctcagcagt ttctagtgaa    300

tcatcagatg tttccagggt gccccaagga cctgaaaatg accctgtacc ttatttgaac    360

taaccaatca gttcgcttct cgcttctgtt cgcgcgcttc cgctctccga gctcaataaa    420

agagcccaca acccctcact cggcgcgcca gtcttccgat agactgcgtc gcccgggtac    480

ccgtattccc aataaagcct cttgctgttt gcatccgaat cgtggtctcg ctgttccttg    540

ggagggtctc ctctgagtga ttgactaccc acgacggggg tctttcattt gggggctcgt    600

ccgggatttg gagacccctg cccagggacc accgacccac caccgggagg taagctggcc    660

agcaacttat ctgtgtctgt ccgattgtct agtgtctatg tttgatgtta tgcgcctgcg    720

tctgtactag ttagctaact agctctgtat ctggcggacc cgtggtggaa ctgacgagtt    780

ctgaacaccc ggccgcaacc ctgggagacg tcccagggac tttgggggcc gtttttgtgg    840

cccgacctga ggaagggagt cgatgtggaa tccgaccccg tcaggatatg tggttctggt    900

aggagacgag aacctaaaac agttcccgcc tccgtctgaa tttttgcttt cggtttggaa    960

ccgaagccgc gcgtcttgtc tgctgcagcg ctgcagcatc gttctgtgtt gtctctgtct   1020

gactgtgttt ctgtatttgt ctgaaaatta gggccagact gttaccactc ccttaagttt   1080

gaccttaggt cactggaaag atgtcgagcg gatcgctcac aaccagtcgg tagatgtcaa   1140

gaagagacgt tgggttacct tctgctctgc agaatggcca acctttaacg tcggatggcc   1200

gcgagacggc acctttaacc gagacctcat cacccaggtt aagatcaagg tcttttcacc   1260

tggcccgcat ggacacccag accaggtccc ctacatcgtg acctgggaag ccttggcttt   1320

tgaccccccct ccctgggtca agccctttgt acaccctaag cctccgcctc ctcttcctcc   1380

atccgccccg tctctccccc ttgaacctcc tcgttcgacc ccgcctcgat cctcccttta   1440

tccagccctc actccttctc taggcgccgg aattccgatc tgatcaagag acaggatgag   1500

gatcgtttcg catgattgaa caagatggat tgcacgcagg ttctccggcc gcttgggtgg   1560

agaggctatt cggctatgac tgggcacaac agacaatcgg ctgctctgat gccgccgtgt   1620

tccggctgtc agcgcagggg cgcccggttc tttttgtcaa gaccgacctg tccggtgccc   1680

tgaatgaact gcaggacgag gcagcgcggc tatcgtggct ggccacgacg ggcgttcctt   1740

gcgcagctgt gctcgacgtt gtcactgaag cgggaaggga ctggctgcta ttgggcgaag   1800
```

-continued

```
tgccggggca ggatctcctg tcatctcacc ttgctcctgc cgagaaagta tccatcatgg   1860
ctgatgcaat gcggcggctg catacgcttg atccggctac ctgcccattc gaccaccaag   1920
cgaaacatcg catcgagcga gcacgtactc ggatggaagc cggtcttgtc gatcaggatg   1980
atctggacga agagcatcag gggctcgcgc cagccgaact gttcgccagg ctcaaggcgc   2040
gcatgcccga cggcgaggat ctcgtcgtga cccatggcga tgcctgcttg ccgaatatca   2100
tggtggaaaa tggccgcttt tctggattca tcgactgtgg ccggctgggt gtggcggacc   2160
gctatcagga catagcgttg gctacccgtg atattgctga agagcttggc ggcgaatggg   2220
ctgaccgctt cctcgtgctt tacggtatcg ccgctcccga ttcgcagcgc atcgccttct   2280
atcgccttct tgacgagttc ttctgagcgg gactctgggg ttcgaaatga ccgaccaagc   2340
gacgcccaac ctgccatcac gagatttcga ttccaccgcc gccttctatg aaaggttggg   2400
cttcggaatc gttttccggg acgccggctg gatgatcctc cagcgcgggg atctcatgct   2460
ggagttcttc gcccaccccg ggctcgatcc cctcgcgagt tggttcagct gctgcctgag   2520
gctggacgac ctcgcggagt tctaccggca gtgcaaatcc gtcggcatcc aggaaaccag   2580
cagcggctat ccgcgcatcc atgcccccga actgcaggag tggggaggca cgatggccgc   2640
tttggtcgag gcggatccgg ccattagcca tattattcat tggttatata gcataaatca   2700
atattggcta ttggccattg catacgttgt atccatatca taatatgtac atttatattg   2760
gctcatgtcc aacattaccg ccatgttgac attgattatt gactagttat taatagtaat   2820
caattacggg gtcattagtt catagcccat atatggagtt ccgcgttaca taacttacgg   2880
taaatggccc gcctggctga ccgcccaacg acccccgccc attgacgtca ataatgacgt   2940
atgttcccat agtaacgcca atagggactt tccattgacg tcaatgggtg gagtatttac   3000
ggtaaactgc ccacttggca gtacatcaag tgtatcatat gccaagtacg ccccctattg   3060
acgtcaatga cggtaaatgg cccgcctggc attatgccca gtacatgacc ttatgggact   3120
ttcctacttg gcagtacatc tacgtattag tcatcgctat taccatggtg atgcggtttt   3180
ggcagtacat caatgggcgt ggatagcggt ttgactcacg gggatttcca agtctccacc   3240
ccattgacgt caatgggagt ttgttttggc accaaaatca acgggacttt ccaaaatgtc   3300
gtaacaactc cgccccattg acgcaaatgg gcggtaggca tgtacggtgg gaggtctata   3360
taagcagagc tcgtttagtg aaccgtcaga tcgcctggag acgccatcca cgctgttttg   3420
acctccatag aagacaccgg gaccgatcca gcctccgcgg ccccaagctt ctcgacggat   3480
ccccgggaat tcaggacctc accatgggat ggagctgtat catcctcttc ttggtagcaa   3540
cagctacagg tgtccactcc caggtccagc tggtccaatc aggggctgaa gtcaagaaac   3600
ctgggtcatc agtgaaggtc tcctgcaagg cttctggcta cacctttact agctactggc   3660
tgcactgggt caggcaggca cctggacagg gtctggaatg gattggatac attaatccta   3720
ggaatgatta tactgagtac aatcagaact tcaaggacaa ggccacaata actgcagacg   3780
aatccaccaa tacagcctac atggagctga gcagcctgag gtctgaggac acggcatttt   3840
atttttgtgc aagaagggat attactacgt tctactgggg ccaaggcacc acggtcaccg   3900
tctcctcagc ctccaccaag ggcccatcgg tcttccccct ggcaccctcc tccaagagca   3960
cctctggggg cacagcggcc ctgggctgcc tggtcaagga ctacttcccc gaaccggtga   4020
cggtgtcgtg gaactcaggc gccctgacca gcggcgtgca caccttcccg gctgtcctac   4080
agtcctcagg actctactcc ctcagcagcg tggtgaccgt gccctccagc agcttgggca   4140
cccagaccta catctgcaac gtgaatcaca agcccagcaa caccaaggtg gacaagagag   4200
```

-continued

```
ttgagcccaa atcttgtgac aaaactcaca catgcccacc gtgcccagca cctgaactcc   4260
tggggggacc gtcagtcttc ctcttccccc caaaacccaa ggacaccctc atgatctccc   4320
ggacccctga ggtcacatgc gtggtggtgg acgtgagcca cgaagaccct gaggtcaagt   4380
tcaactggta cgtggacggc gtggaggtgc ataatgccaa gacaaagccg cgggaggagc   4440
agtacaacag cacgtaccgt gtggtcagcg tcctcaccgt cctgcaccag gactggctga   4500
atggcaagga gtacaagtgc aaggtctcca acaaagccct cccagccccc atcgagaaaa   4560
ccatctccaa agccaaaggg cagccccgag aaccacaggt gtacaccctg cccccatccc   4620
gggaggagat gaccaagaac caggtcagcc tgacctgcct ggtcaaaggc ttctatccca   4680
gcgacatcgc cgtggagtgg gagagcaatg ggcagccgga gaacaactac aagaccacgc   4740
ctcccgtgct ggactccgac ggctccttct tcctctatag caagctcacc gtggacaaga   4800
gcaggtggca gcaggggaac gtcttctcat gctccgtgat gcatgaggct ctgcacaacc   4860
actacacgca gaagagcctc tccctgtctc cgggtaaatg aaagccgaat tcgcccctct   4920
ccctcccccc cccctaacgt tactggccga agccgcttgg aataaggccg gtgtgcgttt   4980
gtctatatgt tattttccac catattgccg tcttttggca atgtgagggc ccggaaacct   5040
ggccctgtct tcttgacgag cattcctagg ggtctttccc ctctcgccaa aggaatgcaa   5100
ggtctgttga atgtcgtgaa ggaagcagtt cctctggaag cttcttgaag acaaacaacg   5160
tctgtagcga ccctttgcag gcagcggaac cccccacctg gcgacaggtg cctctgcggc   5220
caaaagccac gtgtataaga tacacctgca aaggcggcac aaccccagtg ccacgttgtg   5280
agttggatag ttgtggaaag agtcaaatgg ctctcctcaa gcgtattcaa caaggggctg   5340
aaggatgccc agaaggtacc ccattgtatg ggatctgatc tggggcctcg gtgcacatgc   5400
tttacatgtg tttagtcgag gttaaaaaaa cgtctaggcc ccccgaacca cggggacgtg   5460
gttttccttt gaaaaacacg atgataatat ggcctccttt gtctctctgc tcctggtagg   5520
catcctattc catgccaccc aggccgacat ccagctgacc cagtctccat catctctgag   5580
cgcatctgtt ggagataggg tcactatgag ctgtaagtcc agtcaaagtg ttttatacag   5640
tgcaaatcac aagaactact tggcctggta ccagcagaaa ccagggaaag cacctaaact   5700
gctgatctac tgggcatcca ctagggaatc tggtgtccct tcgcgattct ctggcagcgg   5760
atctgggaca gattttactt tcaccatcag ctctcttcaa ccagaagaca ttgcaacata   5820
ttattgtcac caatacctct cctcgtggac gttcggtgga gggaccaagg tgcagatcaa   5880
acgaactgtg gctgcaccat ctgtcttcat cttcccgcca tctgatgagc agttgaaatc   5940
tggaactgcc tctgttgtgt gcctgctgaa taacttctat cccagagagg ccaaagtaca   6000
gtggaaggtg gataacgccc tccaatcggg taactcccag gagagtgtca cagagcagga   6060
cagcaaggac agcacctaca gcctcagcag caccctgacg ctgagcaaag cagactacga   6120
gaaacacaaa gtctacgcct gcgaagtcac ccatcagggc ctgagctcgc ccgtcacaaa   6180
gagcttcaac aggggagagt gttagagatc taggcctcct aggtcgacat cgataaaata   6240
aaagatttta tttagtctcc agaaaaaggg gggaatgaaa gaccccacct gtaggtttgg   6300
caagctagct taagtaacgc cattttgcaa ggcatggaaa aatacataac tgagaataga   6360
gaagttcaga tcaaggtcag gaacagatgg aacagctgaa tatgggccaa acaggatatc   6420
tgtggtaagc agttcctgcc ccggctcagg gccaagaaca gatggaacag ctgaatatgg   6480
gccaaacagg atatctgtgg taagcagttc ctgccccggc tcagggccaa gaacagatgg   6540
```

-continued

```
tccccagatg cggtccagcc ctcagcagtt tctagagaac catcagatgt ttccagggtg   6600

ccccaaggac ctgaaatgac cctgtgcctt atttgaacta accaatcagt tcgcttctcg   6660

cttctgttcg cgcgcttctg ctccccgagc tcaataaaag agcccacaac ccctcactcg   6720

gggcgccagt cctccgattg actgagtcgc ccgggtaccc gtgtatccaa taaaccctct   6780

tgcagttgca tccgacttgt ggtctcgctg ttccttggga gggtctcctc tgagtgattg   6840

actacccgtc agcgggggtc tttcatt                                       6867
```

```
<210> SEQ ID NO 6
<211> LENGTH: 7466
<212> TYPE: DNA
<213> ORGANISM: Artificial Sequence
<220> FEATURE:
<223> OTHER INFORMATION: Synthetic

<400> SEQUENCE: 6

tttgaaagac cccacccgta ggtggcaagc tagcttaagt aacgccactt tgcaaggcat     60

ggaaaaatac ataactgaga atagaaaagt tcagatcaag gtcaggaaca aagaaacagc    120

tgaataccaa acaggatatc tgtggtaagc ggttcctgcc ccggctcagg gccaagaaca    180

gatgagacag ctgagtgatg ggccaaacag gatatctgtg gtaagcagtt cctgccccgg    240

ctcggggcca agaacagatg gtccccagat gcggtccagc cctcagcagt ttctagtgaa    300

tcatcagatg tttccagggt gccccaagga cctgaaaatg accctgtacc ttatttgaac    360

taaccaatca gttcgcttct cgcttctgtt cgcgcgcttc cgctctccga gctcaataaa    420

agagcccaca acccctcact cggcgcgcca gtcttccgat agactgcgtc gcccgggtac    480

ccgtattccc aataaagcct cttgctgttt gcatccgaat cgtggtctcg ctgttccttg    540

ggagggtctc ctctgagtga ttgactaccc acgacggggg tctttcattt gggggctcgt    600

ccgggatttg gagacccctg cccagggacc accgacccac caccgggagg taagctggcc    660

agcaacttat ctgtgtctgt ccgattgtct agtgtctatg tttgatgtta tgcgcctgcg    720

tctgtactag ttagctaact agctctgtat ctggcggacc cgtggtggaa ctgacgagtt    780

ctgaacaccc ggccgcaacc ctgggagacg tcccagggac tttgggggcc gtttttgtgg    840

cccgacctga ggaagggagt cgatgtggaa tccgaccccg tcaggatatg tggttctggt    900

aggagacgag aacctaaaac agttcccgcc tccgtctgaa tttttgcttt cggtttggaa    960

ccgaagccgc gcgtcttgtc tgctgcagcg ctgcagcatc gttctgtgtt gtctctgtct   1020

gactgtgttt ctgtatttgt ctgaaaatta gggccagact gttaccactc ccttaagttt   1080

gaccttaggt cactggaaag atgtcgagcg gatcgctcac aaccagtcgg tagatgtcaa   1140

gaagagacgt tgggttacct tctgctctgc agaatggcca acctttaacg tcggatggcc   1200

gcgagacggc acctttaacc gagacctcat cacccaggtt aagatcaagg tcttttcacc   1260

tggcccgcat ggacacccag accaggtccc ctacatcgtg acctgggaag ccttggcttt   1320

tgaccccccct ccctgggtca agccctttgt acaccctaag cctccgcctc ctcttcctcc   1380

atccgccccg tctctccccc ttgaacctcc tcgttcgacc ccgcctcgat cctcccttta   1440

tccagccctc actccttctc taggcgccgg aattccgatc tgatcaagag acaggatgag   1500

gatcgtttcg catgattgaa caagatggat tgcacgcagg ttctccggcc gcttgggtgg   1560

agaggctatt cggctatgac tgggcacaac agacaatcgg ctgctctgat gccgccgtgt   1620

tccggctgtc agcgcagggg cgcccggttc tttttgtcaa gaccgacctg tccggtgccc   1680

tgaatgaact gcaggacgag gcagcgcggc tatcgtggct ggccacgacg ggcgttcctt   1740
```

-continued

```
gcgcagctgt gctcgacgtt gtcactgaag cgggaaggga ctggctgcta ttgggcgaag   1800
tgccggggca ggatctcctg tcatctcacc ttgctcctgc cgagaaagta tccatcatgg   1860
ctgatgcaat gcggcggctg catacgcttg atccggctac ctgcccattc gaccaccaag   1920
cgaaacatcg catcgagcga gcacgtactc ggatggaagc cggtcttgtc gatcaggatg   1980
atctggacga agagcatcag gggctcgcgc cagccgaact gttcgccagg ctcaaggcgc   2040
gcatgcccga cggcgaggat ctcgtcgtga cccatggcga tgcctgcttg ccgaatatca   2100
tggtggaaaa tggccgcttt tctggattca tcgactgtgg ccggctgggt gtggcggacc   2160
gctatcagga catagcgttg gctacccgtg atattgctga agagcttggc ggcgaatggg   2220
ctgaccgctt cctcgtgctt tacggtatcg ccgctcccga ttcgcagcgc atcgccttct   2280
atcgccttct tgacgagttc ttctgagcgg gactctgggg ttcgaaatga ccgaccaagc   2340
gacgcccaac ctgccatcac gagatttcga ttccaccgcc gccttctatg aaaggttggg   2400
cttcggaatc gttttccggg acgccggctg gatgatcctc cagcgcgggg atctcatgct   2460
ggagttcttc gcccaccccg ggctcgatcc cctcgcgagt tggttcagct gctgcctgag   2520
gctggacgac ctcgcggagt tctaccggca gtgcaaatcc gtcggcatcc aggaaaccag   2580
cagcggctat ccgcgcatcc atgcccccga actgcaggag tggggaggca cgatggccgc   2640
tttggtcgag gcggatccgg ccattagcca tattattcat tggttatata gcataaatca   2700
atattggcta ttggccattg catacgttgt atccatatca taatatgtac atttatattg   2760
gctcatgtcc aacattaccg ccatgttgac attgattatt gactagttat taatagtaat   2820
caattacggg gtcattagtt catagcccat atatggagtt ccgcgttaca taacttacgg   2880
taaatggccc gcctggctga ccgcccaacg acccccgccc attgacgtca ataatgacgt   2940
atgttcccat agtaacgcca atagggactt tccattgacg tcaatgggtg gagtatttac   3000
ggtaaactgc ccacttggca gtacatcaag tgtatcatat gccaagtacg ccccctattg   3060
acgtcaatga cggtaaatgg cccgcctggc attatgccca gtacatgacc ttatgggact   3120
ttcctacttg gcagtacatc tacgtattag tcatcgctat taccatggtg atgcggtttt   3180
ggcagtacat caatgggcgt ggatagcggt ttgactcacg gggatttcca agtctccacc   3240
ccattgacgt caatgggagt ttgttttggc accaaaatca acgggacttt ccaaaatgtc   3300
gtaacaactc cgccccattg acgcaaatgg gcggtaggca tgtacggtgg gaggtctata   3360
taagcagagc tcgtttagtg aaccgtcaga tcgcctggag acgccatcca cgctgttttg   3420
acctccatag aagacaccgg gaccgatcca gcctccgcgg ccccaagctt ggatctcacc   3480
atggagttgg gactgcgctg ggcttcctc gttgctcttt taagaggtgt ccagtgtcag   3540
gtgcaattgg tggagtctgg gggaggcgtg gtccagcctg ggaggtccct gagactctcc   3600
tgtgcagcgt ctggattcgc cttcagtaga tatggcatgc actgggtccg ccaggctcca   3660
ggcaaggggc tggagtgggt ggcagttata tggtatgatg gaagtaataa atactatgca   3720
gactccgtga agggccgatt caccatctcc agagacaatt ccaagaacac gcagtatctg   3780
caaatgaaca gcctgagagc cgaggacacg gctgtgtatt actgtgcgag aggcggtgac   3840
ttcctctact actactatta cggtatggac gtctggggcc aagggaccac ggtcaccgtc   3900
tcctcagcct ccaccaaggg cccatcggtc ttccccctgg caccctctag caagagcacc   3960
tctgggggca cagcggccct gggctgcctg gtcaaggact acttccccga accggtgacg   4020
gtgtcgtgga actcaggcgc cctgaccagc ggcgtgcaca ccttcccggc tgtcctacag   4080
```

-continued

```
tcctcaggac tctactccct cagcagcgtg gtgaccgtgc cctccagcag cttgggcacc   4140
cagacctaca tctgcaacgt gaatcacaag cccagcaaca ccaaggtgga caagagagtt   4200
gagcccaaat cttgtgacaa aactcacaca tgcccaccgt gcccagcacc tgaactcctg   4260
gggggaccgt cagtcttcct cttcccccca aaacccaagg acaccctcat gatctcccgg   4320
acccctgagg tcacatgcgt ggtggtggac gtgagccacg aagaccctga ggtcaagttc   4380
aactggtacg tggacggcgt ggaggtgcat aatgccaaga caaagccgcg ggaggagcag   4440
tacaacagca cgtaccgtgt ggtcagcgtc ctcaccgtcc tgcaccagga ctggctgaat   4500
ggcaaggagt acaagtgcaa ggtctccaac aaagccctcc cagcccccat cgagaaaacc   4560
atctccaaag ccaaagggca gccccgagaa ccacaggtgt acaccctgcc cccatcccgg   4620
gaggagatga ccaagaacca ggtcagcctg acctgcctgg tcaaaggctt ctatcccagc   4680
gacatcgccg tggagtggga gagcaatggg cagccggaga acaactacaa gaccacgcct   4740
cccgtgctgg actccgacgg ctccttcttc ctctatagca agctcaccgt ggacaagagc   4800
aggtggcagc aggggaacgt cttctcatgc tccgtgatgc atgaggctct gcacaaccac   4860
tacacgcaga agagcctctc cctgtctccg ggtaaatgag aattcctcga gttaacagat   4920
ccccgggaat tcgcccctct ccctcccccc cccctaacgt tactggccga agccgcttgg   4980
aataaggccg gtgtgcgttt gtctatatgt tattttccac catattgccg tcttttggca   5040
atgtgagggc ccggaaacct ggccctgtct tcttgacgag cattcctagg ggtctttccc   5100
ctctcgccaa aggaatgcaa ggtctgttga atgtcgtgaa ggaagcagtt cctctggaag   5160
cttcttgaag acaaacaacg tctgtagcga ccctttgcag gcagcggaac cccccacctg   5220
gcgacaggtg cctctgcggc caaaagccac gtgtataaga tacacctgca aaggcggcac   5280
aaccccagtg ccacgttgtg agttggatag ttgtggaaag agtcaaatgg ctctcctcaa   5340
gcgtattcaa caaggggctg aaggatgccc agaaggtacc ccattgtatg ggatctgatc   5400
tggggcctcg gtgcacatgc tttacatgtg tttagtcgag gttaaaaaaa cgtctaggcc   5460
ccccgaacca cggggacgtg gttttccttt gaaaaacacg atgataatat ggcctccttt   5520
gtctctctgc tcctggtagg catcctattc catgccaccc aggccgacat ccagatgacc   5580
cagtctccat cctccctgtc tgcatctgta ggagacagag tcaccatcac ttgccgggcg   5640
agtcagggca ttagcaatta tttagcctgg tatcagcaga aaacagggaa agttcctaag   5700
ttcctgatct atgaagcatc cactttgcaa tcaggggtcc catctcggtt cagtggcggt   5760
ggatctggga cagatttcac tctcaccatc agcagcctgc agcctgaaga tgttgcaact   5820
tattactgtc aaaattataa cagtgcccca ttcactttcg gccctgggac caaagtggat   5880
atcaaacgaa ctgtggctgc accctctgtc ttcatcttcc cgccatctga tgagcagttg   5940
aaatctggaa ctgctagcgt tgtgtgcctg ctgaataact tctatcccag agaggccaaa   6000
gtacagtgga aggtggataa cgccctccaa tcgggtaact cccaggagag tgtcacagag   6060
caggacagca aggacagcac ctacagcctc agcagcaccc tgacgctgag caaagcagac   6120
tacgagaaac acaaagtcta cgcctgcgaa gtcacccatc agggcctgag ctcgcccgtc   6180
acaaagagct tcaacagggg agagtgttag gaattcgcgg ccgctcgaca tcgataatca   6240
acctctggat tacaaaattt gtgaaagatt gactggtatt cttaactatg ttgctccttt   6300
tacgctatgt ggatacgctg ctttaatgcc tttgtatcat gctattgctt cccgtatggc   6360
tttcattttc tcctccttgt ataaatcctg gttgctgtct ctttatgagg agttgtggcc   6420
cgttgtcagg caacgtggcg tggtgtgcac tgtgtttgct gacgcaaccc ccactggttg   6480
```

-continued

```
gggcattgcc accacctgtc agctcctttc cgggactttc gctttccccc tccctattgc   6540

cacggcggaa ctcatcgccg cctgccttgc ccgctgctgg acaggggctc ggctgttggg   6600

cactgacaat tccgtggtgt tgtcggggaa atcatcgtcc tttccttggc tgctcgcctg   6660

tgttgccacc tggattctgc gcgggacgtc cttctgctac gtcccttcgg ccctcaatcc   6720

agcggacctt ccttcccgcg gcctgctgcc ggctctgcgg cctcttccgc gtcttcgcct   6780

tcgccctcag acgagtcgga tctccctttg ggccgcctcc ccgcctgatc gataaaataa   6840

aagattttat ttagtctcca gaaaaagggg ggaatgaaag accccacctg taggtttggc   6900

aagctagctt aagtaacgcc attttgcaag gcatggaaaa atacataact gagaatagag   6960

aagttcagat caaggtcagg aacagatgga acagctgaat atgggccaaa caggatatct   7020

gtggtaagca gttcctgccc cggctcaggg ccaagaacag atggaacagc tgaatatggg   7080

ccaaacagga tatctgtggt aagcagttcc tgccccggct cagggccaag aacagatggt   7140

ccccagatgc ggtccagccc tcagcagttt ctagagaacc atcagatgtt tccagggtgc   7200

cccaaggacc tgaaatgacc ctgtgcctta tttgaactaa ccaatcagtt cgcttctcgc   7260

ttctgttcgc gcgcttctgc tccccgagct caataaaaga gcccacaacc cctcactcgg   7320

ggcgccagtc ctccgattga ctgagtcgcc cgggtacccg tgtatccaat aaaccctctt   7380

gcagttgcat ccgacttgtg gtctcgctgt tccttgggag ggtctcctct gagtgattga   7440

ctacccgtca gcgggggtct ttcatt                                        7466
```

```
<210> SEQ ID NO 7
<211> LENGTH: 7465
<212> TYPE: DNA
<213> ORGANISM: Artificial Sequence
<220> FEATURE:
<223> OTHER INFORMATION: Synthetic

<400> SEQUENCE: 7

tttgaaagac cccacccgta ggtggcaagc tagcttaagt aacgccactt tgcaaggcat     60

ggaaaaatac ataactgaga atagaaaagt tcagatcaag gtcaggaaca aagaaacagc    120

tgaataccaa acaggatatc tgtggtaagc ggttcctgcc ccggctcagg gccaagaaca    180

gatgagacag ctgagtgatg ggccaaacag gatatctgtg gtaagcagtt cctgccccgg    240

ctcggggcca agaacagatg gtccccagat gcggtccagc cctcagcagt ttctagtgaa    300

tcatcagatg tttccagggt gccccaagga cctgaaaatg accctgtacc ttatttgaac    360

taaccaatca gttcgcttct cgcttctgtt cgcgcgcttc cgctctccga gctcaataaa    420

agagcccaca acccctcact cggcgcgcca gtcttccgat agactgcgtc gcccgggtac    480

ccgtattccc aataaagcct cttgctgttt gcatccgaat cgtggtctcg ctgttccttg    540

ggagggtctc ctctgagtga ttgactaccc acgacggggg tctttcattt gggggctcgt    600

ccgggatttg gagacccctg cccagggacc accgacccac caccgggagg taagctggcc    660

agcaacttat ctgtgtctgt ccgattgtct agtgtctatg tttgatgtta tgcgcctgcg    720

tctgtactag ttagctaact agctctgtat ctggcggacc cgtggtggaa ctgacgagtt    780

ctgaacaccc ggccgcaacc ctgggagacg tcccagggac tttgggggcc gtttttgtgg    840

cccgacctga ggaagggagt cgatgtggaa tccgaccccg tcaggatatg tggttctggt    900

aggagacgag aacctaaaac agttcccgcc tccgtctgaa tttttgcttt cggtttggaa    960

ccgaagccgc gcgtcttgtc tgctgcagcg ctgcagcatc gttctgtgtt gtctctgtct   1020
```

-continued

```
gactgtgttt ctgtatttgt ctgaaaatta gggccagact gttaccactc ccttaagttt   1080

gaccttaggt cactggaaag atgtcgagcg gatcgctcac aaccagtcgg tagatgtcaa   1140

gaagagacgt tgggttacct tctgctctgc agaatggcca acctttaacg tcggatggcc   1200

gcgagacggc acctttaacc gagacctcat cacccaggtt aagatcaagg tcttttcacc   1260

tggcccgcat ggacacccag accaggtccc ctacatcgtg acctgggaag ccttggcttt   1320

tgacccccct ccctgggtca agccctttgt acaccctaag cctccgcctc ctcttcctcc   1380

atccgccccg tctctccccc ttgaacctcc tcgttcgacc ccgcctcgat cctcccttta   1440

tccagccctc actccttctc taggcgccgg aattccgatc tgatcaagag acaggatgag   1500

gatcgtttcg catgattgaa caagatggat tgcacgcagg ttctccggcc gcttgggtgg   1560

agaggctatt cggctatgac tgggcacaac agacaatcgg ctgctctgat gccgccgtgt   1620

tccggctgtc agcgcagggg cgcccggttc tttttgtcaa gaccgacctg tccggtgccc   1680

tgaatgaact gcaggacgag gcagcgcggc tatcgtggct ggccacgacg ggcgttcctt   1740

gcgcagctgt gctcgacgtt gtcactgaag cgggaaggga ctggctgcta ttgggcgaag   1800

tgccggggca ggatctcctg tcatctcacc ttgctcctgc cgagaaagta tccatcatgg   1860

ctgatgcaat gcggcggctg catacgcttg atccggctac ctgcccattc gaccaccaag   1920

cgaaacatcg catcgagcga gcacgtactc ggatggaagc cggtcttgtc gatcaggatg   1980

atctggacga agagcatcag gggctcgcgc cagccgaact gttcgccagg ctcaaggcgc   2040

gcatgcccga cggcgaggat ctcgtcgtga cccatggcga tgcctgcttg ccgaatatca   2100

tggtggaaaa tggccgcttt tctggattca tcgactgtgg ccggctgggt gtggcggacc   2160

gctatcagga catagcgttg gctacccgtg atattgctga agagcttggc ggcgaatggg   2220

ctgaccgctt cctcgtgctt tacggtatcg ccgctcccga ttcgcagcgc atcgccttct   2280

atcgccttct tgacgagttc ttctgagcgg gactctgggg ttcgaaatga ccgaccaagc   2340

gacgcccaac ctgccatcac gagatttcga ttccaccgcc gccttctatg aaaggttggg   2400

cttcggaatc gttttccggg acgccggctg gatgatcctc cagcgcgggg atctcatgct   2460

ggagttcttc gcccaccccg ggctcgatcc cctcgcgagt tggttcagct gctgcctgag   2520

gctggacgac ctcgcggagt tctaccggca gtgcaaatcc gtcggcatcc aggaaaccag   2580

cagcggctat ccgcgcatcc atgcccccga actgcaggag tggggaggca cgatggccgc   2640

tttggtcgag gcggatccgg ccattagcca tattattcat tggttatata gcataaatca   2700

atattggcta ttggccattg catacgttgt atccatatca taatatgtac atttatattg   2760

gctcatgtcc aacattaccg ccatgttgac attgattatt gactagttat taatagtaat   2820

caattacggg gtcattagtt catagcccat atatggagtt ccgcgttaca taacttacgg   2880

taaatggccc gcctggctga ccgcccaacg acccccgccc attgacgtca ataatgacgt   2940

atgttcccat agtaacgcca atagggactt tccattgacg tcaatgggtg gagtatttac   3000

ggtaaactgc ccacttggca gtacatcaag tgtatcatat gccaagtacg ccccctattg   3060

acgtcaatga cggtaaatgg cccgcctggc attatgccca gtacatgacc ttatgggact   3120

ttcctacttg gcagtacatc tacgtattag tcatcgctat taccatggtg atgcggtttt   3180

ggcagtacat caatgggcgt ggatagcggt ttgactcacg gggatttcca agtctccacc   3240

ccattgacgt caatgggagt ttgttttggc accaaaatca acgggacttt ccaaaatgtc   3300

gtaacaactc cgccccattg acgcaaatgg gcggtaggca tgtacggtgg gaggtctata   3360

taagcagagc tcgtttagtg aaccgtcaga tcgcctggag acgccatcca cgctgttttg   3420
```

-continued

```
acctccatag aagacaccgg gaccgatcca gcctccgcgg ccccaagctt ctcgagcacc   3480

atggaatgga gcggagtctt tatctttctc ctgtcagtaa ctgcaggtgt ccactccgag   3540

gtgcagctgg tggagtctgg tggaggcttg gtaaagcctg gaggttccct tagactctcc   3600

tgtgcagcct ctggttacac tttcagtaac tattggatcg gatgggtccg ccaggctcca   3660

ggcaaagggc tggagtggat tggcgatatc taccctggag ggaactacat caggaacaat   3720

gagaagttca aggacaagac caccctgtca gcagatactt ccaagaacac agcctatctg   3780

caaatgaaca gcctgaaaac cgaggacaca gccgtgtatt actgtggaag cagcttcggt   3840

agtaactacg tgttcgcctg gtttacttac tggggccaag ggactctggt cacagtctcc   3900

tcagcttcca ccaagggccc atccgtcttc cccctggcgc cctgctccag gagcacctcc   3960

gagagcacag ccgccctggg ctgcctggtc aaggactact tccccgaacc ggtgacggtg   4020

tcgtggaact caggcgccct gaccagcggc gtgcacacct tcccggctgt cctacagtcc   4080

tcaggactct actccctcag cagcgtggtg accgtgccct ccagcagctt gggcacgaag   4140

acctacacct gcaacgtaga tcacaagccc agcaacacca aggtggacaa gagagttgag   4200

tccaaatatg gtcccccatg cccatcatgc ccagcacctg agttcctggg gggaccatca   4260

gtcttcctgt tccccccaaa acccaaggac actctcatga tctcccggac ccctgaggtc   4320

acgtgcgtgg tggtggacgt gagccaggaa gaccccgagg tccagttcaa ctggtacgtg   4380

gatggcgtgg aggtgcataa tgccaagaca aagccgcggg aggagcagtt caacagcacg   4440

taccgtgtgg tcagcgtcct caccgtcctg caccaggact ggctgaacgg caaggagtac   4500

aagtgcaagg tctccaacaa aggcctcccg tcctccatcg agaaaaccat ctccaaagcc   4560

aaagggcagc cccgagagcc acaggtgtac accctgcccc catcccagga ggagatgacc   4620

aagaaccagg tcagcctgac ctgcctggtc aaaggcttct accccagcga catcgccgtg   4680

gagtgggaga gcaatgggca gccggagaac aactacaaga ccacgcctcc cgtgctggac   4740

tccgacggct ccttcttcct ctacagcagg ctaaccgtgg acaagagcag gtggcaggag   4800

gggaatgtct tctcatgctc cgtgatgcat gaggctctgc acaaccacta cacacagaag   4860

agcctctccc tgtctctggg taaatgagtg ccagatcccc gggaattcgc ccctctccct   4920

cccccccccc taacgttact ggccgaagcc gcttggaata aggccggtgt gcgtttgtct   4980

atatgttatt ttccaccata ttgccgtctt ttggcaatgt gagggcccgg aaacctggcc   5040

ctgtcttctt gacgagcatt cctaggggtc tttcccctct cgccaaagga atgcaaggtc   5100

tgttgaatgt cgtgaaggaa gcagttcctc tggaagcttc ttgaagacaa acaacgtctg   5160

tagcgaccct ttgcaggcag cggaaccccc cacctggcga caggtgcctc tgcggccaaa   5220

agccacgtgt ataagataca cctgcaaagg cggcacaacc ccagtgccac gttgtgagtt   5280

ggatagttgt ggaaagagtc aaatggctct cctcaagcgt attcaacaag gggctgaagg   5340

atgcccagaa ggtaccccat tgtatgggat ctgatctggg gcctcggtgc acatgcttta   5400

catgtgttta gtcgaggtta aaaaaacgtc taggcccccc gaaccacggg gacgtggttt   5460

tcctttgaaa aacacgatga taatatggcc tcctttgtct ctctgctcct ggtaggcatc   5520

ctattccatg ccacccaggc cgacattgtg atgacccaat ctccactctc cctgcctgtc   5580

actcctggag agccagcctc catctcttgc agatctagtc agcgccttct gagcagttat   5640

ggacatacct atttacattg gtacctacag aagccaggcc agtctccaca gctcctgatc   5700

tacgaagttt ccaaccgatt ttctggggtc ccagacaggt tcagtggcag tgggtcaggg   5760
```

-continued

```
acagatttca cacttaagat cagtagagtg gaggctgagg atgtgggagt ttattactgc   5820

tctcaaagta cacatgttcc tctcacgttc ggacagggga ccaaggtgga aataaaacga   5880

actgtggctg caccatctgt cttcatcttc ccgccatctg atgagcagtt gaaatctgga   5940

actgcctctg ttgtgtgcct gctgaataac ttctatccca gagaggccaa agtacagtgg   6000

aaggtggata acgccctcca atcgggtaac tcccaggaga gtgtcacaga gcaggacagc   6060

aaggacagca cctacagcct cagcagcacc ctgacgctga gcaaagcaga ctacgagaaa   6120

cacaaagtct acgcctgcga agtcacccat cagggcctga gctcgcccgt cacaaagagc   6180

ttcaacaggg gagagtgtta gagggagaag tgcccccacc tgctcctcga catcgataat   6240

caacctctgg attacaaaat ttgtgaaaga ttgactggta ttcttaacta tgttgctcct   6300

tttacgctat gtggatacgc tgctttaatg cctttgtatc atgctattgc ttcccgtatg   6360

gctttcattt tctcctcctt gtataaatcc tggttgctgt ctctttatga ggagttgtgg   6420

cccgttgtca ggcaacgtgg cgtggtgtgc actgtgtttg ctgacgcaac ccccactggt   6480

tggggcattg ccaccacctg tcagctcctt tccgggactt tcgctttccc cctccctatt   6540

gccacggcgg aactcatcgc cgcctgcctt gcccgctgct ggacaggggc tcggctgttg   6600

ggcactgaca attccgtggt gttgtcgggg aaatcatcgt cctttccttg gctgctcgcc   6660

tgtgttgcca cctggattct gcgcgggacg tccttctgct acgtcccttc ggccctcaat   6720

ccagcggacc ttccttcccg cggcctgctg ccggctctgc ggcctcttcc gcgtcttcgc   6780

cttcgccctc agacgagtcg gatctccctt tgggccgcct ccccgcatcg ataaaataaa   6840

agattttatt tagtctccag aaaaaggggg gaatgaaaga ccccacctgt aggtttggca   6900

agctagctta agtaacgcca ttttgcaagg catggaaaaa tacataactg agaatagaga   6960

agttcagatc aaggtcagga acagatggaa cagctgaata tgggccaaac aggatatctg   7020

tggtaagcag ttcctgcccc ggctcagggc caagaacaga tggaacagct gaatatgggc   7080

caaacaggat atctgtggta agcagttcct gccccggctc agggccaaga acagatggtc   7140

cccagatgcg gtccagccct cagcagtttc tagagaacca tcagatgttt ccagggtgcc   7200

ccaaggacct gaaatgaccc tgtgccttat ttgaactaac caatcagttc gcttctcgct   7260

tctgttcgcg cgcttctgct ccccgagctc aataaaagag cccacaaccc ctcactcggg   7320

gcgccagtcc tccgattgac tgagtcgccc gggtacccgt gtatccaata aaccctcttg   7380

cagttgcatc cgacttgtgg tctcgctgtt ccttgggagg gtctcctctg agtgattgac   7440

tacccgtcag cgggggtctt tcatt                                          7465
```

<210> SEQ ID NO 8
<211> LENGTH: 6232
<212> TYPE: DNA
<213> ORGANISM: Artificial Sequence
<220> FEATURE:
<223> OTHER INFORMATION: Synthetic

<400> SEQUENCE: 8

```
tttgaaagac cccacccgta ggtggcaagc tagcttaagt aacgccactt tgcaaggcat     60

ggaaaaatac ataactgaga atagaaaagt tcagatcaag gtcaggaaca aagaaacagc    120

tgaataccaa acaggatatc tgtggtaagc ggttcctgcc ccggctcagg gccaagaaca    180

gatgagacag ctgagtgatg ggccaaacag gatatctgtg gtaagcagtt cctgccccgg    240

ctcggggcca agaacagatg gtccccagat gcggtccagc cctcagcagt ttctagtgaa    300

tcatcagatg tttccagggt gccccaagga cctgaaaatg accctgtacc ttatttgaac    360
```

-continued

```
taaccaatca gttcgcttct cgcttctgtt cgcgcgcttc cgctctccga gctcaataaa    420
agagcccaca acccctcact cggcgcgcca gtcttccgat agactgcgtc gcccgggtac    480
ccgtattccc aataaagcct cttgctgttt gcatccgaat cgtggtctcg ctgttccttg    540
ggagggtctc ctctgagtga ttgactaccc acgacggggg tctttcattt gggggctcgt    600
ccgggatttg gagacccctg cccagggacc accgacccac caccgggagg taagctggcc    660
agcaacttat ctgtgtctgt ccgattgtct agtgtctatg tttgatgtta tgcgcctgcg    720
tctgtactag ttagctaact agctctgtat ctggcggacc cgtggtggaa ctgacgagtt    780
ctgaacaccc ggccgcaacc ctgggagacg tcccagggac tttgggggcc gtttttgtgg    840
cccgacctga ggaagggagt cgatgtggaa tccgaccccg tcaggatatg tggttctggt    900
aggagacgag aacctaaaac agttcccgcc tccgtctgaa tttttgcttt cggtttggaa    960
ccgaagccgc gcgtcttgtc tgctgcagcg ctgcagcatc gttctgtgtt gtctctgtct   1020
gactgtgttt ctgtatttgt ctgaaaatta gggccagact gttaccactc ccttaagttt   1080
gaccttaggt cactggaaag atgtcgagcg gatcgctcac aaccagtcgg tagatgtcaa   1140
gaagagacgt tgggttacct tctgctctgc agaatggcca acctttaacg tcggatggcc   1200
gcgagacggc acctttaacc gagacctcat cacccaggtt aagatcaagg tcttttcacc   1260
tggcccgcat ggacacccag accaggtccc ctacatcgtg acctgggaag ccttggcttt   1320
tgacccccct ccctgggtca agccctttgt acaccctaag cctccgcctc ctcttcctcc   1380
atccgccccg tctctccccc ttgaacctcc tcgttcgacc ccgcctcgat cctcccttta   1440
tccagccctc actccttctc taggcgccgg aattccgatc tgatcaagag acaggatgag   1500
gatcgtttcg catgattgaa caagatggat tgcacgcagg ttctccggcc gcttgggtgg   1560
agaggctatt cggctatgac tgggcacaac agacaatcgg ctgctctgat gccgccgtgt   1620
tccggctgtc agcgcagggg cgcccggttc tttttgtcaa gaccgacctg tccggtgccc   1680
tgaatgaact gcaggacgag gcagcgcggc tatcgtggct ggccacgacg ggcgttcctt   1740
gcgcagctgt gctcgacgtt gtcactgaag cgggaaggga ctggctgcta ttgggcgaag   1800
tgccggggca ggatctcctg tcatctcacc ttgctcctgc cgagaaagta tccatcatgg   1860
ctgatgcaat gcggcggctg catacgcttg atccggctac ctgcccattc gaccaccaag   1920
cgaaacatcg catcgagcga gcacgtactc ggatggaagc cggtcttgtc gatcaggatg   1980
atctggacga agagcatcag gggctcgcgc cagccgaact gttcgccagg ctcaaggcgc   2040
gcatgcccga cggcgaggat ctcgtcgtga cccatggcga tgcctgcttg ccgaatatca   2100
tggtggaaaa tggccgcttt tctggattca tcgactgtgg ccggctgggt gtggcggacc   2160
gctatcagga catagcgttg gctacccgtg atattgctga agagcttggc ggcgaatggg   2220
ctgaccgctt cctcgtgctt tacggtatcg ccgctcccga ttcgcagcgc atcgccttct   2280
atcgccttct tgacgagttc ttctgagcgg gactctgggg ttcgaaatga ccgaccaagc   2340
gacgcccaac ctgccatcac gagatttcga ttccaccgcc gccttctatg aaaggttggg   2400
cttcggaatc gttttccggg acgccggctg gatgatcctc cagcgcgggg atctcatgct   2460
ggagttcttc gcccaccccg ggctcgatcc cctcgcgagt tggttcagct gctgcctgag   2520
gctggacgac ctcgcggagt tctaccggca gtgcaaatcc gtcggcatcc aggaaaccag   2580
cagcggctat ccgcgcatcc atgcccccga actgcaggag tggggaggca cgatggccgc   2640
tttggtcgag gcggatccgg ccattagcca tattattcat tggttatata gcataaatca   2700
```

-continued atattggcta ttggccattg catacgttgt atccatatca taatatgtac atttatattg 2760
gctcatgtcc aacattaccg ccatgttgac attgattatt gactagttat taatagtaat 2820
caattacggg gtcattagtt catagcccat atatggagtt ccgcgttaca taacttacgg 2880
taaatggccc gcctggctga ccgcccaacg acccccgccc attgacgtca ataatgacgt 2940
atgttcccat agtaacgcca atagggactt tccattgacg tcaatgggtg gagtatttac 3000
ggtaaactgc ccacttggca gtacatcaag tgtatcatat gccaagtacg ccccctattg 3060
acgtcaatga cggtaaatgg cccgcctggc attatgccca gtacatgacc ttatgggact 3120
ttcctacttg gcagtacatc tacgtattag tcatcgctat taccatggtg atgcggtttt 3180
ggcagtacat caatgggcgt ggatagcggt ttgactcacg gggatttcca agtctccacc 3240
ccattgacgt caatgggagt ttgttttggc accaaaatca acgggacttt ccaaaatgtc 3300
gtaacaactc cgccccattg acgcaaatgg gcggtaggca tgtacggtgg gaggtctata 3360
taagcagagc tcgtttagtg aaccgtcaga tcgcctggag acgccatcca cgctgttttg 3420
acctccatag aagacaccgg gaccgatcca gcctccgcgg ccccaagctt ctcgacggat 3480
ccccgggaat tcaggacctc accatgggat ggagctgtat catcctcttc ttggtagcaa 3540
cagctacagg tgtccactcc gaggtccaac tggtggagag cggtggaggt gttgtgcaac 3600
ctggccggtc cctgcgcctg tcctgctccg catctggctt cgatttcacc acatattgga 3660
tgagttgggt gagacaggca cctggaaaag gtcttgagtg gattggagaa attcatccag 3720
atagcagtac gattaactat gcgccgtctc taaaggatag atttacaata tcgcgagaca 3780
acgccaagaa cacattgttc ctgcaaatgg acagcctgag acccgaagac accggggtct 3840
atttttgtgc aagcctttac ttcggcttcc cctggtttgc ttattggggc caagggaccc 3900
cggtcaccgt ctcctcagcc tccaccaagg gcccatcggt cttccccctg gcaccctcct 3960
ccaagagcac ctctgggggc acagcggccc tgggctgcct ggtcaaggac tacttccccg 4020
aaccggtgac ggtgtcgtgg aactcaggcg ccctgaccag cggcgtgcac accttcccgg 4080
ctgtcctaca gtcctcagga ctctactccc tcagcagcgt ggtgaccgtg ccctccagca 4140
gcttgggcac ccagacctac atctgcaacg tgaatcacaa gcccagcaac accaaggtgg 4200
acaagagagt tgagcccaaa tcttgtgaca aaactcacac atgcccaccg tgcccagcac 4260
ctgaactcct ggggggaccg tcagtcttcc tcttcccccc aaaacccaag gacaccctca 4320
tgatctcccg gacccctgag gtcacatgcg tggtggtgga cgtgagccac gaagaccctg 4380
aggtcaagtt caactggtac gtggacggcg tggaggtgca taatgccaag acaaagccgc 4440
gggaggagca gtacaacagc acgtaccgtg tggtcagcgt cctcaccgtc ctgcaccagg 4500
actggctgaa tggcaaggag tacaagtgca aggtctccaa caaagccctc ccagccccca 4560
tcgagaaaac catctccaaa gccaaagggc agccccgaga accacaggtg tacaccctgc 4620
ccccatcccg ggaggagatg accaagaacc aggtcagcct gacctgcctg gtcaaaggct 4680
tctatcccag cgacatcgcc gtggagtggg agagcaatgg gcagccggag aacaactaca 4740
agaccacgcc tcccgtgctg gactccgacg gctccttctt cctctatagc aagctcaccg 4800
tggacaagag caggtggcag caggggaacg tcttctcatg ctccgtgatg catgaggctc 4860
tgcacaacca ctacacgcag aagagcctct ccctgtctcc gggcatccta ttccatgcca 4920
cccaggccga catccagctg acccagagcc caagcagcct gagcgccagc gtgggtgaca 4980
gagtgaccat cacctgtaag gccagtcagg atgtgggtac ttctgtagcc tggtaccagc 5040
agaagccagg taaggctcca aagctgctga tctactggac atccacccgg cacactggtg 5100

-continued

```
tgccaagcag attcagcggt agcggtagcg gtaccgactt caccttcacc atcagcagcc   5160

tccagccaga ggacatcgcc acctactact gccagcaata tagcctctat cggtcgttcg   5220

gccaagggac caaggtggaa atcaaacgaa ctgtggctgc accatctgtc ttcatcttcc   5280

cgccatctga tgagcagttg aaatctggaa ctgcctctgt tgtgtgcctg ctgaataact   5340

tctatcccag agaggccaaa gtacagtgga aggtggataa cgccctccaa tcgggtaact   5400

cccaggagag tgtcacagag caggacagca aggacagcac ctacagcctc agcagcaccc   5460

tgacgctgag caaagcagac tacgagaaac acaaagtcta cgcctgcgaa gtcacccatc   5520

agggcctgag ctcgcccgtc acaaagagct tcaacagggg agagtgttag agatctaggc   5580

ctcctaggtc gacatcgata aaataaaaga ttttatttag tctccagaaa aaggggggaa   5640

tgaaagaccc cacctgtagg tttggcaagc tagcttaagt aacgccattt tgcaaggcat   5700

ggaaaaatac ataactgaga atagagaagt tcagatcaag gtcaggaaca gatggaacag   5760

ctgaatatgg gccaaacagg atatctgtgg taagcagttc ctgccccggc tcagggccaa   5820

gaacagatgg aacagctgaa tatgggccaa acaggatatc tgtggtaagc agttcctgcc   5880

ccggctcagg gccaagaaca gatggtcccc agatgcggtc cagccctcag cagtttctag   5940

agaaccatca gatgtttcca gggtgcccca aggacctgaa atgaccctgt gccttatttg   6000

aactaaccaa tcagttcgct tctcgcttct gttcgcgcgc ttctgctccc cgagctcaat   6060

aaaagagccc acaacccctc actcggggcg ccagtcctcc gattgactga gtcgcccggg   6120

tacccgtgta tccaataaac cctcttgcag ttgcatccga cttgtggtct cgctgttcct   6180

tgggagggtc tcctctgagt gattgactac ccgtcagcgg gggtctttca tt           6232
```

```
<210> SEQ ID NO 9
<211> LENGTH: 6241
<212> TYPE: DNA
<213> ORGANISM: Artificial Sequence
<220> FEATURE:
<223> OTHER INFORMATION: Synthetic

<400> SEQUENCE: 9

tttgaaagac cccacccgta ggtggcaagc tagcttaagt aacgccactt tgcaaggcat     60

ggaaaaatac ataactgaga atagaaaagt tcagatcaag gtcaggaaca aagaaacagc    120

tgaataccaa acaggatatc tgtggtaagc ggttcctgcc ccggctcagg gccaagaaca    180

gatgagacag ctgagtgatg ggccaaacag gatatctgtg gtaagcagtt cctgccccgg    240

ctcggggcca agaacagatg gtccccagat gcggtccagc cctcagcagt ttctagtgaa    300

tcatcagatg tttccagggt gccccaagga cctgaaaatg accctgtacc ttatttgaac    360

taaccaatca gttcgcttct cgcttctgtt cgcgcgcttc cgctctccga gctcaataaa    420

agagcccaca acccctcact cggcgcgcca gtcttccgat agactgcgtc gcccgggtac    480

ccgtattccc aataaagcct cttgctgttt gcatccgaat cgtggtctcg ctgttccttg    540

ggagggtctc ctctgagtga ttgactaccc acgacggggg tctttcattt gggggctcgt    600

ccgggatttg gagacccctg cccagggacc accgacccac caccgggagg taagctggcc    660

agcaacttat ctgtgtctgt ccgattgtct agtgtctatg tttgatgtta tgcgcctgcg    720

tctgtactag ttagctaact agctctgtat ctggcggacc cgtggtggaa ctgacgagtt    780

ctgaacaccc ggccgcaacc ctgggagacg tcccagggac tttgggggcc gtttttgtgg    840

cccgacctga ggaagggagt cgatgtggaa tccgaccccg tcaggatatg tggttctggt    900
```

-continued

```
aggagacgag aacctaaaac agttcccgcc tccgtctgaa tttttgcttt cggtttggaa    960
ccgaagccgc gcgtcttgtc tgctgcagcg ctgcagcatc gttctgtgtt gtctctgtct   1020
gactgtgttt ctgtatttgt ctgaaaatta gggccagact gttaccactc ccttaagttt   1080
gaccttaggt cactggaaag atgtcgagcg gatcgctcac aaccagtcgg tagatgtcaa   1140
gaagagacgt tgggttacct tctgctctgc agaatggcca acctttaacg tcggatggcc   1200
gcgagacggc acctttaacc gagacctcat cacccaggtt aagatcaagg tcttttcacc   1260
tggcccgcat ggacacccag accaggtccc ctacatcgtg acctgggaag ccttggcttt   1320
tgaccccccct ccctgggtca agccctttgt acaccctaag cctccgcctc ctcttcctcc   1380
atccgccccg tctctccccc ttgaacctcc tcgttcgacc ccgcctcgat cctcccttta   1440
tccagccctc actccttctc taggcgccgg aattccgatc tgatcaagag acaggatgag   1500
gatcgtttcg catgattgaa caagatggat tgcacgcagg ttctccggcc gcttgggtgg   1560
agaggctatt cggctatgac tgggcacaac agacaatcgg ctgctctgat gccgccgtgt   1620
tccggctgtc agcgcagggg cgcccggttc tttttgtcaa gaccgacctg tccggtgccc   1680
tgaatgaact gcaggacgag gcagcgcggc tatcgtggct ggccacgacg ggcgttcctt   1740
gcgcagctgt gctcgacgtt gtcactgaag cgggaaggga ctggctgcta ttgggcgaag   1800
tgccggggca ggatctcctg tcatctcacc ttgctcctgc cgagaaagta tccatcatgg   1860
ctgatgcaat gcggcggctg catacgcttg atccggctac ctgcccattc gaccaccaag   1920
cgaaacatcg catcgagcga gcacgtactc ggatggaagc cggtcttgtc gatcaggatg   1980
atctggacga agagcatcag gggctcgcgc cagccgaact gttcgccagg ctcaaggcgc   2040
gcatgcccga cggcgaggat ctcgtcgtga cccatggcga tgcctgcttg ccgaatatca   2100
tggtggaaaa tggccgcttt tctggattca tcgactgtgg ccggctgggt gtggcggacc   2160
gctatcagga catagcgttg gctacccgtg atattgctga agagcttggc ggcgaatggg   2220
ctgaccgctt cctcgtgctt tacggtatcg ccgctcccga ttcgcagcgc atcgccttct   2280
atcgccttct tgacgagttc ttctgagcgg gactctgggg ttcgaaatga ccgaccaagc   2340
gacgcccaac ctgccatcac gagatttcga ttccaccgcc gccttctatg aaaggttggg   2400
cttcggaatc gttttccggg acgccggctg gatgatcctc cagcgcgggg atctcatgct   2460
ggagttcttc gcccaccccg ggctcgatcc cctcgcgagt tggttcagct gctgcctgag   2520
gctggacgac ctcgcggagt tctaccggca gtgcaaatcc gtcggcatcc aggaaaccag   2580
cagcggctat ccgcgcatcc atgcccccga actgcaggag tggggaggca cgatggccgc   2640
tttggtcgag gcggatccgg ccattagcca tattattcat tggttatata gcataaatca   2700
atattggcta ttggccattg catacgttgt atccatatca taatatgtac atttatattg   2760
gctcatgtcc aacattaccg ccatgttgac attgattatt gactagttat taatagtaat   2820
caattacggg gtcattagtt catagcccat atatggagtt ccgcgttaca taacttacgg   2880
taaatggccc gcctggctga ccgcccaacg acccccgccc attgacgtca ataatgacgt   2940
atgttcccat agtaacgcca atagggactt tccattgacg tcaatgggtg gagtatttac   3000
ggtaaactgc ccacttggca gtacatcaag tgtatcatat gccaagtacg ccccctattg   3060
acgtcaatga cggtaaatgg cccgcctggc attatgccca gtacatgacc ttatgggact   3120
ttcctacttg gcagtacatc tacgtattag tcatcgctat taccatggtg atgcggtttt   3180
ggcagtacat caatgggcgt ggatagcggt ttgactcacg gggatttcca agtctccacc   3240
ccattgacgt caatgggagt ttgttttggc accaaaatca acgggacttt ccaaaatgtc   3300
```

-continued

```
gtaacaactc cgccccattg acgcaaatgg gcggtaggca tgtacggtgg gaggtctata   3360
taagcagagc tcgtttagtg aaccgtcaga tcgcctggag acgccatcca cgctgttttg   3420
acctccatag aagacaccgg gaccgatcca gcctccgcgg ccccaagctt ctcgacggat   3480
ccccgggaat tcaggacctc accatgggat ggagctgtat catcctcttc ttggtagcaa   3540
cagctacagg tgtccactcc caggtccagc tggtccaatc aggggctgaa gtcaagaaac   3600
ctgggtcatc agtgaaggtc tcctgcaagg cttctggcta cacctttact agctactggc   3660
tgcactgggt caggcaggca cctggacagg gtctggaatg gattggatac attaatccta   3720
ggaatgatta tactgagtac aatcagaact tcaaggacaa ggccacaata actgcagacg   3780
aatccaccaa tacagcctac atggagctga gcagcctgag gtctgaggac acggcatttt   3840
atttttgtgc aagaagggat attactacgt tctactgggg ccaaggcacc acggtcaccg   3900
tctcctcagc ctccaccaag ggcccatcgg tcttccccct ggcaccctcc tccaagagca   3960
cctctggggg cacagcggcc ctgggctgcc tggtcaagga ctacttcccc gaaccggtga   4020
cggtgtcgtg gaactcaggc gccctgacca gcggcgtgca caccttcccg gctgtcctac   4080
agtcctcagg actctactcc ctcagcagcg tggtgaccgt gccctccagc agcttgggca   4140
cccagaccta catctgcaac gtgaatcaca agcccagcaa caccaaggtg gacaagagag   4200
ttgagcccaa atcttgtgac aaaactcaca catgcccacc gtgcccagca cctgaactcc   4260
tggggggacc gtcagtcttc ctcttccccc caaaacccaa ggacaccctc atgatctccc   4320
ggacccctga ggtcacatgc gtggtggtgg acgtgagcca cgaagaccct gaggtcaagt   4380
tcaactggta cgtggacggc gtggaggtgc ataatgccaa gacaaagccg cgggaggagc   4440
agtacaacag cacgtaccgt gtggtcagcg tcctcaccgt cctgcaccag gactggctga   4500
atggcaagga gtacaagtgc aaggtctcca acaaagccct cccagccccc atcgagaaaa   4560
ccatctccaa agccaaaggg cagccccgag aaccacaggt gtacaccctg cccccatccc   4620
gggaggagat gaccaagaac caggtcagcc tgacctgcct ggtcaaaggc ttctatccca   4680
gcgacatcgc cgtggagtgg gagagcaatg ggcagccgga gaacaactac aagaccacgc   4740
ctcccgtgct ggactccgac ggctccttct tcctctatag caagctcacc gtggacaaga   4800
gcaggtggca gcaggggaac gtcttctcat gctccgtgat gcatgaggct ctgcacaacc   4860
actacacgca gaagagcctc tccctgtctc cgggcatcct attccatgcc acccaggccg   4920
acatccagct gacccagtct ccatcatctc tgagcgcatc tgttggagat agggtcacta   4980
tgagctgtaa gtccagtcaa agtgttttat acagtgcaaa tcacaagaac tacttggcct   5040
ggtaccagca gaaaccaggg aaagcaccta aactgctgat ctactgggca tccactaggg   5100
aatctggtgt cccttcgcga ttctctggca gcggatctgg gacagatttt actttcacca   5160
tcagctctct tcaaccagaa gacattgcaa catattattg tcaccaatac ctctcctcgt   5220
ggacgttcgg tggagggacc aaggtgcaga tcaaacgaac tgtggctgca ccatctgtct   5280
tcatcttccc gccatctgat gagcagttga aatctggaac tgcctctgtt gtgtgcctgc   5340
tgaataactt ctatcccaga gaggccaaag tacagtggaa ggtggataac gccctccaat   5400
cgggtaactc ccaggagagt gtcacagagc aggacagcaa ggacagcacc tacagcctca   5460
gcagcaccct gacgctgagc aaagcagact acgagaaaca caaagtctac gcctgcgaag   5520
tcacccatca gggcctgagc tcgcccgtca caaagagctt caacagggga gagtgttaga   5580
gatctaggcc tcctaggtcg acatcgataa aataaaagat tttatttagt ctccagaaaa   5640
```

-continued agggggggaat gaaagacccc acctgtaggt ttggcaagct agcttaagta acgccatttt 5700
gcaaggcatg gaaaaataca taactgagaa tagagaagtt cagatcaagg tcaggaacag 5760
atggaacagc tgaatatggg ccaaacagga tatctgtggt aagcagttcc tgccccggct 5820
cagggccaag aacagatgga acagctgaat atgggccaaa caggatatct gtggtaagca 5880
gttcctgccc cggctcaggg ccaagaacag atggtcccca gatgcggtcc agccctcagc 5940
agtttctaga gaaccatcag atgtttccag ggtgccccaa ggacctgaaa tgaccctgtg 6000
ccttatttga actaaccaat cagttcgctt ctcgcttctg ttcgcgcgct tctgctcccc 6060
gagctcaata aaagagccca caacccctca ctcggggcgc cagtcctccg attgactgag 6120
tcgcccgggt acccgtgtat ccaataaacc ctcttgcagt tgcatccgac ttgtggtctc 6180
gctgttcctt gggagggtct cctctgagtg attgactacc cgtcagcggg ggtctttcat 6240
t 6241

<210> SEQ ID NO 10
<211> LENGTH: 6818
<212> TYPE: DNA
<213> ORGANISM: Artificial Sequence
<220> FEATURE:
<223> OTHER INFORMATION: Synthetic

<400> SEQUENCE: 10
tttgaaagac cccacccgta ggtggcaagc tagcttaagt aacgccactt tgcaaggcat 60
ggaaaaatac ataactgaga atagaaaagt tcagatcaag gtcaggaaca aagaaacagc 120
tgaataccaa acaggatatc tgtggtaagc ggttcctgcc ccggctcagg gccaagaaca 180
gatgagacag ctgagtgatg ggccaaacag gatatctgtg gtaagcagtt cctgccccgg 240
ctcggggcca agaacagatg gtccccagat gcggtccagc cctcagcagt ttctagtgaa 300
tcatcagatg tttccagggt gccccaagga cctgaaaatg accctgtacc ttatttgaac 360
taaccaatca gttcgcttct cgcttctgtt cgcgcgcttc cgctctccga gctcaataaa 420
agagcccaca acccctcact cggcgcgcca gtcttccgat agactgcgtc gcccgggtac 480
ccgtattccc aataaagcct cttgctgttt gcatccgaat cgtggtctcg ctgttccttg 540
ggagggtctc ctctgagtga ttgactaccc acgacggggg tctttcattt gggggctcgt 600
ccgggatttg gagacccctg cccagggacc accgacccac caccgggagg taagctggcc 660
agcaacttat ctgtgtctgt ccgattgtct agtgtctatg tttgatgtta tgcgcctgcg 720
tctgtactag ttagctaact agctctgtat ctggcggacc cgtggtggaa ctgacgagtt 780
ctgaacaccc ggccgcaacc ctgggagacg tcccagggac tttgggggcc gtttttgtgg 840
cccgacctga ggaagggagt cgatgtggaa tccgaccccg tcaggatatg tggttctggt 900
aggagacgag aacctaaaac agttcccgcc tccgtctgaa tttttgcttt cggtttggaa 960
ccgaagccgc gcgtcttgtc tgctgcagcg ctgcagcatc gttctgtgtt gtctctgtct 1020
gactgtgttt ctgtatttgt ctgaaaatta gggccagact gttaccactc ccttaagttt 1080
gaccttaggt cactggaaag atgtcgagcg gatcgctcac aaccagtcgg tagatgtcaa 1140
gaagagacgt tgggttacct tctgctctgc agaatggcca acctttaacg tcggatggcc 1200
gcgagacggc acctttaacc gagacctcat cacccaggtt aagatcaagg tcttttcacc 1260
tggcccgcat ggacacccag accaggtccc ctacatcgtg acctgggaag ccttggcttt 1320 tgaccccccct ccctgggtca agccctttgt acaccctaag cctccgcctc ctcttcctcc 1380
atccgccccg tctctccccc ttgaacctcc tcgttcgacc ccgcctcgat cctcccttta 1440

-continued

```
tccagccctc actccttctc taggcgccgg aattccgatc tgatcaagag acaggatgag   1500
gatcgtttcg catgattgaa caagatggat tgcacgcagg ttctccggcc gcttgggtgg   1560
agaggctatt cggctatgac tgggcacaac agacaatcgg ctgctctgat gccgccgtgt   1620
tccggctgtc agcgcagggg cgcccggttc tttttgtcaa gaccgacctg tccggtgccc   1680
tgaatgaact gcaggacgag gcagcgcggc tatcgtggct ggccacgacg ggcgttcctt   1740
gcgcagctgt gctcgacgtt gtcactgaag cgggaaggga ctggctgcta ttgggcgaag   1800
tgccggggca ggatctcctg tcatctcacc ttgctcctgc cgagaaagta tccatcatgg   1860
ctgatgcaat gcggcggctg catacgcttg atccggctac ctgcccattc gaccaccaag   1920
cgaaacatcg catcgagcga gcacgtactc ggatggaagc cggtcttgtc gatcaggatg   1980
atctggacga agagcatcag gggctcgcgc cagccgaact gttcgccagg ctcaaggcgc   2040
gcatgcccga cggcgaggat ctcgtcgtga cccatggcga tgcctgcttg ccgaatatca   2100
tggtggaaaa tggccgcttt tctggattca tcgactgtgg ccggctgggt gtggcggacc   2160
gctatcagga catagcgttg gctacccgtg atattgctga agagcttggc ggcgaatggg   2220
ctgaccgctt cctcgtgctt tacggtatcg ccgctcccga ttcgcagcgc atcgccttct   2280
atcgccttct tgacgagttc ttctgagcgg gactctgggg ttcgaaatga ccgaccaagc   2340
gacgcccaac ctgccatcac gagatttcga ttccaccgcc gccttctatg aaaggttggg   2400
cttcggaatc gttttccggg acgccggctg gatgatcctc cagcgcgggg atctcatgct   2460
ggagttcttc gcccacccg ggctcgatcc cctcgcgagt tggttcagct gctgcctgag   2520
gctggacgac ctcgcggagt tctaccggca gtgcaaatcc gtcggcatcc aggaaaccag   2580
cagcggctat ccgcgcatcc atgcccccga actgcaggag tggggaggca cgatggccgc   2640
tttggtcgag gcggatccgg ccattagcca tattattcat tggttatata gcataaatca   2700
atattggcta ttggccattg catacgttgt atccatatca taatatgtac atttatattg   2760
gctcatgtcc aacattaccg ccatgttgac attgattatt gactagttat taatagtaat   2820
caattacggg gtcattagtt catagcccat atatggagtt ccgcgttaca taacttacgg   2880
taaatggccc gcctggctga ccgcccaacg acccccgccc attgacgtca ataatgacgt   2940
atgttcccat agtaacgcca atagggactt tccattgacg tcaatgggtg gagtatttac   3000
ggtaaactgc ccacttggca gtacatcaag tgtatcatat gccaagtacg ccccctattg   3060
acgtcaatga cggtaaatgg cccgcctggc attatgccca gtacatgacc ttatgggact   3120
ttcctacttg gcagtacatc tacgtattag tcatcgctat taccatggtg atgcggtttt   3180
ggcagtacat caatgggcgt ggatagcggt ttgactcacg gggatttcca agtctccacc   3240
ccattgacgt caatgggagt ttgttttggc accaaaatca acgggacttt ccaaaatgtc   3300
gtaacaactc cgccccattg acgcaaatgg gcggtaggca tgtacggtgg gaggtctata   3360
taagcagagc tcgtttagtg aaccgtcaga tcgcctggag acgccatcca cgctgttttg   3420
acctccatag aagacaccgg gaccgatcca gcctccgcgg ccccaagctt ggatctcacc   3480
atggagttgg gactgcgctg ggcttcctc gttgctcttt taagaggtgt ccagtgtcag   3540
gtgcaattgg tggagtctgg gggaggcgtg gtccagcctg ggaggtccct gagactctcc   3600
tgtgcagcgt ctggattcgc cttcagtaga tatggcatgc actgggtccg ccaggctcca   3660
ggcaaggggc tggagtgggt ggcagttata tggtatgatg gaagtaataa atactatgca   3720
gactccgtga agggccgatt caccatctcc agagacaatt ccaagaacac gcagtatctg   3780
```

-continued

```
caaatgaaca gcctgagagc cgaggacacg gctgtgtatt actgtgcgag aggcggtgac   3840
ttcctctact actactatta cggtatggac gtctggggcc aagggaccac ggtcaccgtc   3900
tcctcagcct ccaccaaggg cccatcggtc ttccccctgg caccctctag caagagcacc   3960
tctgggggca cagcggccct gggctgcctg gtcaaggact acttccccga accggtgacg   4020
gtgtcgtgga actcaggcgc cctgaccagc ggcgtgcaca ccttcccggc tgtcctacag   4080
tcctcaggac tctactccct cagcagcgtg gtgaccgtgc cctccagcag cttgggcacc   4140
cagacctaca tctgcaacgt gaatcacaag cccagcaaca ccaaggtgga caagagagtt   4200
gagcccaaat cttgtgacaa aactcacaca tgcccaccgt gcccagcacc tgaactcctg   4260
gggggaccgt cagtcttcct cttcccccca aaacccaagg acaccctcat gatctcccgg   4320
acccctgagg tcacatgcgt ggtggtggac gtgagccacg aagaccctga ggtcaagttc   4380
aactggtacg tggacggcgt ggaggtgcat aatgccaaga caaagccgcg ggaggagcag   4440
tacaacagca cgtaccgtgt ggtcagcgtc ctcaccgtcc tgcaccagga ctggctgaat   4500
ggcaaggagt acaagtgcaa ggtctccaac aaagccctcc cagcccccat cgagaaaacc   4560
atctccaaag ccaaagggca gccccgagaa ccacaggtgt acaccctgcc cccatcccgg   4620
gaggagatga ccaagaacca ggtcagcctg acctgcctgg tcaaaggctt ctatcccagc   4680
gacatcgccg tggagtggga gagcaatggg cagccggaga acaactacaa gaccacgcct   4740
cccgtgctgg actccgacgg ctccttcttc ctctatagca agctcaccgt ggacaagagc   4800
aggtggcagc aggggaacgt cttctcatgc tccgtgatgc atgaggctct gcacaaccac   4860
tacacgcaga agagcctctc cctgtctccg ggcatcctat tccatgccac ccaggccgac   4920
atccagatga cccagtctcc atcctccctg tctgcatctg taggagacag agtcaccatc   4980
acttgccggg cgagtcaggg cattagcaat tatttagcct ggtatcagca gaaaacaggg   5040
aaagttccta agttcctgat ctatgaagca tccactttgc aatcaggggt cccatctcgg   5100
ttcagtggcg gtggatctgg gacagatttc actctcacca tcagcagcct gcagcctgaa   5160
gatgttgcaa cttattactg tcaaaattat aacagtgccc cattcacttt cggccctggg   5220
accaaagtgg atatcaaacg aactgtggct gcaccctctg tcttcatctt cccgccatct   5280
gatgagcagt tgaaatctgg aactgctagc gttgtgtgcc tgctgaataa cttctatccc   5340
agagaggcca aagtacagtg gaaggtggat aacgccctcc aatcgggtaa ctcccaggag   5400
agtgtcacag agcaggacag caaggacagc acctacagcc tcagcagcac cctgacgctg   5460
agcaaagcag actacgagaa acacaaagtc tacgcctgcg aagtcaccca tcagggcctg   5520
agctcgcccg tcacaaagag cttcaacagg ggagagtgtt aggaattcgc ggccgctcga   5580
catcgataat caacctctgg attacaaaat ttgtgaaaga ttgactggta ttcttaacta   5640
tgttgctcct tttacgctat gtggatacgc tgctttaatg cctttgtatc atgctattgc   5700
ttcccgtatg gctttcattt tctcctcctt gtataaatcc tggttgctgt ctctttatga   5760
ggagttgtgg cccgttgtca ggcaacgtgg cgtggtgtgc actgtgtttg ctgacgcaac   5820
ccccactggt tggggcattg ccaccacctg tcagctcctt tccgggactt tcgctttccc   5880
cctccctatt gccacggcgg aactcatcgc cgcctgcctt gcccgctgct ggacaggggc   5940
tcggctgttg ggcactgaca attccgtggt gttgtcgggg aaatcatcgt cctttccttg   6000
gctgctcgcc tgtgttgcca cctggattct gcgcgggacg tccttctgct acgtcccttc   6060
ggccctcaat ccagcggacc ttccttcccg cggcctgctg ccggctctgc ggcctcttcc   6120
gcgtcttcgc cttcgccctc agacgagtcg gatctccctt tgggccgcct ccccgcctga   6180
```

tcgataaaat aaaagatttt atttagtctc cagaaaaagg ggggaatgaa agaccccacc 6240
tgtaggtttg gcaagctagc ttaagtaacg ccattttgca aggcatggaa aaatacataa 6300
ctgagaatag agaagttcag atcaaggtca ggaacagatg gaacagctga atatgggcca 6360
aacaggatat ctgtggtaag cagttcctgc cccggctcag ggccaagaac agatggaaca 6420
gctgaatatg ggccaaacag gatatctgtg gtaagcagtt cctgccccgg ctcagggcca 6480
agaacagatg gtccccagat gcggtccagc cctcagcagt ttctagagaa ccatcagatg 6540
tttccagggt gccccaagga cctgaaatga ccctgtgcct tatttgaact aaccaatcag 6600
ttcgcttctc gcttctgttc gcgcgcttct gctccccgag ctcaataaaa gagcccacaa 6660
cccctcactc ggggcgccag tcctccgatt gactgagtcg cccgggtacc cgtgtatcca 6720
ataaaccctc ttgcagttgc atccgacttg tggtctcgct gttccttggg agggtctcct 6780
ctgagtgatt gactacccgt cagcgggggt ctttcatt 6818

<210> SEQ ID NO 11
<211> LENGTH: 6829
<212> TYPE: DNA
<213> ORGANISM: Artificial Sequence
<220> FEATURE:
<223> OTHER INFORMATION: Synthetic

<400> SEQUENCE: 11
tttgaaagac cccacccgta ggtggcaagc tagcttaagt aacgccactt tgcaaggcat 60
ggaaaaatac ataactgaga atagaaaagt tcagatcaag gtcaggaaca aagaaacagc 120
tgaataccaa acaggatatc tgtggtaagc ggttcctgcc ccggctcagg gccaagaaca 180
gatgagacag ctgagtgatg ggccaaacag gatatctgtg gtaagcagtt cctgccccgg 240
ctcggggcca agaacagatg gtccccagat gcggtccagc cctcagcagt ttctagtgaa 300
tcatcagatg tttccagggt gccccaagga cctgaaaatg accctgtacc ttatttgaac 360
taaccaatca gttcgcttct cgcttctgtt cgcgcgcttc cgctctccga gctcaataaa 420
agagcccaca acccctcact cggcgcgcca gtcttccgat agactgcgtc gcccgggtac 480
ccgtattccc aataaagcct cttgctgttt gcatccgaat cgtggtctcg ctgttccttg 540
ggagggtctc ctctgagtga ttgactaccc acgacggggg tctttcattt gggggctcgt 600
ccgggatttg gagacccctg cccagggacc accgacccac caccgggagg taagctggcc 660
agcaacttat ctgtgtctgt ccgattgtct agtgtctatg tttgatgtta tgcgcctgcg 720
tctgtactag ttagctaact agctctgtat ctggcggacc cgtggtggaa ctgacgagtt 780
ctgaacaccc ggccgcaacc ctgggagacg tcccagggac tttgggggcc gtttttgtgg 840
cccgacctga ggaagggagt cgatgtggaa tccgaccccg tcaggatatg tggttctggt 900
aggagacgag aacctaaaac agttcccgcc tccgtctgaa tttttgcttt cggtttggaa 960
ccgaagccgc gcgtcttgtc tgctgcagcg ctgcagcatc gttctgtgtt gtctctgtct 1020
gactgtgttt ctgtatttgt ctgaaaatta gggccagact gttaccactc ccttaagttt 1080
gaccttaggt cactggaaag atgtcgagcg gatcgctcac aaccagtcgg tagatgtcaa 1140
gaagagacgt tgggttacct tctgctctgc agaatggcca acctttaacg tcggatggcc 1200
gcgagacggc acctttaacc gagacctcat cacccaggtt aagatcaagg tcttttcacc 1260
tggcccgcat ggacacccag accaggtccc ctacatcgtg acctgggaag ccttggcttt 1320 tgaccccccct ccctgggtca agccctttgt acaccctaag cctccgcctc ctcttcctcc 1380

-continued

```
atccgccccg tctctccccc ttgaacctcc tcgttcgacc ccgcctcgat cctcccttta   1440
tccagccctc actccttctc taggcgccgg aattccgatc tgatcaagag acaggatgag   1500
gatcgtttcg catgattgaa caagatggat tgcacgcagg ttctccggcc gcttgggtgg   1560
agaggctatt cggctatgac tgggcacaac agacaatcgg ctgctctgat gccgccgtgt   1620
tccggctgtc agcgcagggg cgcccggttc tttttgtcaa gaccgacctg tccggtgccc   1680
tgaatgaact gcaggacgag gcagcgcggc tatcgtggct ggccacgacg ggcgttcctt   1740
gcgcagctgt gctcgacgtt gtcactgaag cgggaaggga ctggctgcta ttgggcgaag   1800
tgccggggca ggatctcctg tcatctcacc ttgctcctgc cgagaaagta tccatcatgg   1860
ctgatgcaat gcggcggctg catacgcttg atccggctac ctgcccattc gaccaccaag   1920
cgaaacatcg catcgagcga gcacgtactc ggatggaagc cggtcttgtc gatcaggatg   1980
atctggacga agagcatcag gggctcgcgc cagccgaact gttcgccagg ctcaaggcgc   2040
gcatgcccga cggcgaggat ctcgtcgtga cccatggcga tgcctgcttg ccgaatatca   2100
tggtggaaaa tggccgcttt tctggattca tcgactgtgg ccggctgggt gtggcggacc   2160
gctatcagga catagcgttg gctacccgtg atattgctga agagcttggc ggcgaatggg   2220
ctgaccgctt cctcgtgctt tacggtatcg ccgctcccga ttcgcagcgc atcgccttct   2280
atcgccttct tgacgagttc ttctgagcgg gactctgggg ttcgaaatga ccgaccaagc   2340
gacgcccaac ctgccatcac gagatttcga ttccaccgcc gccttctatg aaaggttggg   2400
cttcggaatc gttttccggg acgccggctg gatgatcctc cagcgcgggg atctcatgct   2460
ggagttcttc gcccaccccg ggctcgatcc cctcgcgagt tggttcagct gctgcctgag   2520
gctggacgac ctcgcggagt tctaccggca gtgcaaatcc gtcggcatcc aggaaaccag   2580
cagcggctat ccgcgcatcc atgcccccga actgcaggag tggggaggca cgatggccgc   2640
tttggtcgag gcggatccgg ccattagcca tattattcat tggttatata gcataaatca   2700
atattggcta ttggccattg catacgttgt atccatatca taatatgtac atttatattg   2760
gctcatgtcc aacattaccg ccatgttgac attgattatt gactagttat taatagtaat   2820
caattacggg gtcattagtt catagcccat atatggagtt ccgcgttaca taacttacgg   2880
taaatggccc gcctggctga ccgcccaacg acccccgccc attgacgtca ataatgacgt   2940
atgttcccat agtaacgcca atagggactt tccattgacg tcaatgggtg gagtatttac   3000
ggtaaactgc ccacttggca gtacatcaag tgtatcatat gccaagtacg ccccctattg   3060
acgtcaatga cggtaaatgg cccgcctggc attatgccca gtacatgacc ttatgggact   3120
ttcctacttg gcagtacatc tacgtattag tcatcgctat taccatggtg atgcggtttt   3180
ggcagtacat caatgggcgt ggatagcggt ttgactcacg gggatttcca agtctccacc   3240
ccattgacgt caatgggagt ttgttttggc accaaaatca acgggacttt ccaaaatgtc   3300
gtaacaactc cgccccattg acgcaaatgg gcggtaggca tgtacggtgg gaggtctata   3360
taagcagagc tcgtttagtg aaccgtcaga tcgcctggag acgccatcca cgctgttttg   3420
acctccatag aagacaccgg gaccgatcca gcctccgcgg ccccaagctt ctcgagcacc   3480
atggaatgga gcggagtctt tatctttctc ctgtcagtaa ctgcaggtgt ccactccgag   3540
gtgcagctgg tggagtctgg tggaggcttg gtaaagcctg gaggttccct tagactctcc   3600
tgtgcagcct ctggttacac tttcagtaac tattggatcg gatgggtccg ccaggctcca   3660
ggcaaagggc tggagtggat tggcgatatc taccctggag ggaactacat caggaacaat   3720
gagaagttca aggacaagac caccctgtca gcagatactt ccaagaacac agcctatctg   3780
```

-continued

```
caaatgaaca gcctgaaaac cgaggacaca gccgtgtatt actgtggaag cagcttcggt   3840
agtaactacg tgttcgcctg gtttacttac tggggccaag ggactctggt cacagtctcc   3900
tcagcttcca ccaagggccc atccgtcttc cccctggcgc cctgctccag gagcacctcc   3960
gagagcacag ccgccctggg ctgcctggtc aaggactact tccccgaacc ggtgacggtg   4020
tcgtggaact caggcgccct gaccagcggc gtgcacacct tcccggctgt cctacagtcc   4080
tcaggactct actccctcag cagcgtggtg accgtgccct ccagcagctt gggcacgaag   4140
acctacacct gcaacgtaga tcacaagccc agcaacacca aggtggacaa gagagttgag   4200
tccaaatatg gtcccccatg cccatcatgc ccagcacctg agttcctggg gggaccatca   4260
gtcttcctgt tccccccaaa acccaaggac actctcatga tctcccggac ccctgaggtc   4320
acgtgcgtgg tggtggacgt gagccaggaa gaccccgagg tccagttcaa ctggtacgtg   4380
gatggcgtgg aggtgcataa tgccaagaca aagccgcggg aggagcagtt caacagcacg   4440
taccgtgtgg tcagcgtcct caccgtcctg caccaggact ggctgaacgg caaggagtac   4500
aagtgcaagg tctccaacaa aggcctcccg tcctccatcg agaaaaccat ctccaaagcc   4560
aaagggcagc cccgagagcc acaggtgtac accctgcccc catcccagga ggagatgacc   4620
aagaaccagg tcagcctgac ctgcctggtc aaaggcttct accccagcga catcgccgtg   4680
gagtgggaga gcaatgggca gccggagaac aactacaaga ccacgcctcc cgtgctggac   4740
tccgacggct ccttcttcct ctacagcagg ctaaccgtgg acaagagcag gtggcaggag   4800
gggaatgtct tctcatgctc cgtgatgcat gaggctctgc acaaccacta cacacagaag   4860
agcctctccc tgtctctggg catcctattc catgccaccc aggccgacat tgtgatgacc   4920
caatctccac tctccctgcc tgtcactcct ggagagccag cctccatctc ttgcagatct   4980
agtcagcgcc ttctgagcag ttatggacat acctatttac attggtacct acagaagcca   5040
ggccagtctc cacagctcct gatctacgaa gtttccaacc gattttctgg ggtcccagac   5100
aggttcagtg gcagtgggtc agggacagat ttcacactta agatcagtag agtggaggct   5160
gaggatgtgg gagtttatta ctgctctcaa agtacacatg ttcctctcac gttcggacag   5220
gggaccaagg tggaaataaa acgaactgtg gctgcaccat ctgtcttcat cttcccgcca   5280
tctgatgagc agttgaaatc tggaactgcc tctgttgtgt gcctgctgaa taacttctat   5340
cccagagagg ccaaagtaca gtggaaggtg gataacgccc tccaatcggg taactcccag   5400
gagagtgtca cagagcagga cagcaaggac agcacctaca gcctcagcag caccctgacg   5460
ctgagcaaag cagactacga gaaacacaaa gtctacgcct gcgaagtcac ccatcagggc   5520
ctgagctcgc ccgtcacaaa gagcttcaac aggggagagt gttagaggga gaagtgcccc   5580
cacctgctcc tcgacatcga taatcaacct ctggattaca aaatttgtga aagattgact   5640
ggtattctta actatgttgc tccttttacg ctatgtggat acgctgcttt aatgcctttg   5700
tatcatgcta ttgcttcccg tatggctttc attttctcct ccttgtataa atcctggttg   5760
ctgtctcttt atgaggagtt gtggcccgtt gtcaggcaac gtggcgtggt gtgcactgtg   5820
tttgctgacg caacccccac tggttggggc attgccacca cctgtcagct cctttccggg   5880
actttcgctt tccccctccc tattgccacg gcggaactca tcgccgcctg ccttgcccgc   5940
tgctggacag gggctcggct gttgggcact gacaattccg tggtgttgtc ggggaaatca   6000
tcgtcctttc cttggctgct cgcctgtgtt gccacctgga ttctgcgcgg gacgtccttc   6060
tgctacgtcc cttcggccct caatccagcg gaccttcctt cccgcggcct gctgccggct   6120
```

-continued

```
ctgcggcctc ttccgcgtct tcgccttcgc cctcagacga gtcggatctc cctttgggcc   6180

gcctccccgc atcgataaaa taaaagattt tatttagtct ccagaaaaag gggggaatga   6240

aagaccccac ctgtaggttt ggcaagctag cttaagtaac gccattttgc aaggcatgga   6300

aaaatacata actgagaata gagaagttca gatcaaggtc aggaacagat ggaacagctg   6360

aatatgggcc aaacaggata tctgtggtaa gcagttcctg ccccggctca gggccaagaa   6420

cagatggaac agctgaatat gggccaaaca ggatatctgt ggtaagcagt tcctgccccg   6480

gctcagggcc aagaacagat ggtccccaga tgcggtccag ccctcagcag tttctagaga   6540

accatcagat gtttccaggg tgccccaagg acctgaaatg accctgtgcc ttatttgaac   6600

taaccaatca gttcgcttct cgcttctgtt cgcgcgcttc tgctccccga gctcaataaa   6660

agagcccaca acccctcact cggggcgcca gtcctccgat tgactgagtc gcccgggtac   6720

ccgtgtatcc aataaaccct cttgcagttg catccgactt gtggtctcgc tgttccttgg   6780

gagggtctcc tctgagtgat tgactacccg tcagcggggg tctttcatt               6829
```

<210> SEQ ID NO 12
<211> LENGTH: 6858
<212> TYPE: DNA
<213> ORGANISM: Artificial Sequence
<220> FEATURE:
<223> OTHER INFORMATION: Synthetic

<400> SEQUENCE: 12

```
tttgaaagac ccccacccgta ggtggcaagc tagcttaagt aacgccactt tgcaaggcat     60

ggaaaaatac ataactgaga atagaaaagt tcagatcaag gtcaggaaca aagaaacagc    120

tgaataccaa acaggatatc tgtggtaagc ggttcctgcc ccggctcagg gccaagaaca    180

gatgagacag ctgagtgatg ggccaaacag gatatctgtg gtaagcagtt cctgccccgg    240

ctcggggcca agaacagatg gtccccagat gcggtccagc cctcagcagt ttctagtgaa    300

tcatcagatg tttccagggt gccccaagga cctgaaaatg accctgtacc ttatttgaac    360

taaccaatca gttcgcttct cgcttctgtt cgcgcgcttc cgctctccga gctcaataaa    420

agagcccaca acccctcact cggcgcgcca gtcttccgat agactgcgtc gcccgggtac    480

ccgtattccc aataaagcct cttgctgttt gcatccgaat cgtggtctcg ctgttccttg    540

ggagggtctc ctctgagtga ttgactaccc acgacggggg tctttcattt gggggctcgt    600

ccgggatttg gagacccctg cccagggacc accgacccac caccgggagg taagctggcc    660

agcaacttat ctgtgtctgt ccgattgtct agtgtctatg tttgatgtta tgcgcctgcg    720

tctgtactag ttagctaact agctctgtat ctggcggacc cgtggtggaa ctgacgagtt    780

ctgaacaccc ggccgcaacc ctgggagacg tcccagggac tttgggggcc gtttttgtgg    840

cccgacctga ggaagggagt cgatgtggaa tccgaccccg tcaggatatg tggttctggt    900

aggagacgag aacctaaaac agttcccgcc tccgtctgaa tttttgcttt cggtttggaa    960

ccgaagccgc gcgtcttgtc tgctgcagcg ctgcagcatc gttctgtgtt gtctctgtct   1020

gactgtgttt ctgtatttgt ctgaaaatta gggccagact gttaccactc ccttaagttt   1080

gaccttaggt cactggaaag atgtcgagcg gatcgctcac aaccagtcgg tagatgtcaa   1140

gaagagacgt tgggttacct tctgctctgc agaatggcca acctttaacg tcggatggcc   1200

gcgagacggc acctttaacc gagacctcat cacccaggtt aagatcaagg tcttttcacc   1260

tggcccgcat ggacacccag accaggtccc ctacatcgtg acctgggaag ccttggcttt   1320

tgaccccccct ccctgggtca agccctttgt acaccctaag cctccgcctc ctcttcctcc   1380
```

-continued

```
atccgccccg tctctccccc ttgaacctcc tcgttcgacc ccgcctcgat cctcccttta   1440
tccagccctc actccttctc taggcgccgg aattccgatc tgatcaagag acaggatgag   1500
gatcgtttcg catgattgaa caagatggat tgcacgcagg ttctccggcc gcttgggtgg   1560
agaggctatt cggctatgac tgggcacaac agacaatcgg ctgctctgat gccgccgtgt   1620
tccggctgtc agcgcagggg cgcccggttc tttttgtcaa gaccgacctg tccggtgccc   1680
tgaatgaact gcaggacgag gcagcgcggc tatcgtggct ggccacgacg ggcgttcctt   1740
gcgcagctgt gctcgacgtt gtcactgaag cgggaaggga ctggctgcta ttgggcgaag   1800
tgccggggca ggatctcctg tcatctcacc ttgctcctgc cgagaaagta tccatcatgg   1860
ctgatgcaat gcggcggctg catacgcttg atccggctac ctgcccattc gaccaccaag   1920
cgaaacatcg catcgagcga gcacgtactc ggatggaagc cggtcttgtc gatcaggatg   1980
atctggacga agagcatcag gggctcgcgc cagccgaact gttcgccagg ctcaaggcgc   2040
gcatgcccga cggcgaggat ctcgtcgtga cccatggcga tgcctgcttg ccgaatatca   2100
tggtggaaaa tggccgcttt tctggattca tcgactgtgg ccggctgggt gtggcggacc   2160
gctatcagga catagcgttg gctacccgtg atattgctga agagcttggc ggcgaatggg   2220
ctgaccgctt cctcgtgctt tacggtatcg ccgctcccga ttcgcagcgc atcgccttct   2280
atcgccttct tgacgagttc ttctgagcgg gactctgggg ttcgaaatga ccgaccaagc   2340
gacgcccaac ctgccatcac gagatttcga ttccaccgcc gccttctatg aaaggttggg   2400
cttcggaatc gttttccggg acgccggctg gatgatcctc cagcgcgggg atctcatgct   2460
ggagttcttc gcccaccccg ggctcgatcc cctcgcgagt tggttcagct gctgcctgag   2520
gctggacgac ctcgcggagt tctaccggca gtgcaaatcc gtcggcatcc aggaaaccag   2580
cagcggctat ccgcgcatcc atgcccccga actgcaggag tggggaggca cgatggccgc   2640
tttggtcgag gcggatccgg ccattagcca tattattcat tggttatata gcataaatca   2700
atattggcta ttggccattg catacgttgt atccatatca taatatgtac atttatattg   2760
gctcatgtcc aacattaccg ccatgttgac attgattatt gactagttat taatagtaat   2820
caattacggg gtcattagtt catagcccat atatggagtt ccgcgttaca taacttacgg   2880
taaatggccc gcctggctga ccgcccaacg acccccgccc attgacgtca ataatgacgt   2940
atgttcccat agtaacgcca atagggactt tccattgacg tcaatgggtg gagtatttac   3000
ggtaaactgc ccacttggca gtacatcaag tgtatcatat gccaagtacg ccccctattg   3060
acgtcaatga cggtaaatgg cccgcctggc attatgccca gtacatgacc ttatgggact   3120
ttcctacttg gcagtacatc tacgtattag tcatcgctat taccatggtg atgcggtttt   3180
ggcagtacat caatgggcgt ggatagcggt ttgactcacg gggatttcca agtctccacc   3240
ccattgacgt caatgggagt ttgttttggc accaaaatca acgggacttt ccaaaatgtc   3300
gtaacaactc cgccccattg acgcaaatgg gcggtaggca tgtacggtgg gaggtctata   3360
taagcagagc tcgtttagtg aaccgtcaga tcgcctggag acgccatcca cgctgttttg   3420
acctccatag aagacaccgg gaccgatcca gcctccgcgg ccccaagctt ctcgacggat   3480
ccccgggaat tcaggacctc accatgggat ggagctgtat catcctcttc ttggtagcaa   3540
cagctacagg tgtccactcc gaggtccaac tggtggagag cggtggaggt gttgtgcaac   3600
ctggccggtc cctgcgcctg tcctgctccg catctggctt cgatttcacc acatattgga   3660
tgagttgggt gagacaggca cctggaaaag gtcttgagtg gattggagaa attcatccag   3720
```

-continued

```
atagcagtac gattaactat gcgccgtctc taaaggatag atttacaata tcgcgagaca   3780
acgccaagaa cacattgttc ctgcaaatgg acagcctgag acccgaagac accggggtct   3840
atttttgtgc aagcctttac ttcggcttcc cctggtttgc ttattggggc caagggaccc   3900
cggtcaccgt ctcctcagcc tccaccaagg gcccatcggt cttccccctg gcaccctcct   3960
ccaagagcac ctctgggggc acagcggccc tgggctgcct ggtcaaggac tacttccccg   4020
aaccggtgac ggtgtcgtgg aactcaggcg ccctgaccag cggcgtgcac accttcccgg   4080
ctgtcctaca gtcctcagga ctctactccc tcagcagcgt ggtgaccgtg ccctccagca   4140
gcttgggcac ccagacctac atctgcaacg tgaatcacaa gcccagcaac accaaggtgg   4200
acaagagagt tgagcccaaa tcttgtgaca aaactcacac atgcccaccg tgcccagcac   4260
ctgaactcct ggggggaccg tcagtcttcc tcttcccccc aaaacccaag gacaccctca   4320
tgatctcccg gacccctgag gtcacatgcg tggtggtgga cgtgagccac gaagaccctg   4380
aggtcaagtt caactggtac gtggacggcg tggaggtgca taatgccaag acaaagccgc   4440
gggaggagca gtacaacagc acgtaccgtg tggtcagcgt cctcaccgtc ctgcaccagg   4500
actggctgaa tggcaaggag tacaagtgca aggtctccaa caaagccctc ccagccccca   4560
tcgagaaaac catctccaaa gccaaagggc agccccgaga accacaggtg tacaccctgc   4620
ccccatcccg ggaggagatg accaagaacc aggtcagcct gacctgcctg gtcaaaggct   4680
tctatcccag cgacatcgcc gtggagtggg agagcaatgg gcagccggag aacaactaca   4740
agaccacgcc tcccgtgctg gactccgacg gctccttctt cctctatagc aagctcaccg   4800
tggacaagag caggtggcag caggggaacg tcttctcatg ctccgtgatg catgaggctc   4860
tgcacaacca ctacacgcag aagagcctct ccctgtctcc cgggaaatga aagccgaatt   4920
cgcccctctc cctccccccc ccctaacgtt actggccgaa gccgcttgga ataaggccgg   4980
tgtgcgtttg tctatatgtt attttccacc atattgccgt cttttggcaa tgtgagggcc   5040
cggaaacctg gccctgtctt cttgacgagc attcctaggg gtctttcccc tctcgccaaa   5100
ggaatgcaag gtctgttgaa tgtcgtgaag gaagcagttc ctctggaagc ttcttgaaga   5160
caaacaacgt ctgtagcgac cctttgcagg cagcggaacc ccccacctgg cgacaggtgc   5220
ctctgcggcc aaaagccacg tgtataagat acacctgcaa aggcggcaca accccagtgc   5280
cacgttgtga gttggatagt tgtggaaaga gtcaaatggc tctcctcaag cgtattcaac   5340
aaggggctga aggatgccca gaaggtaccc cattgtatgg gatctgatct ggggcctcgg   5400
tgcacatgct ttacatgtgt ttagtcgagg ttaaaaaaac gtctaggccc cccgaaccac   5460
ggggacgtgg ttttcctttg aaaaacacga tgataatatg gcctcctttg tctctctgct   5520
cctggtaggc atcctattcc atgccaccca ggccgacatc cagctgaccc agagcccaag   5580
cagcctgagc gccagcgtgg gtgacagagt gaccatcacc tgtaaggcca gtcaggatgt   5640
gggtacttct gtagcctggt accagcagaa gccaggtaag gctccaaagc tgctgatcta   5700
ctggacatcc acccggcaca ctggtgtgcc aagcagattc agcggtagcg gtagcggtac   5760
cgacttcacc ttcaccatca gcagcctcca gccagaggac atcgccacct actactgcca   5820
gcaatatagc ctctatcggt cgttcggcca agggaccaag gtggaaatca aacgaactgt   5880
ggctgcacca tctgtcttca tcttcccgcc atctgatgag cagttgaaat ctggaactgc   5940
ctctgttgtg tgcctgctga ataacttcta tcccagagag gccaaagtac agtggaaggt   6000
ggataacgcc ctccaatcgg gtaactccca ggagagtgtc acagagcagg acagcaagga   6060
cagcacctac agcctcagca gcaccctgac gctgagcaaa gcagactacg agaaacacaa   6120
```

-continued agtctacgcc tgcgaagtca cccatcaggg cctgagctcg cccgtcacaa agagcttcaa 6180
caggggagag tgttagagat ctaggcctcc taggtcgaca tcgataaaat aaaagatttt 6240
atttagtctc cagaaaaagg ggggaatgaa agaccccacc tgtaggtttg gcaagctagc 6300
ttaagtaacg ccattttgca aggcatggaa aaatacataa ctgagaatag agaagttcag 6360
atcaaggtca ggaacagatg gaacagctga atatgggcca aacaggatat ctgtggtaag 6420
cagttcctgc cccggctcag ggccaagaac agatggaaca gctgaatatg ggccaaacag 6480
gatatctgtg gtaagcagtt cctgccccgg ctcagggcca agaacagatg gtccccagat 6540
gcggtccagc cctcagcagt ttctagagaa ccatcagatg tttccagggt gccccaagga 6600
cctgaaatga ccctgtgcct tatttgaact aaccaatcag ttcgcttctc gcttctgttc 6660
gcgcgcttct gctccccgag ctcaataaaa gagcccacaa cccctcactc ggggcgccag 6720
tcctccgatt gactgagtcg cccgggtacc cgtgtatcca ataaaccctc ttgcagttgc 6780
atccgacttg tggtctcgct gttccttggg agggtctcct ctgagtgatt gactacccgt 6840
cagcgggggt ctttcatt 6858

<210> SEQ ID NO 13
<211> LENGTH: 6867
<212> TYPE: DNA
<213> ORGANISM: Artificial Sequence
<220> FEATURE:
<223> OTHER INFORMATION: Synthetic

<400> SEQUENCE: 13
tttgaaagac cccacccgta ggtggcaagc tagcttaagt aacgccactt tgcaaggcat 60
ggaaaaatac ataactgaga atagaaaagt tcagatcaag gtcaggaaca aagaaacagc 120
tgaataccaa acaggatatc tgtggtaagc ggttcctgcc ccggctcagg gccaagaaca 180
gatgagacag ctgagtgatg ggccaaacag gatatctgtg gtaagcagtt cctgccccgg 240
ctcggggcca agaacagatg gtccccagat gcggtccagc cctcagcagt ttctagtgaa 300
tcatcagatg tttccagggt gccccaagga cctgaaaatg accctgtacc ttatttgaac 360
taaccaatca gttcgcttct cgcttctgtt cgcgcgcttc cgctctccga gctcaataaa 420
agagcccaca acccctcact cggcgcgcca gtcttccgat agactgcgtc gcccgggtac 480
ccgtattccc aataaagcct cttgctgttt gcatccgaat cgtggtctcg ctgttccttg 540
ggagggtctc ctctgagtga ttgactaccc acgacggggg tctttcattt gggggctcgt 600
ccgggatttg gagacccctg cccagggacc accgacccac caccgggagg taagctggcc 660
agcaacttat ctgtgtctgt ccgattgtct agtgtctatg tttgatgtta tgcgcctgcg 720
tctgtactag ttagctaact agctctgtat ctggcggacc cgtggtggaa ctgacgagtt 780
ctgaacaccc ggccgcaacc ctgggagacg tcccagggac tttgggggcc gtttttgtgg 840
cccgacctga ggaagggagt cgatgtggaa tccgaccccg tcaggatatg tggttctggt 900
aggagacgag aacctaaaac agttcccgcc tccgtctgaa tttttgcttt cggtttggaa 960
ccgaagccgc gcgtcttgtc tgctgcagcg ctgcagcatc gttctgtgtt gtctctgtct 1020
gactgtgttt ctgtatttgt ctgaaaatta gggccagact gttaccactc ccttaagttt 1080
gaccttaggt cactggaaag atgtcgagcg gatcgctcac aaccagtcgg tagatgtcaa 1140
gaagagacgt tgggttacct tctgctctgc agaatggcca acctttaacg tcggatggcc 1200
gcgagacggc acctttaacc gagacctcat cacccaggtt aagatcaagg tcttttcacc 1260

-continued

```
tggcccgcat ggacacccag accaggtccc ctacatcgtg acctgggaag ccttggcttt   1320
tgaccccccct ccctgggtca agccctttgt acaccctaag cctccgcctc ctcttcctcc   1380
atccgccccg tctctccccc ttgaacctcc tcgttcgacc ccgcctcgat cctcccttta   1440
tccagccctc actccttctc taggcgccgg aattccgatc tgatcaagag acaggatgag   1500
gatcgtttcg catgattgaa caagatggat tgcacgcagg ttctccggcc gcttgggtgg   1560
agaggctatt cggctatgac tgggcacaac agacaatcgg ctgctctgat gccgccgtgt   1620
tccggctgtc agcgcagggg cgcccggttc tttttgtcaa gaccgacctg tccggtgccc   1680
tgaatgaact gcaggacgag gcagcgcggc tatcgtggct ggccacgacg ggcgttcctt   1740
gcgcagctgt gctcgacgtt gtcactgaag cgggaaggga ctggctgcta ttgggcgaag   1800
tgccggggca ggatctcctg tcatctcacc ttgctcctgc cgagaaagta tccatcatgg   1860
ctgatgcaat gcggcggctg catacgcttg atccggctac ctgcccattc gaccaccaag   1920
cgaaacatcg catcgagcga gcacgtactc ggatggaagc cggtcttgtc gatcaggatg   1980
atctggacga agagcatcag gggctcgcgc cagccgaact gttcgccagg ctcaaggcgc   2040
gcatgcccga cggcgaggat ctcgtcgtga cccatggcga tgcctgcttg ccgaatatca   2100
tggtggaaaa tggccgcttt tctggattca tcgactgtgg ccggctgggt gtggcggacc   2160
gctatcagga catagcgttg gctacccgtg atattgctga agagcttggc ggcgaatggg   2220
ctgaccgctt cctcgtgctt tacggtatcg ccgctcccga ttcgcagcgc atcgccttct   2280
atcgccttct tgacgagttc ttctgagcgg gactctgggg ttcgaaatga ccgaccaagc   2340
gacgcccaac ctgccatcac gagatttcga ttccaccgcc gccttctatg aaaggttggg   2400
cttcggaatc gttttccggg acgccggctg gatgatcctc cagcgcgggg atctcatgct   2460
ggagttcttc gcccaccccg ggctcgatcc cctcgcgagt tggttcagct gctgcctgag   2520
gctggacgac ctcgcggagt tctaccggca gtgcaaatcc gtcggcatcc aggaaaccag   2580
cagcggctat ccgcgcatcc atgcccccga actgcaggag tggggaggca cgatggccgc   2640
tttggtcgag gcggatccgg ccattagcca tattattcat tggttatata gcataaatca   2700
atattggcta ttggccattg catacgttgt atccatatca taatatgtac atttatattg   2760
gctcatgtcc aacattaccg ccatgttgac attgattatt gactagttat taatagtaat   2820
caattacggg gtcattagtt catagcccat atatggagtt ccgcgttaca taacttacgg   2880
taaatggccc gcctggctga ccgcccaacg acccccgccc attgacgtca ataatgacgt   2940
atgttcccat agtaacgcca atagggactt tccattgacg tcaatgggtg gagtatttac   3000
ggtaaactgc ccacttggca gtacatcaag tgtatcatat gccaagtacg ccccctattg   3060
acgtcaatga cggtaaatgg cccgcctggc attatgccca gtacatgacc ttatgggact   3120
ttcctacttg gcagtacatc tacgtattag tcatcgctat taccatggtg atgcggtttt   3180
ggcagtacat caatgggcgt ggatagcggt ttgactcacg gggatttcca agtctccacc   3240
ccattgacgt caatgggagt ttgttttggc accaaaatca acgggacttt ccaaaatgtc   3300
gtaacaactc cgccccattg acgcaaatgg gcggtaggca tgtacggtgg gaggtctata   3360
taagcagagc tcgtttagtg aaccgtcaga tcgcctggag acgccatcca cgctgttttg   3420
acctccatag aagacaccgg gaccgatcca gcctccgcgg ccccaagctt ctcgacggat   3480
ccccgggaat tcaggacctc accatgggat ggagctgtat catcctcttc ttggtagcaa   3540
cagctacagg tgtccactcc caggtccagc tggtccaatc aggggctgaa gtcaagaaac   3600
ctgggtcatc agtgaaggtc tcctgcaagg cttctggcta cacctttact agctactggc   3660
```

-continued

```
tgcactgggt caggcaggca cctggacagg gtctggaatg gattggatac attaatccta   3720
ggaatgatta tactgagtac aatcagaact tcaaggacaa ggccacaata actgcagacg   3780
aatccaccaa tacagcctac atggagctga gcagcctgag gtctgaggac acggcatttt   3840
atttttgtgc aagaagggat attactacgt tctactgggg ccaaggcacc acggtcaccg   3900
tctcctcagc ctccaccaag ggcccatcgg tcttccccct ggcaccctcc tccaagagca   3960
cctctggggg cacagcggcc ctgggctgcc tggtcaagga ctacttcccc gaaccggtga   4020
cggtgtcgtg gaactcaggc gccctgacca gcggcgtgca caccttcccg gctgtcctac   4080
agtcctcagg actctactcc ctcagcagcg tggtgaccgt gccctccagc agcttgggca   4140
cccagaccta catctgcaac gtgaatcaca agcccagcaa caccaaggtg gacaagagag   4200
ttgagcccaa atcttgtgac aaaactcaca catgcccacc gtgcccagca cctgaactcc   4260
tggggggacc gtcagtcttc ctcttccccc caaaacccaa ggacaccctc atgatctccc   4320
ggacccctga ggtcacatgc gtggtggtgg acgtgagcca cgaagaccct gaggtcaagt   4380
tcaactggta cgtggacggc gtggaggtgc ataatgccaa gacaaagccg cgggaggagc   4440
agtacaacag cacgtaccgt gtggtcagcg tcctcaccgt cctgcaccag gactggctga   4500
atggcaagga gtacaagtgc aaggtctcca acaaagccct cccagccccc atcgagaaaa   4560
ccatctccaa agccaaaggg cagccccgag aaccacaggt gtacaccctg cccccatccc   4620
gggaggagat gaccaagaac caggtcagcc tgacctgcct ggtcaaaggc ttctatccca   4680
gcgacatcgc cgtggagtgg gagagcaatg ggcagccgga gaacaactac aagaccacgc   4740
ctcccgtgct ggactccgac ggctccttct tcctctatag caagctcacc gtggacaaga   4800
gcaggtggca gcaggggaac gtcttctcat gctccgtgat gcatgaggct ctgcacaacc   4860
actacacgca gaagagcctc tccctgtctc ccgggaaatg aaagccgaat tcgcccctct   4920
ccctcccccc cccctaacgt tactggccga agccgcttgg aataaggccg gtgtgcgttt   4980
gtctatatgt tattttccac catattgccg tcttttggca atgtgagggc ccggaaacct   5040
ggccctgtct tcttgacgag cattcctagg ggtctttccc ctctcgccaa aggaatgcaa   5100
ggtctgttga atgtcgtgaa ggaagcagtt cctctggaag cttcttgaag acaaacaacg   5160
tctgtagcga ccctttgcag gcagcggaac cccccacctg gcgacaggtg cctctgcggc   5220
caaaagccac gtgtataaga tacacctgca aaggcggcac aaccccagtg ccacgttgtg   5280
agttggatag ttgtggaaag agtcaaatgg ctctcctcaa gcgtattcaa caaggggctg   5340
aaggatgccc agaaggtacc ccattgtatg ggatctgatc tggggcctcg gtgcacatgc   5400
tttacatgtg tttagtcgag gttaaaaaaa cgtctaggcc ccccgaacca cggggacgtg   5460
gttttccttt gaaaaacacg atgataatat ggcctccttt gtctctctgc tcctggtagg   5520
catcctattc catgccaccc aggccgacat ccagctgacc cagtctccat catctctgag   5580
cgcatctgtt ggagataggg tcactatgag ctgtaagtcc agtcaaagtg ttttatacag   5640
tgcaaatcac aagaactact tggcctggta ccagcagaaa ccagggaaag cacctaaact   5700
gctgatctac tgggcatcca ctagggaatc tggtgtccct tcgcgattct ctggcagcgg   5760
atctgggaca gattttactt tcaccatcag ctctcttcaa ccagaagaca ttgcaacata   5820
ttattgtcac caatacctct cctcgtggac gttcggtgga gggaccaagg tgcagatcaa   5880
acgaactgtg gctgcaccat ctgtcttcat cttcccgcca tctgatgagc agttgaaatc   5940
tggaactgcc tctgttgtgt gcctgctgaa taacttctat cccagagagg ccaaagtaca   6000
```

-continued

```
gtggaaggtg gataacgccc tccaatcggg taactcccag gagagtgtca cagagcagga   6060

cagcaaggac agcacctaca gcctcagcag caccctgacg ctgagcaaag cagactacga   6120

gaaacacaaa gtctacgcct gcgaagtcac ccatcagggc ctgagctcgc ccgtcacaaa   6180

gagcttcaac aggggagagt gttagagatc taggcctcct aggtcgacat cgataaaata   6240

aaagatttta tttagtctcc agaaaaaggg gggaatgaaa gaccccacct gtaggtttgg   6300

caagctagct taagtaacgc cattttgcaa ggcatggaaa aatacataac tgagaataga   6360

gaagttcaga tcaaggtcag gaacagatgg aacagctgaa tatgggccaa acaggatatc   6420

tgtggtaagc agttcctgcc ccggctcagg gccaagaaca gatggaacag ctgaatatgg   6480

gccaaacagg atatctgtgg taagcagttc ctgccccggc tcagggccaa gaacagatgg   6540

tccccagatg cggtccagcc ctcagcagtt tctagagaac catcagatgt ttccagggtg   6600

ccccaaggac ctgaaatgac cctgtgcctt atttgaacta accaatcagt tcgcttctcg   6660

cttctgttcg cgcgcttctg ctccccgagc tcaataaaag agcccacaac ccctcactcg   6720

gggcgccagt cctccgattg actgagtcgc ccgggtaccc gtgtatccaa taaaccctct   6780

tgcagttgca tccgacttgt ggtctcgctg ttccttggga gggtctcctc tgagtgattg   6840

actacccgtc agcgggggtc tttcatt                                       6867
```

<210> SEQ ID NO 14
<211> LENGTH: 7466
<212> TYPE: DNA
<213> ORGANISM: Artificial Sequence
<220> FEATURE:
<223> OTHER INFORMATION: Synthetic

<400> SEQUENCE: 14

```
tttgaaagac cccacccgta ggtggcaagc tagcttaagt aacgccactt tgcaaggcat     60

ggaaaaatac ataactgaga atagaaaagt tcagatcaag gtcaggaaca aagaaacagc    120

tgaataccaa acaggatatc tgtggtaagc ggttcctgcc ccggctcagg gccaagaaca    180

gatgagacag ctgagtgatg ggccaaacag gatatctgtg gtaagcagtt cctgccccgg    240

ctcggggcca agaacagatg gtccccagat gcggtccagc cctcagcagt ttctagtgaa    300

tcatcagatg tttccagggt gccccaagga cctgaaaatg accctgtacc ttatttgaac    360

taaccaatca gttcgcttct cgcttctgtt cgcgcgcttc cgctctccga gctcaataaa    420

agagcccaca acccctcact cggcgcgcca gtcttccgat agactgcgtc gcccgggtac    480

ccgtattccc aataaagcct cttgctgttt gcatccgaat cgtggtctcg ctgttccttg    540

ggagggtctc ctctgagtga ttgactaccc acgacggggg tctttcattt gggggctcgt    600

ccgggatttg gagacccctg cccagggacc accgacccac caccgggagg taagctggcc    660

agcaacttat ctgtgtctgt ccgattgtct agtgtctatg tttgatgtta tgcgcctgcg    720

tctgtactag ttagctaact agctctgtat ctggcggacc cgtggtggaa ctgacgagtt    780

ctgaacaccc ggccgcaacc ctgggagacg tcccagggac tttgggggcc gtttttgtgg    840

cccgacctga ggaagggagt cgatgtggaa tccgaccccg tcaggatatg tggttctggt    900

aggagacgag aacctaaaac agttcccgcc tccgtctgaa tttttgcttt cggtttggaa    960

ccgaagccgc gcgtcttgtc tgctgcagcg ctgcagcatc gttctgtgtt gtctctgtct   1020

gactgtgttt ctgtatttgt ctgaaaatta gggccagact gttaccactc ccttaagttt   1080

gaccttaggt cactggaaag atgtcgagcg gatcgctcac aaccagtcgg tagatgtcaa   1140

gaagagacgt tgggttacct tctgctctgc agaatggcca acctttaacg tcggatggcc   1200
```

-continued

```
gcgagacggc acctttaacc gagacctcat cacccaggtt aagatcaagg tcttttcacc   1260

tggcccgcat ggacacccag accaggtccc ctacatcgtg acctgggaag ccttggcttt   1320

tgaccccccct ccctgggtca agccctttgt acaccctaag cctccgcctc ctcttcctcc   1380

atccgccccg tctctccccc ttgaacctcc tcgttcgacc ccgcctcgat cctcccttta   1440

tccagccctc actccttctc taggcgccgg aattccgatc tgatcaagag acaggatgag   1500

gatcgtttcg catgattgaa caagatggat tgcacgcagg ttctccggcc gcttgggtgg   1560

agaggctatt cggctatgac tgggcacaac agacaatcgg ctgctctgat gccgccgtgt   1620

tccggctgtc agcgcagggg cgcccggttc tttttgtcaa gaccgacctg tccggtgccc   1680

tgaatgaact gcaggacgag gcagcgcggc tatcgtggct ggccacgacg ggcgttcctt   1740

gcgcagctgt gctcgacgtt gtcactgaag cgggaaggga ctggctgcta ttgggcgaag   1800

tgccggggca ggatctcctg tcatctcacc ttgctcctgc cgagaaagta tccatcatgg   1860

ctgatgcaat gcggcggctg catacgcttg atccggctac ctgcccattc gaccaccaag   1920

cgaaacatcg catcgagcga gcacgtactc ggatggaagc cggtcttgtc gatcaggatg   1980

atctggacga agagcatcag gggctcgcgc cagccgaact gttcgccagg ctcaaggcgc   2040

gcatgcccga cggcgaggat ctcgtcgtga cccatggcga tgcctgcttg ccgaatatca   2100

tggtggaaaa tggccgcttt tctggattca tcgactgtgg ccggctgggt gtggcggacc   2160

gctatcagga catagcgttg gctacccgtg atattgctga agagcttggc ggcgaatggg   2220

ctgaccgctt cctcgtgctt tacggtatcg ccgctcccga ttcgcagcgc atcgccttct   2280

atcgccttct tgacgagttc ttctgagcgg gactctgggg ttcgaaatga ccgaccaagc   2340

gacgcccaac ctgccatcac gagatttcga ttccaccgcc gccttctatg aaaggttggg   2400

cttcggaatc gttttccggg acgccggctg gatgatcctc cagcgcgggg atctcatgct   2460

ggagttcttc gcccaccccg ggctcgatcc cctcgcgagt tggttcagct gctgcctgag   2520

gctggacgac ctcgcggagt tctaccggca gtgcaaatcc gtcggcatcc aggaaaccag   2580

cagcggctat ccgcgcatcc atgcccccga actgcaggag tggggaggca cgatggccgc   2640

tttggtcgag gcggatccgg ccattagcca tattattcat tggttatata gcataaatca   2700

atattggcta ttggccattg catacgttgt atccatatca taatatgtac atttatattg   2760

gctcatgtcc aacattaccg ccatgttgac attgattatt gactagttat taatagtaat   2820

caattacggg gtcattagtt catagcccat atatggagtt ccgcgttaca taacttacgg   2880

taaatggccc gcctggctga ccgcccaacg acccccgccc attgacgtca ataatgacgt   2940

atgttcccat agtaacgcca atagggactt tccattgacg tcaatgggtg gagtatttac   3000

ggtaaactgc ccacttggca gtacatcaag tgtatcatat gccaagtacg ccccctattg   3060

acgtcaatga cggtaaatgg cccgcctggc attatgccca gtacatgacc ttatgggact   3120

ttcctacttg gcagtacatc tacgtattag tcatcgctat taccatggtg atgcggtttt   3180

ggcagtacat caatgggcgt ggatagcggt ttgactcacg gggatttcca agtctccacc   3240

ccattgacgt caatgggagt ttgttttggc accaaaatca acgggacttt ccaaaatgtc   3300

gtaacaactc cgccccattg acgcaaatgg gcggtaggca tgtacggtgg gaggtctata   3360

taagcagagc tcgtttagtg aaccgtcaga tcgcctggag acgccatcca cgctgttttg   3420

acctccatag aagacaccgg gaccgatcca gcctccgcgg ccccaagctt ggatctcacc   3480

atggagttgg gactgcgctg ggcttcctc gttgctcttt taagaggtgt ccagtgtcag   3540
```

-continued gtgcaattgg tggagtctgg gggaggcgtg gtccagcctg ggaggtccct gagactctcc 3600
tgtgcagcgt ctggattcgc cttcagtaga tatggcatgc actgggtccg ccaggctcca 3660
ggcaaggggc tggagtgggt ggcagttata tggtatgatg gaagtaataa atactatgca 3720
gactccgtga agggccgatt caccatctcc agagacaatt ccaagaacac gcagtatctg 3780
caaatgaaca gcctgagagc cgaggacacg gctgtgtatt actgtgcgag aggcggtgac 3840
ttcctctact actactatta cggtatggac gtctggggcc aagggaccac ggtcaccgtc 3900
tcctcagcct ccaccaaggg cccatcggtc ttccccctgg caccctctag caagagcacc 3960
tctgggggca cagcggccct gggctgcctg gtcaaggact acttccccga accggtgacg 4020
gtgtcgtgga actcaggcgc cctgaccagc ggcgtgcaca ccttcccggc tgtcctacag 4080
tcctcaggac tctactccct cagcagcgtg gtgaccgtgc cctccagcag cttgggcacc 4140
cagacctaca tctgcaacgt gaatcacaag cccagcaaca ccaaggtgga caagagagtt 4200
gagcccaaat cttgtgacaa aactcacaca tgcccaccgt gcccagcacc tgaactcctg 4260
gggggaccgt cagtcttcct cttcccccca aaacccaagg acaccctcat gatctcccgg 4320
acccctgagg tcacatgcgt ggtggtggac gtgagccacg aagaccctga ggtcaagttc 4380
aactggtacg tggacggcgt ggaggtgcat aatgccaaga caaagccgcg ggaggagcag 4440
tacaacagca cgtaccgtgt ggtcagcgtc ctcaccgtcc tgcaccagga ctggctgaat 4500
ggcaaggagt acaagtgcaa ggtctccaac aaagccctcc cagcccccat cgagaaaacc 4560
atctccaaag ccaaagggca gccccgagaa ccacaggtgt acaccctgcc cccatcccgg 4620
gaggagatga ccaagaacca ggtcagcctg acctgcctgg tcaaaggctt ctatcccagc 4680
gacatcgccg tggagtggga gagcaatggg cagccggaga acaactacaa gaccacgcct 4740
cccgtgctgg actccgacgg ctccttcttc ctctatagca agctcaccgt ggacaagagc 4800
aggtggcagc aggggaacgt cttctcatgc tccgtgatgc atgaggctct gcacaaccac 4860
tacacgcaga agagcctctc cctgtctccc gggaaatgag aattcctcga gttaacagat 4920
ccccgggaat tcgcccctct ccctcccccc cccctaacgt tactggccga agccgcttgg 4980
aataaggccg gtgtgcgttt gtctatatgt tattttccac catattgccg tcttttggca 5040
atgtgagggc ccggaaacct ggccctgtct tcttgacgag cattcctagg ggtctttccc 5100
ctctcgccaa aggaatgcaa ggtctgttga atgtcgtgaa ggaagcagtt cctctggaag 5160
cttcttgaag acaaacaacg tctgtagcga ccctttgcag gcagcggaac cccccacctg 5220
gcgacaggtg cctctgcggc caaaagccac gtgtataaga tacacctgca aaggcggcac 5280
aaccccagtg ccacgttgtg agttggatag ttgtggaaag agtcaaatgg ctctcctcaa 5340
gcgtattcaa caaggggctg aaggatgccc agaaggtacc ccattgtatg ggatctgatc 5400
tggggcctcg gtgcacatgc tttacatgtg tttagtcgag gttaaaaaaa cgtctaggcc 5460
ccccgaacca cggggacgtg gttttccttt gaaaaacacg atgataatat ggcctccttt 5520
gtctctctgc tcctggtagg catcctattc catgccaccc aggccgacat ccagatgacc 5580
cagtctccat cctccctgtc tgcatctgta ggagacagag tcaccatcac ttgccgggcg 5640
agtcagggca ttagcaatta tttagcctgg tatcagcaga aaacagggaa agttcctaag 5700
ttcctgatct atgaagcatc cactttgcaa tcaggggtcc catctcggtt cagtggcggt 5760
ggatctggga cagatttcac tctcaccatc agcagcctgc agcctgaaga tgttgcaact 5820
tattactgtc aaaattataa cagtgcccca ttcactttcg gccctgggac caaagtggat 5880
atcaaacgaa ctgtggctgc accctctgtc ttcatcttcc cgccatctga tgagcagttg 5940

-continued aaatctggaa ctgctagcgt tgtgtgcctg ctgaataact tctatcccag agaggccaaa 6000
gtacagtgga aggtggataa cgccctccaa tcgggtaact cccaggagag tgtcacagag 6060
caggacagca aggacagcac ctacagcctc agcagcaccc tgacgctgag caaagcagac 6120
tacgagaaac acaaagtcta cgcctgcgaa gtcacccatc agggcctgag ctcgcccgtc 6180
acaaagagct tcaacagggg agagtgttag gaattcgcgg ccgctcgaca tcgataatca 6240
acctctggat tacaaaattt gtgaaagatt gactggtatt cttaactatg ttgctccttt 6300
tacgctatgt ggatacgctg ctttaatgcc tttgtatcat gctattgctt cccgtatggc 6360
tttcattttc tcctccttgt ataaatcctg gttgctgtct ctttatgagg agttgtggcc 6420
cgttgtcagg caacgtggcg tggtgtgcac tgtgtttgct gacgcaaccc ccactggttg 6480
gggcattgcc accacctgtc agctcctttc cgggactttc gctttccccc tccctattgc 6540
cacggcggaa ctcatcgccg cctgccttgc ccgctgctgg acaggggctc ggctgttggg 6600
cactgacaat tccgtggtgt tgtcggggaa atcatcgtcc tttccttggc tgctcgcctg 6660
tgttgccacc tggattctgc gcgggacgtc cttctgctac gtcccttcgg ccctcaatcc 6720
agcggacctt ccttcccgcg gcctgctgcc ggctctgcgg cctcttccgc gtcttcgcct 6780
tcgccctcag acgagtcgga tctccctttg ggccgcctcc ccgcctgatc gataaaataa 6840
aagattttat ttagtctcca gaaaaagggg ggaatgaaag accccacctg taggtttggc 6900
aagctagctt aagtaacgcc attttgcaag gcatggaaaa atacataact gagaatagag 6960
aagttcagat caaggtcagg aacagatgga acagctgaat atgggccaaa caggatatct 7020
gtggtaagca gttcctgccc cggctcaggg ccaagaacag atggaacagc tgaatatggg 7080
ccaaacagga tatctgtggt aagcagttcc tgccccggct cagggccaag aacagatggt 7140
ccccagatgc ggtccagccc tcagcagttt ctagagaacc atcagatgtt tccagggtgc 7200
cccaaggacc tgaaatgacc ctgtgcctta tttgaactaa ccaatcagtt cgcttctcgc 7260
ttctgttcgc gcgcttctgc tccccgagct caataaaaga gcccacaacc cctcactcgg 7320
ggcgccagtc ctccgattga ctgagtcgcc cgggtacccg tgtatccaat aaaccctctt 7380
gcagttgcat ccgacttgtg gtctcgctgt tccttgggag ggtctcctct gagtgattga 7440
ctacccgtca gcgggggtct ttcatt 7466

<210> SEQ ID NO 15
<211> LENGTH: 7465
<212> TYPE: DNA
<213> ORGANISM: Artificial Sequence
<220> FEATURE:
<223> OTHER INFORMATION: Synthetic

<400> SEQUENCE: 15
tttgaaagac cccacccgta ggtggcaagc tagcttaagt aacgccactt tgcaaggcat 60
ggaaaaatac ataactgaga atagaaaagt tcagatcaag gtcaggaaca aagaaacagc 120
tgaataccaa acaggatatc tgtggtaagc ggttcctgcc ccggctcagg gccaagaaca 180
gatgagacag ctgagtgatg ggccaaacag gatatctgtg gtaagcagtt cctgccccgg 240
ctcggggcca agaacagatg gtccccagat gcggtccagc cctcagcagt ttctagtgaa 300
tcatcagatg tttccagggt gccccaagga cctgaaaatg accctgtacc ttatttgaac 360
taaccaatca gttcgcttct cgcttctgtt cgcgcgcttc cgctctccga gctcaataaa 420
agagcccaca acccctcact cggcgcgcca gtcttccgat agactgcgtc gcccgggtac 480

-continued

```
ccgtattccc aataaagcct cttgctgttt gcatccgaat cgtggtctcg ctgttccttg    540
ggagggtctc ctctgagtga ttgactaccc acgacggggg tctttcattt gggggctcgt    600
ccgggatttg gagacccctg cccagggacc accgacccac caccgggagg taagctggcc    660
agcaacttat ctgtgtctgt ccgattgtct agtgtctatg tttgatgtta tgcgcctgcg    720
tctgtactag ttagctaact agctctgtat ctggcggacc cgtggtggaa ctgacgagtt    780
ctgaacaccc ggccgcaacc ctgggagacg tcccagggac tttgggggcc gtttttgtgg    840
cccgacctga ggaagggagt cgatgtggaa tccgaccccg tcaggatatg tggttctggt    900
aggagacgag aacctaaaac agttcccgcc tccgtctgaa tttttgcttt cggtttggaa    960
ccgaagccgc gcgtcttgtc tgctgcagcg ctgcagcatc gttctgtgtt gtctctgtct   1020
gactgtgttt ctgtatttgt ctgaaaatta gggccagact gttaccactc ccttaagttt   1080
gaccttaggt cactggaaag atgtcgagcg gatcgctcac aaccagtcgg tagatgtcaa   1140
gaagagacgt tgggttacct tctgctctgc agaatggcca acctttaacg tcggatggcc   1200
gcgagacggc acctttaacc gagacctcat cacccaggtt aagatcaagg tcttttcacc   1260
tggcccgcat ggacacccag accaggtccc ctacatcgtg acctgggaag ccttggcttt   1320
tgaccccccct ccctgggtca agccctttgt acaccctaag cctccgcctc ctcttcctcc   1380
atccgccccg tctctccccc ttgaacctcc tcgttcgacc ccgcctcgat cctcccttta   1440
tccagccctc actccttctc taggcgccgg aattccgatc tgatcaagag acaggatgag   1500
gatcgtttcg catgattgaa caagatggat tgcacgcagg ttctccggcc gcttgggtgg   1560
agaggctatt cggctatgac tgggcacaac agacaatcgg ctgctctgat gccgccgtgt   1620
tccggctgtc agcgcagggg cgcccggttc tttttgtcaa gaccgacctg tccggtgccc   1680
tgaatgaact gcaggacgag gcagcgcggc tatcgtggct ggccacgacg ggcgttcctt   1740
gcgcagctgt gctcgacgtt gtcactgaag cgggaaggga ctggctgcta ttgggcgaag   1800
tgccggggca ggatctcctg tcatctcacc ttgctcctgc cgagaaagta tccatcatgg   1860
ctgatgcaat gcggcggctg catacgcttg atccggctac ctgcccattc gaccaccaag   1920
cgaaacatcg catcgagcga gcacgtactc ggatggaagc cggtcttgtc gatcaggatg   1980
atctggacga agagcatcag gggctcgcgc cagccgaact gttcgccagg ctcaaggcgc   2040
gcatgcccga cggcgaggat ctcgtcgtga cccatggcga tgcctgcttg ccgaatatca   2100
tggtggaaaa tggccgcttt tctggattca tcgactgtgg ccggctgggt gtggcggacc   2160
gctatcagga catagcgttg gctacccgtg atattgctga agagcttggc ggcgaatggg   2220
ctgaccgctt cctcgtgctt tacggtatcg ccgctcccga ttcgcagcgc atcgccttct   2280
atcgccttct tgacgagttc ttctgagcgg gactctgggg ttcgaaatga ccgaccaagc   2340
gacgcccaac ctgccatcac gagatttcga ttccaccgcc gccttctatg aaaggttggg   2400
cttcggaatc gttttccggg acgccggctg gatgatcctc cagcgcgggg atctcatgct   2460
ggagttcttc gcccaccccg ggctcgatcc cctcgcgagt tggttcagct gctgcctgag   2520
gctggacgac ctcgcggagt tctaccggca gtgcaaatcc gtcggcatcc aggaaaccag   2580
cagcggctat ccgcgcatcc atgcccccga actgcaggag tggggaggca cgatggccgc   2640
tttggtcgag gcggatccgg ccattagcca tattattcat tggttatata gcataaatca   2700
atattggcta ttggccattg catacgttgt atccatatca taatatgtac atttatattg   2760
gctcatgtcc aacattaccg ccatgttgac attgattatt gactagttat taatagtaat   2820
caattacggg gtcattagtt catagcccat atatggagtt ccgcgttaca taacttacgg   2880
```

-continued taaatggccc gcctggctga ccgcccaacg acccccgccc attgacgtca ataatgacgt 2940
atgttcccat agtaacgcca atagggactt tccattgacg tcaatgggtg gagtatttac 3000
ggtaaactgc ccacttggca gtacatcaag tgtatcatat gccaagtacg ccccctattg 3060
acgtcaatga cggtaaatgg cccgcctggc attatgccca gtacatgacc ttatgggact 3120
ttcctacttg gcagtacatc tacgtattag tcatcgctat taccatggtg atgcggtttt 3180
ggcagtacat caatgggcgt ggatagcggt ttgactcacg gggatttcca agtctccacc 3240
ccattgacgt caatgggagt ttgttttggc accaaaatca acgggacttt ccaaaatgtc 3300
gtaacaactc cgccccattg acgcaaatgg gcggtaggca tgtacggtgg gaggtctata 3360
taagcagagc tcgtttagtg aaccgtcaga tcgcctggag acgccatcca cgctgttttg 3420
acctccatag aagacaccgg gaccgatcca gcctccgcgg ccccaagctt ctcgagcacc 3480
atggaatgga gcggagtctt tatctttctc ctgtcagtaa ctgcaggtgt ccactccgag 3540
gtgcagctgg tggagtctgg tggaggcttg gtaaagcctg gaggttccct tagactctcc 3600
tgtgcagcct ctggttacac tttcagtaac tattggatcg gatgggtccg ccaggctcca 3660
ggcaaagggc tggagtggat tggcgatatc taccctggag ggaactacat caggaacaat 3720
gagaagttca aggacaagac caccctgtca gcagatactt ccaagaacac agcctatctg 3780
caaatgaaca gcctgaaaac cgaggacaca gccgtgtatt actgtggaag cagcttcggt 3840
agtaactacg tgttcgcctg gtttacttac tggggccaag ggactctggt cacagtctcc 3900
tcagcttcca ccaagggccc atccgtcttc cccctggcgc cctgctccag gagcacctcc 3960
gagagcacag ccgccctggg ctgcctggtc aaggactact tccccgaacc ggtgacggtg 4020
tcgtggaact caggcgccct gaccagcggc gtgcacacct tcccggctgt cctacagtcc 4080
tcaggactct actccctcag cagcgtggtg accgtgccct ccagcagctt gggcacgaag 4140
acctacacct gcaacgtaga tcacaagccc agcaacacca aggtggacaa gagagttgag 4200
tccaaatatg gtccccccatg cccatcatgc ccagcacctg agttcctggg gggaccatca 4260
gtcttcctgt tccccccaaa acccaaggac actctcatga tctcccggac ccctgaggtc 4320
acgtgcgtgg tggtggacgt gagccaggaa gaccccgagg tccagttcaa ctggtacgtg 4380
gatggcgtgg aggtgcataa tgccaagaca aagccgcggg aggagcagtt caacagcacg 4440
taccgtgtgg tcagcgtcct caccgtcctg caccaggact ggctgaacgg caaggagtac 4500
aagtgcaagg tctccaacaa aggcctcccg tcctccatcg agaaaaccat ctccaaagcc 4560
aaagggcagc cccgagagcc acaggtgtac accctgcccc catcccagga ggagatgacc 4620
aagaaccagg tcagcctgac ctgcctggtc aaaggcttct accccagcga catcgccgtg 4680
gagtgggaga gcaatgggca gccggagaac aactacaaga ccacgcctcc cgtgctggac 4740
tccgacggct ccttcttcct ctacagcagg ctaaccgtgg acaagagcag gtggcaggag 4800
gggaatgtct tctcatgctc cgtgatgcat gaggctctgc acaaccacta cacacagaag 4860
agcctctccc tgtctctcgg gaaatgagtg ccagatcccc gggaattcgc ccctctccct 4920
cccccccccc taacgttact ggccgaagcc gcttggaata aggccggtgt gcgtttgtct 4980
atatgttatt ttccaccata ttgccgtctt ttggcaatgt gagggcccgg aaacctggcc 5040
ctgtcttctt gacgagcatt cctaggggtc tttcccctct cgccaaagga atgcaaggtc 5100
tgttgaatgt cgtgaaggaa gcagttcctc tggaagcttc ttgaagacaa acaacgtctg 5160
tagcgaccct ttgcaggcag cggaaccccc cacctggcga caggtgcctc tgcggccaaa 5220

-continued

```
agccacgtgt ataagataca cctgcaaagg cggcacaacc ccagtgccac gttgtgagtt   5280
ggatagttgt ggaaagagtc aaatggctct cctcaagcgt attcaacaag gggctgaagg   5340
atgcccagaa ggtaccccat tgtatgggat ctgatctggg gcctcggtgc acatgcttta   5400
catgtgttta gtcgaggtta aaaaaacgtc taggcccccc gaaccacggg gacgtggttt   5460
tcctttgaaa aacacgatga taatatggcc tcctttgtct ctctgctcct ggtaggcatc   5520
ctattccatg ccacccaggc cgacattgtg atgacccaat ctccactctc cctgcctgtc   5580
actcctggag agccagcctc catctcttgc agatctagtc agcgccttct gagcagttat   5640
ggacatacct atttacattg gtacctacag aagccaggcc agtctccaca gctcctgatc   5700
tacgaagttt ccaaccgatt ttctggggtc ccagacaggt tcagtggcag tgggtcaggg   5760
acagatttca cacttaagat cagtagagtg gaggctgagg atgtgggagt ttattactgc   5820
tctcaaagta cacatgttcc tctcacgttc ggacagggga ccaaggtgga aataaaacga   5880
actgtggctg caccatctgt cttcatcttc ccgccatctg atgagcagtt gaaatctgga   5940
actgcctctg ttgtgtgcct gctgaataac ttctatccca gagaggccaa agtacagtgg   6000
aaggtggata acgccctcca atcgggtaac tcccaggaga gtgtcacaga gcaggacagc   6060
aaggacagca cctacagcct cagcagcacc ctgacgctga gcaaagcaga ctacgagaaa   6120
cacaaagtct acgcctgcga agtcacccat cagggcctga gctcgcccgt cacaaagagc   6180
ttcaacaggg gagagtgtta gagggagaag tgcccccacc tgctcctcga catcgataat   6240
caacctctgg attacaaaat ttgtgaaaga ttgactggta ttcttaacta tgttgctcct   6300
tttacgctat gtggatacgc tgctttaatg cctttgtatc atgctattgc ttcccgtatg   6360
gctttcattt tctcctcctt gtataaatcc tggttgctgt ctctttatga ggagttgtgg   6420
cccgttgtca ggcaacgtgg cgtggtgtgc actgtgtttg ctgacgcaac ccccactggt   6480
tggggcattg ccaccacctg tcagctcctt tccgggactt tcgctttccc cctccctatt   6540
gccacggcgg aactcatcgc cgcctgcctt gcccgctgct ggacaggggc tcggctgttg   6600
ggcactgaca attccgtggt gttgtcgggg aaatcatcgt cctttccttg gctgctcgcc   6660
tgtgttgcca cctggattct gcgcgggacg tccttctgct acgtcccttc ggccctcaat   6720
ccagcggacc ttccttcccg cggcctgctg ccggctctgc ggcctcttcc gcgtcttcgc   6780
cttcgccctc agacgagtcg gatctccctt tgggccgcct ccccgcatcg ataaaataaa   6840
agattttatt tagtctccag aaaaaggggg gaatgaaaga ccccacctgt aggtttggca   6900
agctagctta agtaacgcca ttttgcaagg catggaaaaa tacataactg agaatagaga   6960
agttcagatc aaggtcagga acagatggaa cagctgaata tgggccaaac aggatatctg   7020
tggtaagcag ttcctgcccc ggctcagggc caagaacaga tggaacagct gaatatgggc   7080
caaacaggat atctgtggta agcagttcct gccccggctc agggccaaga acagatggtc   7140
cccagatgcg gtccagccct cagcagtttc tagagaacca tcagatgttt ccagggtgcc   7200
ccaaggacct gaaatgaccc tgtgccttat ttgaactaac caatcagttc gcttctcgct   7260
tctgttcgcg cgcttctgct ccccgagctc aataaaagag cccacaaccc ctcactcggg   7320
gcgccagtcc tccgattgac tgagtcgccc gggtacccgt gtatccaata aaccctcttg   7380
cagttgcatc cgacttgtgg tctcgctgtt ccttgggagg gtctcctctg agtgattgac   7440
tacccgtcag cgggggtctt tcatt                                          7465
```

<210> SEQ ID NO 16
<211> LENGTH: 2082

-continued

<212> TYPE: DNA
<213> ORGANISM: Artificial Sequence
<220> FEATURE:
<223> OTHER INFORMATION: Synthetic

<400> SEQUENCE: 16
atggagttgg gactgcgctg gggcttcctc gttgctcttt taagaggtgt ccagtgtcag 60
gtgcaattgg tggagtctgg gggaggcgtg gtccagcctg ggaggtccct gagactctcc 120
tgtgcagcgt ctggattcgc cttcagtaga tatggcatgc actgggtccg ccaggctcca 180
ggcaaggggc tggagtgggt ggcagttata tggtatgatg gaagtaataa atactatgca 240
gactccgtga agggccgatt caccatctcc agagacaatt ccaagaacac gcagtatctg 300
caaatgaaca gcctgagagc cgaggacacg gctgtgtatt actgtgcgag aggcggtgac 360
ttcctctact actactatta cggtatggac gtctggggcc aagggaccac ggtcaccgtc 420
tcctcagcct ccaccaaggg cccatcggtc ttccccctgg caccctctag caagagcacc 480
tctgggggca cagcggccct gggctgcctg gtcaaggact acttccccga accggtgacg 540
gtgtcgtgga actcaggcgc cctgaccagc ggcgtgcaca ccttcccggc tgtcctacag 600
tcctcaggac tctactccct cagcagcgtg gtgaccgtgc cctccagcag cttgggcacc 660
cagacctaca tctgcaacgt gaatcacaag cccagcaaca ccaaggtgga caagagagtt 720
gagcccaaat cttgtgacaa aactcacaca tgcccaccgt gcccagcacc tgaactcctg 780
gggggaccgt cagtcttcct cttcccccca aaacccaagg acaccctcat gatctcccgg 840
acccctgagg tcacatgcgt ggtggtggac gtgagccacg aagaccctga ggtcaagttc 900
aactggtacg tggacggcgt ggaggtgcat aatgccaaga caaagccgcg ggaggagcag 960
tacaacagca cgtaccgtgt ggtcagcgtc ctcaccgtcc tgcaccagga ctggctgaat 1020
ggcaaggagt acaagtgcaa ggtctccaac aaagccctcc cagcccccat cgagaaaacc 1080
atctccaaag ccaaagggca gccccgagaa ccacaggtgt acaccctgcc cccatcccgg 1140
gaggagatga ccaagaacca ggtcagcctg acctgcctgg tcaaaggctt ctatcccagc 1200
gacatcgccg tggagtggga gagcaatggg cagccggaga acaactacaa gaccacgcct 1260
cccgtgctgg actccgacgg ctccttcttc ctctatagca agctcaccgt ggacaagagc 1320
aggtggcagc aggggaacgt cttctcatgc tccgtgatgc atgaggctct gcacaaccac 1380
tacacgcaga agagcctctc cctgtctccg ggcatcctat tccatgccac ccaggccgac 1440
atccagatga cccagtctcc atcctccctg tctgcatctg taggagacag agtcaccatc 1500
acttgccggg cgagtcaggg cattagcaat tatttagcct ggtatcagca gaaaacaggg 1560
aaagttccta agttcctgat ctatgaagca tccactttgc aatcaggggt cccatctcgg 1620
ttcagtggcg gtggatctgg gacagatttc actctcacca tcagcagcct gcagcctgaa 1680
gatgttgcaa cttattactg tcaaaattat aacagtgccc cattcacttt cggccctggg 1740
accaaagtgg atatcaaacg aactgtggct gcaccctctg tcttcatctt cccgccatct 1800
gatgagcagt tgaaatctgg aactgctagc gttgtgtgcc tgctgaataa cttctatccc 1860
agagaggcca aagtacagtg gaaggtggat aacgccctcc aatcgggtaa ctcccaggag 1920
agtgtcacag agcaggacag caaggacagc acctacagcc tcagcagcac cctgacgctg 1980
agcaaagcag actacgagaa acacaaagtc tacgcctgcg aagtcaccca tcagggcctg 2040
agctcgcccg tcacaaagag cttcaacagg ggagagtgtt ag 2082

<210> SEQ ID NO 17

-continued

<211> LENGTH: 2085
<212> TYPE: DNA
<213> ORGANISM: Artificial Sequence
<220> FEATURE:
<223> OTHER INFORMATION: Synthetic

<400> SEQUENCE: 17
atggaatgga gcggagtctt tatctttctc ctgtcagtaa ctgcaggtgt ccactccgag 60
gtgcagctgg tggagtctgg tggaggcttg gtaaagcctg gaggttccct tagactctcc 120
tgtgcagcct ctggttacac tttcagtaac tattggatcg gatgggtccg ccaggctcca 180
ggcaaagggc tggagtggat tggcgatatc taccctggag ggaactacat caggaacaat 240
gagaagttca aggacaagac caccctgtca gcagatactt ccaagaacac agcctatctg 300
caaatgaaca gcctgaaaac cgaggacaca gccgtgtatt actgtggaag cagcttcggt 360
agtaactacg tgttcgcctg gtttacttac tggggccaag ggactctggt cacagtctcc 420
tcagcttcca ccaagggccc atccgtcttc cccctggcgc cctgctccag gagcacctcc 480
gagagcacag ccgccctggg ctgcctggtc aaggactact tccccgaacc ggtgacggtg 540
tcgtggaact caggcgccct gaccagcggc gtgcacacct tcccggctgt cctacagtcc 600
tcaggactct actccctcag cagcgtggtg accgtgccct ccagcagctt gggcacgaag 660
acctacacct gcaacgtaga tcacaagccc agcaacacca aggtggacaa gagagttgag 720
tccaaatatg gtcccccatg cccatcatgc ccagcacctg agttcctggg gggaccatca 780
gtcttcctgt tccccccaaa acccaaggac actctcatga tctcccggac ccctgaggtc 840
acgtgcgtgg tggtggacgt gagccaggaa gaccccgagg tccagttcaa ctggtacgtg 900
gatggcgtgg aggtgcataa tgccaagaca aagccgcggg aggagcagtt caacagcacg 960
taccgtgtgg tcagcgtcct caccgtcctg caccaggact ggctgaacgg caaggagtac 1020
aagtgcaagg tctccaacaa aggcctcccg tcctccatcg agaaaaccat ctccaaagcc 1080
aaagggcagc cccgagagcc acaggtgtac accctgcccc catcccagga ggagatgacc 1140
aagaaccagg tcagcctgac ctgcctggtc aaaggcttct accccagcga catcgccgtg 1200
gagtgggaga gcaatgggca gccggagaac aactacaaga ccacgcctcc cgtgctggac 1260
tccgacggct ccttcttcct ctacagcagg ctaaccgtgg acaagagcag gtggcaggag 1320
gggaatgtct tctcatgctc cgtgatgcat gaggctctgc acaaccacta cacacagaag 1380
agcctctccc tgtctctggg catcctattc catgccaccc aggccgacat tgtgatgacc 1440
caatctccac tctccctgcc tgtcactcct ggagagccag cctccatctc ttgcagatct 1500
agtcagcgcc ttctgagcag ttatggacat acctatttac attggtacct acagaagcca 1560
ggccagtctc cacagctcct gatctacgaa gtttccaacc gattttctgg ggtcccagac 1620
aggttcagtg gcagtgggtc agggacagat ttcacactta agatcagtag agtggaggct 1680
gaggatgtgg gagtttatta ctgctctcaa agtacacatg ttcctctcac gttcggacag 1740
gggaccaagg tggaaataaa acgaactgtg gctgcaccat ctgtcttcat cttcccgcca 1800
tctgatgagc agttgaaatc tggaactgcc tctgttgtgt gcctgctgaa taacttctat 1860
cccagagagg ccaaagtaca gtggaaggtg gataacgccc tccaatcggg taactcccag 1920
gagagtgtca cagagcagga cagcaaggac agcacctaca gcctcagcag caccctgacg 1980
ctgagcaaag cagactacga gaaacacaaa gtctacgcct gcgaagtcac ccatcagggc 2040
ctgagctcgc ccgtcacaaa gagcttcaac aggggagagt gttag 2085

-continued

```
<210> SEQ ID NO 18
<211> LENGTH: 65
<212> TYPE: DNA
<213> ORGANISM: Artificial Sequence
<220> FEATURE:
<223> OTHER INFORMATION: Synthetic

<400> SEQUENCE: 18

tgaggctctg cacaaccact acacgcagaa gagcctctcc ctgtctcccg ggaaatgaga     60

attcc                                                                 65


<210> SEQ ID NO 19
<211> LENGTH: 60
<212> TYPE: DNA
<213> ORGANISM: Artificial Sequence
<220> FEATURE:
<223> OTHER INFORMATION: Synthetic

<400> SEQUENCE: 19

tcgaggaatt ctcatttccc gggagacagg gagaggctct tctgcgtgta gtggttgtgc     60


<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Ile Leu Phe His Ala Thr Gln Ala
1               5
```

FUSION ANTIBODIES

This Application claims priority to provisional patent application Ser. No. 60/490,569 filed Jul. 28, 2003, which is herein incorporated by reference in its entirety.

FIELD OF THE INVENTION

The present invention provides novel antibodies. In particular, the present invention provides fusion antibodies comprising antibody heavy and light chain fusions. The present invention further provides multivalent antibodies comprising multiple fusion antibody chains. The present invention further provides methods of generating splice resistant antibody genes.

BACKGROUND OF THE INVENTION

The pharmaceutical biotechnology industry is based on the production of recombinant proteins in mammalian cells. These proteins are essential to the therapeutic treatment of many diseases and conditions. In particular, antibodies are of increasing importance in human therapy, assay procedures and diagnostic methods. However, methods of identifying antibodies and production of antibodies is often expensive, particularly where monoclonal antibodies are required. Hybridoma technology has traditionally been employed to produce monoclonal antibodies, but these methods are time-consuming and result in isolation and production of limited numbers of specific antibodies. Additionally, relatively small amounts of antibody are produced; consequently, hybridoma methods have not been developed for a large number of antibodies. This is unfortunate as the potential repertoire of immunoglobulins produced in an immunized animal is quite high, on the order of $>10^{10}$, yet hybridoma technology is too complicated and time consuming to adequately screen and develop large number of useful antibodies. What is needed are methods of generating antibodies with increased activity, thus reducing the quantity of protein that has to be prepared.

SUMMARY OF THE INVENTION

The present invention provides novel antibodies. In particular, the present invention provides fusion antibodies comprising antibody heavy and light chain fusions. The present invention further provides multivalent antibodies comprising multiple fusion antibody chains. The present invention further provides methods of generating splice resistant antibody genes.

For example, in some embodiments, the present invention provides a composition comprising a polypeptide comprising at least one antibody heavy chain fused to at least one antibody light chain. In some embodiments, the antibody heavy chain is separated from the antibody light chain by a linker (e.g., a peptide linker). In some embodiments, the at least one antibody light chain comprises one antibody light chain and the at least one antibody heavy chain comprises one antibody heavy chain. In certain embodiments, the antibody heavy chain is missing the last amino acid relative to the native antibody heavy chain gene.

The present invention also provides a composition comprising a multivalent antibody comprising at least two polypeptides, wherein each of the polypeptides comprises at least one antibody heavy chain fused to at least one antibody light chain. In some embodiments, the polypeptides are joined via di-sulfide bonds. In some embodiments, the multivalent antibody comprises at least 5, preferably at least 10, and even more preferably at least 15 of the polypeptides. In some embodiments, the antibody heavy chain is separated from the antibody light chain by a linker (e.g., a peptide linker). In some embodiments, the at least one antibody light chain comprises one antibody light chain and the at least one antibody heavy chain comprises one antibody heavy chain. In some embodiments, the antibody heavy chain is missing the last amino acid relative to the native antibody heavy chain.

The present invention further provides a composition comprising a nucleic acid comprising at least one antibody heavy chain gene and at least one antibody light chain gene, wherein the nucleic acid encodes a polypeptide comprising at least one antibody heavy chain fused to at least one antibody light chain. In some embodiments, the antibody heavy chain gene is separated from said antibody light chain gene by a linker (e.g., a peptide linker). In some embodiments, the at least one antibody light chain gene comprises one antibody light chain gene and the at least one antibody heavy chain gene comprises one antibody heavy chain gene. In some embodiments, the antibody heavy chain gene is missing the last codon of the native antibody heavy chain gene.

In yet other embodiments, the present invention provides a method of binding an antigen, comprising providing a polypeptide comprising at least one antibody heavy chain fused to at least one antibody light chain; and contacting the polypeptide with a sample comprising an antigen under conditions such that the polypeptide binds to the antigen. In some embodiments, the polypeptide comprises a label. In some embodiments, the antibody heavy chain is separated from the antibody light chain by a linker (e.g., a peptide linker). In some embodiments, the at least one antibody light chain comprises one antibody light chain and the at least one antibody heavy chain comprises one antibody heavy chain. In some embodiments, the antibody heavy chain is missing the last amino acid relative to the native antibody heavy chain gene. In some embodiments, the method utilizes at least two of the polypeptides arranged as a multivalent antibody. In some embodiments, the polypeptides are joined via di-sulfide bonds. In some embodiments, the multivalent antibody comprises at least 5, preferably at least 10, and even more preferably at least 15 of the polypeptides.

In still further embodiments, the present invention provides a method, comprising providing a vector comprising a bicistronic expression construct comprising genes encoding an antibody heavy chain gene and an antibody light chain gene; and altering the nucleic acid sequence of a splice acceptor sequence or a splice donor sequence in the antibody light chain gene or the antibody heavy chain gene under conditions such that splicing is prevented at the splice acceptor sequence or the splice donor sequence. In some embodiments, the splice acceptor sequence or the splice donor sequence is non-canonical. In some embodiments, the method further comprises the step of expressing antibody heavy and light chain polypeptides from the genes.

DESCRIPTION OF THE FIGURES

FIG. 2 shows gene sequences encoding two exemplary antibody fusion proteins of the present invention (SEQ ID NOs: 1 and 2). The underlined sequences are the linker sequences. The start and stop codons are shown in italics.

FIG. 3 shows a protein sequence of the protein product (SEQ ID NO:3) encoded by an exemplary antibody gene sequence of the present invention. The lowercase letters indicate the fusion protein linker between heavy chain and light chain protein. The heavy chain protein is shown in boldface and the light chain protein is shown in italics.

FIG. 5 provides the nucleic acid sequences of initial vectors sequences for the production of four different antibodies (SEQ ID NOs: 4-7).

FIG. 6 provides the nucleic acid sequences of four spliced vector sequences that produce fusion antibodies (SEQ ID NOs: 8-11).

FIG. 7 provides the nucleic acid sequences of four vectors in which a splice donor sequence has been mutated (SEQ ID NOs: 12-15).

FIG. 8 provides the amino acid sequences of the predicted gene sequences of the two additional antibody fusion proteins (3 (SEQ ID NO:16) and 4 (SEQ ID NO:17)). These sequences were not sequenced verified, however protein analysis shows that an active fusion protein was created and sequences needed for fusion splicing to occur were also found in these two gene constructs. The double underlined show the heavy chain genes, the underlined sequences are the linker sequences and the dash underlined sequences are the light chain gene sequences. The start and stop codons are shown in italics.

DEFINITIONS

Figure 1:
FIG. 1 shows a diagram of antibody fusion proteins of some embodiments of the present invention.

To facilitate understanding of the invention, a number of terms are defined below.

As used herein, the term "host cell" refers to any eukaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "vector" refers to any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein, the term "integrating vector" refers to a vector whose integration or insertion into a nucleic acid (e.g., a chromosome) is accomplished via an integrase. Examples of "integrating vectors" include, but are not limited to, retroviral vectors, transposons, and adeno associated virus vectors.

As used herein, the term "integrated" refers to a vector that is stably inserted into the genome (i.e., into a chromosome) of a host cell.

As used herein, the term "multiplicity of infection" or "MOI" refers to the ratio of integrating vectors:host cells used during transfection or transduction of host cells. For example, if 1,000,000 vectors are used to transduce 100,000 host cells, the multiplicity of infection is 10. The use of this term is not limited to events involving transduction, but instead encompasses introduction of a vector into a host by methods such as lipofection, microinjection, calcium phosphate precipitation, and electroporation.

As used herein, the term "genome" refers to the genetic material (e.g., chromosomes) of an organism.

The term "nucleotide sequence of interest" refers to any nucleotide sequence (e.g., RNA or DNA), the manipulation of which may be deemed desirable for any reason (e.g., treat disease, confer improved qualities, expression of a protein of interest in a host cell, expression of a ribozyme, etc.), by one of ordinary skill in the art. Such nucleotide sequences include, but are not limited to, coding sequences of structural genes (e.g., fusion antibodies of the present invention, etc.), and non-coding regulatory sequences which do not encode an mRNA or protein product (e.g., promoter sequence, polyadenylation sequence, termination sequence, enhancer sequence, etc.).

As used herein, the term "protein of interest" refers to a protein encoded by a nucleic acid of interest.

As used herein, the term "signal protein" refers to a protein that is co-expressed with a protein of interest and which, when detected by a suitable assay, provides indirect evidence of expression of the protein of interest. Examples of signal proteins useful in the present invention include, but are not limited to, beta-galactosidase, beta-lactamase, green fluorescent protein, and luciferase.

As used herein, the term "exogenous gene" refers to a gene that is not naturally present in a host organism or cell, or is artificially introduced into a host organism or cell.

The term "gene" refers to a nucleic acid (e.g., DNA or RNA) sequence that comprises coding sequences necessary for the production of a polypeptide or precursor (e.g., proinsulin). The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and includes sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' untranslated sequences. The sequences that are located 3' or downstream of the coding region and which are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decreases production. Molecules (e.g., transcription factors) that are involved in up-regulation or down-regulation are often called "activators" and "repressors," respectively.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the terms "nucleic acid molecule encoding," "DNA sequence encoding," "DNA encoding," "RNA sequence encoding," and "RNA encoding" refer to the order or sequence of deoxyribonucleotides or ribonucleotides along a strand of deoxyribonucleic acid or ribonucleic acid. The order of these deoxyribonucleotides or ribonucleotides determines the order of amino acids along the polypeptide (protein) chain. The DNA or RNA sequence thus codes for the amino acid sequence.

As used herein, the term "variant," when used in reference to a protein, refers to proteins encoded by partially homologous nucleic acids so that the amino acid sequence of the proteins varies. As used herein, the term "variant" encompasses proteins encoded by homologous genes having both conservative and nonconservative amino acid substitutions that do not result in a change in protein function, as well as proteins encoded by homologous genes having amino acid substitutions that cause decreased (e.g., null mutations) protein function or increased protein function.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein, the term "selectable marker" refers to a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that their use must be in conjunction with a cell line that lacks the relevant enzyme activity. Examples of non-dominant selectable markers include the thymidine kinase (tk) gene that is used in conjunction with $tk^-$ cell lines, the CAD gene which is used in conjunction with CAD-deficient cells and the mammalian hypoxanthine-guanine phosphoribosyl transferase (hprt) gene which is used in conjunction with $hprt^-$ cell lines. A review of the use of selectable markers in mammalian cell lines is provided in Sambrook, J. et al., *Molecular Cloning: A Laboratory Manual,* 2nd ed., Cold Spring Harbor Laboratory Press, New York (1989) pp. 16.9-16.15.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, RNA export elements, internal ribosome entry sites, etc. (defined infra).

Transcriptional control signals in eukaryotes comprise "promoter" and "enhancer" elements. Promoters and enhancers consist of short arrays of DNA sequences that interact specifically with cellular proteins involved in transcription (Maniatis et al., Science 236: 1237 [1987]). Promoter and enhancer elements have been isolated from a variety of eukaryotic sources including genes in yeast, insect and mammalian cells, and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (for review see, Voss et al., Trends Biochem. Sci., 11: 287 [1986]; and Maniatis et al., supra). For example, the SV40 early gene enhancer is very active in a wide variety of cell types from many mammalian species and has been widely used for the expression of proteins in mammalian cells (Dijkema et al., EMBO J. 4: 761 [1985]). Two other examples of promoter/enhancer elements active in a broad range of mammalian cell types are those from the human elongation factor 1α gene (Uetsuki et al., J. Biol. Chem., 264: 5791 [1989]; Kim et al., Gene 91: 217 [1990]; and Mizushima and Nagata, Nuc. Acids. Res., 18: 5322 [1990]) and the long terminal repeats of the Rous sarcoma virus (Gorman et al., Proc. Natl. Acad. Sci. USA 79: 6777 [1982]) and the human cytomegalovirus (Boshart et al., Cell 41: 521 [1985]).

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter.

Regulatory elements may be tissue specific or cell specific. The term "tissue specific" as it applies to a regulatory element refers to a regulatory element that is capable of directing selective expression of a nucleotide sequence of interest to a specific type of tissue (e.g., liver) in the relative absence of expression of the same nucleotide sequence of interest in a different type of tissue (e.g., lung).

Tissue specificity of a regulatory element may be evaluated by, for example, operably linking a reporter gene to a promoter sequence (which is not tissue-specific) and to the regulatory element to generate a reporter construct, introducing the reporter construct into the genome of an animal such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the regulatory element is "specific" for the tissues in which greater levels of expression are detected. Thus, the term "tissue-specific" (e.g., liver-specific) as used herein is a relative term that does not require absolute specificity of expression. In other words, the term "tissue-specific" does not require that one tissue have extremely high levels of expression and another tissue have no expression. It is sufficient that expression is greater in one tissue than another. By contrast, "strict" or "absolute" tissue-specific expression is meant to indicate expression in a single tissue type (e.g., liver) with no detectable expression in other tissues.

The term "cell type specific" as applied to a regulatory element refers to a regulatory element that is capable of directing selective expression of a nucleotide sequence of interest in a specific type of cell in the relative absence of expression of the same nucleotide sequence of interest in a different type of cell within the same tissue. The term "cell type specific" when applied to a regulatory element also means a regulatory element capable of promoting selective expression of a nucleotide sequence of interest in a region within a single tissue.

Cell type specificity of a regulatory element may be assessed using methods well known in the art (e.g., immunohistochemical staining and/or Northern blot analysis). Briefly, for immunohistochemical staining, tissue sections are embedded in paraffin, and paraffin sections are reacted with a primary antibody specific for the polypeptide product encoded by the nucleotide sequence of interest whose expression is regulated by the regulatory element. A labeled (e.g., peroxidase conjugated) secondary antibody specific for the primary antibody is allowed to bind to the sectioned tissue and specific binding detected (e.g., with avidin/biotin) by microscopy. Briefly, for Northern blot analysis, RNA is isolated from cells and electrophoresed on agarose gels to fractionate the RNA according to size followed by transfer of the RNA from the gel to a solid support (e.g., nitrocellulose or a nylon membrane). The immobilized RNA is then probed with a labeled oligo-deoxyribonucleotide probe or DNA probe to detect RNA species complementary to the probe used. Northern blots are a standard tool of molecular biologists.

The term "promoter," "promoter element," or "promoter sequence" as used herein, refers to a DNA sequence which when ligated to a nucleotide sequence of interest is capable of controlling the transcription of the nucleotide sequence of interest into mRNA. A promoter is typically, though not necessarily, located 5' (i.e., upstream) of a nucleotide sequence of interest whose transcription into mRNA it controls, and provides a site for specific binding by RNA polymerase and other transcription factors for initiation of transcription.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, etc.). In contrast, a "regulatable" promoter is one that is capable of directing a level of transcription of an operably linked nucleic acid sequence in the presence of a stimulus (e.g., heat shock, chemicals, etc.) that is different from the level of transcription of the operably linked nucleic acid sequence in the absence of the stimulus.

The presence of "splicing signals" on an expression vector often results in higher levels of expression of the recombinant transcript. Splicing signals mediate the removal of introns from the primary RNA transcript and consist of a splice donor and acceptor site (Sambrook et al, *Molecular Cloning: A Laboratory Manual,* 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell). However, it is not intended that expression vectors be limited to any particular viral origin of replication.

As used herein, the term "long terminal repeat" of "LTR" refers to transcriptional control elements located in or isolated from the U3 region 5' and 3' of a retroviral genome. As is known in the art, long terminal repeats may be used as control elements in retroviral vectors, or isolated from the retroviral genome and used to control expression from other types of vectors.

As used herein, the terms "RNA export element" or "Pre-mRNA Processing Enhancer (PPE)" refer to 3' and 5' cis-acting post-transcriptional regulatory elements that enhance export of RNA from the nucleus. "PPE" elements include, but are not limited to Mertz sequences (described in U.S. Pat. Nos. 5,914,267 and 5,686,120, all of which are incorporated herein by reference) and woodchuck mRNA processing enhancer (WPRE; WO99/14310 and U.S. Pat. No. 6,136,597, each of which is incorporated herein by reference).

As used herein, the term "polycistronic" refers to an mRNA encoding more than one polypeptide chain (See, e.g., WO 93/03143, WO 88/05486, and European Pat. No. 117058, all of which are incorporated herein by reference). Likewise, the term "arranged in polycistronic sequence" refers to the arrangement of genes encoding two different polypeptide chains in a single mRNA.

As used herein, the term "internal ribosome entry site" or "IRES" refers to a sequence located between polycistronic genes that permits the production of the expression product originating from the second gene by internal initiation of the translation of the dicistronic mRNA. Examples of internal ribosome entry sites include, but are not limited to, those derived from foot and mouth disease virus (FDV), encephalomyocarditis virus, poliovirus and RDV (Scheper et al., Biochem. 76: 801-809 [1994]; Meyer et al., J. Virol. 69: 2819-2824 [1995]; Jang et al., 1988, J. Virol. 62: 2636-2643 [1998]; Haller et al., J. Virol. 66: 5075-5086 [1995]). Vectors incorporating IRES's may be assembled as is known in the art. For example, a retroviral vector containing a polycistronic sequence may contain the following elements in operable association: nucleotide polylinker, gene of interest, an internal ribosome entry site and a mammalian selectable marker or another gene of interest. The polycistronic cassette is situated within the retroviral vector between the 5' LTR and the 3' LTR at a position such that transcription from the 5' LTR promoter transcribes the polycistronic message cassette. The transcription of the polycistronic message cassette may also be driven by an internal promoter (e.g., cytomegalovirus promoter) or an inducible promoter, which may be preferable depending on the use. The polycistronic message cassette can further comprise a cDNA or genomic DNA (GDNA) sequence operatively associated within the polylinker. Any mammalian selectable marker can be utilized as the polycistronic message cassette mammalian selectable marker. Such mammalian selectable markers are well known to those of skill in the art and can include, but are not limited to, kanamycin/G418, hygromycin B or mycophenolic acid resistance markers.

As used herein, the term "retrovirus" refers to a retroviral particle which is capable of entering a cell (i.e., the particle contains a membrane-associated protein such as an envelope protein or a viral G glycoprotein which can bind to the host cell surface and facilitate entry of the viral particle into the cytoplasm of the host cell) and integrating the retroviral genome (as a double-stranded provirus) into the genome of the host cell. The term "retrovirus" encompasses Oncovirinae (e.g., Moloney murine leukemia virus (MoMOLV), Moloney murine sarcoma virus (MoMSV), and Mouse mammary tumor virus (MMTV), Spumavirinae, and Lentivirinae (e.g., Human immunodeficiency virus, Simian immunodeficiency virus, Equine infection anemia virus, and Caprine arthritis-encephalitis virus; See, e.g., U.S. Pat. Nos. 5,994,136 and 6,013,516, both of which are incorporated herein by reference).

As used herein, the term "retroviral vector" refers to a retrovirus that has been modified to express a gene of interest. Retroviral vectors can be used to transfer genes efficiently into host cells by exploiting the viral infectious process. Foreign or heterologous genes cloned (i.e., inserted using molecular biological techniques) into the retroviral genome can be delivered efficiently to host cells that are susceptible to infection by the retrovirus. Through well known genetic manipulations, the replicative capacity of the retroviral genome can be destroyed. The resulting replication-defective vectors can be used to introduce new genetic material to a cell but they are unable to replicate. A helper virus or packaging cell line can be used to permit vector particle assembly and egress from the cell. Such retroviral vectors comprise a replication-deficient retroviral genome containing a nucleic acid sequence encoding at least one gene of interest (i.e., a polycistronic nucleic acid sequence can encode more than one gene of interest), a 5' retroviral long terminal repeat (5' LTR); and a 3' retroviral long terminal repeat (3' LTR).

The term "pseudotyped retroviral vector" refers to a retroviral vector containing a heterologous membrane protein. The term "membrane-associated protein" refers to a protein (e.g., a viral envelope glycoprotein or the G proteins of viruses in the Rhabdoviridae family such as VSV, Piry, Chandipura and Mokola), which is associated with the membrane surrounding a viral particle; these membrane-associated proteins mediate the entry of the viral particle into the host cell. The membrane associated protein may bind to specific cell surface protein receptors, as is the case for retroviral envelope proteins or the membrane-associated protein may interact with a phospholipid component of the plasma membrane of the host cell, as is the case for the G proteins derived from members of the Rhabdoviridae family.

As used herein, the term "retroviral particle" refers to infections viral particles generated by packaging a retroviral vector in a packaging cell line.

As used herein, the term "plasmid" refers to a circular, extra-chromosomal nucleic acid molecule capable of autonomous replication in a host cell.

The term "heterologous membrane-associated protein" refers to a membrane-associated protein that is derived from a virus that is not a member of the same viral class or family as that from which the nucleocapsid protein of the vector particle is derived. "Viral class or family" refers to the taxonomic rank of class or family, as assigned by the International Committee on Taxonomy of Viruses.

The term "Rhabdoviridae" refers to a family of enveloped RNA viruses that infect animals, including humans, and plants. The Rhabdoviridae family encompasses the genus *Vesiculovirus* that includes vesicular stomatitis virus (VSV), Cocal virus, Piry virus, Chandipura virus, and Spring viremia of carp virus (sequences encoding the Spring viremia of carp virus are available under GenBank accession number U18101). The G proteins of viruses in the *Vesiculovirus genera* are virally-encoded integral membrane proteins that form externally projecting homotrimeric spike glycoproteins complexes that are required for receptor binding and membrane fusion. The G proteins of viruses in the *Vesiculovirus genera* have a covalently bound palmititic acid ($C_{16}$) moiety. The amino acid sequences of the G proteins from the Vesiculoviruses are fairly well conserved. For example, the Piry virus G proteins share about 38% identity and about 55% similarity with the VSV G proteins (several strains of VSV are known, e.g., Indiana, New Jersey, Orsay, San Juan, etc., and their G proteins are highly homologous). The Chandipura virus G protein and the VSV G proteins share about 37% identity and 52% similarity. Given the high degree of conservation (amino acid sequence) and the related functional characteristics (e.g., binding of the virus to the host cell and fusion of membranes, including syncytia formation) of the G proteins of the Vesiculoviruses, the G proteins from non-VSV Vesiculoviruses may be used in place of the VSV G protein for the pseudotyping of viral particles. The G proteins of the Lyssa viruses (another genera within the Rhabdoviridae family) also share a fair degree of conservation with the VSV G proteins and function in a similar manner (e.g., mediate fusion of membranes) and therefore may be used in place of the VSV G protein for the pseudotyping of viral particles. The Lyssa viruses include the Mokola virus and the Rabies viruses (several strains of Rabies virus are known and their G proteins have been cloned and sequenced). The Mokola virus G protein shares stretches of homology (particularly over the extracellular and transmembrane domains) with the VSV G proteins, which show about 31% identity, and 48% similarity with the VSV G proteins. Preferred G proteins share at least 25% identity, preferably at least 30% identity and most preferably at least 35% identity with the VSV G proteins. The VSV G protein from which New Jersey strain (the sequence of this G protein is provided in GenBank accession numbers M27165 and M21557) is employed as the reference VSV G protein.

As used herein, the term "lentivirus vector" refers to retroviral vectors derived from the Lentiviridae family (e.g., human immunodeficiency virus, simian immunodeficiency virus, equine infectious anemia virus, and caprine arthritis-encephalitis virus) that are capable of integrating into non-dividing cells (See, e.g., U.S. Pat. Nos. 5,994,136 and 6,013,516, both of which are incorporated herein by reference).

The term "pseudotyped lentivirus vector" refers to lentivirus vector containing a heterologous membrane protein (e.g., a viral envelope glycoprotein or the G proteins of viruses in the Rhabdoviridae family such as VSV, Piry, Chandipura and Mokola).

As used herein the term, the term "in vitro" refers to an artificial environment and to processes or reactions that occur within an artificial environment. In vitro environments can consist of, but are not limited to, test tubes and cell cultures. The term "in vivo" refers to the natural environment (e.g., an animal or a cell) and to processes or reactions that occur within a natural environment.

As used herein, the term "immunoglobulin" refers to proteins that bind a specific antigen. Immunoglobulins include, but are not limited to, polyclonal, monoclonal, chimeric, and humanized antibodies, Fab fragments, $F(ab')_2$ fragments, and includes immunoglobulins of the following classes: IgG, IgA, IgM, IgD, IbE, and secreted immunoglobulins (sIg). Immunoglobulins generally, but not always, comprise two identical heavy chains and two light chains.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, $F(ab')_2$ fragments, and Fab expression libraries; and single chain (e.g., fusion) antibodies.

As used herein, the term "purified" refers to molecules, either nucleic or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

The term "test compound" refers to any chemical entity, pharmaceutical, drug, and the like contemplated to be useful in the treatment and/or prevention of a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

DETAILED DESCRIPTION OF THE INVENTION

In some embodiments, the present invention provides antibody fusions. The antibody fusions of the present invention comprise antibody light chains fused to antibody heavy chains in a single polypeptide. Such fusion antibodies find use in a variety of applications including, but not limited to, the exemplary applications described below.

I. Generation of Antibody Fusions

In some embodiments, the present invention provides methods of generating antibody fusion polypeptides.

A. Antibody Fusion Genes

The present invention is not limited to a particular antibody. Any desired antibody may be generated as a fusion polypeptide. In some embodiments, antibody heavy and/or light chain genes are obtained commercially. Commercially available antibodies (e.g., available as antibody libraries) include, but are not limited to, those available from Cambridge Antibody Technology (Cambridgeshire, United Kingdom), HUCAL libraries (See e.g., U.S. Pat. No. 5,514,548, herein incorporated by reference), Morphosys (Munich, Germany), Bioinvent (Lund, Sweden), and INTRACEL (Rockville, Md.). In other embodiments, antibody heavy and light chain genes are obtained by PCR (e.g., including but not limited to, the method disclosed in U.S. Pat. No. 6,291,650, herein incorporated by reference).

In some embodiments, the antibodies are recombinant antibodies or fragments thereof. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

In some embodiments, expression vectors comprise a single antibody light chain gene fused to a single antibody heavy chain gene. In other embodiments, expression vectors comprise greater than one (e.g., two or more) antibody light chain genes and greater than one (e.g., two or more) antibody heavy chain genes.

In some preferred embodiments, the antibody fusions of the present invention comprise an entire antibody heavy chain and an entire antibody light chain. In other embodiments, the antibody heavy chain is missing the last codon. In still further embodiments, the antibody fusion genes comprise fragments or portions of the antibody heavy and/or light chain genes. The antibody heavy and light chain genes can be from any type of antibody including, but not limited to, IgG, IgM, IgE, IgA, etc.

In some embodiments, the light and heavy chain genes are separated by a linker (e.g., a peptide linker). In some embodiments, the linker is a peptide linker comprising between approximately 5 and 20 amino acids. The present invention is not limited to the use of a peptide linker. Any suitable linker may be utilized. In other embodiments, antibody light and heavy chain genes are fused without a linker.

B. Expression Vectors

Antibody fusion genes of the present invention may be expressed in any suitable vector including, but not limited to, those disclosed herein.

i. Retroviral Vectors

In some embodiments, antibody fusions are expressed in retroviral vectors. Retroviruses (family Retroviridae) are divided into three groups: the spumaviruses (e.g., human foamy virus); the lentiviruses (e.g., human immunodeficiency virus and sheep visna virus) and the oncoviruses (e.g., MLV, Rous sarcoma virus).

Retroviruses are enveloped (i.e., surrounded by a host cell-derived lipid bilayer membrane) single-stranded RNA viruses that infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products), which is surrounded by a lipid bilayer membrane derived from the host cell containing the viral envelope glycoproteins (also referred to as membrane-associated proteins).

The organization of the genomes of numerous retroviruses is well known to the art and this has allowed the adaptation of the retroviral genome to produce retroviral vectors. The production of a recombinant retroviral vector carrying antibody fusion genes of interest is typically achieved in two stages.

First, the antibody fusion gene is inserted into a retroviral vector which contains the sequences necessary for the efficient expression of the antibody fusion gene of interest (including promoter and/or enhancer elements which may be provided by the viral long terminal repeats (LTRs) or by an internal promoter/enhancer and relevant splicing signals), sequences required for the efficient packaging of the viral RNA into infectious virions (e.g., the packaging signal (Psi), the tRNA primer binding site (−PBS), the 3' regulatory sequences required for reverse transcription (+PBS)) and the viral LTRs. The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); therefore, the resulting virus is said to be replication defective.

Second, following the construction of the recombinant vector, the vector DNA is introduced into a packaging cell line. Packaging cell lines provide proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles that lack a membrane-associated protein (e.g., an env protein). In order to produce viral particles containing a membrane associated protein that will permit entry of the virus into a cell, the packaging cell line containing the retroviral sequences is transfected with sequences encoding a membrane-associated protein (e.g., the G protein of vesicular stomatitis virus (VSV)). The transfected packaging cell will then produce viral particles that contain the membrane-associated protein expressed by the transfected packaging cell line; these viral particles, which contain viral genomic RNA derived from one virus encapsidated by the envelope proteins of another virus, are said to be pseudotyped virus particles.

The retroviral vectors utilized in the methods and compositions of the present invention can be further modified to include additional regulatory sequences. For example, in some embodiments, the retroviral vectors include the following elements in operable association: a) a 5' LTR; b) a packaging signal; c) a 3' LTR and d) a nucleic acid encoding a antibody fusion protein of interest located between the 5' and 3' LTRs. In some embodiments of the present invention, the nucleic acid of interest may be arranged in opposite orientation to the 5' LTR when transcription from an internal promoter is desired. Suitable internal promoters include, but are not limited to, the alpha-lactalbumin promoter, the CMV promoter (human or ape), and the thymidine kinase promoter.

In other embodiments of the present invention, where secretion of the fusion antibody is desired, the vector is modified by including a signal peptide sequence in operable association with the fusion protein of interest. The sequences of several suitable signal peptides are known to those in the art, including, but not limited to, those derived from tissue plasminogen activator, human growth hormone, lactoferrin, alpha-casein, and alpha-lactalbumin. In other embodiments, the native signal peptide sequence of the antibody heavy and/or light chain gene included in the fusion is utilized.

In other embodiments of the present invention, the vectors are modified by incorporating an RNA export element (See, e.g., U.S. Pat. Nos. 5,914,267; 6,136,597; and 5,686,120; and WO 99/14310, all of which are incorporated herein by reference) either 3' or 5' to the nucleic acid sequence encoding the antibody fusion protein of interest. It is contemplated that the use of RNA export elements allows high levels of expression of the antibody fusions without incorporating splice signals or introns in the nucleic acid sequence encoding the antibody fusion protein of interest.

In still other embodiments, the vector further comprises at least one internal ribosome entry site (IRES) sequence. The sequences of several suitable IRES's are available, including, but not limited to, those derived from foot and mouth disease virus (FDV), encephalomyocarditis virus, and poliovirus. The IRES sequence can be interposed between two transcriptional units (e.g., nucleic acids encoding different fusion proteins of interest) to form a polycistronic sequence so that the two transcriptional units are transcribed from the same promoter.

The retroviral vectors of the present invention may also further comprise a selectable marker allowing selection of transformed cells. A number of selectable markers find use in the present invention, including, but not limited to the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid.

In still other embodiments of the present invention, the retroviral vectors may comprise recombination elements recognized by a recombination system (e.g., the cre/loxP or flp recombinase systems, see, e.g., Hoess et al., Nucleic Acids Res. 14: 2287-2300 [1986], O'Gorman et al., Science 251: 1351-55 [1991], van Deursen et al., Proc. Natl. Acad. Sci. USA 92: 7376-80 [1995], and U.S. Pat. No. 6,025,192, herein incorporated by reference). After integration of the vectors into the genome of the host cell, the host cell can be transiently transfected (e.g., by electroporation, lipofection, or microinjection) with either a recombinase enzyme (e.g., Cre recombinase) or a nucleic acid sequence encoding the recombinase enzyme and one or more nucleic acid sequences encoding antibody fusion genes of interest flanked by sequences recognized by the recombination enzyme so that the nucleic acid sequence is inserted into the integrated vector.

Viral vectors, including recombinant retroviral vectors, provide a more efficient means of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation are subject to rearrangement and degradation.

The most commonly used recombinant retroviral vectors are derived from the amphotropic Moloney murine leukemia virus (MOMLV) (See e.g., Miller and Baltimore Mol. Cell. Biol. 6: 2895 [1986]). The MoMLV system has several advantages: 1) this specific retrovirus can infect many different cell types, 2) established packaging cell lines are available for the production of recombinant MoMLV viral particles and 3) the transferred genes are permanently integrated into the target cell chromosome. The established MoMLV vector systems comprise a DNA vector containing a small portion of the retroviral sequence (e.g., the viral long terminal repeat or "LTR" and the packaging or "psi" signal) and a packaging cell line. The antibody fusion gene to be transferred is inserted into the DNA vector. The viral sequences present on the DNA vector provide the signals necessary for the insertion or packaging of the vector RNA into the viral particle and for the expression of the inserted gene. The packaging cell line provides the proteins required for particle assembly (Markowitz et al., J. Virol. 62: 1120 [1988]).

Despite these advantages, existing retroviral vectors based upon MoMLV are limited by several intrinsic problems: 1) they do not infect non-dividing cells (Miller et al., Mol. Cell. Biol. 10: 4239 [1990]), except, perhaps, oocytes; 2) they produce low titers of the recombinant virus (Miller and Rosman, BioTechniques 7: 980 [1980] and Miller, Nature 357: 455 [1990]); and 3) they infect certain cell types (e.g., human lymphocytes) with low efficiency (Adams et al., Proc. Natl. Acad. Sci. USA 89: 8981 [1992]). The low titers associated with MoMLV-based vectors have been attributed, at least in part, to the instability of the virus-encoded envelope protein. Concentration of retrovirus stocks by physical means (e.g., ultracentrifugation and ultrafiltration) leads to a severe loss of infectious virus.

The low titer and inefficient infection of certain cell types by MoMLV-based vectors has been overcome by the use of pseudotyped retroviral vectors that contain the G protein of VSV as the membrane associated protein. Unlike retroviral envelope proteins, which bind to a specific cell surface protein receptor to gain entry into a cell, the VSV G protein interacts with a phospholipid component of the plasma membrane (Mastromarino et al., J. Gen. Virol. 68: 2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al. Proc. Natl. Acad. Sci. USA 90: 8033 [1993]).

The present invention is not limited to the use of the VSV G protein when a viral G protein is employed as the heterologous membrane-associated protein within a viral particle (See, e.g., U.S. Pat. No. 5,512,421, which is incorporated herein by reference). The G proteins of viruses in the *Vesiculovirus genera* other than VSV, such as the Piry and Chandipura viruses, that are highly homologous to the VSV G protein and, like the VSV G protein, contain covalently linked palmitic acid (Brun et al. Intervirol. 38: 274 [1995] and Masters et al., Virol. 171: 285 (1990]). Thus, the G protein of the Piry and Chandipura viruses can be used in place of the VSV G protein for the pseudotyping of viral particles. In addition, the VSV G proteins of viruses within the Lyssa virus genera such as Rabies and Mokola viruses show a high degree of conservation (amino acid sequence as well as functional conservation) with the VSV G proteins. For example, the Mokola virus G protein has been shown to function in a manner similar to the VSV G protein (i.e., to mediate membrane fusion) and therefore may be used in place of the VSV G protein for the pseudotyping of viral particles (Mebatsion et al., J. Virol. 69: 1444 [1995]). Viral particles may be pseudotyped using either the Piry, Chandipura or Mokola G protein using a plasmid containing sequences encoding either the Piry, Chandipura or Mokola G protein under the transcriptional control of a suitable promoter element (e.g., the CMV intermediate-early promoter; numerous expression vectors containing the CMV IE promoter are available, such as the pcDNA3.1 vectors (Invitrogen)) is used in place of pHCMV-G. Sequences encoding other G proteins derived from other members of the Rhabdoviridae family may be used; sequences encoding numerous rhabdoviral G proteins are available from the GenBank database.

The majority of retroviruses can transfer or integrate a double-stranded linear form of the virus (the provirus) into the genome of the recipient cell only if the recipient cell is cycling (i.e., dividing) at the time of infection. Retroviruses that have been shown to infect dividing cells exclusively, or more efficiently, include MLV, spleen necrosis virus, Rous sarcoma virus and human immunodeficiency virus (HIV; while HIV infects dividing cells more efficiently, HIV can infect non-dividing cells).

It has been shown that the integration of MLV virus DNA depends upon the host cell's progression through mitosis and it has been postulated that the dependence upon mitosis reflects a requirement for the breakdown of the nuclear envelope in order for the viral integration complex to gain entry into the nucleus (Roe et al., EMBO J. 12: 2099 [1993]). However, as integration does not occur in cells arrested in metaphase, the breakdown of the nuclear envelope alone may not be sufficient to permit viral integration; there may be additional requirements such as the state of condensation of the genomic DNA (Roe et al., supra).

The present invention also contemplates the use of lentiviral vectors to express antibody fusion genes. The *lentiviruses* (e.g., equine infectious anemia virus, caprine arthritis-encephalitis virus, human immunodeficiency virus) are a subfamily of retroviruses that are able to integrate into non-dividing cells. The lentiviral genome and the proviral DNA have the three genes found in all retroviruses: gag, pol, and env, which are flanked by two LTR sequences. The gag gene encodes the internal structural proteins (e.g., matrix, capsid, and nucleocapsid proteins); the pol gene encodes the reverse transcriptase, protease, and integrase proteins; and the pol gene encodes the viral envelope glycoproteins. The 5' and 3' LTRs control transcription and polyadenylation of the viral RNAs. Additional genes in the lentiviral genome include the vif vpr, tat, rev, vpu, nef, and vpx genes.

A variety of lentiviral vectors and packaging cell lines are known in the art and find use in the present invention (See, e.g., U.S. Pat. Nos. 5,994,136 and 6,013,516, both of which are herein incorporated by reference). Furthermore, the VSV G protein has also been used to pseudotype retroviral vectors based upon the human immunodeficiency virus (HIV) (Naldini et al., Science 272: 263 [1996]). Thus, the VSV G protein may be used to generate a variety of pseudotyped retroviral vectors and is not limited to vectors based on MoMLV. The lentiviral vectors may also be modified as described above to contain various regulatory sequences (e.g., signal peptide sequences, RNA export elements, and IRES's). After the lentiviral vectors are produced, they may be used to transfect host cells as described below for retroviral vectors.

Once integrating vectors (e.g., retroviral vectors) encoding antibody fusions have been produced, they may be used to transfect or transduce host cells (examples of which are described below). Preferably, host cells are transfected or transduced with integrating vectors at a multiplicity of infection sufficient to result in the integration of the desired number of vectors. When non-pseudotyped retroviral vectors are utilized for infection, the host cells are incubated with the culture medium from the retroviral producing cells containing the desired titer (i.e., colony forming units, CFUs) of infectious vectors. When pseudotyped retroviral vectors are utilized, the vectors are concentrated to the appropriate titer by ultracentrifugation and then added to the host cell culture. Alternatively, the concentrated vectors can be diluted in a culture medium appropriate for the cell type.

In each case, the host cells are exposed to medium containing the infectious retroviral vectors for a sufficient period of time to allow infection and subsequent integration of the vectors. In general, the amount of medium used to overlay the cells should be kept to as small a volume as possible so as to encourage the maximum amount of integration events per cell. As a general guideline, the number of colony forming units (cfu) per milliliter should be about $10^5$ to $10^7$ cfu/ml, depending upon the number of integration events desired. The host cells (See below description of host cells) are then cultured (e.g., according to the methods described below).

ii. Additional Vectors

The present invention is not limited to the use of retroviral vectors. Indeed, the use of a variety of vectors is contemplated, including, but not limited to plasmids, cosmids, bacterial artificial chromosomes, yeast artificial chromosomes, adeno-associated virus vectors, and adenovirus vectors. Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In some embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In other embodiments, the expression vector also contains a ribosome binding site for translation initiation and a transcription terminator. In still other embodiments of the present invention, the vector may also include appropriate sequences for amplifying expression.

C. Host Cells

The present invention contemplates the transfection of a variety of host cells with vectors to generate the antibody fusion polypeptides of the present invention. A number of mammalian host cell lines are known in the art. In general, these host cells are capable of growth and survival when placed in either monolayer culture or in suspension culture in a medium containing the appropriate nutrients and growth factors, as is described in more detail below. Typically, the cells are capable of expressing and secreting large quantities of a particular antibody fusion of interest into the culture medium. Examples of suitable mammalian host cells include, but are not limited to Chinese hamster ovary cells (CHO-K1, ATCC CCl-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36: 59 [1977]); baby hamster kidney cells (BHK, ATCC CCL 10); mouse sertoli cells (TM4, Mather, Biol. Reprod. 23: 243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383: 44-68 [1982]); MRC 5 cells; FS4 cells; rat fibroblasts (208F cells); MDBK cells (bovine kidney cells); and a human hepatoma line (Hep G2).

The present invention also contemplates the use of amphibian and insect host cell lines. Examples of suitable insect host cell lines include, but are not limited to, mosquito cell lines (e.g., ATCC CRL-1660). Examples of suitable amphibian host cell lines include, but are not limited to, toad cell lines (e.g., ATCC CCL-102).

In other embodiments of the present invention, the host cell is a lower eukaryotic cell (e.g., a yeast cell). In still other embodiments of the present invention, the host cell can be a prokaryotic cell (e.g., a bacterial cell). Specific examples include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae*, and *Schizosaccharomycees pombe*.

D. Host Cell Culture

The transfected host cells are cultured according to methods known in the art. Suitable culture conditions for mammalian cells are well known in the art (See e.g., J. Immunol. Methods (1983)56: 221-234 [1983*], Animal Cell Culture: A Practical Approach* 2nd Ed., Rickwood, D. and Hames, B. D., eds. Oxford University Press, New York [1992]).

The host cell cultures of the present invention are prepared in a media suitable for the particular cell being cultured. Commercially available media such as Ham's F10 (Sigma, St. Louis, Mo.), Minimal Essential Medium (MEM, Sigma), RPMI-1640 (Sigma), and Dulbecco's Modified Eagle's Medium (DMEM, Sigma) are exemplary nutrient solutions. Suitable media are also described in U.S. Pat. Nos. 4,767,704; 4,657,866; 4,927,762; 5,122,469; 4,560,655; and WO 90/03430 and WO 87/00195; the disclosures of which are herein incorporated by reference. Any of these media may be supplemented as necessary with serum, hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin (gentamicin), trace elements (defined as inorganic compounds usually present at final concentrations in the micromolar range) lipids (such as linoleic or other fatty acids) and their suitable carriers, and glucose or an equivalent energy source. Any other necessary supplements may also be included at appropriate concentrations that would be known to those skilled in the art. For mammalian cell culture, the osmolality of the culture medium is generally about 290-330 mOsm.

The present invention also contemplates the use of a variety of culture systems (e.g., petri dishes, 96 well plates, roller bottles, and bioreactors) for the transfected host cells. For example, the transfected host cells can be cultured in a perfusion system. Perfusion culture refers to providing a continuous flow of culture medium through a culture maintained at high cell density. The cells are suspended and do not require a solid support to grow on. Generally, fresh nutrients must be supplied continuously with concomitant removal of toxic metabolites and, ideally, selective removal of dead cells. Filtering, entrapment and micro-capsulation methods are all suitable for refreshing the culture environment at sufficient rates.

As another example, in some embodiments a fed batch culture procedure can be employed. In the preferred fed batch culture the mammalian host, cells and culture medium are supplied to a culturing vessel initially and additional culture nutrients are fed, continuously or in discrete increments, to the culture during culturing, with or without periodic cell and/or product harvest before termination of culture. The fed batch culture can include, for example, a semi-continuous fed batch culture, wherein periodically whole culture (including cells and medium) is removed and replaced by fresh medium. Fed batch culture is distinguished from simple batch culture in which all components for cell culturing (including the cells and all culture nutrients) are supplied to the culturing vessel at the start of the culturing process. Fed batch culture can be further distinguished from perfusion culturing insofar as the supernatant is not removed from the culturing vessel during the process (in perfusion culturing, the cells are restrained in the culture by, e.g., filtration, encapsulation, anchoring to microcarriers etc. and the culture medium is continuously or intermittently introduced and removed from the culturing vessel). In some particularly preferred embodiments, the batch cultures are performed in roller bottles.

Further, the cells of the culture may be propagated according to any scheme or routine that may be suitable for the particular host cell and the particular production plan contemplated. Therefore, the present invention contemplates a single step or multiple step culture procedure. In a single step culture the host cells are inoculated into a culture environment and the processes of the instant invention are employed during a single production phase of the cell culture. Alternatively, a multi-stage culture is envisioned. In the multi-stage culture cells may be cultivated in a number of steps or phases. For instance, cells may be grown in a first step or growth phase culture wherein cells, possibly removed from storage, are inoculated into a medium suitable for promoting growth and high viability. The cells may be maintained in the growth phase for a suitable period of time by the addition of fresh medium to the host cell culture.

Fed batch or continuous cell culture conditions are devised to enhance growth of the mammalian cells in the growth phase of the cell culture. In the growth phase cells are grown under conditions and for a period of time that is maximized for growth. Culture conditions, such as temperature, pH, dissolved oxygen ($dO_2$) and the like, are those used with the particular host and will be apparent to the ordinarily skilled artisan. Generally, the pH is adjusted to a level between about 6.5 and 7.5 using either an acid (e.g., $CO_2$) or a base (e.g., $Na_2CO_3$ or NaOH). A suitable temperature range for culturing mammalian cells such as CHO cells is between about 30 to 38° C. and a suitable $dO_2$ is between 5-90% of air saturation.

In some embodiments, following the antibody fusion production phase, the antibody fusion proteins of interest are recovered from the culture medium using techniques that are well established in the art. In some embodiments, the fusion proteins are preferably recovered from the culture medium as secreted polypeptides (e.g., the secretion of the antibody fusion polypeptides of interest is directed by a signal peptide sequence), although it also may be recovered from host cell lysates. As a first step, the culture medium or lysate is centrifuged to remove particulate cell debris. The polypeptide thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG. A protease inhibitor such as phenyl methyl sulfonyl fluoride (PMSF) also may be useful to inhibit proteolytic degradation during purification. Additionally, the protein of interest can be fused in frame to a marker sequence, which allows for purification of the protein of interest. Non-limiting examples of marker sequences include a hexahistidine tag that may be supplied by a vector, preferably a pQE-9 vector, and a hemagglutinin (HA) tag. The HA tag corresponds to an epitope derived from the influenza hemagglutinin protein (See e.g., Wilson et al., Cell, 37: 767 [1984]). One skilled in the art will appreciate that purification methods suitable for the polypeptide of interest may require modification to account for changes in the character of the polypeptide upon expression in recombinant cell culture.

II. Uses of Antibody Fusion Proteins

Figure 4:
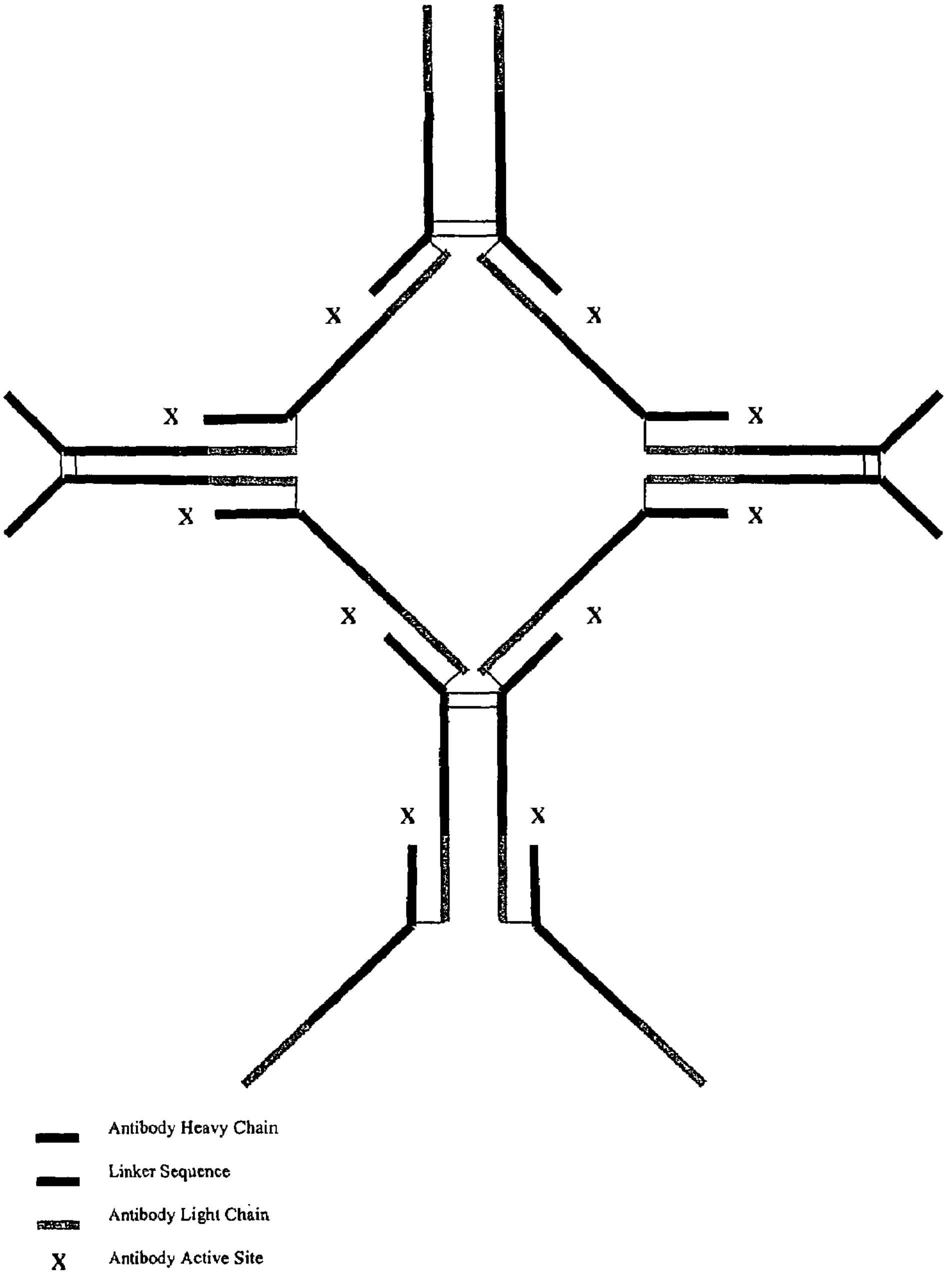
FIG. 4 shows an exemplary multivalent antibody of the present invention.

The antibody fusion of the present invention find use in a variety of applications. In general, the antibody fusions of the present invention are suitable for use in any application requiring antibodies. The present invention is not limited to a particular mechanism. Indeed, an understanding of the mechanism of the present invention is not necessary to practice the present invention. However, it is contemplated that the antibody fusions of the present invention form multivalent structures through disulfide bonds. In some embodiments, it is contemplated that disulfide bonds form between the same amino acids involved in the formation of disulfide bonds in non-fusion antibodies. Experiments conducted during the course of the development of the present invention led to the unexpected result that the fusion antibodies of the present invention assemble into multivalent structures. Such higher order structures may have at least two (e.g., at least 5, or even 10 or more) antibody fusion polypeptides. One exemplary multivalent structure is shown in FIG. 4.

Experiments conducted during the course of development of the present invention led to the unexpected result that the fusion antibodies of the present invention retained functional binding to antigens. The present invention is not limited to a particular mechanism. Indeed, an understanding of the mechanism is not necessary to practice the present invention. Nonetheless, it is contemplated that the antibody fusions of the present invention, as well as multivalent complexes thereof are contemplated to have several advantages over traditional antibodies including, but not limited to, longer half-life after injection, increased immune response, more potent drug or isotope delivery to a specific antigen, IgM like function, increased immunogenicity if used as a vaccine, and an increase in the sensitivity of assays that use antibodies.

Accordingly, it is contemplated that the antibody fusions of the present invention find use in both in vitro (e.g., diagnostic and research) applications, as well as in vivo (vaccine and pharmaceutical) applications.

A. In Vitro Applications

For example, in some embodiments, the fusion antibodies of the present invention are utilized in in vitro binding assays. Such assays find use in a wide variety of diagnostic and research applications including, but not limited to, identification of antigens in a mixture and determining the presence or absence of expression of a particular protein. Antibody binding is detected by techniques known in the art, including, but not limited to, radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary fusion antibody. In another embodiment, the primary fusion antibody is detected by detecting binding of a secondary antibody or reagent to the primary fusion antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the result of the immunoassay is utilized.

In other embodiments, the immunoassay described in U.S. Pat. Nos. 5,599,677 and 5,672,480; each of which is herein incorporated by reference it utilized.

B. In Vivo Applications

In other embodiments, the fusion antibodies of the present invention are used in a variety of in vivo applications. For example, in some embodiments, the fusion antibodies of the present invention are used in vaccines. Immunoglobulins may be altered for use as vaccines (See e.g., U.S. Pat. Nos. 6,132,718, 5,792,455, 5,798,100, 5,658,762, and 5,583,202; each of which is herein incorporated by reference). Fusion antibodies of the present invention are suitable as vaccines for any number of pathogens (e.g., viral or bacterial pathogens).

In other embodiments, fusion antibodies are utilized as cancer vaccines. In some embodiments, the present invention provides cancer vaccines comprising fusion antibodies directed against a specific cancer. Cancer vaccines induce a systemic tumor-specific immune response. Such a response is capable of eradicating tumor cells anywhere in the body (e.g., metastatic tumor cells). Methods for generating cancer vaccines are well known in the art (See e.g., U.S. Pat. Nos. 5,994,523; 5,972,334; 5,904,920; 5,674,486; and 6,207,147; each of which is herein incorporated by reference).

In some embodiments, cancer vaccines are administered when cancer is first detected (e.g., concurrently with other therapeutics such as chemotherapy). In other embodiments, cancer vaccines are administered following treatment (e.g., surgical resection, radiation or chemotherapy) to prevent relapse or metastases. In yet other embodiments, cancer vaccines are administered prophylactically (e.g., to those at risk of a certain cancer).

The vaccines of the present invention may be administered using any suitable method, including but not limited to, those described above. In preferred embodiments, administration of a cancer vaccine of the present invention results in elimination (e.g., decrease or elimination of tumors) or prevention of detectable cancer cells.

In other embodiments, the present invention provides therapy for cancer comprising the administration of therapeutic antibodies (See e.g., U.S. Pat. Nos. 6,180,357; and 6,051,230; both of which are herein incorporated by reference).

In some embodiments, the therapeutic antibodies comprise a fusion antibody of the present invention (e.g., generated against a tumor antigen or tumor marker) conjugated to a cytotoxic agent. Such antibodies are particularly suited for targeting markers expressed on tumor cells but not normal cells. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies or growth factors, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-11, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include a plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93: 280 [1983]).

For example, in some embodiments the present invention provides immunotoxins targeted to tumor markers. Imunotoxins are conjugates of a specific targeting agent typically a tumor-directed fusion antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48: 6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

C. Pharmaceutical Compositions

In preferred embodiments, antibody based therapeutics are formulated as pharmaceutical compositions. In preferred embodiments, administration of an antibody composition of the present invention results in a measurable decrease in cancer (e.g., decrease or elimination of tumors.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, antibody fusion proteins can be administered to a patient alone, or in combination with other drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, antibody fusion proteins may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts the level of the antibody fusion protein.

A therapeutically effective dose refers to that amount of antibody fusion protein that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Administration to the bone marrow may necessitate delivery in a manner different from intravenous injections.

III. Deletion of Antibody Splice Junctions

Experiments conducted during the course of development of the present invention demonstrated that the presence of donor or acceptor splice junctions in bicistronic constructs for the expression of antibody heavy and light chain genes resulted in the spontaneous formation of antibody fusions. Accordingly, in some embodiments, the present invention provides methods of preventing spontaneous or unwanted fusion of antibody heavy and light chain genes in biscistronic constructs comprising the deletion of antibody splice donor or acceptor sites. Experiments conducted during the course of development of the present invention (See e.g., Example 2) demonstrated that the removal of splice donor sites resulted in the elimination of unwanted fusion polypeptides.

Experimental

The following examples serve to illustrate certain preferred embodiments and aspects of the present invention and are not to be construed as limiting the scope thereof.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml (milliliters); μl (microliters); cm (centimeters); mm (millimeters); μm (micrometers); nm (nanometers); ° C. (degrees Centigrade).

EXAMPLE 1

Generation of Antibody Fusion Genes

The gene that produces the antibody fusion protein was created as follows: The heavy chain gene of a specific antibody was fused to a linker sequence and the linker sequence was fused to the light chain gene sequence. This fusion gene encodes a single protein. A diagram of the actual gene construct is shown in FIG. 1. The complete sequence of two specific antibody fusions are shown in FIG. 2. The linker sequence is made from a portion of the bovine α-lactalbumin signal peptide. The antibody fusions contain the whole heavy chain gene, but are lacking the last codon, which typically encodes a lysine. The linker gene sequence encodes the following protein sequence: Ile-Leu-Phe-His-Ala-Thr-Gln -Ala (SEQ ID NO:20). The whole light chain sequence without modifications is then encoded by the fusion gene sequence.

Cell lines were transduced with retroviral vectors containing the gene constructs. The production of the fusion protein was analyzed via western blots. Western blots indicated that the fusion protein was produced and was the correct molecular weight. ELISA assays that measure the ability of the antibody to bind to the antigen indicate that the fusion antibody product binds the antigen effectively.

The fusion gene constructs were not created intentionally, but by an RNA splicing event that occurred during our retroviral vector production process. An initial gene construct was made for each antibody. The initial vectors that were used to transduce cell lines are shown in FIG. 5. The sequences of the spliced retrovectors are shown in FIG. 6. The splicing location and sequence was verified by gene sequencing for antibody #1 and #2. Since the splicing signals were the same for antibodies #3 and #4 and the same mutational fix corrected the problem, it is predicted that the spliced sequence is the same as antibody #1 and #2. The nucleic acid sequences of the fusions for antibodies 3 and 4 are provided in FIG. 8.

EXAMPLE 2

Removal of Splice Junction Sequences

This Example describes the removal of non-canonical splice donor sites of the PSMA heavy chain gene in order to avoid unwanted splicing. The splice site at 5038-5041 of pLNC-PSMAhc-Ires-LC-WPREFixed was mutated from GG GT to CG GG. The mutation was introduced with an oligonucleotide pair (5' TGAGGCTCTGCACAACCACTACACGCAGAAGAGCCTCTCCCTGTCTCCCGGG AAATGAGAATTCC-3' (SEQ ID NO:18) and 5'TCGAGGAAT- TCTCATTTCCCGGGAGACAGGGAGAGGCTCTTCTG CGTGTAG TGGTTGTGC-3' (SEQ ID NO:19)) that was ligated with pLNC-PSMAhc-Ires-LC-WPREFixed that had been digested with NsiI and XhoI. The sequence of the new clone was verified by sequencing. This construct was shown to successfully produce antibody. The antibody was shown to bind the PSMA antigen.

The sequences of vectors containing antibody genes in which the splice donor sites have been removed are provided in FIG. 7. These vectors were used to transduce host CHO cells. Media was isolated from clonal populations of CHO cells that had been infected with fixed/mutated retroviral vector and subsequently placed under G418 selection. Each of the cells are G418 resistant and are expected to contain a fixed retrovector gene insert. Media was collected from the cells, run on gels, and blotted. The blots were probed with HRP labeled anti-human heavy chain constant region and HRP labeled anti-human IgG Kappa light chain antibodies. The results indicated that the heavy and light chains were not expressed as fusions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, protein fermentation, biochemistry, or related fields are intended to be within the scope of the following claims.

What is claimed is:

1. A composition comprising at least two identical polypeptides, each polypeptide comprising an entire antibody heavy chain fused to an entire antibody light chain in a single polypeptide, wherein said light chain is fused at the C-terminus of said heavy chain, wherein said entire antibody heavy chain and said entire antibody light chain are from the same parental immunoglobulin that binds a specific antigen, and wherein said antibody heavy chain is fused to said antibody light chain by the peptide linker of SEQ ID NO:20.

2. A composition comprising a multivalent protein comprising at least five identical polypeptides, wherein each of said polypeptides comprises an entire antibody heavy chain fused to an entire antibody light chain, wherein said light chain is fused at the C-terminus of said heavy chain, and wherein said entire antibody heavy chain and said entire antibody light chain are from the same parental immunoglobulin that binds a specific antigen, and wherein said antibody heavy chain is fused to said antibody light chain by the peptide linker of SEQ ID NO:20.

* * * * *